(12) United States Patent
Pelletier et al.

(10) Patent No.: US 6,783,930 B1
(45) Date of Patent: Aug. 31, 2004

(54) DEVELOPMENT OF NOVEL ANTI-MICROBIAL AGENTS BASED ON BACTERIOPHAGE GENOMICS

(76) Inventors: Jerry Pelletier, 8 Lakeview, Baie-D'Urfe, Quebec (CA), H9X 3B1; Philippe Gros, 107 Montrose, St. Lambert, Quebec (CA), J4R 1X4; Michael DuBow, 4901 Coolbrook Avenue, Montreal, Quebec (CA), H3X 2K8

(*) Notice: Subject to any disclaimer, the term of this patent is extended or adjusted under 35 U.S.C. 154(b) by 0 days.

(21) Appl. No.: 09/454,252

(22) Filed: Dec. 2, 1999

Related U.S. Application Data

(63) Continuation-in-part of application No. 09/407,804, filed on Sep. 28, 1999.

(60) Provisional application No. 60/110,992, filed on Dec. 3, 1998.

(51) Int. Cl.$^7$ .................. C12Q 1/68; G01N 33/569; C07H 21/04; C07K 14/00

(52) U.S. Cl. .................. 435/5; 435/7.1; 435/7.33; 435/7.8; 435/883; 536/23.7; 530/350; 530/820

(58) Field of Search ............... 435/5, 7.1, 7.33, 435/7.8, 883, 7.3; 536/23.7; 530/350, 820; 424/9.1, 9.2

(56) References Cited

U.S. PATENT DOCUMENTS

| | | | |
|---|---|---|---|
| 3,691,016 A | 9/1972 | Patel | 195/68 |
| 3,969,287 A | 7/1976 | Jaworek et al. | 260/8 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,330,440 A | 5/1982 | Ayers et al. | 525/54.31 |

FOREIGN PATENT DOCUMENTS

| | | |
|---|---|---|
| EP | 0 072 925 A2 | 3/1983 |
| EP | 0 786 519 A2 | 7/1997 |
| WO | WO 89/00199 | 1/1989 |
| WO | WO 95/27043 | 10/1995 |

OTHER PUBLICATIONS

Adelman et al., "In Vitro Deletional Mutagenesis For Bacterial Production Of The 20,000–Dalton Form Of Human Pituitary Growth Hormone", DNA, 2(3):183–93, 1983.

Altschul et al., "Gapped BLAST and PSI–BLAST: a new generation of protein database search programs", Nucleic Acids Research, 1997, vol. 25, No. 17, pp. 3389–3402.

Cohen, "Epidemiology of Drug Resistance: Implications for a Post–Antimicrobial Era", ML Science, vol. 257, Aug. 21, 1992, pp. 1050–1055.

Diaz et al., "Construction of a broad–host–range pneumococcal promoter–probe plasmid", Gene, 90: 163–167, 1990.

Durfee et al., "The retinoblastoma protein associates with the protein phosphatase type 1 catalytic subunit", Genes & Development, 7:555–569, 1993.

Eichenbaum et al., "Use of Lactococcal nisA Promoter To Regulate Gene Expression in Gram–Positive Bacteria: Comparison of Induction Level and Promoter Strength", Applied and Environmental Microbiology, 64:2763–2769, 1998.

Endo et al., "A new protein containing an SH2 domain that inhibits JAK kinases", Nature, 387:921–924, 1997.

Field et al., "Purifications Of A RAS–Responsive Adenylyl Cyclase Complex From *Saccharomyces Cerevisiae* By Use Of An Epitope Addition Method", Mol. Cell. Biol., 8:2159–2165, 1988.

Fink, "Where are the Limits of Life?", Book Reviews, 322:469–470, 1998.

Garvey et al., "The complete sequence of Bacillus phage Ø29 gene 16: a protein required for the genome encapsidation reaction", Gene, 40:311–316, 1985.

Gutierrez et al., "Signals in the Ø29 DNA–Terminal Protein Template for the Initiation of Phage Ø29 DNA Replication", Virology, 155:474–483, 1986.

Jorgensen et al., "Antimicrobial Resistance among Respiratory isolates of *Haemophilus influenza, Moraxella catarrhalis,* and *Streptococcus pneumonia* in the United States", Antimicrobial Agents and Chemotherapy, 34:2075–2080, 1990.

Kaneko et al., "Complete nucleotide sequence and molecular characterization of the temperature staphylococcal bacteriophage ΦPVL carrying Pantom–Valentine leukocidin genes", Genes 215:57–67, 1998.

Karimova et al., "A bacterial two–hybrid system based on a reconstituted signal transduction pathway", Proc. Natl. Acad. Sci., 95:5752–5756, 1998.

Katagari et al., "Multiple Possible Sites of BRCA2 Interacting With DNA Repair Protein RAD5 1", Genes, Chromosomes & Cancer, 21:217–222, 1998.

Kreiswirth et al., "The Toxic Shock Syndrome Exotoxin Structural Gene Is Not Detectably Transmitted By A Prophage", Nature, Oct. 20–26, 1983;305(5936):709–12, 1983.

Kodaira et al., "The dnaX gene Encodes the DNA Polymerase III Holoenzyme τ Submit, the dnaZ Gene Product", Mol Gen Genet, 192:80–86, 1983.

(List continued on next page.)

*Primary Examiner*—Robert A. Wax
*Assistant Examiner*—Rita Mitra

(57) ABSTRACT

A method for identifying suitable targets for antibacterial agents based on identifying targets of bacteriophage-encoded proteins is described. Also described are compositions useful in the identification methods and in inhibiting bacterial growth, and methods for preparing and using such compositions.

10 Claims, 8 Drawing Sheets

OTHER PUBLICATIONS

Lee et al., "*Escherichia coli* DnaX product, the τ subunit of DNA polymerase III, is a multifunctional protein with single–stranded DNA–dependent ATPase activity", Proc. Natl. Acad. Sci., 84:2713–2717, 1987.

Loessner et al., "The Two–Component Lysis System Of *Staphylococcus Aureus* Bacteriophage Twort: A Large TTG–Start Holin And An Associated Amidase Endolysin", FEMS Microbiol Lett., May 15;162(2):265–74, 1998.

Maki et al., "DNA Polymerase III Holoenzyme of *Escherichia coli*", The Journal of Biological Chemistry, 263:6547–6554, 1988.

Mancini et al., "Complementation of the fol2 Deletion in *Sccharmoyces cerevisiae* by Human and *Escherichia coli* Genes Encoding GTP Cyclohydrolase I", Biochemical and Biophysical Research Communications, 255:521–527, 1999.

Martin et al., "Analysis of the Complete Nucleotide Sequence and Functional Organization of the Genome of *Streptococcus pneumoniae* Bacteriophage Cp–1", Journal of Virology, 70:3678–3687, 1996.

McDonnell et al., ""Diplophage": A Bacteriophage of *Diplococcus pneumoniae*", Virology, 63:577–582, 1975.

Nardese et al., "Disruption of the GTP–Cyclohidrolase I Gene in *Saccharomyces cerevisiae*", Biochemical and Biophysical Research Communications, 218:273–279, 1996.

Neu, "The Crisis in Antibiotic Resistance", Science, 257:1064–1073, 1992.

Oskouian et al., "Repression And Catabolite Repression Of The Lactose Operon Of *Staphylococcus Aureus*", J. Bacteriol, Jul., 172(7):3804–12, 1990.

Pickett et al., "Encapsidation of Heterologous RNAs by Bacteriophage MS2 Coat Protein", Nucleic Acids Research, 21:4621–4626, 1993.

Qin et al., "A Strategy for Rapid, High–Confidence Protein Identification", Anal. Chem., 69:3995–4001, 1997.

Qui et al., "Dimerization by Translation Initiation Factor 2 Kinase GCN2 Is Mediated by Interactions in the C–Terminal Ribosome–Binding Region and the Protein Kinase Domain", Molecular and Cellular Biology, 18:2697–2711, 1988.

Reisinger et al., "Lambda Kil–Mediated Lysis Requires the Phage Context", Virology, 193:1033–1036, 1993.

Rost et al., "Bridging The Protein Sequence–Structure Gap By Structure Predictions", Annu. Rev.Biophys, Biomol. Struct., 25:113–36, 1996.

Salamov et al., "Combining Sensitive Database Searches With Multiple Intermediates to Detect Distant Homologues", Protein Eng., 12:95–100, 1999.

Schenk et al., "Improved Method For Electroporation of *Staphylococcus aureus*", FEMS Microbiology Letters, 94:133–138, 1992.

Sheehan et al., "The lytic enzyme of the pneumococcal phage Dp–1: a chimeric lysin of intergeneric origin", Molecular Microbiology, 25:717–725, 1997.

Smidt et al., "Physiologic Importance of Pyrroloquinoline Quinone", P.S.E.B.M., 197:19–26, 1991.

Sopta et al., "Isolation of Three Proteins That Bind to Mammalian RNA Polymerase II", 260:10353–10360, 1985.

Steiner et al., "The Missing Link in Phage Lysis of Gram-Positive Bacteria: Gene 14 of *Bacillus subtilis* Phage Φ29 Encodes the Functional Homolog of Lambda S Protein", Journal of Bacteriology, 175:1038–1942, 1993.

Swanstrom et al., "Agar Layer Method for Production of High Titer Phage Stocks", Proc. Soc. Exptl. Biol. & Med., 78:372–375, 1951.

Tauriainen et al., "Recombinant Luminescent Bacterial for Measuring Bioavailable Arsenite and Antimonite", Applied and Environmental Microbiology, 63:4456–4461, 1997.

Tomasz, "Model for the Mechanism Controlling the Expression of Competent State in Pneumococcus Cultures", Journal of Bacteriology, 91:1050–1061, 1966.

Tsuchihashi et al., "Translational frameshifting generates the Γ subunit of DNA polymerase II holoenzyme", Proc. Natl. Acad. Sci., 87:2516–2520, 1990.

Yoshikawa et al., "Nucleotide sequence analysis of DNA replication origins of the small Bacillus bacteriphages: evolutionary relationships", Gene, 1985.

A) Functional assay on semi-solid support media

B) Functional assay in liquid medium

DEVELOPMENT OF NOVEL ANTI-MICROBIAL AGENTS BASED ON BACTERIOPHAGE GENOMICS

RELATED APPLICATIONS

This application is a continuation-in-part of U.S. application Ser. No. 09/407,804, filed Sep. 28, 1999, entitled DNA SEQUENCES FROM *STAPYLOCOCCUS AUREUS* BACTERIOPHAGE 77 THAT ENCODE ANTI-MICROBIAL POLYPEPTIDES, and claims the benefit of U.S. Provisional Application No. 60/110,992, filed Dec. 3, 1998, entitled DEVELOPMENT OF NOVEL ANTIMICROBIAL AGENTS BASED ON BACTERIOPHAGE GENOMICS, which are hereby incorporated by reference in their entireties, including drawings.

BACKGROUND OF THE INVENTION

The present invention relates to the field of antibacterial agents and the treatment of infections of animals or other complex organisms by bacteria.

The frequency and spectrum of antibiotic-resistant infections have, in recent years, increased in both the hospital and community. Certain infections have become essentially untreatable and are growing to epidemic proportions in the developing world as well as in institutional settings in the developed world. The staggering spread of antibiotic resistance in pathogenic bacteria has been attributed to microbial genetic characteristics, widespread use of antibiotic drugs, and changes in society that enhance the transmission of drug-resistant organisms. This spread of drug resistant microbes is leading to ever increasing morbidity, mortality and health-care costs.

Ironically, it is the very success of antibiotics, resulting in their widespread use, that has contributed the most to rising numbers of drug resistant bacterial strains. The longer a bacterial strain is exposed to a drug, the more likely it is to acquire resistance. Today, a total of 160 antibiotics, all based on a few basic chemical structures and targeting a small number of metabolic pathways, have found their way to market. Over-prescription of these drugs, as well as the failure of patients to comply with the complete antibiotic regimen, has lead to the rapid emergence of antibiotic resistant strains. Such misuse of prescriptions, careless use of antibiotics in virtually all commercial production of beef and fowl, and changing societal conditions, such as the growth of day-care centers, increased long-term care in hospitals, and increased mobility of the population, has provided an environment where drug-resistant microbes can emerge and spread. Thus, virtually all common infectious bacteria are becoming, or have already become, resistant to one or more groups of antibiotics. Such resistance now reaches all classes of antibiotics currently in use, including: β-lactams, fluoroquinolones, aminoglycosides, macrolide peptides, chloramphenicol, tetracyclines, rifampicin, folate inhibitors, glycopeptides, and mupirocin.

Over the last 45 years bacteria have adapted genetically to avoid the destruction/alteration of the essential pathways that these chemotherapeutic agents target. Antibiotic resistant bacterial strains are now emerging at a higher rate than the rate at which new antibiotics are being developed. The consequence of this dilemma has been a dramatic increase in the cost of treating infections what would otherwise easily succumb to routine antibiotic therapy. Furthermore, and perhaps most importantly, the emergence of multiple drug resistant pathogenic bacteria has led to a significant increase in morbidity and mortality, particularly in institutional settings.

Most major pharmaceutical companies have on-going drug discovery programs for novel anti-microbials. These are based on screens for small molecule inhibitors (natural products, bacterial culture media, libraries of small molecules, combinatorial chemistry) of crucial metabolic pathways of the micro-organism of interest (e.g., bacteria, fungi, parasites, worms). The screening process is largely for cytotoxic compounds and in most cases is not based on a known mechanism of action of the compounds. Pharmaceutical companies have large programs in this area Classical drug screening programs are being exhausted and many of these pharmaceutical companies are looking towards rational drug design programs.

Several small to mid-size biotechnology companies as well as large pharmaceutical companies have developed systematic high-throughput sequencing programs to decipher the genetic code of specific microorganisms of interest. The goal is to identify, through sequencing, unique biochemical pathways or intermediates that are unique to the microorganism. Knowledge of this may, in turn, form the rationale for a drug discovery program based on the mechanism of action of the identified enzymes/proteins. Genome Therapeutics Corp., The Institute for Genome Research, Human Genome Sciences Inc., and other companies have such sequencing programs in place. However, one of the most critical steps in this approach is the ascertainment that the identified proteins and biochemical pathways are 1) non-redundant and essential for bacterial survival, and 2) constitute suitable and accessible targets for drug discovery.

SUMMARY OF THE INVENTION

While animals such as humans are, on occasion, infected by pathogenic bacteria, bacteria also have natural enemies. A number of host-specific viruses, known as bacteriophages or phages, infect and kill bacteria in the natural environment. Such bacteriophages generally have small compact genomes and bacteria are their exclusive hosts. Many known bacteria are host to a large number of bacteriophages that have been described in the literature. During the 1940's–1960's, phage biology was an area of active research. As a testimony to this, the study of phages which infect and inhibit the enteric bacterium *Escherichia coli* (*E. coli*) contributed much to the early understanding of molecular biology and virology.

This invention utilizes the observation that bacteriophages successfully infect and inhibit or kill host bacteria, targeting a variety of normal host metabolic and physiological traits, some of which are shared by all bacteria, pathogenic and nonpathogenic alike. The term "pathogenic" as used herein denotes a contribution to or implication in disease or a morbid state of an infected organism. The invention thus involves identifying and elucidating the molecular mechanisms by which phages interfere with host bacterial metabolism, an objective being to provide novel targets for drug design. Whether the phage blocks bacterial RNA transcription or translation, or attacks other important metabolic pathways, such as cell wall assembly or membrane integrity, the basic blueprint for a phage's bacteria-inhibiting ability is encoded in its genome and can be unlocked using bioinformatics, functional genomics, and proteorics. By these means, the invention utilizes sequence information from the genomics of bacteriophage to identify novel antimicrobials that can be further used to actively and/or prophylactically treat bacterial infection.

Two important components of the invention thus are: i) the identification of bacteria-inhibiting phage open reading frames ("ORF"s) and corresponding products that can be used to develop antibiotics based on amino acid sequence and secondary structural characteristics of the ORF products, and ii) the use of bacteriophages to map out essential bacterial target genes and homologs, which can in turn lead to the development of suitable anti-microbial agents. These two avenues represent new and general methods for developing novel antimicrobials.

The invention thus concerns the identification of bacteriophage ORFs that supply bacteria-inhibiting functions. In this regard, use of the terms "inhibit", "inhibition", "inhibitory", and "inhibitor" all refer to a function of reducing a biological activity or function. Such reduction in activity or function can, for example, be in connection with a cellular component, e.g., an enzyme, or in connection with a cellular process, e.g., synthesis of a particular protein, or in connection with an overall process of a cell, e.g., cell growth. In reference to bacterial cell growth, for example, an inhibitory effect (i.e., a bacteria-inhibiting effect) may be bacteriocidal (killing of bacterial cells) or bacteriostatic (i.e., stopping or at least slowing bacterial cell growth). The latter slows or prevents cell growth such that fewer cells of the strain are produced relative to uninhibited cells over a given period of time. From a molecular standpoint, such inhibition may equate with a reduction in the level of, or elimination of, the transcription and/or translation of a specific bacterial target(s), or reduction or elimination of activity of a particular target biomolecule.

It is particularly advantageous to evaluate a plurality of different phage ORFs for inhibitory activity which may be from one, but is preferably from a plurality of different phage. For example, evaluating ORFs from a number of different phage of the same bacterial host provides at least two advantages. One is that the multiple phages will provide identification of a variety of different targets. Second, it is likely that multiple phage will utilize the same cellular target.

As used herein, the terms "bacteriophage" and "phage" are used interchangeably to refer to a virus which can infect a bacterial strain or a number of different bacterial strains.

In the context of this invention, the term "bacteriophage ORF" or "phage ORF" or similar term refers to a nucleotide sequence in or from a bacteriophage. In connection with a particular ORF, the terms refer an open reading frame which has at least 95% sequence identity, preferably at least 97% sequence identity, more preferably at least 98% sequence identity with an ORF from the particular phage identified herein (e.g., with an ORF as identified herein) or to a nucleic acid sequence which has the specified sequence identify percentage with such an ORF sequence.

A first aspect of the invention thus provides a method for identifying a bacteriophage nucleic acid coding region encoding a product active on an essential bacterial target by identifying a nucleic acid sequence encoding a gene product which provides a bacteria-inhibiting function when the bacteriophage infects a host bacterium, preferably one that is an animal or plant pathogen, more preferably a bird or mammalian pathogen, and most preferably a human pathogen. The bacteriophage is an uncharacterized bacteriophage. Thus, the method excludes, for example, phage λ, φx174, m13 and other E. coli-specific bacteriophage that have been studied with respect to gene number and/or function. It also excludes, for example, the nucleic acid coding regions described in Tables 13–14, and in preferred embodiments, excludes the phage in which those regions are naturally located. In preferred embodiments of this and the other aspects of the present invention, the phage is Staphylococcus aureus phage 77, 3A, or 96.

In connection with bacteriophage, the term "uncharacterized" means that a certain bacteriophage's genome has not yet been fully identified such that the genes having function involved in inhibiting host cells have not been identified. In particular, phage for which the description of genomic or protein sequence was first provided herein are uncharacterized. Phage sequences for which host bacteria-inhibiting functions have been identified prior to the filing of the present application (or alternatively prior to the present invention) are specifically excluded from the aspects involving utilization of sequences from uncharacterized bacteriophage, except that aspects may involve a plurality of phage where one or more of those phage are uncharacterized and one or more others have been characterized to some extent. A number of different bacteria-inhibiting phage ORFs are indicated in Tables 12–14. The phage ORFs or sequences identified therein are not within the term "uncharacterized; alternatively, in preferred embodiments the phage containing those ORFs are excluded from this term. Further, any additional phage ORFs (or alternatively the phage which contain those ORFs) which have previously been described in the art as bacteria-inhibiting ORFs are expressly excluded; those ORFs or phage are known to those skilled in the art and the exclusion can be made express by specifically naming such ORFs or phage as needed (likewise for uncharacterized targets as described below). For the sake of brevity, such a listing is not expressly presented, as such information is readily available to those skilled in the art Stating that an agent or compound is "active on" a particular cellular target, such as the product of a particular gene, means that the target is an important part of a cellular pathway which includes that target and that the agent acts on that pathway. Thus, in some cases the agent may act on a component upstream or downstream of the stated target, including on a regulator of that pathway or a component of that pathway.

By "essential", in connection with a gene or gene product, is meant that the host cannot survive without, or is significantly growth compromised, in the absence depletion, or alteration of functional product An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly, preferably less than 20%, more preferably less than 10%, most preferably less than 5% of the growth rate of the uninhibited wild-type, or not at all, in the growth medium. Preferably, in the absence of activity provided by a product of the gene, the cell will not grow at all or will be non-viable, at least under culture conditions similar to the in vivo conditions normally encountered by the bacterial cell during an infection. For example, absence of the biological activity of certain enzymes involved in bacterial cell wall synthesis can result in the lysis of cells under normal osmotic conditions, even though protoplasts can be maintained under controlled osmotic conditions. In the context of the invention, essential genes are generally the preferred targets of antimicrobial agents. Essential genes can encode target molecules directly or can encode a product involved in the production, modification, or maintenance of a target molecule.

A "target" refers to a biomolecule that can be acted on by an exogenous agent, thereby modulating, preferably inhibiting, growth or viability of a cell. In most cases such a target will be a nucleic acid sequence or molecule, or a polypeptide or protein. However, other types of biomolecules can also be targets, e.g., membrane lipids and mri cell wall structural components.

The term "bacterium" refers to a single bacterial strain, and includes a single cell, and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different phage ORF inserts.

Preferred embodiments involve expressing at least one recombinant phage ORF(s) in a bacterial host followed by inhibition analysis of that host. Inhibition following expression of the phage ORF is indicative that the product of the ORF is active on an essential bacterial target. Such evaluation can be carried out in a variety of different formats, such as on a support matrix such as a solidified medium in a petri dish, or in liquid culture. Preferably a plurality of phage ORFs are expressed in at least one bacterium. The plurality of phage ORFs can be from one or a plurality of phage. With respect to a single phage or at least one phage in a plurality of phages, the plurality of expressed ORFs preferably represents at least 10%, more preferably at least 20%, 40%, or 60%, still more preferably at least 80% or 90%, and most preferably at least 95% of the ORFs in the phage genome. Preferably, for a plurality of phage, the plurality of expressed ORFs preferably represents at least 10%, more preferably at least 20%, 40%, or 60%, still more preferably at least 80% or 90%, and most preferably at least 95% of the ORFs in the phage genome of each phage. The plurality of phage ORFs can be expressed in a single bacterium, or in a plurality of bacteria where one ORF is expressed in each bacterium, or in a plurality of bacteria where a plurality of ORFs are expressed in at least one or in all of the plurality of bacteria, or combinations of these.

In embodiments of the above aspect (as well as in other aspects herein) in which a plurality of phage are utilized, a plurality of phage have the same bacterial host species; have different bacterial host species; or both. The plurality of phage includes at least two different phage, preferably at least 3,4,5,6,8,10,15,20, or more different phage. Indeed, more preferably, the plurality of phage will include 50, 75, 100, or more phage. As described herein, the larger number of phage is useful to provide additional target and target evaluation information useful in developing antibacterial agents, for example, by providing identification of a larger range of bacterial targets, and/or providing further indication of the suitability of a particular target (for example, utilization of a target by a number of different unrelated phage can suggest that the target is particularly stable and accessible and effective) and/or can indicate alternate sites on a target which interact with different inhibitors.

Further embodiments involve confirmation of the inhibitor function of the phage ORF, such as by utilizing or incorporating a control(s) designed to confirm the inhibitory nature of the ORF(s) being evaluated. The control can, for example, be provided by expression of an inactive or partially inactive form of the ORF or ORF product, and/or by the absence of expression of the ORF or ORF product in the same or a closely comparable bacterial strain as that used for expression of the test ORF. The reduced level of activity or the absence of active ORF product in the control will thus not provide the inhibition provided by a corresponding inhibitory ORF, or will provide a distinguishably lower level of inhibition. An inactivated or partially inactivated control has a mutation(s), e.g., in the coding region or in flanking regulatory elements, that reduce(s) or eliminate(s) the normal function of the ORF. Thus, the inhibition of a bacterium following expression of a phage ORF is determined by comparison with the effects of expression of an inactivated ORF or the response of the bacteria in the absence of expression in the same or similar type bacterium. Such determination of inhibition of the bacterium following expression of the ORF is indicative of a bacteria-inhibiting function. These manipulations are routinely understood and accomplished by those of skill in the art using standard techniques. In embodiments utilizing absence of expression of the ORF, the bacteria can, for example, contain an empty vector or a vector which allows expression of an unrelated sequence which is preferably non-inhibitory. Alternatively, the bacteria may have no vector at all. Combinations of such controls or other controls may also be utilized as recognized by those skilled in the art.

In embodiments involving expression of a phage ORF in a bacterial strain, in preferred embodiments that expression is inducible. By "inducible" is meant that expression is absent or occurs at a low level until the occurrence of an appropriate environmental stimulus provides otherwise. For the present invention such induction is preferably controlled by an artificial environmental change, such as by contacting a bacterial strain population with an inducing compound (i.e., an inducer). However, induction could also occur, for example, in response to build-up of a compound produced by the bacteria in the bacterial culture, e.g., in the medium. As uncontrolled or constitutive expression of inhibitory ORFs can severely compromise bacteria to the point of eradication, such expression is therefore undesirable in many cases because it would prevent effective evaluation of the strain and inhibitor being studied. For example, such uncontrolled expression could prevent any growth of the strain following insertion of a recombinant ORF, thus preventing determination of effective tansfection or transformation. A controlled or inducible expression is therefore advantageous and is generally provided through the provision of suitable regulatory elements, e.g., promoter/operator sequences that can be conveniently transcriptionally linked to a coding sequence to be evaluate. In most cases, the vector will also contain sequences suitable for efficient replication of the vector in the same or different host cells and/or sequences allowing selection of cells containing the vector, i.e., "selectable markers." Further, preferred vectors include convenient primer sequences flanking the cloning region from which PCR and/or sequencing may be performed.

As knowledge of the nucleotide sequence of phage ORFs is useful, e.g. for assisting in the identification of phage proteins active against essential bacterial host targets, preferred embodiments involve the sequencing of at least a portion of the phage genome in combination with the above methods. This can be done either before or after or independent of expression and inhibition of the ORF in the bacteria, and provides information on the nature and characteristics of the ORF. Such a portion is preferably at least 10%, 20%, 40%, 80%, 90%, or 100% of the phage genome. For embodiments in which a plurality of phage are utilized, preferably each phage is sequenced to an extent as just specified.

Such sequencing is preferably accompanied by computer sequence analysis to define and evaluate ORF(s), ORF products, structural motifs or functional properties of ORF products, and/or their genetic control elements. Thus, certain embodiments incorporate computer sequence analyses or nucleic acid and/or amino acid sequences. Further, existing data banks can provide phage sequence and product information which can be utilized for analysis and identification of ORFs in the sequence. Computer analysis may further employ known homologous sequences from other species that suggest or indicate conserved underlying biochemical function(s) for the inhibitory or potentially inhibitory ORF sequence(s) being evaluated. This can include the sequences of signature motifs of identified classes of inhibitors.

In the context of the phage nucleic acid sequences, e.g., gene sequences, of this invention, the terms "homolog" and "homologous" denote nucleotide sequences from different bacteria or phage strains or species or from other types of organisms that have significantly related nucleotide sequences, and consequently significantly related encoded gene products, preferably having related function. Homologous gene sequences or coding sequences have at least 70% sequence identity (as defined by the maximal base match in a computer-generated alignment of two or more nucleic acid sequences) over at least one sequence window of 48 nucleotides, more preferably at least 80 or 85%, still more preferably at least 90%, and most preferably at least 95%. The polypeptide products of homologous genes have at least 35% amino acid sequence identity over at least one sequence window of 18 amino acid residues, more preferably at least 40%, still more preferably at least 50% or 60%, and most preferably at least 70%, 80%, or 90%. Preferably, the homologous gene product is also a functional homolog, meaning that the homolog will functionally complement one or more biological activities of the product being compared. For nucleotide or amino acid sequence comparisons where a homology is defined by a % sequence identity, the percentage is determined using BLAST programs (with default parameters (Altschul et al., 1997, "Gapped BLAST and PSI-BLAST: a new generation of protein database search programs, Nucleic Acid Res. 25:3389–3402). Any of a variety of algorithms known in the art which provide comparable results can also be used, preferably using default parameters. Performance characteristics for three different algorithms in homology searching is described in Salamov et al., 1999, "Combining sensitive database searches with multiple intermediates to detect distant homologues." *Protein Eng.* 12:95–100. Another exemplary program package is the GCG™ package from the University of Wisconsin.

Homologs may also or in addition be characterized by the ability of two complementary nucleic acid strands to hybridize to each other under appropriately stringent conditions. Hybridizations are typically and preferably conducted with probe-length nucleic acid molecules, preferably 20–100 nucleotides in length. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g.,. Maniatis, T. et al. (1989) *Molecular Cloning: A Laboratory Manual*, Cold Spring Harbor University Press, Cold Spring, N.Y.; Ausubel, F. M. et al. (1994) *Current Protocols in Molecular Biology*. John Wiley & Sons, Secaucus, N.J. Homologs and homologous gene sequences may thus be identified using any nucleic acid sequence of interest, including the phage ORFs and bacterial target genes of the present invention.

A typical hybridization, for example, utilizes, besides the labeled probe of interest, a salt solution such as 6×SSC (NaCl and Sodium Citrate base) to stabilize nucleic acid strand interaction, a mild detergent such as 0.5% SDS, together with other typical additives such as Denhardt's solution and salmon sperm DNA. The solution is added to the immobilized sequence to be probed and incubated at suitable temperatures to preferably permit specific binding while minimizing nonspecific binding. The temperature of the incubations and ensuing washes is critical to the success and clarity of the hybridization. Stringent conditions employ relatively higher temperatures, lower salt concentrations, and/or more detergent than do non-stringent conditions. Hybridization temperatures also depend on the length, complementarity level, and nature (ie, "GC content") of the sequences to be tested. Typical stringent hybridizations and washes are conducted at temperatures of at least 40° C., while lower stringency hybridizations and washes are typically conducted at 37° C. down to room temperature (~25° C.). One of skill in the art is aware that these conditions may vary according to the parameters indicated above, and that certain additives such as formamide and dextran sulphate may also be added to affect the conditions.

By "stringent hybridization conditions" is meant hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C.

In sequence comparison analyses, an ORF, or motif, or set of motifs in a bacteriophage sequence can be compared to known inhibitor sequences, e.g., homologous sequences encoding homologous inhibitors of bacterial function. Likewise, the analysis can include comparison with the structure of essential bacterial gene products, as structural similarities can be indicative of similar or replacement biological function. Such analysis can include the identification of a signature, or characteristic motif(s) of an inhibitor or inhibitor class.

Also, the identification of structural motifs in an encoded product, based on nucleotide or amino acid sequence analysis, can be used to infer a biochemical function for the product. A database containing identified structural motifs in a large number of sequences is available for identification of motifs in phage sequences. The database is PROSITE, which is available at www.expasy.cb/cgi~bin/scanprosite. The identification of motifs can, for example, include the identification of signature motifs for a class or classes of inhibitory proteins. Other such databases may also be used.

In aspects and preferred embodiments described herein, in which a bacterium or host bacterium is specified, the bacterium or host bacterium is preferably selected from a pathogenic bacterial species, for example, one selected from Table 1. Preferably, an animal or plant pathogen is used. For animals, preferably the bacterium is a bird or mammalian pathogen, still more preferably a human pathogen.

In aspects and preferred embodiments involving a bacteriophage or sequences from a bacteriophage, one or more bacteriophage are preferably selected from those listed in Table 1 in the Detailed Description below. Those exemplary bacteriophge are readily obtained from the indicated sources.

In some cases, it is advantageous to utilize phage with non-pathogenic host bacteria. The genome, structural motif, ORF, homolog, and other analyses described herein can be performed on such phage and bacteria. Such analysis provides useful information and compositions. The results of such analyses can also be utilized in aspects of the present invention to identify homologous ORFs, especially inhibitor ORFs in phage with pathogenic bacterial hosts. Similarly, identification of a target in a non-pathogenic host can be used to identify homologous sequences and targets in pathogenic bacteria, especially in genetically closely related bacteria. Those skilled in the art are familiar with bacterial genetic relationships and with how to determine relatedness based on levels of genomic identity or other measures of nucleotide sequence and/or amino acid sequence similarity, and/or other physical and culture characteristics such as morphology, nutritional requirements, or minimal media to support growth.

Also in preferred embodiments, an embodiments of this aspect is combined with an embodiment of the following aspect.

A related aspect of the invention provides methods for identifying a target for antibacterial agents by identifying the bacterial target(s) of at least one uncharacterized or untargeted inhibitor protein or RNA from a bacteriophage. Such identification allows the development of antibacterial agents active on such targets. Preferred embodiments for identifying such targets involve the identification of binding of target and phage ORF products to one another. The phage ORF products may be subportions of a larger ORF product that also binds the host target. In preferred embodiments, the phage protein or RNA is from an uncharacterized bacteriophage in Table 1. This aspect preferably includes the identification of a plurality of such targets in one or a plurality of different bacteria, preferably in one or a plurality of bacteria listed in Table 1.

In preferred embodiments of this aspect and other aspects of this invention involving particular phage ORFs or phage sequences, the ORF is *Staphylococcus aureus* phage 77 ORF 17, 19, 43, 102, 104, or 182 as identified in U.S. application Ser. No. 09/407,804.

As indicated for the above aspect, preferably the method involves the use of a plurality of different phage, and thus a plurality of different phage inhibitors and/or inhibitor ORFs.

In addition to uncharacterized phage ORF products, it is also useful to identify the targets of phage ORF products which are known to be inhibitors of host bacteria, but where the target has not been identified. Thus, such inhibitors can likewise be utilized as "untargeted" inhibitor phage ORFs and ORF products, e.g., proteins or RNAS.

In the context of inhibitor proteins or RNAs from a phage, the term "uncharacterized" means that a bacteria-inhibiting function for the protein has not previously been identified. Preferably, but not necessarily, the sequence of the protein or the corresponding coding region or ORF was not described in the art before the filing of the present application for patent (or alternatively prior to the present invention). Thus, this term specifically excludes any bacteria-inhibiting phage protein and its associated bacterial target which has been identified as inhibitory before the present invention or alternatively before the filing of the present application, for example those identified in Tables 12–14 or otherwise identified herein. For example, from *E. coli*, phage T7 genes 0.7 and 2.0 target the host RNA polymerase, phage T4 gp55/gp33 alter the specificity of host RNA polymerase. The T4 regB gene product also targets the host translation apparatus. As with the uncharacterized bacteriophage ORFs or bacteriophage above, for such identified proteins, the sequences encoding those proteins are excluded from the uncharacterized inhibitor proteins.

The term "fragment" refers to a portion of a larger molecule or assembly. For proteins, the term "fragment" refers to a molecule which includes at least 5 contiguous amino acids from the reference polypeptide or protein, preferably at least 8, 10, 12, 15, 20, 30, 50 or more contiguous amino acids. In connection with oligo- or polynucleotides, the term "fragment" refers to a molecule which includes at least 15 contiguous nucleotides from a reference polynucleotide, preferably at least 24, 30, 36, 45, 60, 90, 150, or more contiguous nucleotides.

Preferred embodiments involve identification of binding that include methods for distinguishing bound molecules, for example, affinity chromatography, immunoprecipitation, crosslinking, and/or genetic screen methods that permit protein:protein interactions to be monitored. One of skill in the art is familiar with these techniques and common materials utilized (see, e.g., Coligan, J. et al. (eds.) (1995) *Current Protocols in Protein Science*. John Wiley & Sons, Secaucus, N.J.).

Genetic screening for the identification of protein:protein interactions typically involves the co-introduction of both a chimeric bait nucleic acid sequence (here, the phage ORF to be tested) and a chimeric target nucleic acid sequence that, when co-expressed and having affinity for one another in a host cell, stimulate reporter gene expression to indicate the relationship. A "positive" can thus suggest a potential inhibitory effect in bacteria. This is discussed in further detail in the Detailed Description section below. In this way, new bacterial targets can be identified that are inhibited by specific phage ORF products or derivatives, fragments, mimetics, or other molecules.

Other embodiments involve the identification and/or utilization of mutant targets by virtue of their host's relatively unresponsive nature in the presence of expression of ORFs previously identified as inhibitory to the non-mutant or wild-type strain. Such mutants have the effect of protecting the host from an inhibition that would otherwise occur and indirectly allow identification of the precise responsible target for follow-up studies and anti-microbial development. In certain embodiments, rescue from inhibition occurs under conditions in which a bacterial target or mutant target is highly expressed. This is performed, for example, through coupling of the sequence with regulatory element promoters, e.g., as known in the art, which regulate expression at levels higher than wild-type, e.g., at a level sufficiently higher that the inhibitor can be competitively bound to the highly expressed target such that the bacterium is detectably less inhibited.

Identification of the bacterial target can involve identification of a phage-specific site of action. This can involve a newly identified target, or a target where the phage site of action differs from the site of action of a previously known antibacterial agent or inhibitor. For example, phage T7 genes 0.7 and 2.0 target the host RNA polymerase, which is also the cellular target for the antibacterial agent, rifampin. To the extent that a phage product is found to act at a different site than previously described inhibitors, aspects of the present invention can utilize those new, phage-specific sites for identification and use of new agents. The site of action can be identified by techniques well-known to those skilled in the art, for example, by mutational analysis, binding competition analysis, and/or other appropriate techniques.

Once a bacterial host target protein or nucleic acid or mutant target sequence has been identified and/or isolated, it too can be conveniently sequenced, sequence analyzed (e.g., by computer), and the underlying gene(s), and corresponding translated product(s) further characterized. Preferred embodiments include such analysis and identification. Preferably such a target has not previously been identified as an appropriate target for antibacterial action.

Certain embodiments include the identification of at least one inhibitory phage ORF or ORF product, e.g., as described for the above aspect, and thus are a combination of the two aspects.

Additionally, the invention provides methods for identifying targets for antibacterial agents by identifying homologs of a Enterococcus sp. target of a bacteriophage inhibitory ORF product. Such homologs may be utilized in the various aspects and embodiments described herein as described for the host Enterococcus sp. for bacteriophage 182.

Other aspects of the invention provide isolated, purified, or enriched specific phage nucleic acid and amino acid sequences, subsequences, and homologs thereof for phage selected from uncharacterized phage listed in Table 1, preferably from bacteriophage 77, 3A, 96. For example, such sequences do not include sequences identified in any of Tables 11–14. Such nucleotide sequences are at least 15 nucleotides in length, preferably at least 18, 21, 24, or 27 nucleotides in length, more preferably at least 30, 50, or 90 nucleotides in length. In certain embodiments, longer nucleic acids are preferred, for example those of at least 120, 150, 200, 300, 600, 900 or more nucleotides. Such sequences can, for example, be amplification oligonucleotides (e.g., PCR primers), oligonucleotide probes, sequences encoding a portion or all of a phage-encoded protein, or a fragment or all of a phage-encoded protein. In preferred embodiments, the nucleic acid sequence contains a sequence which is within a length range with a lower length as specified above, and an upper length limit which is no more than 50, 60, 70, 80, or 90% of the length of the corresponding full-length ORF. The upper length limit can also be expressed in terms of the number of base pairs of the ORF (coding region). In preferred embodiments, the nucleic acid sequence is from *Staphylococcus aureus* phage 77 ORF 17, 19, 43, 102, 104, or 182 as identified in U.S. application Ser. No. 09/407,804.

As it is recognized that alternate codons will encode the same amino acid for most amino acids due to the degeneracy of the genetic code, the sequences of this aspect includes nucleic acid sequences utilizing such alternate codon usage for one or more codons of a coding sequence. For example, all four nucleic acid sequences GCT, GCC, GCA, and GCG encode the amino acid, alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified (e.g., a nucleic acid sequence from a phage as specified above) to form a second nucleic acid sequence encoding the same polypeptide as encoded by the first nucleic acid sequence using routine procedures and without undue experimentation. Thus, all possible nucleic acid sequences that encode the specified amino acid sequences are also fully described herein, as if all were written out in full, taking into account the codon usage, especially that preferred in the host bacterium. The alternate codon descriptions are available in common textbooks, for example, Stryer, BIOCHEMISTRY $3^{rd}$ ed., and Lehninger, BIOCHEMISTRY $3^{rd}$ ed. Codon preference tables for various types of organisms are available in the literature. Sequences with alternate codons at one or more sites can also be utilized in the computer-related aspects and embodiments herein. Because of the number of sequence variations involving alternate codon usage, for the sake of brevity, individual sequences are not separately listed herein. Instead the alternate sequences are described by reference to the natural sequence with replacement of one or more (up to all) of the degenerate codons with alternate codons from the alternate codon table (Table 6), preferably with selection according to preferred codon usage for the normal host organism or a host organism in which a sequence is intended to be expressed. Those skilled in the art also understand how to alter the alternate codons to be used for expression in organisms where certain codons code differently than shown in the "universal" codon table.

For amino acid sequences or polypeptides, sequences contain at least 5 peptide-linked amino acid residues, and preferably at least 6, 7, 10, 15, 20, 30, or 40, amino acids having identical amino acid sequence as the same number of contiguous amino acid residues in a particular phage ORF product. In some cases longer sequences may be preferred, for example, those of at least 50, 60, 70, 80, or 100 amino acids in length. In preferred embodiments, the amino acid sequence contains a sequence which is within a length range with a lower length as specified above, and an upper length limit which is no more than 50, 60, 70, 80, or 90% of the length of the corresponding full-length ORF product. The upper length limit can also be expressed in terms of the number of amino acid residues of the ORF product. In preferred embodiments, the amino acid sequence or polypeptide has bacteria-inhibiting function when expressed or otherwise present in a bacterial cell that is a host for the bacteriophage from which the sequence was derived.

By "isolated" in reference to a nucleic acid is meant that a naturally occurring sequence has been removed from its normal cellular (e.g., chromosomal) environment or is synthesized in a non-natural environment (e.g., artificially synthesized). Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched" means that the specific DNA or RNA sequence constitutes a significantly higher fraction (2–5 fold) of the total DNA or RNA present in the cells or solution of interest than in normal or diseased cells or in cells from which the sequence was originally taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

The term "significant" is used to indicate that the level of increase is useful to the person making such an increase and an increase relative to other nucleic acids of about at least 2-fold, more preferably at least 5- to 10-fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level, this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message Thus, purification of at least one order of magnitude, preferably two or three orders, and more preferably four or five orders of magnitude is expressly contemplated.

The terms "isolated", "enriched", and "purified" as used with respect to nucleic acids, above, may similarly be used to denote the relative purity and abundance of polypeptides (multimers of amino acids joined one to another by α-carboxyl:α-amino group (peptide) bonds). These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other tagging" techniques, conventional chromatography and/or electrophoretic methods. Some of the above utilize the corresponding nucleic acid sequence.

As indicated above, aspects and embodiments of the invention are not limited to entire genes and proteins. The invention also provides and utilizes fragments and portions thereof, preferably those which are "active" in the inhibitory sense described above. Such peptides or oligopeptides and oligo or polynucleotides have preferred lengths as specified above for nucleic acid and amino acid sequences from phage; corresponding recombinant constructs can be made to express the encoded same. Also included are homologous sequences and fragments thereof.

The nucleotide and amino acid sequences identified herein are believed to be correct, however, certain sequences may contain a small percentage of errors, e.g., 1–5%. In the event that any of the sequences have errors, the corrected sequences can be readily provided by one skilled in the art using routine methods. For example, the nucleotide sequences can be confirmed or corrected by obtaining and culturing the relevant phage, and purifying phage genomic nucleic acids. A region or regions of interest can be amplified, e.g., by PCR from the appropriate genomic template, using primers based on the described sequence. The amplified regions can then be sequenced using any of the available methods (e.g., a dideoxy termination method). This can be done redundantly to provide the corrected sequence or to confirm that the described sequence is correct. Alternatively, a particular sequence or sequences can be identified and isolated as an insert or inserts in a phage genomic library and isolated, amplified, and sequenced by standard methods. Confirmation or correction of a nucleotide sequence for a phage gene provides an amino acid sequence of the encoded product by merely reading off the amino acid sequence according to the normal codon relationships and/or expressed in a standard expression system and the polypeptide product sequenced by standard techniques. The sequences described herein thus provide unique identification of the corresponding genes and other sequences, allowing those sequences to be used in the various aspects of the present invention.

In other aspects the invention provides recombinant vectors and cells harboring at least one of the phage ORFs or portion thereof, or bacterial target sequences described herein. As understood by those skilled in the art, vectors may be provided in different forms, including, for example, plasmids, cosmids, and virus-based vectors. See, e.g., Maniatis, T. et al. (1989) *Molecular Cloning: A Laboratory Manual*, Cold Spring Harbor University Press, Cold Spring, N.Y.; See also, Ausubel, F. M. et al. (eds.) (1994) *Current Protocols in Molecular Biology*. John Wiley & Sons, Secaucus, N.J.

In preferred embodiments, the vectors will be expression vectors, preferably shuttle vectors that permit cloning, replication, and expression within bacteria. An "expression vector" is one having regulatory nucleotide sequences containing transcriptional and translational regulatory information that controls expression of the nucleotide sequence in a host cell. Preferably the vector is constructed to allow amplification from vector sequences flanking an insert locus. In certain embodiments, the expression vectors may additionally or alternatively support expression, and/or replication in animal, plant and/or yeast cells due to the presence of suitable regulatory sequences, e.g., promoters, enhancers, 3' stabilizing sequences, primer sequences, etc. In preferred embodiments, the promoters are inducible and specific for the system in which expression is desired, e.g., bacteria, animal, plant, or yeast. The vectors may optionally encode a "tag" sequence or sequences to facilitate protein purification. Convenient restriction enzyme cloning sites and suitable selective marker(s) are also optionally included. Such selective markers can be, for example, antibiotic resistance markers or markers which supply an essential nutritive growth factor to an otherwise deficient mutant host, e.g., tryptophan, histidine, or leucine in the Yeast Two-Hybrid systems described below.

The term "recombinant vector" relates to a single- or double-stranded circular nucleic acid molecule that can be transfected into cells and replicated within or independently of a cell genome. A circular double-stranded nucleic acid molecule can be cut and thereby linearized upon treatment with appropriate restriction enzymes. An assortment of nucleic acid vectors, restriction enzymes, and the knowledge of the nucleotide sequences cut by restriction enzymes are readily available to those skilled in the art. A nucleic acid molecule encoding a desired product can be inserted into a vector by cutting the vector with restriction enzymes and ligating the two pieces together. Preferably the vector is an expression vector, e.g., a shuttle expression vector as described above.

By "recombinant cell" is meant a cell possessing introduced or engineered nucleic acid sequences, e.g., as described above. The sequence may be in the form of or part of a vector or may be integrated into the host cell genome. Preferably the cell is a bacterial cell.

In another aspect, the invention also provides methods for identifying and/or screening compounds "active on" at least one bacterial target of a bacteriophage inhibitor protein or RNA. Preferred embodiments involve contacting such a bacterial target or targets (e.g., bacterial target proteins) with a test compound, and determining whether the compound binds to or reduces the level of activity of the bacterial target (e.g., a bacterial target protein). Preferably this is done either in vivo (i.e., in a cell-based assay) or in vitro, e.g., in a cell-free system under approximately physiological conditions.

The compounds that can be used may be large or small, synthetic or natural, organic or inorganic, proteinaceous or non-proteinaceous. In preferred embodiments, the compound is a peptidomimetic, as described herein, a bacteriophage inhibitor protein or fragment or derivative thereof, preferably an "active portion", or a small molecule.

In particular embodiments, the methods include the identification of bacterial targets or the site of action of an inhibitor on a bacterial target as described above or otherwise described herein.

In embodiments involving binding assays, preferably binding is to a fragment or portion of a bacterial target protein, where the fragment includes less than 90%, 80%, 70%, 60%, 50%, 40%, or 30% of an intact bacterial target protein. Preferably, the at least one bacterial target includes a plurality of different targets of bacteriophage inhibitor proteins, preferably a plurality of different targets. The plurality of targets can be in or from a plurality of different bacteria, but preferably is from a single bacterial species.

A "method of screening" refers to a method for evaluating a relevant activity or property of a large plurality of compounds (e.g., a bacteria-inhibiting activity), rather than just one or a few compounds. For example, a method of screening can be used to conveniently test at least 100, more preferably at least 1000, still more preferably at least 10,000, and most preferably at least 100,000 different compounds, or even more.

In the context of this invention, the term "small molecule" refers to compounds having molecular mass of less than 2000 Daltons, preferably less than 1500, still more preferably less than 1000, and most preferably less than 600 Daltons. Preferably but not necessarily, a small molecule is not an oligopeptide.

In a related aspect or in preferred embodiments, the invention provides a method of screening for potential antibacterial agents by determining whether any of a plurality of compounds, preferably a plurality of small molecules, is active on at least one target of a bacteriophage inhibitor protein or RNA. Preferred embodiments include those described for the above aspect, including embodiments which involve determining whether one or more test compounds bind to or reduce the level of activity of a bacterial target, and embodiments which utilize a plurality of different targets as described above.

The identification of bacteria-inhibiting phage ORFs and their encoded products also provides a method for identifying an active portion of such an encoded product. This also provides a method for identifying a potential antibacterial agent by identifying such an active portion of a phage ORF or ORF product. In preferred embodiments, the identification of an active portion involves one or more of mutational analysis, deletion analysis, or analysis of fragments of such products. The method can also include determination of a 3-dimensional structure of an active portion, such as by analysis of crystal diffraction patterns. In further embodiments, the method involves constructing or synthesizing a peptidomimetic compound, where the structure of the peptidomimetic compound corresponds to the structure of the active portion. In this context, "corresponds" means that the peptidomimetic compound structure has sufficient similarities to the structure of the active portion that the peptidomimetic will interact with the same molecule as the phage protein and preferably will elicit at least one cellular response in common which relates to the inhibition of the cell by the phage protein.

The methods for identifying or screening for compounds or agents active on a bacterial target of a phage-encoded inhibitor can also involve identification of a phage-specific site of action on the target.

Preferably in the methods for identifying or screening for compounds active on such a bacterial target, the target is uncharacterized; the target is from an uncharacterized bacterium from Table 1; the site of action is a phage-specific site of action.

Further embodiments include the identification of inhibitor phage ORFs and bacterial targets as in aspects above.

An "active portion" as used herein denotes an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

By "mimetic" is meant a compound structurally and functionally related to a reference compound that can be natural, synthetic, or chimeric. In terms of the present invention, a "peptidomimetic," for example, is a compound that mimics the activity-related aspects of the 3-dimensional structure of a peptide or polypeptide in a non-peptide compound, for example mimics the structure of a peptide or active portion of a phage- or bacterial ORF-encoded polypeptide.

A related aspect provides a method for inhibiting a bacterial cell by contacting the bacterial cell with a compound active on a bacterial target of a bacteriophage inhibitor protein or RNA, where the target was uncharacterized. In preferred embodiments, the compound is such a protein, or a fragment or derivative thereof; a structural mimetic, e.g., a peptidomimetic, of such a protein or fragment; a small molecule; the contacting is performed in vitro, the contacting is performed in vivo in an infected or at risk organism, e.g., an animal such as a mammal or bird, for example, a human, or other mammal described herein; the bacterium is selected from a genus and/or species listed in Table 1; the bacteriophage inhibitor protein is uncharacterized; and the bacteriophage inhibitor protein is from an uncharacterized phage listed in Table 1.

In the context of targets in this invention, the term "uncharacterized" means that the target was not recognized as an appropriate target for an antibacterial agent prior to the filing of the present application or alternatively prior to the present invention. Such lack of recognition can include, for example, situations where the target and/or a nucleotide sequence encoding the target were unknown, situations where the target was known, but where it had not been identified as an appropriate target or as an essential cellular component, and situations where the target was known as essential but had not been recognized as an appropriate target due to a belief that the target would be inaccessible or otherwise that contacting the cell with a compound active on the target in vitro would be ineffective in cellular inhibition, or ineffective in treatment of an infection. Methods described herein utilizing bacterial targets, e.g., for inhibiting bacteria or treating bacterial infections, can also utilize "uncharacterized target sites", meaning that the target has been previously recognized as an appropriate target for an antibacterial agent, but where an agent or inhibitor of the invention is used which acts at a different site than that at which the previously utilized antibacterial agent, i.e., a phage-specific site. Preferably the phage-specific site has different functional characteristics from the previously utilized site. In the context of targets or target sites, the term "phage-specific" indicates that the target or site is utilized by at least one bacteriophage as an inhibitory target and is different from previously identified targets or target sites.

In the context of this invention, the term "bacteriophage inhibitor protein" refers to a protein encoded by a bacteriophage nucleic acid sequence which inhibits bacterial function in a host bacterium. Thus, it is a bacteria-inhibiting phage product.

In the context of this invention, the phrase "contacting the bacterial cell with a compound active on a bacterial target of a bacteriophage inhibitor protein" or equivalent phrases refer to contacting with an isolated, purified, or enriched compound or a composition including such a compound, but specifically does not rely on contacting the bacterial cell with an intact phage which encodes the compound. Preferably no intact phage are involved in the contacting.

Related aspects provide methods for prophylactic or therapeutic treatment of a bacterial infection by administering to an infected, challenged or at risk organism a therapeutically or prophylactically effective amount of a compound active on a target of a bacteriophage inhibitor protein or RNA, or as described for the previous aspect. Preferably the bacterium involved in the infection or risk of infection produces the identified target of the bacteriophage inhibitor protein or alternatively produces a homologous target compound. In preferred embodiments, the host organism is a plant or animal, preferably a mammal or bird, and more preferably, a human or other mammal described herein. Preferred embodiments include, without limitation, those as described for the preceding aspect.

Compounds useful for the methods of inhibiting, methods of treating, and pharmaceutical compositions can include novel compounds, but can also include compounds which had previously been identified for a purpose other than inhibition of bacteria. Such compounds can be utilized as described and can be included in pharmaceutical compositions.

In preferred embodiments of this and other aspects of the invention utilizing bacterial target sequences of a bacteriophage inhibitory ORF product, the target sequence is encoded by a Staphylococcus nucleic acid coding sequence, preferably *S. aureus*. Possible target sequences are described herein by reference to sequence source sites.

The amino acid sequence of a polypeptide target is readily provided by translating the corresponding coding region. For the sake of brevity, the sequences are not reproduced herein. For the sake of brevity, the sequences are described by reference to the GenBank entries instead of being written out in full herein. In cases where the TIGR or GenBank entry for a coding region is not complete, the complete sequence can be readily obtained by routine methods, e.g., by isolating a clone in a phage host genomic library, and sequencing the clone insert to provide the relevant coding region. The boundaries of the coding region can be identified by conventional sequence analysis and/or by expression in a bacterium in which the endogenous copy of the coding region has been inactivated and using subcloning to identify the functional start and stop codons for the coding region.

In the context of nucleic acid or amino acid sequences of this invention, the term "corresponding" indicates that the sequence is at least 95% identical, preferably at least 97% identical, and more preferably at least 99% identical to a sequence from the specified phage genome, a ribonucleotide equivalent, a degenerate equivalent (utilizing one or more degenerate codons), or a homologous sequence, where the homolog provides functionally equivalent biological function.

By "treatment" or "treating" is meant administering a compound or pharmaceutical composition for prophylactic and/or therapeutic purposes. The term "prophylactic treatment" refers to treating a patient or animal that is not yet infected but is susceptible to or otherwise at risk of a bacterial infection. The term "therapeutic treatment" refers to administering treatment to a patient already suffering from infection.

The term "bacterial infection" refers to the invasion of the host organism, animal or plant, by pathogenic bacteria. This includes the excessive growth of bacteria which are normally present in or on the body of the organism, but more generally, a bacterial infection can be any situation in which the presence of a bacterial population(s) is damaging to a host organism. Thus, for example, an organism suffers from a bacterial population when excessive numbers of a bacterial population are present in or on the organism's body, or when the effects of the presence of a bacterial population(s) is damaging to the cells, tissue, or organs of the organism.

The terms "administer", "administering", and "administration" refer to a method of giving a dosage of a compound or composition, e.g., an antibacterial pharmaceutical composition, to an organism. Where the organism is a mammal, the method is, e.g., topical, oral, intravenous, transdermal, intraperitoneal, intramuscular, or intrathecal. The preferred method of administration can vary depending on various factors, e.g., the components of the pharmaceutical composition, the site of the potential or actual bacterial infection, the bacterium involved, and the infection severity.

The term "mammal" has its usual biological meaning referring to any organism of the Class Mammalia of higher vertebrates that nourish their young with milk secreted by mammary glands, e.g., mouse, rat, and, in particular, human, bovine, sheep, swine, dog, and cat.

In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells that renders or contributes to bacterial infection.

The dose of antibacterial agent that is useful as a treatment is a "therapeutically effective amount." Thus, as used herein, a therapeutically effective amount means an amount of an antibacterial agent that produces the desired therapeutic effect as judged by clinical trial results and/or animal models. This amount can be routinely determined by one skilled in the art and will vary depending on several factors, such as the particular bacterial strain involved and the particular antibacterial agent used.

In connection with claims to methods of inhibiting bacteria and therapeutic or prophylactic treatments, "a compound active on a target of a bacteriophage inhibitor protein" or terms of equivalent meaning differ from administration of or contact with an intact phage naturally encoding the full-length inhibitor compound. While an intact phage may conceivably be incorporated in the present methods, the method at least includes the use of an active compound as specified different from a full length inhibitor protein naturally encoded by a bacteriophage and/or a delivery or contacting method different from administration of or contact with an intact phage encoding the full-length protein. Similarly, pharmaceutical compositions described herein at least include an active compound different from a full-length inhibitor protein naturally encoded by a bacteriophage or such a full-length protein is provided in the composition in a form different from being encoded by an intact phage. Preferably the methods and compositions do not include an intact phage.

In accord with the above aspects, the invention also provides antibacterial agents and compounds active on bacterial targets of bacteriophage inhibitor proteins or RNAs, where the target was uncharacterized as indicated above. As previously indicated, such active compounds include both novel compounds and compounds which had previously been identified for a purpose other than inhibition of bacteria. Such previously identified biologically active compounds can be used in embodiments of the above methods of inhibiting and treating. In preferred embodiments, the targets, bacteriophage, and active compound are as described herein for methods of inhibiting and methods of treating. Preferably the agent or compound is formulated in a pharmaceutical composition which includes a pharmaceutically acceptable carrier, excipient, or diluent. In addition, the invention provides agents, compounds, and pharmaceutical compositions where an active compound is active on an uncharacterized phage-specific site.

In preferred embodiments, the target is as described for embodiments of aspects above.

Likewise, the invention provides a method of making an antibacterial agent. The method involves identifying a target of a bacteriophage inhibitor polypeptide or protein or RNA, screening a plurality of compounds to identify a compound active on the target, and synthesizing the compound in an amount sufficient to provide a therapeutic effect when administered to an organism infected by a bacterium naturally producing the target. In preferred embodiments, the identification of the target and identification of active compounds include steps or methods and/or components as described above (or otherwise herein) for such identification. Likewise, the active compound can be as described above, including fragments and derivatives of phage inhibitor proteins, peptidomimetics, and small molecules. As recognized by those skilled in the art, peptides can be synthesized by expression systems and purified, or can be synthesized artificially.

As indicated above, sequence analysis of nucleotide and/or amino acid sequences can beneficially utilize computer analysis. Thus, in additional aspects the invention provides computer-related hardware and media and methods utilizing and incorporating sequence data from uncharacterized phage, e.g., uncharacterized phage listed in Table 1, preferably at least one of bacteriophage 77, 3A, and 96, (*Staphylococcus aureus* phage). In general, such aspects can facilitate the above described aspects. Various embodiments involve the analysis of genetic sequence and encoded products, as applied to the evaluating bacteriophage inhibitor ORFs and compounds and fragments related thereto. The various sequence analyses, as well as function analyses, can be used separately or in combination, as well as in preceding aspects and embodiments. Use in combination is often advantageous as the additional information allows more efficient prioritizing of phage ORFs for identification of those ORFs that provide bacteria-inhibiting function.

In one aspect, the invention provides a computer-readable device which includes at least one recorded amino acid or nucleotide sequence corresponding to one of the specified phage and a sequence analysis program for analyzing a nucleotide and/or amino acid sequence. The device is arranged such that the sequence information can be retrieved and analyzed using the analysis program. The analysis can identify, for example, homologous sequences or the indicated %s of the phage genome and structural motifs. Preferably the sequence includes at least 1 phage ORF or encoded product, more preferably at least 10%, 20%, 30%, 40%, 50%, 70%, 90%, or 100% of the genomic phage ORFs and/or equivalent cDNA, RNA, or amino acid sequences. Preferably the sequence or sequences in the device are recorded in a medium such as a floppy disk, a computer hard drive, an optical disk, computer random access memory (RAM), or magnetic tape. The program ay also be recorded in such medium. The sequences can also include sequences from a plurality of different phage.

In this context, the term "corresponding" indicates that the sequence is at least 95% identical, preferably at least 97% identical, and more preferably at least 99% identical to a sequence from the specified phage genome, a ribonucleotide equivalent, a degenerate equivalent (utilizing one or more degenerate codons), or a homologous sequence, where the homolog provides functionally equivalent biological function.

Similarly, the invention provides a computer analysis system for identifying biologically important portions of a bacteriophage genome. The system includes a data storage medium, e.g., as identified above, which has recorded thereon a nucleotide sequence corresponding to at least a portion of at least one uncharacterized bacteriophage genome, a set of program instructions to allow searching of the sequence or sequences to analyze the sequence, and an output device where the portion includes at least the sequence length as specified in the preceding aspect. The output device is preferably a printer, a video display, or a recording medium. More one than one output device may be included. For each of the present computer-related aspects, the bacteriophage are preferably selected from the uncharacterized phage listed in Table 1, more preferably from bacteriophage 77, 3A, and 96.

In keeping with the computer device aspects, the invention also provides a method for identifying or characterizing a bacteriophage ORF by providing a computer-based system for analyzing nucleotide or amino acid sequences, e.g., as describe above. The system includes a data storage medium which has recorded a sequences or sequences as described for the above devices, a set of instructions as in the preceding aspect, and an output device as in the preceding aspect. The method further involves analyzing at least one sequence, and outputting the analysis results to at least one output device.

In preferred embodiments, the analysis identifies a sequence similarity or homology with a sequence or sequences selected from bacterial ORFs encoding products with related biological function; ORFs encoding known inhibitors; and essential bacterial ORFs. Preferably the analysis identifies a probable biological function based on identification of structural elements or characteristic or signature motifs of an encoded product or on sequence similarity or homology. Preferably the uncharacterized bacteriophage is from Table 1, more preferably at least one of bacteriophage 77, 3A, and 96. In preferred embodiments, the method also involves determining at least a portion of the nucleotide sequence of at least one uncharacterized bacteriophage as indicated, and recording that sequence on data storage medium of the computer-based system.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Further embodiments will be apparent from the following Detailed Description and from the claims.

BRIEF DESCRIPTION OF THE DRAWINGS

FIG. 3A) Functional assay on semi-solid support media. FIG. 3B) Functional assay in liquid culture.

DETAILED DESCRIPTION OF THE PREFERRED EMBODIMENTS

Figure 1A:
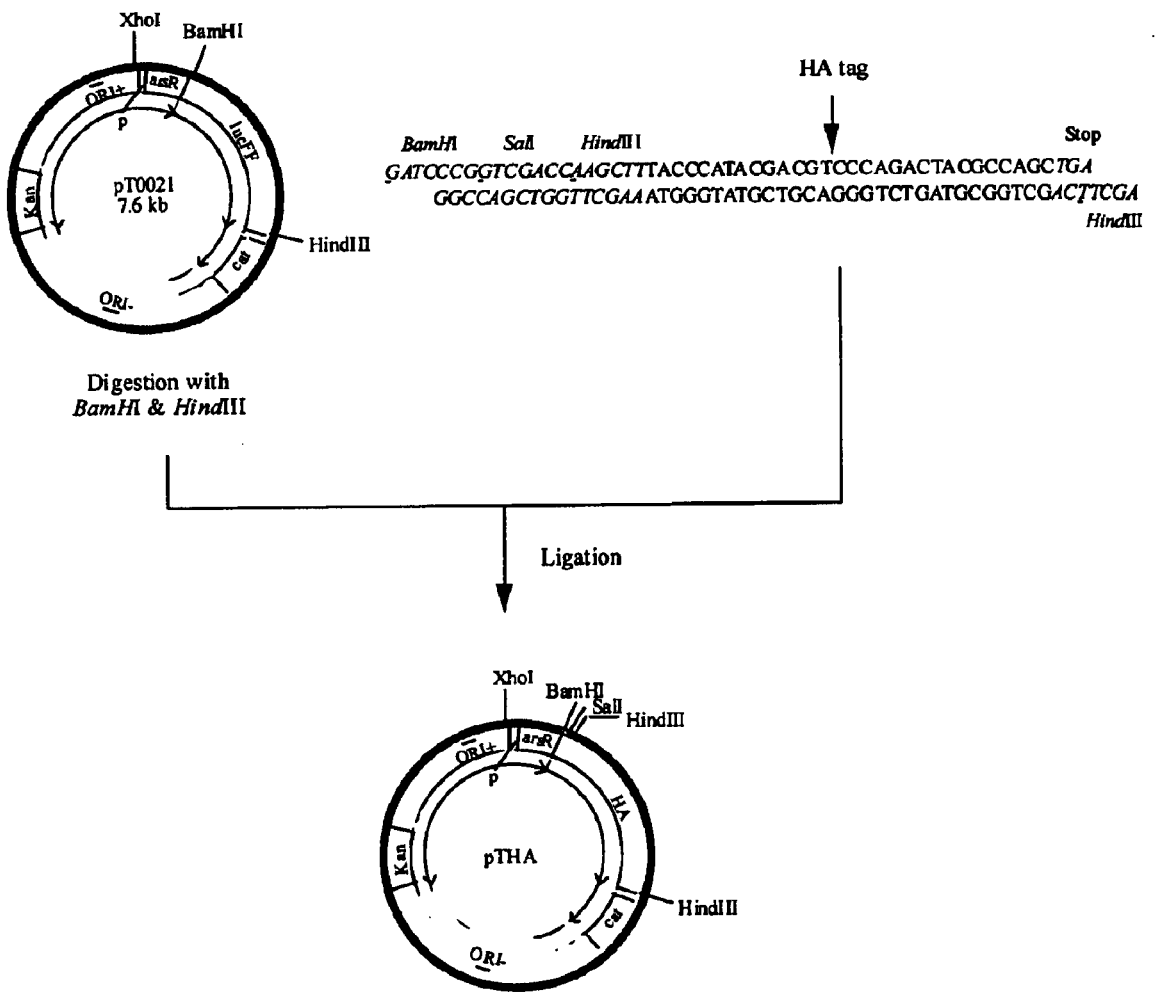
FIGS. 1A and 1B are flow schematics showing the manipulations necessary to convert pT0021, an arsenite inducible vector containing the luciferase gene, into pTHA or pTM, two ars inducible vectors. Vector pTHA contains BamHI, SalI, and HindIII cloning sites and a downstream HA epitope tag. Vector pTM contains BamHI and HindIII cloning sites and no HA epitope tag.

The invention may be more clearly understood from the following description.

The tables will first be briefly described.

Table 1 is a listing of a large number of available bacteriophage that can be readily obtained and used in the present invention.

Table 2 shows the complete nucleotide sequence of the genome of *Staphylococcus aureus* bacteriophage 77.

Table 3 shows a list of all the ORFs from Bacteriophage 77 that were screened in the functional assay to identify those with anti-microbial activity.

Table 4 shows the predicted nucleotide sequence, predicted amino acid sequence, and physiochemical parameters of ORF 17/ 19/ 43/ 102/ 104/ 182]. These include the primary amino acid sequence of the predicted protein, the average molecular weight, amino acid composition, theoretical pI, hydrophobicity map, and predicted secondary structure map.

Table 5 shows homology search results. BLAST analysis was performed with ORFs 17/ 19/ 43/ 102/ 104/ 182 against NCBI non-redundant nucleotide and Swissprot databases. The results of this search indicate that: I) ORF 17 has no significant homology to any gene in the NCBI non-NCBI non-redundant nucleotide database, II) ORF 19 has significant homology to one gene in the NCBI non-redundant nucleotide database—the gene encoding ORF 59 of bacteriophage phi PVL, III) ORF 43 has significant homology to one gene in the NCBI non-redundant nucleotide database—the gene encoding ORF 39 of phi PVL, IV) ORF 102 has significant homology to one gene in the NCBI non-redundant nucleotide database—the gene encoding ORF 38 of phi PVL, V) ORF 104 has no significant homology to any gene in the NCBI non-redundant nucleotide database, VI) ORF 182 has significant homology to one gene in the NCBI non-redundant nucleotide database—the gene encoding ORF 39 of phi PVL.

Table 6 is a table from Alberts et al., MOLECULAR BIOLOGY OF THE CELL $3^{rd}$ ed., showing the redundancy of the "universal" genetic code.

Table 7 shows the complete nucleotide sequence of *Staphylococcus aureus* bacteriophage 3A.

Table 8 is a listing of the ORFs identified in *Staphylococcus aureus* bacteriophage 3A.

Table 9 shows the complete nucleotide sequence of *Staphylococcus aureus* bacteriophage 96.

Table 10 is a listing of the ORFs identified in *Staphylococcus aureus* bacteriophage 96.

Table 11 is a listing of sequences deposited in the NCBI public database (GeneBank) for bacteriophage listed in Table 1.

Table 12 is a listing of phage which encode a known lysis function, including the identified lysis gene.

Table 13 is a listing of bacteriophage which encode holin genes, where holin genes encode proteins which form pores and eventually enable other enzymes to kill the host bacterium.

Table 14 is a listing of bacteriophage which encode kil genes.

Table 15 is a list of *Staphylococcus aureus* sequences which may include sequences from genes coding for target sequences for the phage 77-encoded antimicrobial proteins or peptides.

Background

As indicated in the Summary above, the present invention is concerned with the use of bacteriophage coding sequences and the encoded polypeptides or RNA transcripts to identify bacterial targets for potential new antibacterial agents. Thus, the invention concerns the selection of relevant bacteria. Particularly relevant bacteria are those which are pathogens of a complex organism such as an animal, e.g., mammals, reptiles, and birds, and plants. However, the invention can be applied to any bacterium (whether pathogenic or not) for which bacteriophage are available or which are found to have cellular components closely homologous to components targeted by phage of another bacterium, e.g., a pathogenic bacterium, e.g., a pathogenic bacterium.

Thus, the invention also concerns the bacteriophage which can infect a selected bacterium. Identification of ORFs or products from the phage which inhibit the host bacterium both provides an inhibitor compound and allows identification of the bacterial target affected by the phage-encoded inhibitor. Such targets are thus identified as potential targets for development of other antibacterial agents or inhibitors and the use of those targets to inhibit those bacteria. As indicated above, even if such a target is not initially identified in a particular bacterium, such a target can still be identified if a homologous target is identified in another bacterium. Usually, but not necessarily, such another bacterium would be a genetically closely related bacterium. Indeed, in some cases, a phage-encoded inhibitor can also inhibit such a homologous bacterial cellular component.

The demonstration that bacteriophage have adapted to inhibiting a host bacterium by acting on a particular cellular component or target provides a strong indication that that component is an appropriate target for developing and using antibacterial agents, e.g., in therapeutic treatments. Thus, the present invention provides additional guidance over mere identification of bacterial essential genes, as the present invention also provides an indication of accessability of the target to an inhibitor, and an indication that the target is sufficiently stable over time (e.g., not subject to high rates of mutation) as phage acting on that target were able to develop and persist. Thus, the present invention identifies a subset of essential cellular components which are particularly likely to be appropriate targets for development of antibacterial agents.

The invention also, therefore, concerns the development or identification of inhibitors of bacteria, in addition to the phage-encoded inhibitory proteins (or RNA transcripts), which are active on the targets of bacteriophage-encoded inhibitors. As described herein, such inhibitors can be of a variety of different types, but are preferably small molecules.

The following description provides preferred methods for developing the various aspects of the invention. However, as those skilled in the art will readily recognize, other approaches can be used to obtain and process relevant information. Thus the invention is not limited to the specifically described methods. In addition, the following description provides a set of steps in a particular order. That series of steps describes the overall development involved in the present invention. However, it is clear that individual steps or portions of steps may be usefully practiced separately, and, further, that certain steps may be performed in a different order or even bypassed if appropriate information is already available or is provided by other sources or methods.

Selecting and Growing Phage, and Isolating DNA

Conceptually, the first step involves selecting bacterial hosts of interest. Preferably, but not necessarily, such hosts will be pathogens of clinical importance. Alternatively, because bacteria all share certain fundamental metabolic and structural features, these features can be targeted for study in one strain, for example a nonpathogenic one, and extrapolated to similarly succeed in pathogenic ones. Nonpathogenic strains may also exhibit initial advantages in being not only less dangerous, but also, for example, in having better growth and culturing characteristics and/or better developed molecular biology techniques and reagents. Consequently, advantageously the invention provides the ability target virtually any bacteria, but preferably pathogenic bacteria, with antimicrobial compounds designed and/or developed using bacteriophage inhibitory proteins and peptides from phage with non-pathogenic and/or pathogenic hosts.

We have selected *Staphylococcus aureus, Streptococcus pneumoniae*, various Enterococci, and *Pseudomonas aeruginosa* as initial exemplary pathogens. These bacteria are a major cause of morbidity and mortality in hospital-based infections, and the appearance of antibiotics resistance in all three organisms makes it increasingly difficult to treat benign infections involving these organisms. Such infections can include, for example, otitis media, sinusitis, and skin, and airway infections (Neu, H. C. (1992). *Science* 257, 1064–1073). However, the approach described below is clearly applicable to any human bacterial pathogens including but not restricted to *Mycobacterium tuberculosis, Nesseria gonorrhoeae, Haemophilus influenza*, Acinobacter, *Escherichia coli, Shigella dysenteria, Streptococcus pyogenes, Helicobacter pylori*, and Mycoplasma species. This invention can also be applied to the discovery of anti-bacterial compounds directed against pathogens of animals other than humans, for example, sheep, cattle, swine, dogs, cats, birds, and reptiles. Similarly, the invention is not limited to animals, but also applies to plants.

The bacteria are grown according to standard methodologies employed in the art, including solid, semi-solid or liquid culturing, which procedures can be found in or extrapolated from standard sources such as Maloy, S. R., Stewart, V. J., and Taylor, R. K. *Genetic Analysis of Pathogenic Bacteria* (1996) Cold Spring Harbor Laboratory Press, or Maniatis, T. et al. (1989) *Molecular Cloning: A Laboratory Manual*, Cold Spring Harbor University Press, Cold Spring, N.Y.; or Ausubel, F. M. et al. (1994) *Current Protocols in Molecular Biology*. John Wiley & Sons, Secaucus, N.J. Culture conditions are selected which are adapted to the particular bacterium generally using culture conditions known in the art as appropriate, or adaptations of those conditions.

Nucleic acids within these bacteria can be routinely extracted through common procedures such as described in the above-referenced manuals and as generally known to those skilled in the art. Those nucleic acid stocks can then be used to practice the other inventive aspects described below.

Selection and Growth of Bacteriophage, and Isolation of DNA

The second step involves assembling a group of bacteriophages (phage collection) for each of the targeted bacterial hosts. While the invention can be utilized with a single bacteriophage for a pathogen or other bacterium, it is preferable to utilize a plurality of phage for each bacterium, as comparisons between a plurality of such phage provides useful additional information. Non-limiting examples of phage and sources for some of the above-mentioned pathogenic bacteria are found in Table 1. The criteria used to select such phages is that they are infectious for the microbe targeted, and replicate in, lyse, or otherwise inhibit growth of the bacterium in a measurable fashion. These phages can be very different from one another (representing different families), as judged by criteria such as morphology (head, tail, plate, etc.), and similarity of genome nucleotide sequence (cross-hybridization). Since such diverse bacteriophages are expected to block bacterial host metabolism and ultimately inhibit by a variety of mechanisms, their combined study will lead to the identification of different mechanisms by which the phages independently inhibit bacterial targets. Examples include degradation of host DNA (Parson K. A., and Snustad, D. P. (1975). *J. Virol.* 15, 221–444) and inhibition of host RNA transcription (Severinova, E., Severinov, K. and Darst, S. A. (1998). *J. Mol. Biol.* 279, 9–18). This, in turn, yields novel information on phage proteins that can inhibit the targeted microbe. As explained below, this 1) forms the basis of novel drug discovery efforts based on knowledge of the primary amino acid sequence of the phage inhibitor protein (e.g., peptide fragments or peptidomimetics) and/or 2) leads to the identification of bacterial biochemical pathways, the proteins of which are essential or significant for survival of the targeted microbe, and which enzymatic steps or chemical reactions can be targeted by classical drug discovery methods using molecular inhibitors, for example, small molecule inhibitors.

Bacteriophage are generally either of two types, lytic or filamentous, meaning they either outright destroy their host and seek out new hosts after replication, or else continuously propogate and extrude progeny phage from the same host without destroying it. Regardless of the phage life cycle and type, preferred embodiments incorporate phage which impede cell growth in measurable fashion and preferably stop cell growth. To this end, lytic phage are preferred, although certain nonlytic species may also suffice, e.g., if sufficiently bacteriostatic.

Various procedures that are commonly understood by those of skill in the art can be routinely employed to grow, isolate, and purify phage. Such procedures are exemplified by those found in such common laboratory aids such as Maloy, S. R., Stewart, V. J., and Taylor, R. K. *Genetic Analysis of Pathogenic Bacteria* (1996) Cold Spring Harbor Laboratory Press; Maniatis, T. et al. (1989) *Molecular Cloning: A Laboratory Manual*, Cold Spring Harbor University Press, Cold Spring, N.Y.; and Ausubel, F. M. et al. (eds.) (1994) *Current Protocols in Molecular Biology*. John Wiley & Sons, Secaucus, N.J. The techniques generally involve the culturing of infected bacterial cells that are lysed naturally and/or chemically assisted, for example, by the use of an organic solvent such as chloroform that destroys the host cells thereby liberating the phage within. Following this, the cellular debris is centrifuged away from the supernatant containing the phage particles, and the phage then subsequently and selectively precipitated out of the supernatant using various methods usually employing the use of alcohols and/or other chemical compounds such as polyethylene glycol (PEG). The resulting phage can be further purified using various density gradient/centrifugation methodologies. The resulting phage are then chemically lysed, thereby releasing their nucleic acids that can be conveniently precipitated out of the supernatant to yield a viral nucleic acid supply of the phage of interest.

Exemplary bacteriophage are indicated in Table 1, along with sources where those phage may be obtained.

Exemplary bacteria include the reference bacteria for the identified viral strains, available from the same sources.

Characterizing Bacteriophage Genomes for ORFs

The third step involves systematically characterizing the genetic information contained in the phage genome. Within this genetic information is the sequence of all RNAs and proteins encoded by the phage, including those that are essential or instrumental in inhibiting their host. This characterization is preferably done in a systematic fashion. For example, this can be done by first isolating high molecular weight genomic DNA from the phage using standard bacterial lysis methods, followed by phage purification using density gradient ultracentrifugation, and extraction of nucleic acid from the purified phage preparation. The high molecular weight DNA is then analyzed to determine its size and to evaluate a proper strategy for its sequencing. The DNA is broken down into smaller size fragments by sonication or partial digestion with frequently cutting restriction enzymes such as Sau3A to yield predominantly 1 to 2 kilobase length DNA, which DNA can then be resolved by gel electrophores is followed by extraction from the gel.

The ends of the fragments are enzymatically treated to render them suitable for cloning and the pools of fragments are cloned in a bacterial plasmid to generate a library of the phage genome. Several hundred of these random DNA fragments contained in the plasmid vector are isolated as clones after introduction into an appropriate bacterium, usually *Escherichia coli*. They are then individually expanded in culture and the DNA from each individual clone is purified. The nucleotide sequences of the inserts of these clones are determined by standard automated or manual methods, using oligonucleotide primers located on either side of the cloning site to direct polymerase mediated sequencing (e.g., the Sanger sequencing method or a modification of that method). Other sequencing methods can also be used.

The sequence of individual clones is then deposited in a computer, and specific software programs (for example Sequencher™, Gene Codes Corp.) are used to look for overlap between the various sequences, resulting in ordering of contig sequences and ultimately providing the complete sequence of the entire bacteriophage genome (one such example is given in Table 2 for *Staphylococcus aureus* bacteriophage 77). This complete nucleotide sequence is preferably determined with a redundancy of 3- to 5-fold (number of independent sequencing events covering the same region) in order to minimize sequencing errors.

Preferably, the bacterial strain used as a phage host should not possess any other innate plasmids, transposons, or other phage or incompatible sequences that would complicate or otherwise make the various manipulations and analyses more difficult.

Commercially available computer software programs are used to translate the nucleotide sequence of the phage to identify all protein sequences encoded by the phage (hereafter called open reading frames or ORFs). As phages are known to transcribe their genome into RNA from both strands, in both directions, and sometimes in more than one frame for the same sequence, this exercise is done for both strands and in all six possible reading frames. As evolutionary constraints have forced the phage to conserve all of its vital protein sequences in as small a genome as possible, it is straightforward to identify all the proteins encoded by the phage by simple examination of the 6 translation frames of the genome. Once these ORFs are identified, they are cataloged into a phage proteome database (Table 3 lists ORFs identified from phage 77). This analysis is preferably performed for each phage under study. The process of ORF identification can be varied depending on the desired results. For example, the minimum length for the putative encoded polypeptide can be varied, and/or putative coding regions that have an associated Shine-Dalgarno sequence can be selected. In the case of phage 77 ORFs, such parameter adjustment was performed and resulted in the identification of ORFs as listed herein. Different parameters had resulted in the identification of the ORFs listed in the preceding U.S. Provisional Application No. 60/110,992, filed Dec. 3, 1998, which is hereby incorporated by reference in its entirety.

Correlation of exemplary ORFs identified in that provisional application and as identified herein are shown in the following table:

| ORF ID from 60/110,992 | Genomic position | a.a. size | Start codon | ORF ID from 09/407,804 | Genomic position | a.a. size | Start codon |
|---|---|---|---|---|---|---|---|
| 77ORF016 | 2369–24024 | 251 | TTG | 77ORF017 | 23269–23982 | 237 | ATG |
| 77ORF019 | 39845–40501 | 218 | ATA | 77ORF019 | 3985–40501 | 216 | ATG |
| 77ORF050 | 29268–29564 | 98 | ATG | 77ORF182 | 29268–29564 | 98 | ATG |
| 77ORF050 | 29268–29564 | 98 | ATG | 77ORF043 | 29304–29564 | 86 | ATG |
| 77ORF067 | 34312–34551 | 79 | CTG | 77ORF104 | 34393–34551 | 52 | ATG |
| 77ORF146 | 29051–29212 | 53 | ATG | 77ORF102 | 29051–29212 | 53 | ATG |

Identifying and Characterizing Inhibitory Phage ORFs

The fourth step entails identifying the phage protein or proteins or RNA transcripts that have the ability to inhibit their bacterial hosts. This can be accomplished, for example, by either or both of two non-mutually exclusive methods. The first method makes use of bioinformatics. Over the past few years, a large amount of nucleotide sequence information and corresponding translated products have become available through large genome sequencing projects for a variety of organisms including mammals, insects, plants, unicellular eukaryotes (yeast and fungi), as well as several bacterial genomes such as E. coli, Mycobacterium tuberculosis, Bacillus subtilis, Staphylococcus aureus and many others. Such sequences have been deposited in public databases (for example, non-redundant sequence database at GenBank and SwissProt protein sequence database) (http://www.ncbi.nlm.nih.gov)) and can be freely accessed to compare any specific query sequence to those present in such databases. For example, GenBank contains over 1.6 billion nucleotides corresponding to 2.3 million sequence records. Several computer programs and servers (e.g., TBLASTN) have been created to allow the rapid identification of homology between any given sequence from one organism to that of another present in such databases, and such programs are public and available free of charge.

In addition, it has been well established that basic biochemical pathways can be conserved in very distant organisms (for example bacteria and man), and that the proteins performing the various enzymatic steps in these pathways are themselves conserved at the amino acid sequence level. Thus, proteins performing similar functions (e.g. DNA repair, RNA transcription, RNA translation) have frequently preserved key structural signatures, identifiable by similarities across regions of proteins (domains and motifs). The antimicrobials of the present invention will preferably target features and targets that are highly characteristic or conserved in microbes, and not higher organisms.

Most genomes encode individual proteins or groups of proteins that can be assembled into protein families that have been evolutionarily conserved. Therefore, similarity between a new query sequence and that of a member of a protein family (reference sequences from public databases) can immediately suggest a biochemical function for the novel query sequence, which in our case is a phage ORF.

The sequence homology between individual members of evolutionarily distant members of a protein family is usually not randomly distributed along the entire length of the sequence but is often clustered into "motifs". These correspond to key three-dimensional folds that form key catalytic and/or regulatory structures that perform key biochemical function(s) for the group of proteins. Commercially available computer software programs can identify such motifs in a new query sequence, again providing functional information for the query sequence. Such structural and functional motifs have also been derived from the combined analysis of primary sequence databases (protein sequences) and protein structure databases (X-ray crystallography, nuclear magnetic resonance) using so-called "reading" methods (Rost B,l and Sander C. (1996). Ann. Rev. Biophy. Biomol. Struct. 25, 113–136).

Such motifs and folds are themselves deposited in public databases which can be directly accessed (for example, SwissProt database; 3D-ALI at EMBL, Heidelberg; PROSITE). This basic exercise leads to a structural homology map in which each of the phage ORFs has been probed for such similarities, and where initial structural and functional hits are identified (selected examples of sequence homologies detected between individual ORFs from the genome of Staphylococcus aureus bacteriophage 77 and sequences deposited in public databases are shown in Table 5; listed are the proteins showing homologies and the TBLASTN scores quantifying the degree of sequence similarity between the two compared sequences).

This analysis can point out phage proteins with similarity to proteins from other phages (such as those for E. coli) playing an important role in the basic biochemical pathways of the phage (such as DNA replication, RNA transcription, tRNAs, coat protein and assembly). Selected examples of such proteins are shown in Tble 5. Therefore, this analysis enables identification and elimination of non-essential ORFs as candidates for an inhibitor function, as well as the identification of (potentially) useful ones.

In addition, this analysis can point out specific ORFs as possible inhibitor ORFs. For example these ORFs may encode proteins or enzymes that alter bacterial cell structure, metabolism or physiology, and ultimately viability. Examples of such proteins present in the genome of Staphylococcus aureus bacteriophage 77 include orf14 (deoxyuridine triphosphatase from bacteriophage T5), and orf15 (sialidase).

In addition, it is well known that bacterial and eukaryotic viruses can usurp pathways from their host in order to use them to their advantage in blocking host cellular pathways upon infection. The phage can achieve this, for example, by overexpressing part or whole host-related sequences which are themselves regulating or rate limiting in key biochemical pathways of the host. The identification of sequence similarity between phage ORFs and bacterial host genome sequences will be highly indicative of such a mechanism (Selected examples of such homologies are listed in Table 5, e.g. orf4 (homologous to autolysin), orf20 (hypothetical protein from Staphyloccus aureus) and orf29 (hypothetical protein from Staphyloccus aureus). These ORFs can be analyzed by a standard biochemical approach to directly test their inhibitor functions (e.g., as described below).

Alternatively, a homology search may reveal that a given phage ORF is related to a protein present in the databases having an activity known to be inhibitory, (e.g. inhibitor of host RNA polymerase by *E. coli* bacteriophage T7. Such a finding would implicate the phage ORF product in a related activity. This will also suggest that a new antimicrobial could be derived by a mimetic approach (e.g., peptidomimetic) imitating this function or by a small molecule inhibitor to the bacterial target of the phage ORF, or any steps in the relevant host metabolic pathway, e.g., high throughput screening of small molecule libraries. Selected examples of such similarity between ORFs of *Staphyloccus aureus* bacteriophage 77 and proteins with inhibitor functions for bacterial hosts are listed in Table 5. These include orf9 (similar to bacteriophage P1 kilA function), and orf4 (autolysin of *Staphylococcus aureus*, amidase enzymatic activity).

A reason for the biochemical study of individual ORFs for inhibitor function is that their expression or overexpression will block cellular pathways of the host, ultimately leading to arrest and/or inhibition of host metabolism. In addition, such ORFs can alter host metabolism in different ways, including modification of pathogenicity. Therefore, individual ORFs identified above are expressed, preferably overexpressed, in the host and the effect of this expression or overexpression on host metabolism and viability is measured. This approach can be systematically applied to every ORF of the phage, if necessary, and does not rely on the absolute identification of candidate ORFs by bioinformatics. Individual ORFs are resynthesized from the phage genomic DNA, e.g., by the polymerase chain reaction (PCR), preferably using oligonucleotide primers flanking the ORF on either side. These single ORFs are preferably engineered so that they contain appropriate cloning sites at their extremities to allow their introduction into a new bacterial expression plasmid, allowing propagation in a standard bacterial host such as *E. coli*, but containing the necessary information for plasmid replication in the target microbe such as *S. aureus* (hereafter referred to as shuttle vector). Shuttle vectors and their use are well known in the art.

Figure 1B:
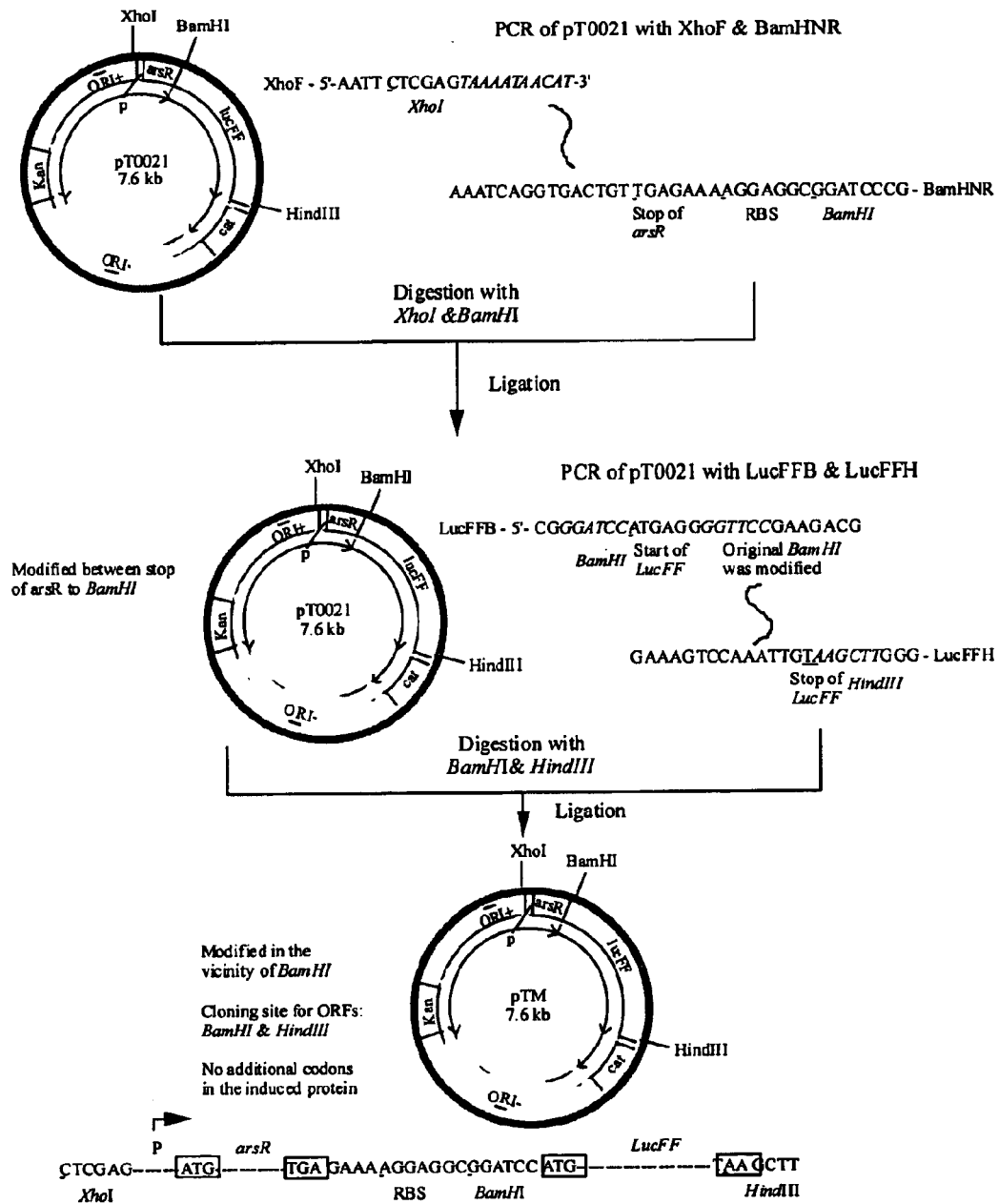
Figure 2:
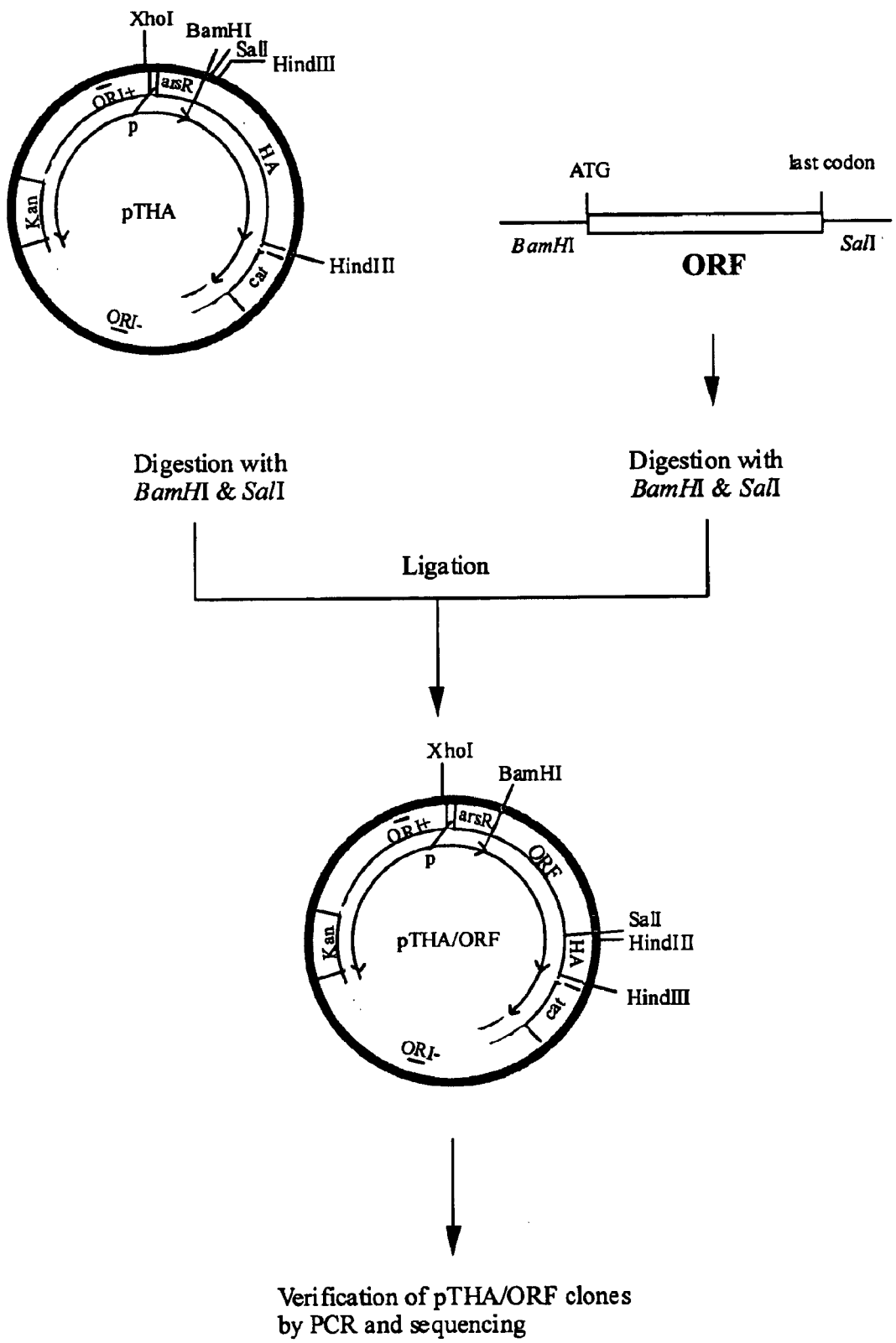
FIG. 2 is a schematic representation of the cloning steps involved to place the DNA segments of any of ORFs 17/ 19/ 43/ 102/104/182 or other sequences into pTHA to assess inhibitory potential. For subcloning into pTM or pT0021, Individual ORFs were amplified by the PCR using oligonucleotides targeting the ATG and stop codons of the ORFs. Using this strategy, BamHI and HindIII sites were positioned immediately upstream or downstream, respectively of the start and stop codons of each ORF. Following digestion with BamHI and HindIII, the PCR fragments were subcloned into the same sites of pT0021 or pTM. Clones were verified by PCR and direct sequencing.
Figure 3:
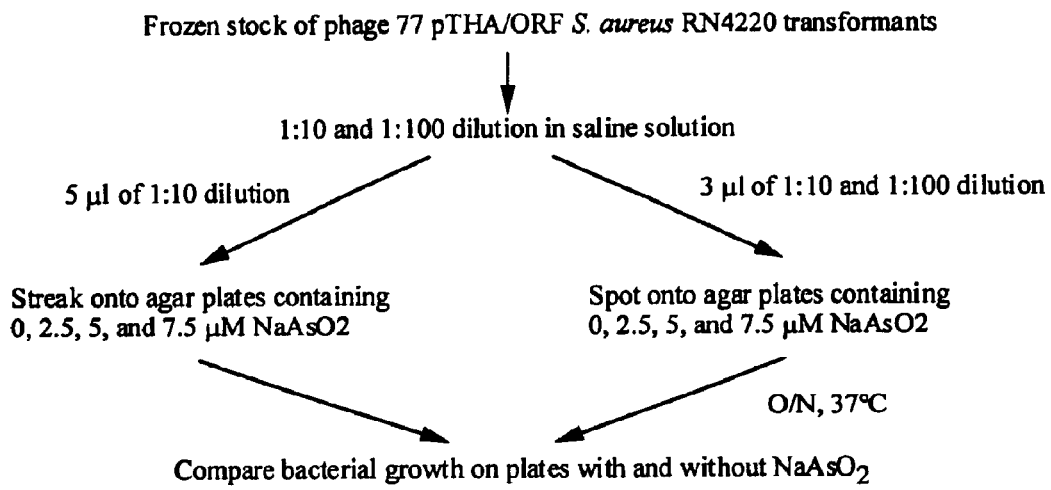
FIG. 3 shows a schematic representation of the functional assays used to characterize the bactericidal and bacteriostatic potential of all predicted ORFs (>33 amino acids) encoded by bacteriophage 77.
Figure 3:
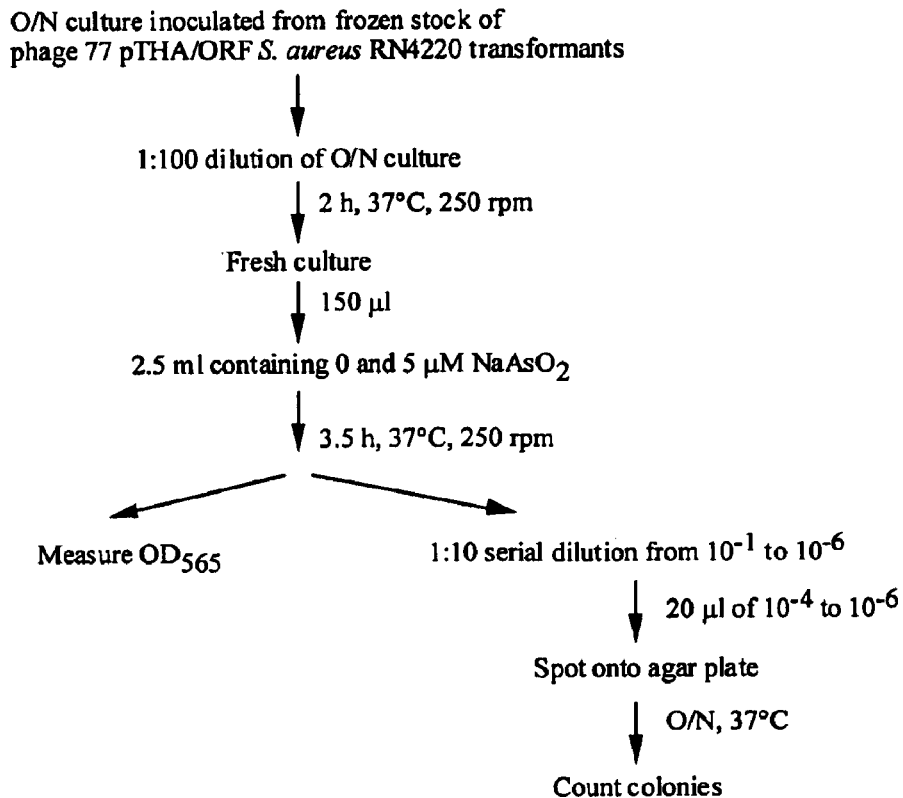
Figure 4A:
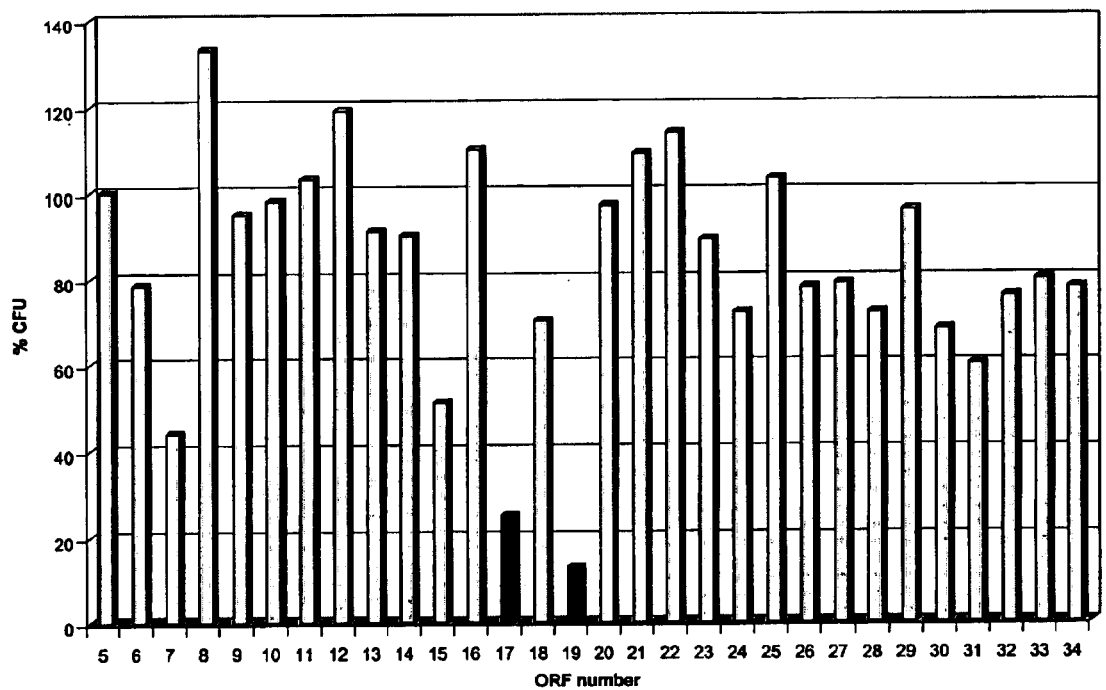
FIGS. 4A, B, and C is a bar graph showing the results of a screen in liquid media to assess bacteriostatic or bactericidal activity of 93 predicted ORFs (>33 amino acids) encoded by bacteriophage 77. Growth inhibition assays were performed as detailed in the Detailed Description. The relative growth of *Staphylococcus aureus* transformants harboring a given bacteriophage 77 ORF (identified on the bottom of the graph), in the absence or presence of arsenite, is plotted relative to growth of a *Staphylococcus aureus* transformant containing ORF 5, a non-toxic bacteriophage 77 ORF (which is set at 100%). Each bar represents the average obtained from three Staph A transformants grown in duplicate. Bacteriophage 77 ORFs showing significant growth inhibition are plotted in red and consist or ORF 17, 19, 102, 104, and 182.
Figure 4B:
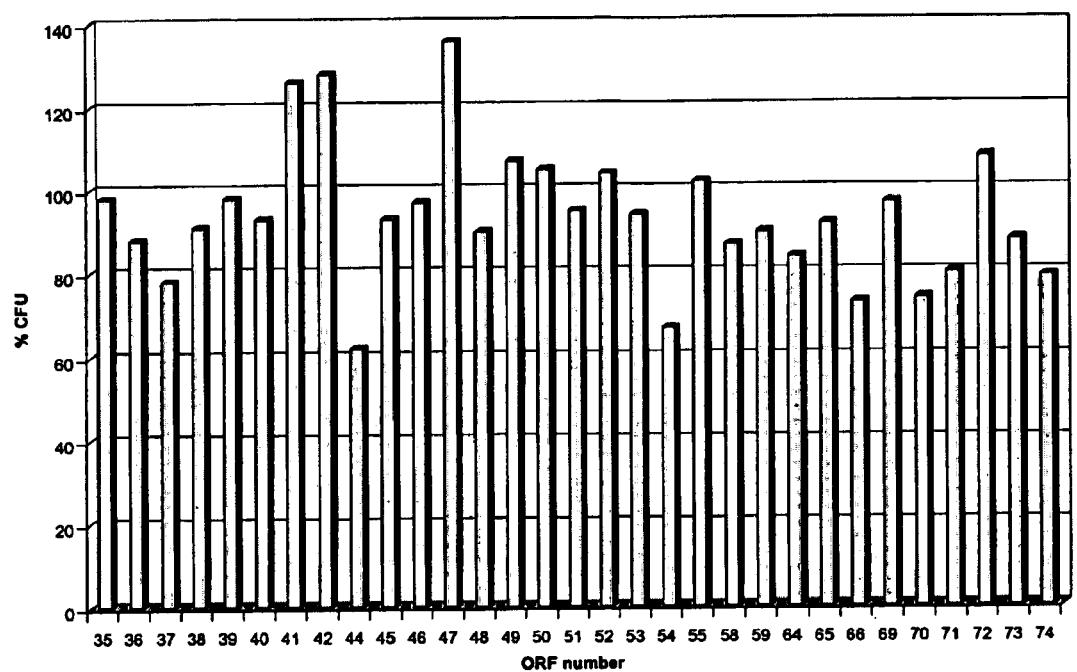
Figure 4C:
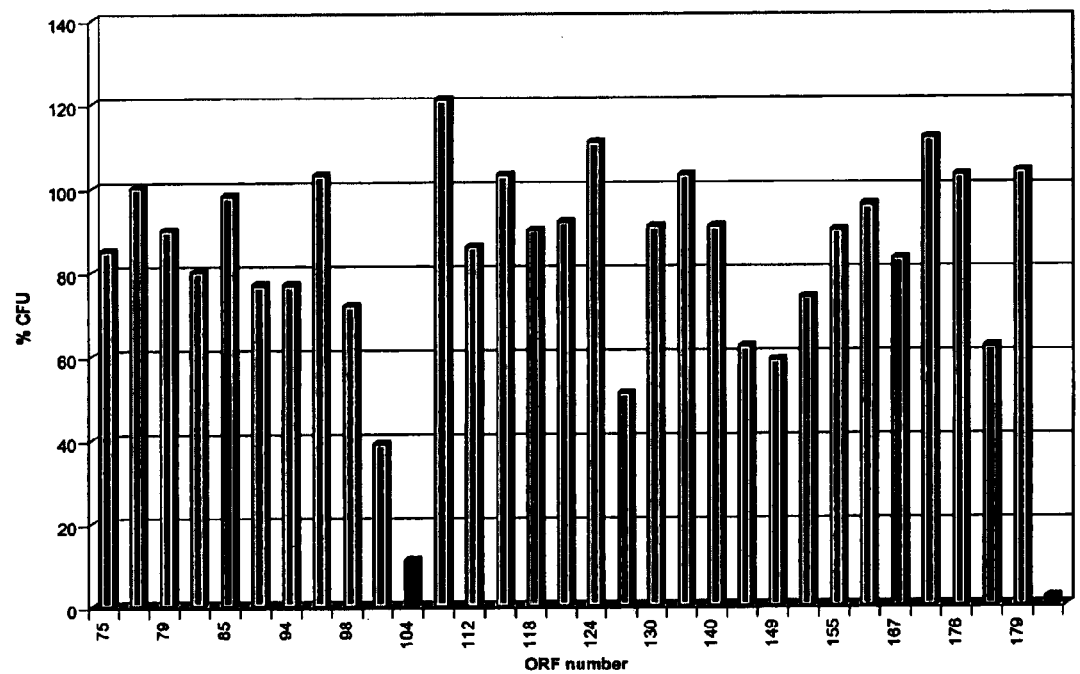

Such shuttle vectors preferably also contain regulatory sequences that allow inducible expression of the introduced ORF. As the candidate ORF may encode an inhibitor function that will eliminate the host, it is beneficial that it not be expressed prior to testing for activity. Thus, screening for such sequences when expressed in a constitutive fashion is less likely to be successful when the inhibitor is lethal. In the exemplary inducible system presented in FIGS. 1A, 1B, and 2, regulatory sequences from the ars operon of *S. aureus* are used to direct individual ORF expression in *S. aureus*. The ars operon encodes a series of proteins which normally mediate the extrusion of arsenite and other trivalent oxyanions from tie cells when they are exposed to such toxic substances in their environment. The operon encoding this detoxifying mechanism is normally silent and only induced when arsenite-related compounds are present. (Tauriainen, S. et al. (1997) *App. Env. Microb.*, Vol. 63, No. 11, p. 4456–4461.)

Therefore, individual phage ORFs can be expressed in *S. aureus* in an inducible fashion by adding to the culture medium non-toxic arsenite concentrations during the growth of individual *S. aureus* clones expressing such individual phage ORFs. Toxicity of the phage inhibitor ORF for the host is monitored by reduction or arrest of growth under induction conditions, as measured by optical density in liquid culture or after plating the induced cultures on solid medium. Subsequently, interference of the phage ORF with the host biochemical pathways ultimately leading to reduced or arrested host metabolism can be measured by pulse-chase experiments using radiolabeled precursors of either DNA replication, RNA transcription, or protein synthesis.

Those skilled in the art are familiar with a variety of other inducible systems which can also be used for the controlled expression of phage ORFs, including, for example, lactose (see e.g., Stratagene's LacSwitch™II system; La Jolla, Calif.) and tetracycline-based systems (see, e.g. Clontech's Tet On/Tet Off™ system; Palo Alto, Calif.). The arsenite-inducible system described is further depicted in FIGS. 1A, 1B, and 2.

The selection or construction of shuttle vectors and the selection and use of inducible systems are well known and thus other shuttle vectors appropriate for other bacteria can be readily provided by those skilled in the art.

Standard methodologies for expressing proteins from constructs, and isolating and manipulating those proteins, for example in cross-linking and affinity chromatography studies, may be found in various commonly available and known laboratory manuals. See, e.g., *Current Protocols in Protein Science*. John Wiley & Sons, Secaucus, N.J., and Maniatis, T. et al. (1989) *Molecular Cloning: A Laboratory Manual*, Cold Spring Harbor University Press, Cold Spring, N.Y.

It has been found that certain phage or other viruses inhibit host cells, at least in part, by producing an antisense RNA which binds to and inhibits translation from a bacterial RNA seqeunce. Thus, in the case of potentially inhibitor RNA transcripts encoded by the phage genome, a strong indicator of a possible inhibitory function is provided by the identification of phage sequence which is the identical to or fully complementary (or with only a small percentage of mismatch, e.g., <10%, preferably less than 5%, most preferably less than 3%, to a bacterial sequence. This approach is convenient in the case of bacteria which have been essentially completely sequenced, as the comparison can be performed by computer using public database information.

The inhibitory effect of the transcript can be confirmed using expression of the phage sequence in a host bacterium. If needed, such inhibitory can also be tested by transfecting the cells with a vector which will transcribe the phage sequence to form RNA in such manner that the RNA produced will not be translated into a polypeptide. Inhibition under such conditions provides a strong indication that the inhibition is due to the transcript rather than to an encoded polypeptide.

In an alternative, the expression of an ORF in a host bacterium is found to be inhibitory, but the inhibition if found to be due to an RNA product of the genomic coding region. For antisense inhibition, the sequence of the bacterial target nucleic acid sequence can be identified by inspection of the phage sequence, and the full sequence of the relevant coding region for the bacterial product can be found from a database of the bacterial genomic sequence or can be isolated by standard techniques (e.g., a clone in a genomic library can be isolated which contains the full bacterial ORF, and then sequenced).

In either case, the identification of a target which is inhibited by an RNA transcript produced by a phage provides both the possible inhibition of bacteria naturally containing the same target nucleic acid sequence, as well as the ability to use the target sequence in screening for other types of compounds which will act directly on the target nucleic acid sequence or on a polypeptide product expressed or regulated, at least in part, by the target of the inhibitory phage RNA.

In some cases it will be found that the target of an inhibitory phage RNA or protein has previously been found to be a target of an inhibitory phage RNA or protein has previously been found to be a target for an antibacterial agent. In such cases, the phage inhibitor can still provide useful information if it is found that the phage-encoded product acts at a different site than the previously identified antibacterial agent or inhibitor, i.e., acts at a phage-specific site. For many targets, action at a different site provides highly beneficial characteristics and/or information. For example, an alternate site of inhibitor action can at least partially overcome a resistance mechanism in a bacterium. As an illustration, in many cases, resistance is due, in large part, to altered binding characteristics of the immediate target to the antibacterial agent. The altered binding is due to a structural change which prevents or destabilizes the binding. However, the structural change is frequently quite local, so that compounds which bind at different local sites will b unaffected or affected to a much lesser degree. Indeed, in some cases the local sites will be on a different molecule and so may be completely unaffected by the local structural change creating resistance to the original agent(s). An example of resistance due to altered binding is provided by methicillin-resistant *Staphylococcus aureus*, in which the resistance is due to an altered penicillin-binding protein.

In other cases, a new site of action can have improved accessibility as compared to a site acted on by a previously identified agent. This can, for example, assist in allowing effective treatment at lower doses, or in allowing access by a larger range of types of compounds, potentially allowing identification of more potential active agents.

Another advantage is that the structural characteristics of a different site of action will lead to identification and/or development of inhibitors with different structures and different pharmacological parameter. This can allow a greater range of possibilities when selecting an antibacterial agent.

Yet further, different sites often produce different inhibitory characteristics in the target organism. This is commonly the case for multi-domain target proteins. Thus, inhibition targeting an alternate site can produce more efficacious action, e.g., faster killing, slower development of resistance, lower numbers of surviving cells, and different secondary effects (for example, different nutrient utilization).

Validating Identified Inhibitory Phage ORFs

A fifth step involves validating the identified phage inhibitor ORF by independent methods, and delineating further possible smaller segments of the ORFs that have inhibitory activity. Several methods exist to validate the role of the identified ORF as an inhibitor ORF.

One example utilizes the creation of a mutant variant of the phage ORF in which the candidate ORF carries a partial or complete loss-of-function mutation that is measurable as compared with the non-mutant ORF. Comparison of the effects of expression of the loss of function mutant with the normal ORF provides confirmation of the identification of an inhibitor ORF where the loss of function mutant provides a measurably lower level of inhibition, preferably no inhibition. The loss of function may be conditional, e.g., temperature sensitive.

Once validation of the inhibitor ORF is achieved, a bidirectional deletion analysis can be carried out using the same experimental system to identify the minimal polypeptide segment that has inhibitor activity. This may be carried out by a variety of means, e.g., by exonuclease or PCR methodologies, and is used to determine if a relatively small segment of the ORF (i.e., the product of the ORF) still possesses inhibitory activity when isolated away from its native sequence. If so, a portion of the ORF encoding this "active portion" can be used as a template for the synthesis of novel anti-microbial agents and further allowing derivation of the peptide sequence, e.g., using modified peptides and/or peptidomimetics.

In creation of certain peptidomimetics, the peptide backbone is transformed into a carbon-based hydrophobic structure that can retain inhibitor activity against the bacterium. This is done by standard medicinal chemistry methods, typically monitored by measuring growth inhibition of the various molecules in liquid cultures or on solid medium. These mimetics can also represent lead compounds for the development of novel antibiotics.

Recently, a major effort has been undertaken by the pharmaceutical industry and their biotechnology partners for the sequencing of bacterial pathogen genomes. The rationale is that the systematic sequencing of the genome will identify all of the bacterial proteins and therefore this proteome will be the target for designing novel inhibitor antibiotics. Although systematic, this approach has several major problems. The first is that analysis of primary amino acid sequences of bacterial proteins does not immediately reveal which protein will be essential for viability of the bacterium, and target validation is thus a major issue. The second problem is one of redundancy, as several biochemical pathways arc either structurally duplicated in bacteria (different isoforms of the same enzyme), or functionally duplicated by the presence of salvage pathways in the event of a metabolic block in one pathway (different nutritional conditions). The third is that even a valid target may not be structurally or functionally amenable to inhibition by small molecules because of inaccessibility (sequestration of target).

Therefore, there is considerable interest within the pharmaceutical and biotechnology industry in identifying key targets for drug discovery amongst the mass of novel targets generated by large-scale genomic sequencing projects.

On the other hand, and underscoring the instant invention, the phages herein described have, over millions of years, evolved specific mechanisms to target such key biochemical pathways and proteins. In the few cases where inhibition by phages has been elucidated (e.g., see ref. 3), such bacterial targets are invariably rate-limiting in their respective biochemical pathways, are not redundant, and/or arc readily accessible for inhibition by the phage (or by another inhibitory compound). Therefore, the sixth step of this invention involves identifying the host biochemical pathways and proteins that are targeted by the phage inhibitory mechanisms.

Identifing, Validating, and Characterizing Bacterial Host Target Proteins and Affected Pathways A rationale for this step is that the inhibitor ORF product from the phage physically interacts with and/or modifies certain microbial host components to block their function. Exemplary approaches which can be used to identify the host bacterial pathways and proteins that interact with, and preferably also are inhibited by, phage ORF product(s) are described below.

The first approach is a genetic screen to determine physiological protein:protein interaction, for example, using a yeast two hybrid system. In this assay, the phage ORF is fused to the carboxyl terminus of the yeast Gal4 activation domain II (amino acids 768–881) to create a bait vector. A cDNA library of cloned *S. aureus* sequences which have been engineered into a plasmid where the *S. aureus* sequences are fused to the DNA binding domain of Gal4 is also generated. These plasmids are introduced alone, or in combination, into yeast strain Y190—previously engineered with chromosomally integrated copies of the *E. coli* lacZ and the selectable HIS3 genes, both under Gal4 regulation (Durfee, T., Becherer, K., Chen, P.-L., Yeh, S.-H., Yang, Y., Kilburn, A. E., Lee, W.-H., and Elledge, S. J. (1993). *Genes & Dev.* 7, 555–569). If the two proteins expressed in yeast interact, the resulting complex will activate transcription from promoters containing Gal4 binding sites. A lacZ and His3 gene, each driven by a promoter containing Gal4 binding sites, have been integrated into the genome of the host yeast system used for measuring protein-protein interactions. Such a system provides a physiological environment in which to detect potential protein interactions. This system has been extensively used to identify novel protein-protein interaction partners and to map the sites required for interaction (for example, to identify interacting partners of translation factors (Qiu, H., Garcia-Barrio, M. T., and Hinnebusch, A. G. (1998). *Mol & Cell Biology* 18, 2697–2711), transcription factors (Katagiri, T., Saito, H., Shinohara, A., Ogawa, H., Kamada, N., Nakamura , Y., and Miki, Y. (1998). Genes, *Chromosomes & Cancer* 21, 217–222), and proteins involved in signal transduction (Endo, T. A., Masuhara, M., Yokouchi, M., Suzuki, R., Sakamoto, H., Mitsui, K., Matsumoto, A., Tanimura, S., Ohtsubo, M., Misawa, H., Miyazaki, T., Leonor N., Taniguchi, T., Fujita, T., Kanakura, Y., Komiya, S., and Yoshimura, A. *Nature*. 387, 921–924). This approach has also been used in many published reports to identify interaction between mammalian viral and mammalian cell proteins.

For example, the non-structural protein NS1 of parvovirus is essential for viral DNA amplification and gene expression and is also the major cytopathic effector of these viruses. A yeast two-hybrid screen with NS1 identified a novel cellular protein of unknown function that interacts with NS-1, called SGT, for small glutamine-rich tetratricopeptide repeat (TPR)-containing protein (Czieplich C. Kordes E. Poirey R. Grewenig A. Rommelaere, J, and Jauniaux J C. (1998) *J Virol*. 72, 4149–4156). In another screen, the adenovirus E3 protein was recently shown to interact with a novel tumor necrosis factor alpha-inducible protein and to modulate some of the activities of E3 (Li Y. Kang J. and Horwitz M. S. (1998). *Mol & Cell Biol*. 18, 1601–1610). In yet another recent screen, the herpes simplex virus 1 alpha regulatory protein ICP0 was found to interact with (and stabilize) the cell cycle regulator cyclin D3 (Kawaguchi Y. Van Sant C. and Roizman B. (1997). *J Virol*. 71, 7328–7336).

Another two-hybrid system for identifying protein:protein interactions is commercially available from STRATE-GENE™ as the CYTO-TRAP™ system (Chang et al., *Strategies Newsletter* 11(3), 65–68 (1998)(from Stratagene)). The system is a yeast-based method for detecting protein:protein interactions in vivo, using activation of the Ras signal transduction cascade by localizing a signal pathway component, human Sos (hSos), to its activation site in the yeast plasma membrane. The system uses a temperature-sensitive *Saccharomyces cerevisiae* mutant, strain cdc25H, which contains a point mutation at amino acid residue 1328 of the cdc25 gene. This gene encodes a guanyl nucleotide exchange factor which binds and activates Ras, leading to cell growth. The mutation in the cdc25 gene prevents host growth at 37° C., but at a permissive temperature of 25° C., growth is normal. The system utilizes the ability of (hSos) to complement the cdc25 defect and activate the yeast Ras signaling pathway. Once (hSos) is expressed and localized to the plasma membrane, the cdc25H yeast strain grows at 37° C. Localizing hSos to the plasma membrane occurs through a protein:protein interaction. A protein of interest, or bait, is expressed as a fusion protein with hSos. The library, or target proteins are expressed with the myristylation membrane-localization signal. The yeast cells are then incubated under restrictive conditions (37° C.). If the bait and the target protein interact, the hSos protein is recruited to the membrane, activating the Ras signaling pathway and allowing the cdc25H yeast strain to grow at the restrictive temperature.

The second approach is based on identifying protein:protein interactions between the phage ORF product and bacterial, e.g., *S. aureus*, proteins using a biochemical approach based, for example, on affinity chromatography. This approach has been described, for example, in Sopta, M., Carthew, R. W., and Greenblatt, J. (1985) *J. Biol. Chem.* 260, 10353–10369. The phage ORF is fused to a peptide tag (e.g. glutathione-S-transferase ("GST"), 6×HIS ("HIS") and/or calmodulin binding protein ("CPB") within a commercially available plasmid vector that directs high level expression on induction of a suitably responsive promoter driving the fuision's expression. The translated fusion protein is expressed in *E. coli*, purified, and immobilized on a solid phase matrix via, for example, the tag. Total cell extracts from the host bacterium, e.g., *S. aureus*, are then passed through the affinity matrix containing the immobilized phage ORF fusion protein; host proteins retained on the column are then eluted under different conditions of ionic strength, pH, detergents, etc., and characterized by gel electrophoresis and other techniques. Appropriate controls are run to guard against nonspecific binding to the resin. Target proteins thus recovered should be enriched for the phage protein/peptide of interest and are subsequently electrophoretically or otherwise separated, purified, sequenced, or biochemically analyzed. Usually sequencing entails individual digestion of the proteins to completion with a protease (e.g., trypsin), followed by molecular mass and amino acid composition and sequence determination using, for example, mass spectrometry, e.g., by MALDI-TOF technology (Qin, J., Fenyo, D., Zhao, Y., Hall, W. W., Chao, D. M., Wilson, C. J., Young, R. A. and Chait, B. T. (1997). *Anal. Chem.* 69:3995–4001).

The sequence of the individual peptides from a single protein are then analyzed by the bioinformatics approach described above to identify the *S. aureus* protein interacting with the phage ORF. This analysis is performed by a computer search of the *S. aureus* genome for an identified sequence. Alternatively, all tryptic peptide fragments of the *S. aureus* genome can be predicted by computer software, and the molecular mass of such fragments compared to the molecular mass of the peptides obtained from each interacting protein eluted from the affinity matrix. The responsible gene sequence can be obtained, for example by using synthetic degenerate nucleic acid sequences to pull out the corresponding homologous bacterial sequence. Alternatively, antibodies can be generated against the peptide and used to isolate nascent peptide/mRNA transcript complexes, from which the mRNA can be reverse transcribed, cloned, and further characterized using the procedures discussed herein.

A variety of other binding assay methods are known in the art and can be used to identify interactions between phage proteins and bacterial proteins or other bacterial cell components. Such methods which allow or provide identification of the bacterial component can be used in this invention for identifying putative targets.

Validation of the interaction between the phage ORF product and the bacterial proteins or other components can be obtained by a second independent assay (e.g., co-immunoprecipitation or protein-protein crosslinking experiments (Qiu, H., Garcia-Barrio, M. T., and Hinnebusch, A. G. (1998). *Mol & Cell Biology* 18, 2697–2711; Brown, S. and Blumenthal, T. (1976). *Proc. Natl. Acad. Sci. USA* 73, 1131–1135)).

Finally, the essential nature of the identified bacterial proteins is preferably determined genetically by creating a constitutive or inducible partial or complete loss-of-function mutation in the gene encoding the identified interacting bacterial protein. This mutant is then tested for bacterial survival and replication.

The protein target of the phage inhibitor function can also be identified using a genetic approach. Two exemplary approaches will be delineated here. The first approach involves the overexpression of a predetermined phage inhibitor protein in mutagenized host bacteria, e.g., S. aureus, followed by plating the cells and searching for colonies that can survive the inhibitor. These colonies will then be grown, their DNA extracted and cloned into an expression vector that contains a replicon of a different incompatibility group, and preferably having a different selectible marker than the plasmid expressing the phage inhibitor. Thus, host DNA fragments from the mutant that can protect the cell from phage ORF inhibition can be sequenced and compared with that of the bacterial host to determine in which gene the mutation lies. This approach allows rapid determination of the targets and pathways that are affected by the inhibitor.

Alternatively, the bacterial targets can be determined in the absence of selecting for mutations using an approach known as "multicopy suppression". In this approach, the DNA from the wild type host is cloned into an expression vector that can coexist, as previously described, with one containing a predetermined phage inhibitor. Those plasmids that contain host DNA fragments and genes that protect the host from the phage inhibitor can then be isolated and sequenced to identify putative targets and pathways in the host bacteria.

Regardless of the specific mode of identification, screening assays may additionally utilize gene fusions to specific "reporter genes" to identify a bacterial gene(s) whose expression is affected when the host target pathway is affected by the phage inhibitor. Such gene fusions can be used to search a number of small molecule compounds for inhibitors that may affect this pathway and thus cause cell inhibition. This approach will allow the screening of a large number of molecules on petri dishes or 96-well format by monitoring for a simple colorchange in the bacterial colonies. In this manner, we can validate host targets and classes of compounds for further study and clinical development. These inhibitors also represent lead compounds for the development of other antibiotics.

Bioinformatics and comparative genomics are preferably then applied to the identified bacterial gene products to predict biochemical function. The biochemical activity of the protein can be verified in vitro in cell free assays or in vivo in intact cells. In vitro biochemical assays utilizing cell-free extracts or purified protein are established as a basis for the screening and development of inhibitors.

These inhibitors, preferably small molecule inhibitors, may comprise peptides, antibodies, products from natural sources such as fungal or plant extracts or small molecule organic compounds. In general, small molecule organic compounds are preferred. These compounds may, for example, be identified within large compound libraries, including combinatorial libraries. For example, a plurality of compounds, preferably a large number of compounds can be screened to determine whether any of the compounds binds or otherwise disrupts or inhibits the identified bacterial target. Compounds identified as having any of these activities can then be evaluated further in cell culture and/or animal model systems to determine the pharmacological properties of the compound, including the specific antimicrobial ability of the compound.

For mixtures of natural products, including crude preparations, once a preparation or fraction of a preparation is shown the have an anti-microbial activity, the active substance can be isolated and identified using techniques well known in the art, if the compound is not already available in a purified form.

Identified compounds possessing anti-microbial activity and similar compounds having structural similarity can be further evaluated and, if necessary, derivatized according to synthesis and/or modification methods available in the art selected as appropriate for the particular starting molecule.

Derivatization of Identified Anti-microbials

In cases where the identified anti-microbials above might represent peptidal compounds, the in vivo effectiveness of such compounds may be advantageously enhanced by chemical modification using the natural polypeptide as a starting point and incorporating changes that provide advantages for use, for example, increased stability to proteolytic degradation, reduced antigenicity, improved tissue penetration, and/or improved delivery characteristics.

In addition to active modifications and derivative creations, it can also be useful to provide inactive modifications or derivatives for use as negative controls or introduction of immunologic tolerance. For example, a biologically inactive derivative which has essentially the same epitopes as the corresponding natural antimicrobial can be used to induce immunological tolerance in a patient being treated. The induction of tolerance can then allow uninterrupted treatment with the active anti-microbial to continue for a significantly longer period of time.

Modified anti-microbial polypeptides and derivatives can be produced using a number of different types of modifications to the amino acid chain. Many such methods are known to those skilled in the art. The changes can include, for example, reduction of the size of the molecule, and/or the modification of the amino acid sequence of the molecule. In addition, a variety of different chemical modifications of the naturally occurring polypeptide can be used, either with or without modifications to the amino acid sequence or size of the molecule. Such chemical modifications can, for example, include the incorporation of modified or non-natural amino acids or non-amino acid moieties during synthesis of the peptide chain, or the post-synthesis modification of incorporated chain moieties.

The oligopeptides of this invention can be synthesized chemically or through an appropriate gene expression system. Synthetic peptides can include both naturally occurring amino acids and laboratory synthesized, modified amino acids.

Also provided herein are functional derivatives of anti-microbial proteins or polypeptides. By "functional derivative" is meant a "chemical derivative," "fragment," "variant," "chimera," or "hybrid" of the polypeptide or protein, which terms are defined below. A functional derivative retains at least a portion of the function of the protein, for example reactivity with a specific antibody, enzymatic activity or binding activity.

A "chemical derivative" of the complex contains additional chemical moieties not normally a part of the protein or peptide. Such moieties may improve the molecule's solubility, absorption, biological half-life, and the like. The moieties may alternatively decrease the toxicity of the molecule, eliminate or attenuate any undesirable side effect of the molecule, and the like. Moieties capable of mediating such effects are disclosed in Alfonso and Gennaro (1995).

Procedures for coupling such moieties to a molecule are well known in the art. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing primary amine-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking component peptides to each other or the complex to a water-insoluble support matrix or to other macromolecular carriers. Commonly used cross-linking agents include, for example, 1,1-bis (diazoacetyl)-2-phenylethane, glutaraldehyde, N-hydroxysuccinimide esters, for example, esters with 4-azidosalicylic acid, homobi-functional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecular Properties*, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex. Moieties capable of mediating such effects are disclosed, for example, in Alfonso and Gennaro (1995).

The term "fragment" is used to indicate a polypeptide derived from the amino acid sequence of the protein or polypeptide having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Another functional derivative intended to be within the scope of the present invention is a "variant" polypeptide which either lacks one or more amino acids or contains additional or substituted amino acids relative to the native polypeptide. The variant may be derived from a naturally occurring polypeptide by appropriately modifying the protein DNA coding sequence to add, remove, and/or to modify codons for one or more amino acids at one or more sites of the C-terminus, N-terminus, and/or within the native sequence.

A functional derivative of a protein or polypeptide with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183; Sambrook et al., 1989) wherein nucleotides in the DNA coding sequence are modified such that a modified coding sequence is produced, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art.

Insofar as other anti-microbial inhibitor compounds identified by the invention described herein may not be peptidal in nature, other chemical techniques exist to allow their suitable modification, as well, and according the desirable principles discussed above.

Administration and Pharmaceutical Compositions

For the therapeutic and prophylactic treatment of infection, the preferred method of preparation or administration of anti-microbial compounds will generally vary depending on the precise identity and nature of the antimicrobial being delivered. Thus, those skilled in the art will understand that administration methods known in the art will also be appropriate for the compounds of this invention.

The particularly desired anti-microbial can be administered to a patient either by itself, or in pharmaceutical compositions where it is mixed with suitable carriers or excipient(s). In treating an infection, a therapeutically effective amount of an agent or agents is administered. A therapeutically effective dose refers to that amount of the compound that results in amelioration of one or more symptoms of bacterial infection and/or a prolongation of patient survival or patient comfort.

Toxicity, therapeutic and prophylactic efficacy of anti-microbials can be determined by standard pharmaceutical procedures in cell cultures and/or experimental organisms such as animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound identified and used in the method of the invention, the therapeutically effective dose can be estimated initially from cell culture assays. Such information can be used to more accurately determine useful doses in organisms such as plants and animals, preferably mammals, and most preferably humans. Levels in plasma may be measured, for example, by HPLC or other means appropriate for detection of the particular compound.

The exact formulation, route of administration and dosage can be chosen by the individual physician in view of the patient's condition (see e.g. Fingi et. al., in *The Pharmacological Basis of Therapeutics*, 1975, Ch. 1 p.1).

It should be noted that the attending physician would know how and when to terminate, interrupt, or adjust administration due to toxicity, organ dysfunction, or other systemic malady. Conversely, the attending physician would also know to adjust treatment to higher levels if the clinical response were not adequate (precluding toxicity). The magnitude of an administered dose in the management of the disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary or phyto medicine.

Depending on the specific infection target being treated and the method selected, such agents may be formulated and administered systemically or locally, i.e., topically. Techniques for formulation and administration may be found in Alfonso and Gennaro (1995). Suitable routes may include, for example, oral, rectal, transdermal, vaginal, transmucosal, intestinal, parenteral, intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate identified anti-microbials of the present invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active anti-microbial compounds in water-soluble form. Alternatively, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The above methodologies may be employed either actively or prophylactically against an infection of interest.
Computer-related Aspects and Embodiments In addition to the provision of compounds as chemical entities, nucleotide sequences, or fragments thereof at least 95%, preferably at least 97%, more preferably at least 99%, and most preferably at least 99.9% identical to phage inhibitor sequences can also be provided in a variety of additional media to facilitate various uses.

Thus, as used in this section, "provided" refers to an article of manufacture, rather than an actual nucleic acid molecule, which contains a nucleotide sequence of the present invention; e.g., a nucleotide sequence of an exemplary bacteriophage or a sequence encoding a bacterial target or a fragment thereof, preferably a nucleotide sequence at least 95%, more preferably at least 99% and most preferably at least 99.9% identical to such a bacteriophage or bacterial sequence, for example, to a polynucleotide of an unsequenced phage listed in Table 1, preferably of bacteriophage 77 (S. aureus host) or bacteriophage 3A (S. aureus host) or bacteriophage 96 (S. aureus host). Such an article provides a large portion of the particular bacteriophage genome or bacterial gene and parts thereof (e.g., a bacteriophage open reading frame (ORF)) in a form which allows a skilled artisan to examine and/or analyze the sequence using means not directly applicable to examining the actual genome or gene or subset thereof as it exists in nature or in purified form as a chemical entity.

In one application of this aspect, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, magnetic tape; optical storage media such as CD-ROM; electrical storage media such as RAM and ROM; and hybrids of these categories, such as magnetic/optical storage media A skilled artisan can readily appreciate how any of the presently known computer readable mediums can be used to create an article of manufacture which includes one or more computer readable media having recorded thereon a nucleotide sequence or sequences of the present invention. Likewise, it will be clear to those of skill how additional computer readable media that may be developed also can be used to create analogous manufactures having recorded thereon a nucleotide sequence of the present invention.

As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can, for example, be presented in a word processing test file, formatted in commercially available software such as WordPerfect and Microsoft Word, or represented in the form of an ASCII file, stored in a database application, such as DB2, Sybase, Oracle, or the like. A skilled artisan can readily adapt any number of data processor structuring formats (e.g., text file or database) in order to obtain computer readable medium having recorded thereon the nucleotide sequence information of the present invention.

Computer software is publicly available which allows a skilled artisan to access sequence information provided in a computer readable medium. Thus, by providing in computer readable form a nucleotide sequence of an unsequenced bacteriophage, such as an exemplary bacteriophage listed in Table 1 or of a sequence encoding a bacterial target or a fragment thereof, preferably a nucleotide sequence at least 95%, more preferably at least 99% and most preferably at least 99.9% identical to such a bacteriophage or bacterial sequence, for example, to a polynucleotide of bacteriophage 77 (S. aureus host) or bacteriophage 3A (S. aureus host) or bacteriophage 96 (S. aureus host), the present invention enables the skilled artisan to routinely access the provided sequence information for a wide variety of purposes.

Those skilled in the art understand that software can implement a variety of different search or analysis software which implement sequence search and analysis algorithms, e.g., the BLAST (Altschul et al., J. Mol. Biol. 215:403410 (1990) and BLAZE (Brutlag et al., Comp. Chem 17:203–207 (1993)) search algorithms. For example, such search algorithms can be implemented on a Sybase system and used to identify open reading frames (ORFs) within the bacteriophage genome which contain homology to ORFs or proteins from other viruses, e.g, other bacteriophage, and other organisms, e.g., the host bacterium. Among the ORFs discussed herein are protein encoding fragments of the bacteriophage genomes which encode bacteria-inhibiting proteins or fragments.

The present invention further provides systems, particularly computer-based systems, which contain the sequence information described. Such systems are designed to identify, among other things, useful fragments of the bacteriophage genomes.

As used herein, "a computer-based system" refers to the hardware, software, and data storage media used to analyze the nucleotide sequence information of the present invention. The minimum hardware of the computer-based systems of the present invention comprises a central processing unit (CPU), input device, output device, and data storage medium or media. A skilled artisan will readily recognize that any of the currently available general purpose computer-based system are suitable for use in the present invention, as well as a variety of different specialized or dedicated computer-based systems.

As stated above, the computer-based systems of the present invention comprise data storage media having stored therein a nucleotide sequence of the present invention and the necessary hardware and software for supporting and implementing a search and/or analysis program.

As used herein, "data storage media" refers to memory which can store nucleotide sequence information of the present invention, or a memory access means which can access manufactures having recorded thereon the nucleotide sequence information of the present invention.

As used herein, "search program" refers to one or more programs which are implemented on the computer-based system to compare a target sequence or target structural motif with the sequence information stored within the data storage means. Search means are used to identify fragments or regions of the present genomic sequences which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA). A skilled artisan can readily recognize that any one of the available algorithms or implementing software packages for conducting homology searches and/or sequence analyses can be adapted for use in the present computer-based systems.

As used herein in connection with sequence searches and analyses, a "target sequence" can be any DNA or amino acid sequence of six or more nucleotides or two or more amino acids. A skilled artisan can readily recognize that the longer a target sequence is, the less likely a target sequence will be present as a random occurrence in the database. Also, the target sequence length is preferably selected to include sequence corresponding to a biologically relevant portion of an encoded product, for example a region which is expected to be conserved across a range of source organisms. Preferably the sequence length of a target polypeptide sequence is from 5–100 amino acids, more preferably 7–50 or 7–100 amino acids, and still more preferably 10–80 or 10–100 amino acids. Preferably the sequence length of a target polynucleotide sequence is from 15–300 nucleotide residues, more preferably from 21–240 or 21–300, and still more preferably 30–150 or 30–300 nucleotide residues. However, it is well recognized that searches for commercially important fragments, such as sequence fragments involved in gene expression and protein processing, may be of shorter length. Likewise, it may be desirable to search and/or analyze longer sequences.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to promoter sequences, hairpin structures and inducible expression elements (protein binding sequences).

A variety of structural formats for the input and output devices can be used to input and output the information in the computer-based systems of the present invention. A preferred format for an output device ranks fragments of the bacteriophage or bacterial sequences possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing methods and/or devices and/or formats can be used to compare a target sequence or target motif with the sequence stored in data storage media to identify sequence fragments of the bacteriophage or bacterium in question. One skilled in the art can readily recognize that any one of the publicly available homology search programs can be used as the search program for the computer-based systems of the present invention. Of course, suitable proprietary systems that may be known to those of skill, or later developed, also may be employed in this regard.

Figure 5:
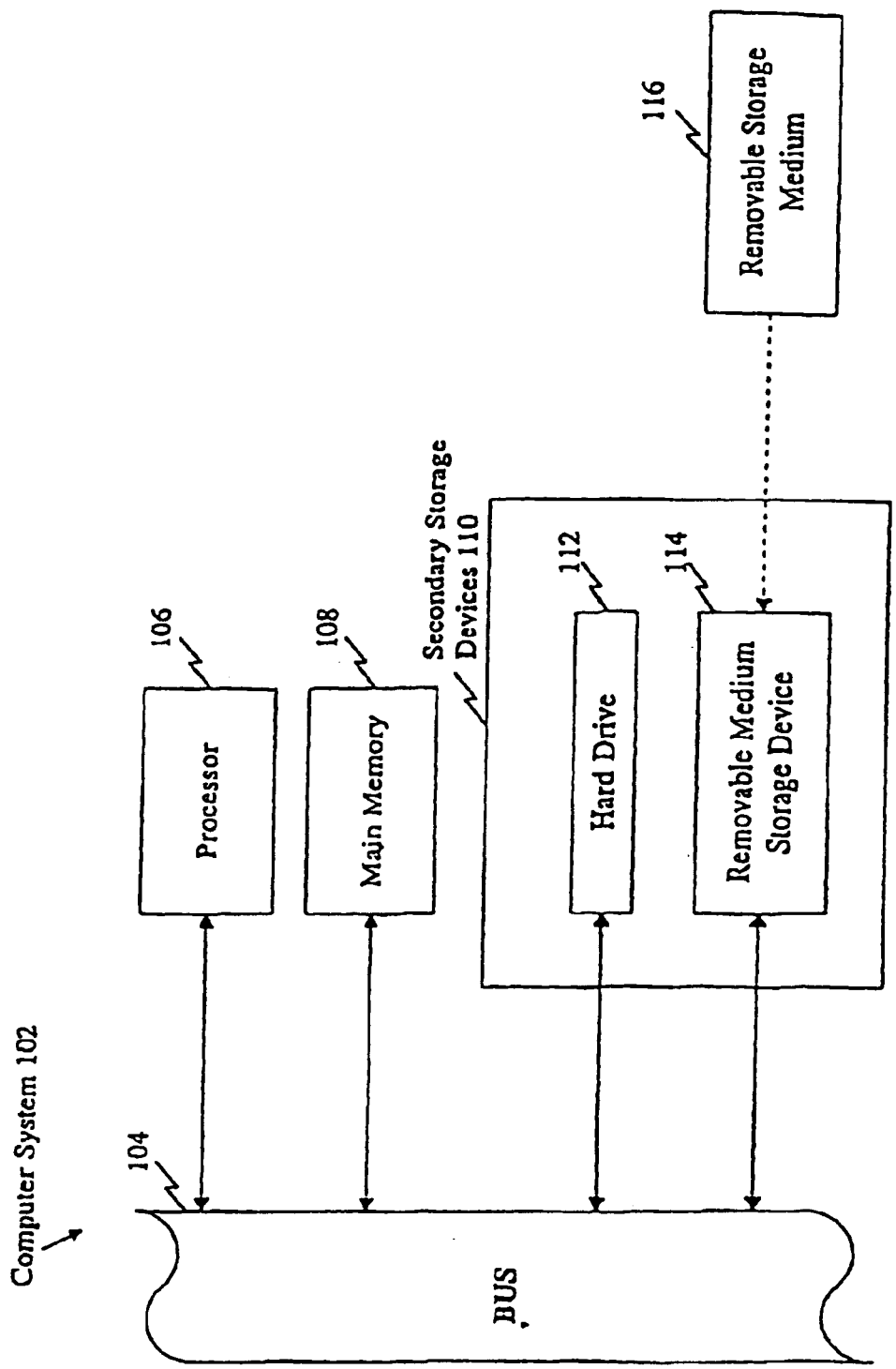
FIG. 5 shows a block diagram of major components of a general purpose computer.

FIG. 5 provides a block diagram of a computer system illustrative of embodiments of this aspect of present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114, once it is inserted into the removable medium storage device 114.

A nucleotide sequence of the present invention may be stored in a well-known manner in the main memory 108, any of the secondary storage devices 110, and/or a removable storage medium 116. During execution, software for accessing and processing the sequence (such as search tools, comparing tools, etc.) reside in main memory 108, in accordance with the requirements and operating parameters of the operating system, the hardware system and the software program or programs.

The data storage medium in which the sequence is embodied and the central processor need not be part of a single stand-alone computer, but may be separated so long as data transfer can occur. For example, the processor or processors being utilized for a search or analysis can be part of one general purpose computer, and the data storage medium can be part of a second general purpose computer connected to a network, or the data storage medium can be part of a network server. As another example the data storage medium can be part of a computer system or network accessible over telephone lines or other remote connection method.

EXAMPLES

Example 1

Propagation of Bacteriophage 77 of *Staphylococcus aureus*

Bacterial Propagating Strain and Bacteriophage:

The *Staphylococcus aureus* propagating strain 77 (PS 77) was used as a host to propagate its respective phage 77 (ATCC # 27699-B1).

Purification of Bacteriophage and Prepradon of Phage DNA:

The propagation method was carried out by using the agar layer method described by Swanström and Adams (Swanström, M. and Adams, M. H. (1951). Agar layer method for production of high titer phage stocks. *Proc. Soc. Exptl. Bio. & Med.* 78: 372–375). Briefly, the PS 77 strain was grown overnight at 37° C. in Nutrient broth [NB: 3 g Bacto Beef Extract, 5 g Bacto Peptone per liter, (Difco Laboratories)]. The culture was then diluted 20× in NB and incubated at 37° C. until the $OD_{540}$=0.2. The suspension ($15 \times 10^7$ Bacteria) was then mixed with $15 \times 10^5$ phage particles to give a ratio of 100 bacteria/phage particle in the presence of 400 µg/ml of $CaCl_2$. After incubation of 15 min at room temperature, 7.5 ml of melted soft agar (NB supplemented with 0.6% of agar), were added to the mixture and poured onto the surface of 100 mm nutrient agar plates (3 g Bacto Beef Extract, 5 g Bacto Peptone and 15 g of Bacto Agar per liter) and incubated overnight at 30° C. To collect the lysate, 20 ml of NB were added to each plate and the soft agar layer was collected by scrapping off with a clean microscope slide and shaken vigorously for 5 min to break up the agar. The mixture was then centrifuged for 10 min at 4,000 rpm and the supernatent (lysate) is collected and subjected to a treatment with 10 µg/ml of DNase I and RNase A for 30 min at 37° C. To precipitate the phages particles, 10% (w/v) of PEG 8000 and 0.5 M of NaCl were added to the lysate and the mixture was incubated on ice for 16 h. The phages were recovered by centrifugation at 4,000 rpm for 20 min at 4° C. on a GS-6R table top centrifuge (Beclanan). The pellet was resuspended with 2 ml of phage buffer (1 mM $MgSO_4$, 5 mM $MgCl_2$, 80 mM NaCl and 0.1 % Gelatin). The phage suspension was extracted with 1 volume of chloroform and purified by centrifugation using a TLS 55 rotor and the Optima TLX ultracentrifuge (Beckman), for 2 h at 28,000 Rpm at 4° C. in preformed cesium chloride gradient as described in Sambrook et al. (Sambrook, J., Fritsch, E. F. and Maniatis, T (1989). Molecular cloning: A laboratory Manual. Cold Spring Harbor Laboratory, New York. Cold Spring Harbor Laboratory Press). Banded phages were collected and ultracentrifuged again on an isopycnic cesium chloride gradient at 40,000 rpm for 24 h rpm at 4° C. using a TLV rotor (Beckman). The phage was dialyzed for 4 h at room temperature against 4 L of dialysis buffer consisting of 10 mM NaCl, 50 mM Tris-HCl pH 8 and 10 mM $MgCl_2$. Phage DNA was prepared from the phages by adding 20 mM EDTA, 50 mg/ml Proteinase K and 0.5% SDS and incubating for 1 h at 65° C., followed by successive extractions with 1 volume of phenol, 1 volume of phenol-chloroform and 1 volume of chloroform. The DNA was then dialyzed overnight at 4° C. against 4 L of T.E (10 mM $Tris_{8.0}$, 1 mM EDTA).

Example 2

Preparation of Bacteriophage 77 DNA for Sequencing

Sonication of DNA:

4 µg of phage DNA was diluted in 200 µl of T.E pH 8.0 in a 1.5 ml Eppendorf tube and sonication was performed (550 Sonic Dismembrator, Fisher Scientific). Samples were sonicated under an amplitude of 3 µm with bursts of 5 s spaced by 15 s cooling in ice/water for 3 to 4 cycles and size-fractioned on 1% agarose gels. Fractions ranging from 1 to 2 kbp were isolated and gel purified by using the Qiagen kit according to the instructions of the manufacturer (Qiagen) and eluted in 50 µl of Tris 1 mM, pH 8.5.

Repair of Fragmented DNA Ends:

The ends of the sonicated DNA fragments were repaired with a combination of T4 DNA polymerase and Klenov as follows. Reactions were performed in a final volume of 100 µl containing DNA, 10 mM Tris-HCl pH 8.0, 50 mM NaCl, 10 mM $MgCl_2$, 1 mM DTT, 5 µg BSA, 100 µM of each dNTP and 15 units of T4 DNA polymerase (New England Biolabs) for 20 min at 12° C. followed by addition of 12.5 units of Klenow large fragment (New England Biolabs) for 15 min at room temperature. The reaction was stopped by two phenol/chloroform extractions and the DNA was ethanol precipitated and resuspended in 20 µl of $H_2O$.

Cloning Into pKSII and Transformation:

Blunt-ended DNA fragments were cloned by ligation directly into HinII (New England Biolabs) and calf intestinal phosphatase (New England Biolabs)-treated pKSII vector (Stratagene). A typical reaction contained 100 ng of vector, 2 to 5 µl of repaired sonicated phage DNA in a final volume of 20 µl containing, 800 units of T4 DNA ligase (New England Biolabs) for overnight at 16 ° C. Transformation and selection of positive clones was performed in the host strain DH10 β of *E. coli* using ampicillin as a selective antibiotic as described in Sambrook et al. (supra)

Preparation of Sequencing Templates:

Recombinant clones were picked from agar plates into 96-well plates. The presence of foreign insert was confirmed by PCR analysis using T3 and T7 primers. PCR amplification of foreign insert was performed in a 15-µl reaction volume containing 10 mM Tris (pH 8.3), 50 mM KCl, 1.5 mM $MgCl_2$, 0.02% gelatin, 1 µM primer, 187.5 µM each dNTP, and 0.75 units Taq polymerase (BRL). The thermocycling parameters were as follows: 2 min initial denaturation at 94° C. for 2 min, followed by 20 cycles of 30 sec denaturation at 94° C., 30 sec annealing at 58° C., and 2 min extension at 72° C., followed by a single extension step at 72° C. for 10 min. Clones with insert sizes of 1 to 2 kbp were selected and miniprep DNA of the selected clones were prepared using QIAprep spin miniprep kit (Qiagen).

Example 3

DNA Sequencing

DNA sequencing:

The ends of each recombinant clone were sequenced on an ABI 377-36 automated sequencer with two types of chemistry: ABI prism bigdye primer or ABI prism bigdye terminator cycle sequencing ready reaction kit (Applied Biosystems). To ensure co-linearity of the sequence data and the genome, all regions of phage genome were sequenced at least once from both directions on two separate clones. In areas that this criteria was not met, a sequencing primer was selected and phage DNA was used directly as sequencing template employing ABI prism bigdye terminator cycle sequencing ready reaction kit.

Sequence Contig Assembly:

Sequence contigs were assembled using Sequencher 3.1 software (GeneCodes). To close contig gaps, sequencing primers were selected near the edge of the contigs. Phage DNA was used directly as sequencing template employing ABI prism bigdye terminator cycle sequencing ready reaction kit.

The sequence obtained for phage 77 is shown in Table 2. The sequences for phage 3A and 96 were obtained by similar sequencing methods; the sequences of those phage genomes are shown in Tables 7 & 9 respectively.

Example 4

Sequence Analysis

Sequence Analysis:

An implementation of the publicly available program SEQUIN, available for download at ftp://negi.nlm.nih.gov/sequin/, was used on phage genome sequence to identify all putative ORFs larger than 33 codons. A listing of such ORFs for S. aureus phage 77 is shown in Table 3, with predicted amino acid sequences for selected ORFs shown in Table 4. Listings of ORFs for phage 3A and 96 are provided in Tables 8 and 10 respectively. A variety of other ORF identification could be used as alternatives and are known to those skilled in the art. Sequence homology searches for each ORF are then carried out using a standard implementation of blast programs. Downloaded public databases used for sequence analysis include:

non-redundant GenBank (ftp://ncbi.nlm.nih.gov/blast/db/nr.Z),

Swissprot (ftp://ncbi.nlm.nih.gov/blast/db/swissprot.Z);

vector (ftp://ncbi.nlm.nih.gov/blast/db/vector.Z);

pdbaa databases (ftp://ncbi.nlm.nih.gov/blast/db/pdbaa.Z);

*staphylococcus aureus* NCTC 8325 (ftp://ftp.genome.ou.edu/pub/staph/staph-1k.fa);

*streptococcus pyogenes* (ftp://ftp.genome.ou.edu/pub/strep/strep-1k.fa);

*streptococcus pneumoniae* (ftp://ftp.tigr.org/pub/data/s_pneumoniae/gsp.contigs.112197.Z);

*mycobacterium tuberculosis* CSU#9 (ftp://ftp.tigr.org/pub/data/m_tuberculosis/TB_091097.Z); and

*pseudomonas aeruginosa* (htp://www.genome.washington.edu/pseudo/data.html).

Exemplary results of homology searches are shown in Table 5 for bacteriophage 77.

Example 5

Identification of Cecronin Signature Motif in *Staphylococcus aureus* Bacteriophage 3A ORF The genome for *S. aureus* bacteriophage 3A was determined and the sequence was analyzed essentially as described for bacteriophage 77 in the examples above. Upon blast analysis of the identified open reading frames of phage 3A, the presence of an amino acid sequence corresponding to a cecropin signature motif was observed. This motif (WDGHKTLEK) is located at position aa 481–489. Cecropins were originally identified in proteins from the cecropia moth and are recognized as potent antibacterial proteins that constitute an important part of the cell-free immunity of insects. Cecropins are small proteins (31–39 amino acid residues) that are active against both Gram-positive and Gram-negative bacteria by disrupting the bacterial membranes. Although the mechanisms by which the cecropons cause cell death are not fully understood, it is generally thought to involve channel formation and membrane destabilization.

The identification of a motif corresponding to a known inhibitor suggests that the product of ORF002 is also an inhibitory compound. Such inhibitory activity can be confirmed as described herein or by other methods known in the art. Confirmation of the inhibitory activity would indicate that the ORF product could serve as the basis for construction of mimetic compounds and other inhibitors directed to the target of the ORF002 product.

Boman & Hultmnark, 1987, *Ann. Rev. Microbiol.* 41:103–126.

Boman, 1991, *Cell* 65:205–207.

Boman et al., 1991, *Eur. J. Bioichem.* 201:23–31.

Wang et al., *J. Biol. Chem.* 273:27438–27448.

Example 6

Bacteriophage 77 ORF Expression

Bacteriophage ORFs are prepared and expressed as generally described in the Detailed Description above, utilizing a shuttle expression vector with a locus for insertion of a phage ORF subject to inducible expression in an appropriate host bacterium.

Preparation of Shuttle Expression Vector:

The shuttle vector pT0021, in which the firefly luciferase (lucFF) expression is controlled by the ars promoter/operator from a *S. aureus* plasmid (Tauriainen, S., Karp, M., Chang, W and Virta, M. (1997). Recombinant luminescent bacteria for measuring bioavailable arsenite and antimonite. *Appl. Environ. Microbiol.* 63:4456–4461), was modified as below to suit our specific application. Two oligonucleotides corresponding to the influenza HA tag were synthesized. The sense strand HA tag sequence (with BamHI, SalI and HindIII cloning sites) is: 5'-gatcccggtcgaccaagcttTACCCATACGACGTCCCAGAC TACGCCAGCTGA-3'; the antisense strand HA tag sequence (with HindIII cloning site) is: 5'-agctTCAGCTGGCGTAGTCTGGGACGTCGTATGGG TAaagcttggtcgaccgg-3'. The two HA tag oligonucleotides were annealed following a standard protocol (supra) and ligated to pT0021 vector that was digested with BamHI and HindIII (the lucFF gene was released from the vector and replaced by the HA tag). This modified shuttle vector containing the ars promoter, arsR gene and HA tag was named pTHA vector.

Cloning of ORFs with a Shine-Dalgarno Sequence:

ORFs with a Shine-Dalgarno sequence were selected for functional analysis of bacterial killing. Each ORF, from initiation codon to last codon (excluding the stop codon), was PCR amplified from phage genomic DNA. For PCR amplification of ORFs, each sense strand primer starts at the initiation codon and is preceded by a BamHI restriction site and each antisense strand starts at the last codon (excluding the stop codon) and is preceded by a SalI restriction site. PCR product of each ORF was gel purified and digested with BamHI and SalI overnight. The digested PCR product was then gel purified, ligated into BamHI and SalI digested pTHA vector, and used to transform bacterial strain DH10β. As a result, HA tag is inframe with the ORF and a fusion protein with ORF begins at N-terminal and HA tag ends at the C-terminal is produced. Recombinant ORF clones were picked and their sizes were confirmed by PCR analysis using primers flanking the cloning site. The sequence fidelity of cloned ORFs was verified by DNA sequencing using the same primers as used for PCR. In the cases that the verification of ORFs could not be achieved by one path of sequencing using primers flanking the cloning site, internal primers were selected and used for sequencing.

Transformation of *Staphylococcus aureus* with Expression Constructs

*Staphylococcus aureus* strain RN4220 (Kreiswirth et al., 1983, *Nature* 305:709–712) was used as a recipient for the expression of recombinant plasmids. Electroporation was performed essentially as previously described (Schenk and Laddaga, 1992, *FEMS Microbiology Letters* 94:133–138). Selection of recombinant clones was performed on Luria-Broth agar (LB-agar) plates containing 30 µg/ml of Kanamycin.

Chemical Inducers

Sodium arsenite ($NaAsO_2$), sodium arsenate ($Na_2HAsO_4$), and antimony potassium tartrate (K(SbO) $C_4H_4O_6$) were purchased from Sigma (Sigma-Aldrich Canada LTD, Oakville) and were used as heavy metals to induce gene expression from the ars promoter/operator.

Induction of Gene Expression from the Ars Operon

Cells containing different recombinant plasmids were grown overnight at 37° C. in LB medium supplemented with 30 µg/ml of Kanamycin. The cells were then diluted to the mid log phase ($OD_{540}$ approx. 0.2) with fresh LB media containing Kanamycin and transferred to 96-well microtitration plates (100 µl/well). Inducers were then added at different final concentrations (ranging from 2.5 to 10 µM) and the culture was incubated for an additional 2 h at 37° C. Control cultures without inducers were cultured in separate wells. The effect of expression of the phage 77 ORFs on bacterial cell growth was then monitored by measuring the OD540 and comparing the rate of growth of the culture containing inducer to the rate of growth of the culture not containing inducer. As positive controls for growth inhibition, the kilA gene of phage lambda (Reisinger et al., 1993, *Virology* 193:1033–1036), and the holin/lsinI genes of the *Staphylococcus aureus* phage Twort (Loessner et al., 1998, *FEMS Microbiology Letters* 162:265–274) were subcloned into the ars inducible vector and included in separate wells of the microtitration plate.

Expression of ORFs from a large variety of other phage can be accomplished using the above vector, or other vector adapted for an appropriate bacterium and preferably for inducible expression of the insert ORF or ORFs.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using a variety of different bacteria, bacteriophage, and sequencing methods within the general descriptions provided.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C. Thus, for example, for the bacteria and phage specified herein, the embodiments expressly include any subset or subgroup of those bacteria and/or phage. While each such subset or subgroup could be listed separately, for the sake of brevity, such a listing is replaced by the present description.

Thus, additional embodiments are within the scope of the invention and within the following claims.

TABLE 1

Phages against human and animal pathogenic bacteria

| Pathogen name | Phage name | Catalog # | Origin/ reference |
|---|---|---|---|
| Acinetobacter calcoaceticus | A3/2<br>A10/45<br>A36<br>B9GP<br>B9PP<br>BS46<br>E13<br>E14<br>531 | | Felix d'Herelle Reference Centre, Quebec, Quebec |
| | Ap3 | | J. Bacteriol 1984. 157: 179–183 |
| | P78 | | J. Gen. Microbiol 1986. 132: 2633–2636 |
| Acinetobacter haemolyticus | 2213/73 | | Felix d'Herelle Reference Centre, Quebec, Quebec |
| Acinetobacter johnsonii | 133 | | Felix d'Herelle Reference Centre, Quebec, Quebec |
| Acinetobacter sp. | BP1<br>G4,<br>HP2,<br>HP3 &<br>HP4 | | J. Virol. 1968. 2: 716–722<br>Can. J. Microbiol.<br>1966. 12: 1023–1030 &<br>J. Virol. 1974. 13: 46–52 &<br>Arch. Virol. 1994.<br>135: 345–354 |
| | A1, A4,<br>A9 &<br>196 | | Arch. Virol. 1994.<br>135: 345–354 |
| | HP1 | | Can. J. Microbio. 1966.<br>12: 1023–1030 |
| | A19,,<br>A23, | | J. Microsc (Paris) 1973. 16: 215–224 &<br>CR. Hebdo Seances Acad. Sci.<br>Ser D. Sci |
| | A29,<br>A31, | | D. Sci Natur(Paris)278: 1907–1909 &<br>Arch. Virol. 1994. 135: 345–354 & |

TABLE 1-continued

Phages against human and animal pathogenic bacteria

| Pathogen name | Phage name | Catalog # | Origin/reference |
|---|---|---|---|
| | A33, A34, A3759 & 2845 | | Rev. Can. Biol. 1970. 29: 317–320 |
| Actinobacillus actinomycetecomitans | φAa φAa17 Aaφ23 Aaφ247 | | FEMS Microbiol Lett 1994. 119: 329–337 Infec. Immmun. 1982. 35: 343–349 Mol. Gen. Genet 1998. 258: 323–325 Oral Micriol. Immunol 1997. 12: 40–46 |
| Actinomyces viscosus | Av-1 AV-2, AV-3 & 1281 BF307 & CT7 phi225 | 43146-B1 | The American Type Culture Collection Infect. Immun. 1985. 48: 228–233 Infect. Immun. 1988. 56: 54–59 Plasmid 1997. 37 : 141–153 |
| Aeromonas hydrophila | PM2** & PM3 Aeh1 Aeh2 PM4 PM5 PM6 T7-ah | | FEMS Microbiol. Lett. 1990. 57: 277–282 Felix d'Herelle Reference Centre, Quebec, Quebec |
| Aeromonas salmonicida | 3 25 29 31 32 40R-R$_{2,8}$t 43 51 56 59.1 65 Asp37 55R.1 | | Felix d'Herelle Reference Centre, Quebec, Quebec Can. J. Microbiol. 1983. 29: 1458–1461 |
| Alteromonas espejiana | PM2** | 27025-B1 | The American Type Culture Collection |
| Asticacaulis biprosthecum | B1a | | Felix d'Herelle Reference Centre, Quebec, Quebec |
| Asticcacaulis excentricus | φAc20 φAc21 φAc24 | 15261-B1 15261-B2 15261-B3 | The American Type Culture Collection |
| Azotobacter vinelandii | A12 A14 A21 A31 A41 PAV1 | 12518-B1 12518-B4 12518-B5 12518-B9 12518-B10 13705-B1 | The American Type Culture Collection |
| Azotobacter sp. | A12 | | Virology 1972. 49: 439–452 |
| Bacteroides fragilis | Bf-1 B40-8 HSP40 phiA1 | | Rev. Infect. Dis. 1979. 1: 325–336 FEMS Microbiol. Lett. 1991. 66: 61–67 Appl. Environ. Microbiol. 1989. 55: 2696–2701 Zentralbl.bakteriol. 1972. 222: 57–63 |
| Bdellovibrio bacteriovorus | MAC-1 | | J. Gen. Microbiol. 1987. 133: 3065–3070 |
| Bdellovibrio sp. | VL-1 | | J. Virol. 1973. 12: 1522–1533 |
| Bordetella brochiseptica | 214 | | Zh. Mikrobiol. Epidemiol. Immuno. 1987. 5:9–13 |
| Bordetella parapertussis | L-1 Tohama phiT 134 41405 | | Felix d'Herelle Reference Centre, Quebec, Quebec Mol. Gen. Mikrobiol. Virusol. 1988. 4: 22–25 Zh. Mikrobiol. Epidemiol. Immuno. 1987. 5: 9–13 Zh. Mikrobiol. Epidemiol. Immuno. 1987. 5: 9–13 |
| Brucella abortus | S708 Fi75/13 Tbilisi 10/I 24/II 212/XV 371/ XXLX BK-2, TB & Fi** R/c & R/O | 23448-B1 23448-B2 23448-B3 17385-B1 17385-B2 | Felix d'Herelle Reference Centre, Quebec, Quebec The American Type Culture Collection Zh. Mikrobiol. Epidemiol. Immunobiol. 1983. 2: 48–52 Dev. Biol. Stand. 1984. 56: 55–62 |
| Brucella canis | R/c | | Dev. Biol. Stand. 1984. 56: 55–62 |
| Brucella melitensis | BK-2 | 23456-B1 | The American Type Culture Collection |
| Brucella suis | Wb Fi** & TB | | Zentralbl. Veterinarmed. 1975. 22: 866–867 Zh. Mikrobiol. Epidemiol. Immunobiol. 1983. 2: 48–52 |
| Brucella sp. | Np (Nepean) & Iz Iz-1 R | | Can. J. Vet. Res. 1989. 53: 319–325 Res. Vet. Sci. 1988. 44: 45–49 Zh. Mikrtobiol. Epidemiol. Immunobiol. 1983. 2: 48 |
| Campylobacter coli | 17 18 19 20 | 43133-B1 43134-B1 43135-B1 43136-B1 | The American Type Culture Collection |
| Campylobacter jejuni | 1 2 3 4 5 6 7 8 9 10 11 12 13 14 17 18 19 20 | 35918-B1 35919-B1 35920-B1 35921-B1 35918-B2 35920-B2 35922-B2 35923-B1 35924-B1 35925-B1 35925-B2 35922-B2 35924-B2 35922-B3 43133-B1 43134-B1 43135-B1 43136-B1 | The American Type Culture Collection |
| Campylobacter (Helicobacter) pylori | HP1 | | J. Med. Microbiol. 1993. 38: 245–249 |
| Chlamydia psittaci | Chp1** | | J. Gen. Virol. 1989. 70: 3381–3390 |
| Clostridium acetobutylicum | CAK-1 | | J. Bacteriol. 1993. 175: 3838–3843 |
| Clostridium botulinum | C** & D** C-ST** | | Nucleic Acids Res. 1990. 18: 1291 Bioch. Biophys. res. Commun. 1990. 171. 1304–1311 |

TABLE 1-continued

Phages against human and animal pathogenic bacteria

| Pathogen name | Phage name | Catalog # | Origin/reference |
|---|---|---|---|
| | α1 & α2 | | Microbiol. immonol. 1981. 25: 915–927 |
| | d-16 phi**, d-1', CE β & CE γ | | J. Vet. Med. Sci. 1992. 54: 675–684 |
| Clostridium difficile | 41 & 56 | | J. Clini. Microbiol. 1985. 21: 251–254 |
| Clostridium perfringens | PF1, PF2, PF3 & PF4 | | Rev. Can. Biol. 1977. 36: 205–215 |
| | φ29** & φ59 | | FEMS Microbiol. Lett. 1990. 54: 323–326 |
| Clostridium sporogenes | J | 8074-B11 | The American Type Culture Collection |
| | 59 | 17886-B1 | |
| | 70 | 17886-B3 | |
| | 71 | 17886-B4 | |
| | 72S | 17886-B5 | |
| | 72L | 17886-B6 | |
| Clostridium tetani | A & B | | Rev. Can. Biol. 1978. 37: 43–46 |
| Corynebacterium diphteriae | BF, φ9 & φ 984 | | Vopr. Virusol. 1986. 31: 577–584 |
| Corynebacterium pseudotuberculosis | NN | 12319-B1 | The American Type Culture Collection |
| Corynebacterium sp | DLC 2921/49 | 12052-B1 | The American Type Culture Collection |
| Enterococcus faecalis | 42 | 19948-B1 | The American Type Culture Collection |
| Enterococcus faecium | 113 | 19950-B1 | The American Type Culture Collection |
| | 124 | 19953-b2 | |
| | 133 | 19953-B1 | |
| Escherichia coli | AP211 | 11303-B14 | The American Type Culture Collection |
| | BG3 | 11303-B10 | |
| | C33 | 11303-B21 | |
| | C36 | 8677-B1 | |
| | C204 | 11303-B13 | |
| | E1 | 13706-B4 | |
| | f1** | 15766-B1 | |
| | f2** | 15766-B1 | |
| | FCZ | 1242-B5 | |
| | fd** | 15669-B2 | |
| | fr** | 15767-B1 | |
| | G178 | 11303-B16 | |
| | If1** | 27-65-B1 | |
| | If2 | 25065-B2 | |
| | M13** | 15669-B1 | |
| | MS2** | 15597-B1 | |
| | MU9 | 21816-B1 | |
| | Mu-1 | 23724-B9 | |
| | Ox6 | 15593-B1 | |
| | P1** | 25404-B1 | |
| | P4 | 29746-B1 | |
| | sid$_i$** | | |
| | Q-β** | 23631-B1 | |
| | R17** | 25868-B1 | |
| | Z1K/1 | 25298-B1 | |
| | ZJ/2 | 25298-B2 | |
| | rA105 | 11303-B37 | |
| | rEDa41 | 11303-B24 | |
| | rED220 | 11303-B26 | |
| | rEDb44 | 11303-B27 | |
| | rEDb45 | 11303-B28 | |
| | rEDb50 | 11303-B29 | |
| | rH23 | 11303-B30 | |
| | rH88 | 11303-B33 | |
| | r33 | 11303-B31 | |
| | r71 | 11303-B25 | |
| | r187 | 11303-B35 | |
| | r196 | 11303-B34 | |
| | r638 | 11303-B36 | |
| | r1589 | 11303-B32 | |
| | S13** | 13706-B5 | |
| | T$_1$** | 11303-B1 | |
| | T$_2$** | 11303-B2 | |
| | T$_3$** | 11303-B3 | |
| | T$_4$** | 11303-B4 | |
| | T$_4$am-A453 | 35060-B1 | |
| | T$_4$am-B17 | 35060-B2 | |
| | T$_4$am-N120 | 35060-B3 | |
| | T5** | 11303-B5 | |
| | T6** | 11303-B6 | |
| | T7** | 11303-B7 | |
| | T$_7$M | 11303-B38 | |
| | 5 | 12141-B1 | |
| | 6A | 12144-B3 | |
| | 250 | 11303-B20 | |
| | 547 | 11303-B17 | |
| | UV1 | 11303-B15 | |
| | UV47 | 11303-B11 | |
| | UV375 | 11303-B18 | |
| | α3** | 13706-B2 | |
| | λ ** | 23724-B2 | |
| | λ C-17 | 23724-B1 | |
| | λ sus P-3 | 23724-B3 | |
| | λ sus R-5 | 23724-B4 | |
| | λ sus J-6 | 23724-B5 | |
| | λ sus O-8 | 23724-B6 | |
| | λ sus A-11 | 23724-B7 | |
| | λ ind | 23724-B8 | |
| | φ92 | 35860-B1 | |
| | φR | 13706-B3 | |
| | φV-1 | 15597-B2 | |
| | φX- | 13706-B1 | |

TABLE 1-continued

Phages against human and animal pathogenic bacteria

| Pathogen name | Phage name | Catalog # | Origin/reference |
|---|---|---|---|
| | 174** | | |
| | φXcs-70am-3 | 49696-B1 | |
| | G4** & φK** | | Biochim. Biophysica Acta. 1992. 1130: 277–288 |
| | BF23** | | J. Bacteriol. 1977. 129: 265–275 |
| | Mu1 | | J. Ultrastruct. Res. 1966. 14: 441–448 |
| | Hp17 | | J. Mol. Biol. 1991. 218: 705–721 |
| | K3** & Ox2** | | FEBS Lett. 1987. 215: 145–150 |
| | Rb-18**, Rb51 & Rb69** | | J. Bacteriol. 1990. 172: 180–186 |
| | H1**, H3, H8, K9, K18 & Ox1 | | Mol. Gen. Genet. 1990. 221: 491–494 |
| | M1**, TuIa** & TuIb** | | J. Mol. Biol. 1987. 196: 165–174 |
| | K10 | | J. Bacteriol. 1979. 140: 680–686 |
| | Qsr' | | J. Bacteriol. 1985. 162: 256–262 |
| | B278 | | J. Gen. Microbiol. 1988. 134: 1333–1338 |
| | phi 80** | | FEMS Microbiol. Lett. 1994. 119: 71–76 |
| | phi m173 | | Genetika 1985. 21: 673–675 |
| | tf-1 | | J. Gen. Microbiol. 1987. 133: 953–960 |
| | P4 & phiR73 | | Mol. Microbiol. 1995. 18: 201–208 |
| | I$_2$-2 | | J. Gen. Microbiol. 1982. 128: 2797–2804 |
| | PRD1 | | Virology 1990. 177: 445–451 |
| | K3hx | | Mol. Gen. Genet. 1987. 206: 110–115 |
| | 933-J** & 933-W** | | Infect. Immunity. 1986. 53: 135–140 |
| | H19-B** | | J. Bacteriol. 1987. 169: 4308–4312 |
| | Tcp-111 | | Zentralbnl. Bakteriol. Mikrobiol. Hyg. 1988. 270: 41–51 |
| | N4** | | Vet. Microbiol. 1992. 30: 203–212 |
| | Phi 80 trp | | Ann. Inst. Pasteur. 1971. 120: 121–125 |
| | Obeta 1 | | J. Bacteriol. 1978. 133: 172–177 |
| | P1CM | | J. Gen. Microbiol. 1978. 107: 73–83 |
| | PA 2** | | J. Bacteriol. 1990. 172: 1660–1662 |
| | 186** | | Mol. Gen. Genet. 1982. 187: 87–95 |
| | 186.-IX.B | | Mol. Microbiol. 1992. 6: 2629–2642 |
| | 21** | | Virology 1983. 129: 484–489 |
| | P4** | | Microbiol Rev. 1993. 57: 683–702 |
| | 82** | | J. Biol. Chem. 1987. 262: 11721–11725 |
| | PSP3 | | J. Bacteriol. 1996. 178: 5668–5675 |
| | HK-022** | | Nucleic Acids Res. 1994. 22: 354–356 |
| | D108** | | Nucleic Acids Res. 1986. 14: 3813–3825 |
| | Rb49 | | J. Mol. Biol. 1997. 267: 237–249 |
| | Ike** | | J. Mol. Biol. 1985. 181: 27–39 |
| | P22dis | | Mol. Gen. Genet. 1978. 166: 233–243 |
| | N15** | | J. Bacteriol. 1996. 178: 1484–1486 |
| | If1** | | Proc. R. Soc. Lond. B. Biol. Sci. 1991. 245: 23–30 |
| | Stx-Phi-I & Stx2-Phi-II | | Infect. Immun. 1998. 66: 4100–4107 |
| | 18 | | Virology 1987. 156: 122–126 |
| | X | | J. Gen. Microbiol. 1981. 126: 389–396 |
| | AC3 | | Mol. Microbiol. 1991. 5: 715–725 |
| | BW-1 | | Felix d'Herelle Reference Centre, Quebec, Quebec |
| | C-1 | | |
| | E920g | | |
| | Esc-7-11 | | |
| | H19J | | |
| | Haiti | | |
| | HK243 | | |
| | Iα | | |
| | K20 | | |
| | K30 | | |
| | KL$_3$ | | |
| | M | | |
| | Mu** | | |
| | O103 | | |
| | O157:-H7 | | |
| | P1D | | |
| | pt1 | | |
| | PilHα | | |
| | PR64FS | | |
| | PR772 | | |
| | SS4 | | |
| | β4Q | | |
| | λvir** | | |
| | Ω8 | | |
| | 09-1 | | |
| | 92 | | |
| Haemophilus | HP1** | | Nucleic Acids Res. 1996. 24: 2360–2368 |
| Halobacterium cutirubrum | S2** S45 | | Gene 1997. 196: 139–144 Felix d'Herelle Reference Centre, Quebec, Quebec |
| Halobacterium halobium | φH & φN Hh1 & Hh3 | | Felix d'Herelle Reference Centre, Quebec, Quebec Can. J. Microbiol. 1982. 28: 916–921 |
| Halobacterium salinarium | Phi H | | Biol. Chem. Hoppe Seyler 1994. 375: 747–757 |
| Klebsiella oxytoca | tf-1 | | J. Gen. Microbiol. 1987. 133: 953–960 |
| Klebsiella pneumoniae | 60 92 K19Q | 23356-B1 23357-B1 | The American Type Culture Collection Felix d'Herelle Reference Centre, Quebec, Quebec Can. J. Microbiol. 1991. 37: 270–275 |
| | FC3-1 & FC3-9 FC3-10 | | FEMS Microbiol. Lett. 1991. 67: 291–297 |
| Klebsiella sp. | K11** | | Mol. Gen. Genet. 1990. 221: 283–286 |
| Leptospira sp. | LE1, LE3 & LE4 | | Res. Microbiol. 1990. 141: 1131–1138 |
| Listeria monocytogenes | 243 197, 1313 & 9425 | 23074-B1 | The American Type Culture Collection Appl. Environ. Microbiol. 1997. 63: 3374–3377 |
| | H387 & H387-A 5775, 6223 & 12682 2389, 2671, 4211 & 2685 | | Appl. Environ. Microbiol. 1993. 59: 2914–2917 APMIS. 1993. 101: 160–167 Intervirology 1994. 37: 31–35 & Zentralbl. Bakterial. Mikrobiol. Hyg. 1986. 261: 12–28 |
| | 4b, 4ab, 4g & 3c | | Ann. Microbiol (Paris) 1977. 128: 185–198 |

TABLE 1-continued

Phages against human and animal pathogenic bacteria

| Pathogen name | Phage name | Catalog # | Origin/reference |
|---|---|---|---|
| | A118, A500 & A511** | | Mol. Microbiol. 1995. 16: 1231–1241-992 |
| | 1, 3, 4, 5, 6, 7, 8, 9, 10, 11, 14, 15, 16 17, 19 & 20 | | Ann. Microbiol. (Paris) 1979. 130B: 179–189 |
| | ½a, ½b, 3c, 4ab, 6a & 6b | | Clin. Invest. Med. 1984. 7: 229–232 |
| | φLMU-P35 2685 | | Felix d'Herelle Reference Centre, Quebec, Quebec |
| Listeria innocua | 4211 | | Felix d'Herelle Reference Centre, Quebec, Quebec |
| Micrococcus luteus | N1 N3 N4 N8 | 4698-B1 4698-B4 4698-2 4698-B3 | The American Type Culture Collection |
| Micro coccus luteus | N17 | | Can. J. Microbiol. 1979. 25: 1027–1035 |
| Myco-bacterium smegmatis | BK-3 Bo1 Bo 6 Bo 6II Bo 6III Mc-2 Mc-4 NN Phagus lacti-cola R1 33D BK1 Clark DNA III Legendre Leo Roy Sedge L5 D29 L1 I3 TM4 29M, 31M, 122, 154, 37, 29D, 46, 139, 110, 141, 74D, AG1 & DS6A | 27203-B1 27204-B1 27205-B1 27205-B2 27205-B3 607-B6 607-B7 11727-B1 11759-B1 607-B1 HER 317 HER 330 HER 333 HER 335 HER 334 HER 331 HER 316 HER 332 | The American Type Culture Collection Felix d'Herelle Reference Centre, Quebec, Quebec Mol. Microbiol. 1993. 7: 395–405 J. Mol. Biol. 1998. 279: 143–164 Proc. Natl. Acad. Sci USA. 1988. 84: 2833–2837 Mol. Biol. Rep. 1981. 30: 11–15 Proc. Natl. Acad. Sci. USA 1997. 94: 10961–10966 Arch. Virol. 1993. 133: 39–49 & Am. Rev. Respir. Dis. 1975. 112: 17–22 |
| Myco-bacterium fartuitum | NN Bo 4 Bo 7 | 23052-B1 27207-B1 27207-B2 | The American Type Culture Collection |
| Myco-baterium leprae | BK1, Clark, Sedge, Baits, Watson & D29 | | Ann. Microbiol. (Paris) 1982. 133: 93–97 |
| Myco-bacterium tuber-culosis | LG DS6A D-34 110, 139 & 33D AG1, GS4E, BG1, PH & BK1 | 25618-B1 25618-B2 4243-B1 | The American Type Culture Collection Arch. Virol. 1993. 133: 39–49

The Biology of Mycobacteria. Academic Press, Toronto 1982 (Ratledge & Stanford) 1982. 309–351 |
| Myco-bacterium sp | Phagus pelle-grini NN B1 TM4, ph60, ph72, PhA-E39, phA-E40 & Bxb1 C2 18 & I15 63 phlei & buty-ricum MyF3P-59a Bo2a D4, D28 & D32 HC | 11760-B1 11761-B1 23239-B1 | The American Type Collection Culture Microbiology 1995. 141: 1173–1181

Experentia 1969. 25: 1112–1113 J. Gen. Virol. 1987. 68: 949–956 Gruzlica 1968. 36: 617–622 J. Gen. Virol. 1975. 29: 235–238

Z. Allg. Mikrobiol. 1968. 8:29–37 J. Gen. Virol. 1973. 20: 75–87 J. Exptl. Med. 1966. 123: 327–340

J. Bacteriol. 1963. 86: 608–609 |
| Myco-bacterium vaccae | B5 | 15483-B1 | The American Type Culture Collection |
| Myco-bacterium phlei | NN NN Bo 2 Bo 2h Bo 3 | 11728-B1 11758-B1 27086-B2 27086-B1 27206 B1 | The American Type Culture Collection |
| Myco-plasma arthritidis | MA-V1** | | Infect. Immunity. 1995. 63: 4016–4023 |
| Myco-plasma hyorhinis | Hr-1 | | Arch. Virol. 1983. 77: 81–85 |
| Myco-plasma pneu-moniae | Br-1 | | Arch. Virol. 1983. 75: 1–15 |
| Myco-plasma pulmonis | P1 | | Plasmid 1995. 33: 41–49 |
| Myco-plasma sp. | MV-01 L1 L2** L3 (MV-L3) MAV-1 | | J. Gen. Microbiol. 1985: 131: 3117–3126 J. Virol. 1986. 59: 584–590 Gene 1994. 141: 1–8 Microbios 1990. 64: 111–125

Infection & Immunity 1995. 63: 4016–4023 |

TABLE 1-continued

Phages against human and animal pathogenic bacteria

| Pathogen name | Phage name | Catalog # | Origin/reference |
|---|---|---|---|
| | 20-P | | Med. Biol. 1982. 60: 116–120 |
| | MV-L2 & MV-1g-pS2-L172 | | Arch. Virol. 1979. 61: 289–296 |
| | MV-1g-L 172 | | Acta. Virol. 1978. 22: 443–450 |
| | BN1 | | J. Gen. Virol. 1979. 42: 315–322 |
| | MVL51 | | Virology 1973. 55: 118–126 |
| | MVL1, MVL52 & MVG51 | | Science 1971. 173: 725–727 |
| Neisseria perflava | NP-1 | | J. Clin. Microbiol. 1976. 4: 87–91 |
| Nocardia erythrypolis | φC | | J. Gen. Virol. 1974. 23: 247–254 |
| | φEC | | J. Bacteriol. 1976. 126: 1104–1107 |
| Pasteurella multocida | B225 | | Arch. Exp. Veteriarmed. 1981. 35: 433–436 |
| | B939a | | Am. J. Vet. Res. 1978. 39: 1565–1566 |
| | Nos. 115, 32, 967 & 1075 | | Vet. Med. Nauki. 1977. 14: 33–36 |
| Propionibacterium acnes | NN | 29399-B1 | The American Type Collection Culture |
| Pseudomonas aeruginosa | 1 | 12175-B | The American Type Culture Collection |
| | 2 | 12175-B2 | |
| | 2A | 12175-B3 | |
| | 2B | 12175-B4 | |
| | 11 | 14205-B1 | |
| | 16 | 14206-B1 | |
| | 24 | 14207-B1 | |
| | 27 | 14208-B1 | |
| | 44 | 14209-B1 | |
| | 73 | 14210-B1 | |
| | 95 | 14211-B1 | |
| | 109 | 14212-B1 | |
| | 113 | 14213-B1 | |
| | 249 | 14214-B1 | |
| | B3 | 15692-B1 | |
| | Hoff 2 | 14203-B1 | |
| | Hoff 3 | 14204-B1 | |
| | Pa | 12055-B1 | |
| | Pb | 12055-B2 | |
| | PB-1 | 15692-B3 | |
| | Pc | 12055-B3 | |
| | Pf | 25102-B1 | |
| | PP7** | 15692-B2 | |
| | SD1-M, φw14, 7 & 31 | | Felix d'Herelle Reference Centre, Quebec, Quebec |
| | Pf3** | | J. Virol. 1983. 47: 221–223 |
| | φ-MC | | Can. J. Microbiol. 1969. 15: 1179–1186 |
| | Pf1** | | J. Mol. Biol. 1991. 218: 349–364 |
| | PR4** | | J. Gen. Virol. 1979. 43: 583–592 |
| | A7 | | J. Bacteriol. 1992. 174: 2407–2411 |
| | KF1 | | J. Biochem. 1983. 93: 61–71 |
| | φC-TX** | | Mol. Microbiol. 1993. 4: 1703–1709 |
| | f2** | | J. Virol. 1977. 24: 135–141 |
| | φKZ, 21, φNZ, PM-N17, PTB80, 68, PB-1, E79, 16, 109, 352, 1214, F8, 71, 337, M4, φC17, SL2, B17, Li-24, φmn-P78, PS17**, φ1, 73, M6, Li-2, 7, φmn-F82, PTB2, PTB20, PTB42, φKF77, 31, PTB21, 119x, φPLS-27, B3, 258, Hw12, PM57, PM62, PM105, 148, PM681, 198, 218, 222, 242, 246, PC131, φC11, SL5, D-3112**, Jb19, F7, PM69, PM13, PM61, PM113, φ240, 249 & 269 297, 309, 318, 11, PH51, 342, 351, PH93, 357-1, 13, 14, PC11-1, 267, D 3**, PC351, KF, PM63, PH132, 1°, | | Arch. Virol. 1993. 131: 141–151 |

TABLE 1-continued

Phages against human and animal pathogenic bacteria

| Pathogen name | Phage name | Catalog # | Origin/reference |
|---|---|---|---|
| | φX, 400-1 45, SM, SL3, SL1, φ11, F10, φC15, 160, 336, 350, φC5, φC11-1 φC13, 295, , SL4, G101, F116, B26, φBS, 53, 145, 284 & 308 | | |
| Pseudomonas cepacia | 42 & 83-24 | | Felix d'Herelle Reference Centre, Quebec, Quebec |
| Pseudomonas fragi | ps1 wy | 27362-B1 27363 B1 | The American Type Culture Collection |
| Pseudomonas phaseolicola | φ6 | | Felix d'Herelle Reference Centre, Quebec, Quebec |
| Pseudomonas putida | gh-1 | 12633-B1 | The American Type Culture Collection |
| Pseudomonas syringae | NN φ-6 | 40492-B1 21781-B1 | The American Type Culture Collection |
| Pseudomonas sp. | PPs-G3 | 49780-B1 | The American Type Culture Collection |
| Salmonella bareilly | Sab 2 | | Felix d'Herelle Reference Centre, Quebec, Quebec |
| Salmonella enteritidis | 1, 2, 3 & 6 2a, 3a, 4a, 5a, 6a, 7a, 8a, 9a, 15, 19, 20 & 21** | | Epidemiol. Infect. 1995. 114: 227–236 Vet. Med. Nauki. 1975. 12: 55–60 |
| Salmonella newington | Epsilon 34 | | J. Struct. Biol. 1995. 115: 283–289 |
| Salmonella newport | 7–11 16–19 2.5a | 27869-B1 27869-B2 | The American Type Culture Collection Felix d'Herelle Reference Centre, Quebec, Quebec |
| Salmonella paratyphi | 31 Paratyphoid A Jersey | 19940-B1 12176-B1 | The American Type Culture Collection Felix d'Herelle Reference Centre, Quebec, Quebec |
| Salmonella senftenberg | SasL1, SaL2, Sal3, SaL4, SaL5, SasL6 | | Indian J. Med. Res. 1997. 105: 47–52 |
| Salmonella typhimurium | P22** SL-1 MB-78** SE1 LT2 ES18** L** P1CM clr-100 F22 Fels 1 Fels 2 Px P1kc A3 & A4 HT IRA Mud1 P22 (cir4-1, cir5-1, & cir6-1) BF23** Kb1 P221dis PRD-1** I₂-2 tf-1 X** | 19585-B1 40282 | The American Type Cuture Collection J. Virol. 1982. 41: 1038–1043 J. Gen. Microbiol. 1986. 132: 1035–1041 Virology 1971. 45: 835–836 Virology 1970. 42: 621–632 J. Virol. 1985. 56: 1034–1036 Mol. Gen. Genet. 1975. 138: 113–126 Genet. Res. 1986. 48: 139–143 J. Gen. Virol. 1978. 38: 263–272 Genet. Res. 1986. 48: 139–143 Mol. Gen. Genet. 1970. 108: 184–202 Virology 1974. 60: 503–514 J. Bacteriol. 1987. 169: 1003–1009 Genet. Res. 1976. 27: 315–322 J. Basic Microbiol. 1990.30: 707–716 Mol. Gen. Genet. 1986. 202: 327–330 Mol. Gen. Genet. 1984. 198: 105–109 Mol. Gen. Genet. 1976. 147: 195–202 J. Bacteriol. 1974. 117: 907–908 J. Gen. Virol. 1978. 41: 367–376 Virology 1990. 177: 445–451 J. Gen. Microbio. 1982. 128: 2797–2804 J. Gen. Microbiol. 1987. 133: 953–960 J. Gen. Microbiol. 1981. 126: 389–396 |
| Salmonella typhosa/ typhi | 8 23 25 46 53 163 175 ViI ViVI O1 ViII j2 | 19937-B1 19938-B1 19939-B1 19942-B1 19943-B1 19946-B1 19947-B1 27870-B1 27870-B2 | The American Type Culture Collection Felix d'Herelle Reference Centre, Quebec, Quebec Chung Hua Liu Hsing Ping H.T.C. 1992. 13: 288 J. Gen. Microbiol. 1983. 129: 3395–33400 |
| Salmonella sp. | P3 P4** P9a P9c P10 102 Chi(χ) R34 MG40 P14 PSP3 Ike** P27 & 9NA | 25957-B1 25957-B2 25957-B3 25957-B4 25957-B5 19945-B1 9842-B1 97541 | The American Type Culture Collection Virology 1968. 34: 521–530 Microb. Pathog. 1990. 8:393–402 Virology 1992. 188: 414 Zentralb1. Bakteriol. 1976. 234: 294–304 J. Virol. 1986. 12: 921–931 |
| Sphaerotilus natans | SN1 | | Appl. Environ. Microbiol. 1979. 37: 1025–1030 |
| Shigella dysenteriae | 2 P2 φ-80 | 23351-B1 11456b 11456a-B1 | The American Type Culture Collection |
| Shigella flexeneri | D20 SfII** SfV** | 12661-B1 | The American Type Culture Collection Mol. Microbiol. 1997. 26: 939–950 Gene 1997. 22: 217–227 |

TABLE 1-continued

Phages against human and animal pathogenic bacteria

| Pathogen name | Phage name | Catalog # | Origin/reference |
|---|---|---|---|
| | Sf6** | | Mol. Microbiol. 1995. 18: 201–208 |
| | SfX | | Gene 1993. 129: 99–101 |
| Shigella sonnei | C16** | | |
| | Ufa | | Mol. .Biol (Mosk) 1977. 11: 323–331 |
| Shigella sp | 37 | 23354-B1 | The American Type Culture Collection |
| Spiroplasma citri | SpV1 | | Plasmid 1993. 29: 193–205 |
| Spiroplasma sp. | SpV1-R8A2B | | Nucleic Acids Res. 1990. 18: 1293 |
| | SpV3 | | Isr. J. Med. Sci. 1987. 23: 429–433 |
| | Sp V4 | | J. Bacteriol. 1987. 169: 4950–4961 |
| Staphylococcus albus | 1 to 18, 20, 21 to 25, 27, 29 to 36 & 39 | | Staphylococci & Staphylococcal Infections. 1997. Vol1: 503–508 (Karger, Basel) |
| Staphylococcus aureus | 3A | 27702-B1 | The American Type Culture Collection |
| | 3C | 27703-B1 | |
| | 6 | 27704-B1 | |
| | 15 | 23360-B1 | |
| | 17 | 23361-B1 | |
| | 29 | 27705-B1 | |
| | 42D** | 27712-B1 | |
| | 42E | 27690-B1 | |
| | 47 | 27691-B1 | |
| | 52 | 27692-B1 | |
| | 52A | 27693-B1 | |
| | 53 | 27694-B1 | |
| | 54 | 27695-B1 | |
| | 55 | 27696-B1 | |
| | 71 | 27697-B1 | |
| | 75 | 27698-B1 | |
| | 77 | 27699-B1 | |
| | 79 | 27693-B2 | |
| | 80 | 27700-B1 | |
| | 81 | 27701-B1 | |
| | 83A | 27706-B1 | |
| | 84 | 27707-B1 | |
| | 85** | 27708-B1 | |
| | 88 | 33742 | |
| | 92 | 33741-B1 | |
| | 5504* | 15565 | |
| | K | 19685-B1 | |
| | P1 | 11987-B1 | |
| | P14 | 11988-B1 | |
| | UC18 | 15752-B1 | |
| | 44A-HJD | HER 101 | Felix d'Herelle Reference Centre, Quebec, Quebec |
| | 187 | HER 239 | |
| | 2638A/2854 | HER 283 | |
| | p68 | HER 49 | |
| | Tw-ort** | HER 48 | |
| | φ11** | | J. Bacteriol. 1988. 170: 2409–2411 |
| | φ13** & φ42** | | J. Gen. .Microbiol. 1989. 135: 1679–1697 |
| | L54a** | | J. Bateriol. 1986. 166: 385–391 |
| | | | Can. J. Microbiol. 1996. 43: 612–616 |
| | 94, 95 & 96 | | J. Clin. Microbiol. 1988. 26: 2395–2401 |
| | φ131, A₃ & A₅ | | Staphylococci & Staphylococcal Infections. 1997. Vol1: 503–508 (Karger, Basel) |
| | Phi PVL** | | Gene 1998. 215: 57–67 |
| Staphylococcus | Ba-STC2 | | Felix d'Herelle Reference Centre, Quebec, Quebec |
| carnosus | | | |
| Staphylococcus epidermidis | 1a, 2b, 3a, 4b, 5a, 6b, 7b, 8c, 9a, 10a, 11b, 12a & 13b | | Can. J. Microbiol. 1988. 34: 1358–1361 |
| | 41, 63, 118II, 138, 245, 336, 392 & 550 | | Res. Virol. 1994. 145: 111–121 |
| Staphylococcus saprophyticus | 1154A, 1405, 1314, 1139 & 1259 | | Res. Virol. 1990. 141: 625–635 & Res. Virol. 1994. 145: 111–121 |
| Staphyloccus sp. | Phi 812, Phi 131, SK311 & U16 | | Virology 1998. 246: 241–252 |
| Streptococcus faecalis | VD13 | HER44 | Felix d'Herelle Reference Centre, Quebec, Quebec |
| Streptococcus faecium | PE1 | | Zentra1bl. Bakteriol. 1975. 231: 421–425 |
| Streptococcus oralis | Cp-1** & Cp-7** | | FEMS Microbiol. Lett. 1989. 65: 187–192 |
| Streptococcus pneumoniae | CP-1** | Her223 | Felix d'Herelle Reference Centre, Quebec, Quebec |
| | Cp-1**, Cp-5**, Cp-7**, Cp-9**, ω-1 & ω-2 | | J. Virol. 1981. 40: 551–559 & Eur. J. Biochem. 1979. 101: 59–64 & Microbial Drug Resistance 1997. 3: 165–176 |
| | HB-623 & HB-746 | | J. Virol. 1990. 64: 5149–5155 |
| | EJ-1** | | J. Bacteriol. 1992. 174: 5516–5525 |
| | Dp-2 & Dp-4 | | J. Virol. 1978. 26: 221–225 |
| | Dp-1 | | Virology 1975. 63: 577–582 |
| | ω-3 & ω-8 | | J. Virol. 1976. 19: 659–667 |
| | 304 | | J. Bacteriol. 1980. 141: 1298–1304 |
| | HB-1, HB-2, HB-3**, HB-4, HB-5 & HB-6 | | J. Bacteriol. 1979. 138: 618–624 |
| Streptococcus pyogenes | T12** | | Mol. Microbiology. 1997 #23: 719–728 |
| | A-1 | 12202-B1 | The American Type Culture Collection |
| | A-6 | 12203-B1 | |
| | A-25 | 12204-B1 | |
| | Kjem | 14918 | |
| Streptococcus sp./Enterococcus | 1 | HER 339 | Felix d'Herelle Reference Centre, Quebec, Quebec |
| | 182 | HER 80 | |
| | VD-1884 | HER 323 | |
| | 1A | 12169-B1 | The American Type Culture Collection |
| | 1B | 12170-B1 | |
| | NN | 21597-B1 | |
| | 42 | 19948-B1 | |

TABLE 1-continued

Phages against human and animal pathogenic bacteria

| Pathogen name | Phage name | Catalog # | Origin/reference |
|---|---|---|---|
| | 118 | 19951-B2 | |
| | 120 | 19952-B1 | |
| Veillonella rodentium | N2 | | Antonie Van Leeuwenhoek 1989. 56: 263–271 |
| Vibrio cholerae | Psi 92 | | Intervirology 1993. 36: 237–244 |
| | VCB-1, 2, 3 & 4 | | J. Infetion 1998. 36: 131 |
| | CP-T1** | | J. Virol. 1984. 51: 163–169 |
| | VSK | | FEMS Microbiol. Lett. 1996. 145: 17–22 |
| | Phi138 | | J. Virol. 1986. 57: 960–967 |
| | Phi149 | | J. Virol. 1985. 140: 217–223 |
| | Fs-2** | | Microbiology 1998. 144: 1901–1906 |
| | e4 | | Felix d'Herelle Reference Centre, Quebec, Quebec |
| | e5 | | |
| | X29 | | |
| | β | | |
| | κ | | |
| | 13 | | |
| | 14 | | |
| | 16 | | |
| | 24 | | |
| | 32 | | |
| | 57 | | |
| | 138 | 14100-B1 | The American Type Culture Collection |
| | 145 | 14100-B2 | |
| | 149 | 14100-B30 | |
| | 163 | 14100-B4 | |
| | N-4 | 51352-B1 | |
| | S-5 | 51352-B2 | |
| | S-20 | 51352-B3 | |
| | M-4 | 51352-B4 | |
| | D-10 | 51352-B5 | |
| | I | 51352-b6 | |
| | II | 51352-B7 | |
| | III | 51352-B8 | |
| | IV | 51352-B9 | |
| | V | 51352-B10 | |
| Vibrio costicola | UTAK | | Felix d'Herelle Reference Centre, Quebec, Quebec |
| Vibrio eltor | e₄ | | J. Gen. Virol. 1987. 68: 1411–1416 |
| Vibrio natrigens | nt1, nt6 | | Felix d'Herelle Reference Centre, Quebec, Quebec |
| Vibrio parahaemolyticus | KVP-40** | | Felix d'Herelle Reference Centre, Quebec, Quebec |
| | VF33 | | |
| | VP1 | | |
| | φ60 | | |
| | φHA-WI-5 | | |
| | φPEL-8C-1 | | |
| Vibrio sp. | α3a | | Felix d'Herelle Reference Centre, Quebec, Quebec |
| | NN | 11985-B1 | The American Type Culture Collection |
| | ph1 | 51582-B1 | |
| | Phi149 | | J. Virol. 1987. 61: 3999–4006 |
| Veillonella rodentium | N2 | | Antonie V. Leeuwenhoek. 1989. 56: 263–271 |
| Yersinia enterocolitica | 1 | | Felix d'Herelle Reference Centre, Quebec, Quebec |
| | 2 | | |
| | 3 | | |
| | 4 | | |
| | 5 | | |
| | 6 | | |
| | 7 | | |
| | 8 | | |
| | 9 | | |
| | φYeO3-12 | | |
| | I, IV & VIII | | Zentralbl. Bakteriol. Mikrobiol. Hyg. 1982. 253: 102 |
| Yersinia pestis | R | 23208-B1 | The American Type Culture Collection |
| | S | 11593-B1 | |
| | Y | 23053-B1 | |
| | II | | Zh. Mikrobiol. Epidemiol. Immunobiol. 1990. 11: 9 |
| Yersinia pseudotuberculosis | PST** | 23207-B1 | The American Type Culture Collection |
| Yersinia sp. | RD2 | | Mol. Gen. Mikrobiol. Virusol. 1990. 8: 18–21 |

TABLE 2

>Bacteriophage 77, complete genome sequence, 41708 nucleotides

```
  1    gatcaaaata cttggggaac ggttagggag taaacttcgc gataatttta aaaattcatg
 61    tataaccccc ctcttataac cattttaagg caggtgatga aatggagatt atagtcgatg
121    aaaatttagt gcttaaagaa aaagaaaggc tacaagtatt atataaagac atacctagca
181    ataaattaaa agtagttgat ggtttaatta ttcaagcagc aaggctacgt gtaatgcttg
241    attacatgtg ggaagacata aaagaaaaag gtgattatga tttatttact caatctgaaa
301    aggcgccacc atatgaaagg gaaagaccag tagccaaact atttaatgct agagatgctg
361    catatcaaaa aataatcaaa caattatcgg atttattgcc cgaagagaaa gaagacacag
```

TABLE 2-continued

>Bacteriophage 77, complete genome sequence, 41708 nucleotides

```
 421   aaacgccatc tgatgattac ctatgattag taataaatac gttgatgaat atataaattt
 481   gtggaaacaa ggaaagataa ttttaaataa agaaagaatt gatctcttta attatctaca
 541   aaaacatata tattcacgag atgatgtata ttttgatgaa cagaaaatcg aggattgtat
 601   caaatttatt gaaaaatggt attttccaac attaccattt caaaggttta tcatagctaa
 661   tatatttctt atagataaaa atacagatga agctttcttt acagaatttg ctattttcat
 721   gggacgtgga ggcgggaaaa acggtctaat aagtgctatt agtgattttc tttctacgcc
 781   cttacacgga gttaaagaat atcacatctc cattgttgct aatagtgaag atcaagcaaa
 841   aacatcgttt gatgaaatca gaaccgtttt aatggataac aaacgaaata agacgggtaa
 901   aacgccaaaa gctccttatg aagttagtaa agcaaaaata ataaaccgtc aactaaatc
 961   ggttattcga tataacacat caaacacaaa aaccaaagac ggtggacgtg agggtgtgt
1021   tattttgat gaaattcatt atttctttgg tcctgaaatg gtaaacgtca aacgtggtgg
1081   attaggtaaa aagaaaaata gaagaacgtt ttatataagt actgatggtt tgttagaga
1141   gggttatatc gatgcaatga agcacaaaat tgcaagtgta ttaagtggca aggttaaaaa
1201   tagtagattg tttgcttttt attgtaagtt agacgatcca aaagaagttg atgacagaca
1261   gacgtgggaa aaggcgaacc caatgttaca taaaccgtta tcagaatacg ctaaaacact
1321   gctaagcacg attgaagaag aatataacga tttaccattc aaccgttcaa ataagcccga
1381   attcatgact aagcgaatga atttgcctga agttgacctt gaaaaagtaa tagcaccatg
1441   gaaagaaata ctagcgacta atagagagat accaaattta gataatcaaa tgtgtattgg
1501   tggtttagac tttgcaaaca ttcgagattt tgcaagtgta gggctattat tccgaaaaaa
1561   cgatgattac atttggttag acattcgtt tgtaagacaa gggttttttgg atgatgtcaa
1621   attagaacct cctattaaag aatgggaaaa aatgggatta ttgaccattg tcgatgatga
1681   tgtcattgaa attgaatata tagttgattg gttttttaaag gctagagaaa aatatgggct
1741   tgaaaaagtc atagctgata attatagaac tgatattgta agacgtgcgt tgaggatgc
1801   tggcataaaa cttgaagtac ttagaaatcc aaaagcaata catggattac ttgcaccacg
1861   tatcgataca atgtttgcga aacataacgt aatatatgga gacaatcctt gatgcgttg
1921   gtttactaat aatgttgctg taaaaatcaa gccggatgga aataaagagt atatcaaaaa
1981   agatgaagtc agacgtaaaa cggatggatt catggctttt gttcacgcat tatatagagc
2041   agacgatata gtagacaaag acatgtctaa agcgcttgat gcattaatga gtatagattt
2101   ctaatagagg aggtgagaca tgagtattct agaaaagata tttaaaacta ggaaagatat
2161   aacatatatg cttgatttag atatgataga agatctatca caacaagcgt atgtgaaacg
2221   tttagcgatt gatagttgta ttgaatttgt tgcgcgagct gtcgctcaaa gtcattttaa
2281   agtattggaa ggtaatagaa ttcaaaagaa tgatgtttac tacaagttaa atataaaacc
2341   aaatactgac ttatcaagcg atagtttttg gcaacaagtt atatataaac taatttatga
2401   taacgaggtt ttaatcgtag taagtgacag caaagaatta cttatcgcag atagctttta
2461   cagagaagag tacgctttgt atgatgatat attcaaagat gtaacggtta aagattatac
2521   ttatcaacgt actttcacaa tgcaagaggt catatattta aagtacaaca acaataaagt
2581   gacacacttt gtagaaagtc tattcgaaga ttacgggaaa atattcggaa gaatgatagg
2641   tgcacaatta aaaaactatc aaataagagg gattttgaaa tctgcctcta gcgcatatga
2701   cgaaaagaat atagaaaaat tacaagcgtt cacaaataaa ttattcaata cttttaataa
```

TABLE 2-continued

>Bacteriophage 77, complete genome sequence, 41708 nucleotides

| | | | | | |
|---|---|---|---|---|---|
| 2761 | aaatcaacta | gcaatcgcgc | ctttgataga | aggttttgat | tatgaggaat tatctaatgg |
| 2821 | tggtaagaat | agtaacatgc | cttttctga | attgagtgag | ctaatgagag atgcaataaa |
| 2881 | aaatgttgcg | ttgatgattg | gtatacctcc | aggtttgatt | tacggagaaa cagctgattt |
| 2941 | ggaaaaaaac | acgcttgtat | ttgagaagtt | ctgtttaaca | cctttattaa aaaagattca |
| 3001 | gaacgaatta | aacgcgaaac | tcataacaca | aagcatgtat | ttgaaagata caagaataga |
| 3061 | aattgtcggt | gtgaataaaa | aagacccact | tcaatatgct | gaagcaattg acaaacttgt |
| 3121 | aagttctggt | tcatttacaa | ggaatgaggt | gcggattatg | ttaggtgaag aaccatcaga |
| 3181 | caatcctgaa | ttagacgaat | acctgattac | taaaaactac | gaaaaagcta acagtggtga |
| 3241 | aaatgatgaa | aaagaaaaag | atgaaaacac | tttgaaaggt | ggtgatgaag atgaaagcgg |
| 3301 | agattaaagg | cgtcatcgtt | tccaacgaag | ataaatgggt | ttacgaaatg cttggtatgg |
| 3361 | attcgacttg | tcctaaagat | gttttaacac | aactagaatt | tagtgatgaa gatgttgata |
| 3421 | ttataattaa | ctcaaatggt | ggtaacctag | tagctggtag | tgaaatatat acacatttaa |
| 3481 | gagctcataa | aggcaaagtg | aatgttcgta | tcacagcaat | agcagcaagt gcggcatcgc |
| 3541 | ttatcgcaat | ggctggtgac | cacatcgaaa | tgagtccggt | tgctagaatg atgattcaca |
| 3601 | atccttcaag | tattgcgcaa | ggagaagtga | aagatctaaa | tcatgctgca gaaacattag |
| 3661 | aacatgttgg | tcaaataatg | gctgaggcat | atgcggttag | agctggtaaa acaaacaag |
| 3721 | aacttataga | aatgatggct | aaggaaacgt | ggctaaatgc | tgatgaagcc attgaacaag |
| 3781 | gttttgcgga | tagtaaaatg | tttgaaaacg | acaatatgca | aattgtagca agcgatacac |
| 3841 | aagtgttatc | gaaagatgta | ttaaatcgtg | taacagcttt | ggtaagtaaa acgccagagg |
| 3901 | ttaacattga | tattgacgca | atagcaaata | aagtaattga | aaaataaat atgaaagaaa |
| 3961 | aggaatcaga | aatcgatgtt | gcagatagta | aattatcagc | aaatggattt tcaagattcc |
| 4021 | ttttttaata | caaaaatagg | aggtcataaa | atgactataa | atttatcgga acattcgca |
| 4081 | aatgcgaaaa | acgaatttat | taatgcagta | acaacggtg | aaccgcaaga aagacaaaat |
| 4141 | gaattgtacg | gtgacatgat | taaccaacta | tttgaagaaa | ctaaattaca agcaaaagca |
| 4201 | gaagctgaaa | gagtttctag | tttacctaaa | tcagcacaaa | ctttgagtgc aaaccaaga |
| 4261 | aatttcttta | tggatatcaa | taagagtgtt | ggatataaag | aagaaaaact tttaccagaa |
| 4321 | gaaacaattg | atagaatctt | cgaagattta | acaacgaatc | atccattatt agctgactta |
| 4381 | ggtattaaaa | atgctggttt | gcgtttgaag | ttcttaaaat | ccgaaacttc tggcgtggct |
| 4441 | gtttggggta | aaatctatgg | tgaaattaaa | ggtcaattag | atgctgcgtt cagtgaagaa |
| 4501 | acagcaattc | aaaataaatt | gacagcgttt | gttgtttac | caaaagattt aaatgatttt |
| 4561 | ggtcctgcgt | ggattgaaag | atttgttcgt | gttcaaatcg | aagaagcatt tgcagtggcg |
| 4621 | cttgaaactg | cgttcttaaa | aggtactggt | aaagaccaac | cgattggctt aaaccgtcaa |
| 4681 | gtacaaaaag | gtgtatcggt | aactgatggt | gcttatccag | agaaagaaga acaaggtacg |
| 4741 | cttacatttg | ctaatccgcg | cgctacggtt | aatgaattga | cgcaagtgtt taaataccac |
| 4801 | tcaactaacg | agaaaggtaa | atcagtagcg | gttaaggta | atgtaacaat ggttgttaat |
| 4861 | ccgtccgatg | cttttgaggt | tcaagcacag | tatacacatt | taaatgcaaa tggcgtatat |
| 4921 | gttactgctt | taccacttaa | tttgaatgtt | attgagtcta | cagttcaaga agcaggtaag |
| 4981 | gttttaacgt | acgttaaagg | tctatatgat | ggttatttag | ctggtggtat taatgttcag |

TABLE 2-continued

>Bacteriophage 77, complete genome sequence, 41708 nucleotides

```
5041  aaatttaaag aaacacttgc gttagatgat atggatttat acactgcaaa acaatttgct
5101  tacggcaaag cgaaagataa taaagttgct gctgtttgga aattagattt aaaaggacat
5161  aaaccagctt tagaagatac cgaagaaaca ctataaaatt ttatgaggtg ataaaatggt
5221  gaaatttaaa gttgttagag aatttaaaga catagagcac aatcaacaca agtacaaagt
5281  aggggagttg tatccagctg aagggtataa caatcctcgt gttgaattgt tgacaaatca
5341  aatcaaaaat aagtacgaca aagtttatat cgtacccttta gataagctga caaaacaaga
5401  actattagaa ctatgcgaat cattacaaaa aaaagcgtct agttcaatgg ttaaaagtga
5461  aatcatcgac ttattgaatg gtgaagacaa tgacgattga tgatttgctt gtcaaattta
5521  aatcacttga aaagattgac cataattcag aggatgagta cttaaagcag ttgttaaaaa
5581  tgtcgtacga gcgtataaaa aatcagtgcg gagtttttga attagagaat ttaataggtc
5641  aagaattgat acttatacgc gctagatatg cttatcaaga tttattagaa cacttcaacg
5701  acaattacag acctgaaata atagattttt cgttatctct aatggaggta tcagaagatg
5761  aagaaagtgt ttaagaaacc tagaattaca actaaacgtt taaatacgcg tgttcatttt
5821  tataagtata ctgaaaataa tggtccagaa gctggagaaa aagaagaaaa attattatat
5881  agctgttggg cgagtattga tggtgtctgg ttacgtgaat tagaacaagc tatctcaaac
5941  ggaacgcaaa atgacattaa attgtatatt cgtgatccgc aaggtgatta tttacccagt
6001  g8agaacatt atcttgaaat tgaatcaaga tatttcaaaa atcgtttgaa taca&agcaa
6061  gtatcaccag atttggataa taaagacttt attatgattc gcggaggata tagttcatga
6121  gtgtgaaagt gacaggtgat aaagcattag aaagagaatt agaaaaacat ttcggcataa
6181  aagagatggt aaaagttcaa gataaggcgt taatagctgg tgctaaggta attgttgaag
6241  aaataaaaaa acaactcaaa ccttcagaag actcaggagc actgattagt gagattggtc
6301  gtactgaacc tgaatggata aaggggaaac gtactgttac aattaggtgg cgtgggcctt
6361  ttgaacgatt tagaatagta catttaattg aaaatggtca tgttgagaaa aagtcaggaa
6421  aatttgtaaa acctaaagct atgggtggga ttaatagagc aataagacaa gggcaaaata
6481  agtattttga gacgctaaaa agggagttga aaaaattgtg attgatattt tgtacaaagt
6541  tcatgaagtg attagtcaag acagaattat tagagagcac gtaaatatca ataatattaa
6601  gttcaataaa taccctaatg taaaagatac tgatgtaccct tttattgtta ttgacgatat
6661  cgacgaccca atacctacaa cttatactga cggagatgag tgtgcatata gttatattgt
6721  ccaaatagat gttttttgtta agtacaatga tgaatataat gcgagaatca taagaaataa
6781  gatatctaat cgcattcaaa agttattatg gtctgaacta aaaatgggaa atgtttcaaa
6841  tggaaaaccg gaatatatag aagaatttaa aacatataga agctctcgcg tttacgaggg
6901  cattttttat aaggaggaaa attaaatggc agtaaaacat gcaagtgcgc caaaggcgta
6961  tattaacatt actggtttag gtttcgctaa attaacgaaa gaaggcgcgg aattaaaata
7021  tagtgatatt acaaaaacaa gaggattaca aaaaattggt gttgaaactg gtggagaact
7081  aaaaacagct tatgctgatg gcggtccaat tgaatcaggg aatacagacg gagaaggtaa
7141  aatctcatta caaatgcatg cgttccctaa agagattcgc aaaattgttt ttaatgaaga
7201  ttatgatgaa gatggcgttt acgaagagaa acaaggtaaa caaaacaatt acgtagctgt
7261  atggttcaga caagagcgta aagacgtac atttagaaca gttttattac ctaaagttat
7321  gtttacaaat cctaaaatcg atggagaaac ggctgagaaa gattgggatt tctcaagtga
```

TABLE 2-continued

>Bacteriophage 77, complete genome sequence, 41708 nucleotides

```
7381   agaggttgaa ggtgaggcac tttttcccttt agttgataat aaaaagtcag tacgtaagta
7441   tatctttgat tcagctaaca tgacaaatca tgatggagac ggtgaaaaag gcgaagaggc
7501   tttcttaaag aaaattttag gcgaagaata tactggaaac gtgacagagg gtaacgaaga
7561   aactttgtaa caaaaccggc ttcatcggaa actgcggtaa agtcggttaa tataccagat
7621   agcattaaaa cacttaaagt tggcgacaca tacgatttaa atgttgtagt agagccatct
7681   aatcaaagta agttattgaa atacacaaca gatcaaacga atattgtatc aatcaatagt
7741   gatggtcaag ttactgcgga agcacaaggc attgctacgg ttaaagcaac agttggtaat
7801   atgagtgaca ctataacaat aaatgtagaa gcataagagg gggcaacccc tctattttat
7861   ttgaaaataa ggagagtatt ataaaatggc aaaattaaaa cgtaacatta ttcaattagt
7921   agaagatcca aaagcaaatg aaattaaatt acaacgtac ttaacaccac acttcatttc
7981   atttgaaatt gtatacgaag caatggattt aatcgatgat attgaggacg aaaatagcac
8041   gatgaagcca agagaaatcg ctgacagatt gatggatatg gttgtaaaaa tttacgataa
8101   ccaattcaca gttaaagacc taaagaacg tatgcatgca cctgatggaa tgaatgcact
8161   tcgtgaacaa gtgattttca ttactcaagg tcaacaaact gaggaaacta gaaattttat
8221   ccagaacatg aaataaagcc tgaagattta acatataaag caatgttgaa aaatatggat
8281   actctcatga tggacttaat tgaaaatggt aaagacgcta acgaagtttt aaaaatgcca
8341   tttcattatg tgctttccat atatcaaaat aaaaataatg acatttctga agaaaaagca
8401   gaggctttaa ttgatgcatt ttaaccttaa ccgtttggtt agggttattt ttttgaactt
8461   ttttagaaag gaggtaaaaa atgggagaaa gaataaaagg tttatctata ggtttggatt
8521   tagatgcagc aaatttaaat agatcatttg cagaaatcaa acgaaacttt aaaactttaa
8581   attctgactt aaaattaaca ggcaacaact tcaaatatac cgaaaaatca actgatagtt
8641   acaaacaaag gattaaagaa cttgatggaa ctatcacagg ttataagaaa aacgttgatg
8701   atttagccaa gcaatatgac aaggtatctc aagaacaggg cgaaaacagt gcagaagctc
8761   aaaagttacg acaagaatat aacaaacaag caaatgagct gaattatta gaaagagaat
8821   tacaaaaaac atcagccgaa tttgaagagt tcaaaaaagc tcaagttgaa gctcaaagaa
8881   tggcagaaag tggctgggga aaaaccagta agttttttga agtatggga cctaaattaa
8941   caaaaatggg tgatggttta aaatccattg gtaaaggttt gatgattggt gtaactgcac
9001   ctgttttagg tattgcagca gcatcaggaa aagcttttgc agaagttgat aaaggtttag
9061   atactgtt&c tcaagcaaca ggcgcaacag gcagtgaatt aaaaaaattg cagaactcat
9121   ttaaagatgt ttatggcaat tttccagcag atgctgaaac tgttggtgga gtttttaggag
9181   aagttaatac aaggttaggt tttacaggta agaacttga aaatgccaca gagtcattct
9241   tgaaattcag tcatataaca ggttctgacg gtgtgcaagc cgtacagtta attacccgtg
9301   caatgggcga tgcaggtatc gaagcaagtg aatatcaaag tgttttggat atggtagcaa
9361   aagcggcgca agctagtggg ataagtgttg atacattagc tgatagtatt actaaatacg
9421   gcgctccaat gagagctatg ggctttgaga tgaaagaatc aattgcttta ttctctcaat
9481   gggaaaagtc aggcgttaat actgaaatag cattcagtgg tttgaaaaaa gctatatcaa
9541   attggggtaa agctggtaaa aacccaagag aagaatttaa gaagacatta gcagaaattg
9601   aaaagacgcc ggatatagct agcgcaacaa gtttagcgat tgaagcattt ggtgcaaagg
```

TABLE 2-continued

>Bacteriophage 77, complete genome sequence, 41708 nucleotides

```
9661   caggtcctga tttagcagac gctattaaag gtggtcgctt tagttatcaa gaattttaa
9721   aaactattga agattcccaa ggcacagtaa accaaacatt taaagattct gaaagtggct
9781   ccgaaagatt taaagtagca atgaataaat taaaattagt aggtgctgat gtatgggctt
9841   ctattgaaag tgcgtttgct cccgtaatgg aagaattaat caaaaagcta tctatagcgg
9901   ttgattggtt ttccaattta agtgatggtt ctaaaagatc aattgttatt ttcagtggta
9961   ttgctgctgc aattggtcct gtagttttg ggttaggtgc atttataagt acaattggca
10021  atgcagtaac tgtattagct ccattgttag ctagtattgc aaaggctggt ggattgatta
10081  gttttttatc gactaaagta cctatattag gaactgtctt cacagcttta actggtccaa
10141  ttggcattgt attaggtgta ttggctggtt tagcagtcgc atttacaatt gcttataaga
10201  aatctgaaac atttagaaat tttgttaatg gtgcaattga agtgttaaa caaacattta
10261  gtaattttat tcaatttatt caacctttcg ttgattctgt taaaaacatc tttaaacaag
10321  cgatatcagc aatagttgat ttcgcaaaag atatttggag tcaaatcaat ggattcttta
10381  atgaaaacgg aatttccatt gttcaagcac ttcaaaatat atgcaacttt attaaagcga
10441  tatttgaatt tattttaaat tttgtaatta aaccaattat gttcgcgatt tggcaagtga
10501  tgcaatttat ttggccggcg gttaaagcct tgattgtcag tacttgggag aacataaaag
10561  gtgtaataca aggtgcttta aatatcatac ttggcttgat taagttcttc tcaagtttat
10621  tcgttggtga ttggcgagga gtttgggacg ccgttgtgat gattcttaaa ggagcagttc
10681  aattaatttg gaatttagtt caattatggt ttgtaggtaa aatacttggt gttgttaggt
10741  actttggcgg gttgctaaaa ggattgatga caggaatttg ggacgtaata agaagtatat
10801  tcagtaaatc tttatcagca atttggaatg caacaaaaag tattttttgga ttttatttta
10861  atagcgtaaa atcaattttc acaaatatga aaaattggtt atctaatact tggagcagta
10921  tccgtacgaa tacaatagga aaagcgcagt cattatttag tggcgtcaaa tcaaaattta
10981  ctaattatg gaatgcgacg aaagaaattt ttagtaattt aagaaattgg atgtcaaata
11041  tttggaattc cattaaagat aatacggtag gaattgcaag ccgtttatgg agtaaggtac
11101  gtggaattt cacaaatatg cgcgatggct tgagttccat tatagataag attaaaagtc
11161  atatcggcgg tatggtaagc gctattaaaa aaggacttaa taaattaatc gacggtttaa
11221  actgggtcgg tggtaagttg ggaatggata aaatacctaa gttacacact ggtacagagc
11281  acacacatac tactacaaga ttagttaaga acggtaagat tgcacgtgac acattcgcta
11341  cagttgggga taagggacgc ggaaatggtc caaatggttt tagaaatgaa atgattgaat
11401  tccctaacgg taaacgtgta atcacaccta atacagatac taccgcttat ttacctaaag
11461  gctcaaaagt ataacaggt gcacaaactt attcaatgtt aaacggaacg cttccaagat
11521  ttagtttagg tactatgtgg aaagatatta aatctggtgc atcatcggca tttaactgga
11581  caaaagataa aataggtaaa ggtaccaaat ggcttggcga taaagttggc gatgttttag
11641  atttttatgga aaatccaggc aaacttttaa attatatact tgaagctttt ggaattgatt
11701  tcaattcttt aactaaaggt atgggaattg caggcgacat aacaaaagct gcatggtcta
11761  agattaagaa aagtgctact gattggataa agaaaattt agaagctatg gcggtggcg
11821  atttagtcgg cggaatatta gaccctgaca aaattaatta tcattatgga cgtaccgcag
11881  cttataccgc tgcaactgga agaccatttc atgaaggtgt cgatttcca tttgtatatc
11941  aagaagttag aacgccgatg ggtggcagac ttacaagaat gccatttatg tctggtggtt
```

TABLE 2-continued

>Bacteriophage 77, complete genome sequence, 41708 nucleotides

```
12001   atggtaatta tgtaaaaatt actagtggcg ttatcgatat gctatttgcg catttgaaaa
12061   actttagcaa atcaccacct agtggcacga tggtaaagcc cggtgatgtt gttggtttaa
12121   ctggtaatac cggatttagt acaggaccac atttacatttt tgaaatgagg agaaatggac
12181   gacattttga ccctgaacca tatttaagga atgctaagaa aaaggaaga ttatcaatag
12241   gtggtggcgg tgctacttct ggaagtggcg caacttatgc cagtcgagta atccgacaag
12301   cgcaaagtat tttaggtggt cgttataaag gtaaatggat tcatgaccaa atgatgcgcg
12361   ttgcaaaacg tgaaagtaac taccagtcaa atgcagtgaa taactgggat ataaatgctc
12421   aaagaggaga cccatcaaga ggattattcc aaatcatcgg ctcaacttt agcaaacg
12481   ctaaacgtgg atatactaac tttaataatc cagtacatca aggtatctca gcaatgcagt
12541   acattgttag acgatatggt tggggtggtt ttaaacgtgc tggtgattac gcatatgcta
12601   caggtggaaa agttttttgat ggttggtata acttaggtga agacggtcat ccagaatgga
12661   ttattccaac agatccagct cgtagaaatg atgcaatgaa gattttgcat tatgcagcag
12721   cagaagtaag agggaaaaaa gcgagtaaaa ataagcgtcc tagccaatta tcagacttaa
12781   acgggtttga tgatcctagc ttattattga aaatgattga acaacagcaa caacaaatag
12841   ctttattact gaaaatagca caatctaacg atgtgattgc agataaagat tatcagccga
12901   ttattgacga atacgctttt gataaaaagg tgaacgcgtc tatagaaaag cgagaaaggc
12961   aagaatcaac aaaagtaaag tttagaaaag gaggaattgc tattcaatga tagacactat
13021   taaagtgaac aacaaaacaa ttccttggtt gtatgtcgaa agagggtttg aaatacctc
13081   ttttaattat gttttaaaaa cagaaaatgt agatggacgt tcggggtcta tatataaagg
13141   gcgtaggctt gaatcttata gttttgatat acctttggtg gtacgtaatg actatttatc
13201   tcacaacggc attaaaacac atgatgacgt cttgaatgaa ttagtaaagt tttttaacta
13261   cgaggaacaa gttaaattac aattcaaatc taaagattgg tactggaacg cttatttcga
13321   aggaccaata aagctgcaca agaatttac aatacctgtt aagttcacta tcaaagtagt
13381   actaacagac ccttacaaat attcagtaac aggaaataaa aatactgcga tttcagacca
13441   agtttcagtt gtaaatagtg ggactgctga cactccttta attgttgaag cccgagcaat
13501   taaaccatct agttacttta tgattactaa aaatgatgaa gattattta tggttggtga
13561   tgatgaggta accaaagaag ttaaggatta catgcctcct gtttatcata gtgagtttcg
13621   tgatttcaaa ggttggacta agatgattac tgaagatatt ccaagtaatg acttaggtgg
13681   taaggtcggc ggtgacttg tgatatccaa tcttggcgaa ggatataaag caactaattt
13741   tcctgatgca aaaggttggg ttggtgctgg cacgaaacga gggctcccta agcgatgac
13801   agattttcaa attacctata atgtattgt tgaacaaaaa ggtaaaggtg ccggaagaac
13861   agcacaacat atttatgata gtgatggtaa gttacttgct tctattggtt atgaaaataa
13921   atatcatgat agaaaaatag gacatattgt tgttacgttg tataaccaaa aaggagaccc
13981   caaaaagata tacgactatc agaataaacc gataatgtat aacttggaca gaatcgttgt
14041   ttatatgcgg ctcagaagag taggtaataa attttctatt aaaacttgga aatttgatca
14101   cattaaagac ccagatagac gtaaacctat tgatatggat gagaaagagt ggatagatgg
14161   cggtaagttt tatcagcgtc cagcttctat catagctgtc tatagtgcga agtataacgg
14221   ttataagtgg atggagatga atgggttagg ttcattcaat acggagattc taccgaaacc
```

TABLE 2-continued

>Bacteriophage 77, complete genome sequence, 41708 nucleotides

```
14281   gaaaggcgca aggggatgtca ttatacaaaa aggtgattta gtaaaaatag atatgcaagc
14341   aaaaagtgtt gtcatcaatg aggaaccaat gttgagcgag aaatcgtttg gaagtaatta
14401   tttcaatgtt gattctgggt acagtgaatt aatcatacaa cctgaaaacg tctttgatac
14461   gacggttaaa tggcaagata gatatttata gaaggagat gagagtgtga tacatgtttt
14521   agattttaac gacaagatta tagatttcct ttctactgat gacccttcct tagttagagc
14581   gattcataaa cgtaatgtta atgacaattc agaaatgctt gaactgctca tatcatcaga
14641   aagagctgaa aagttccgtg aacgacatcg tgttattata agggattcaa acaaacaatg
14701   gcgtgaattt attattaact gggttcaaga tacgatggac ggctacacag agatagaatg
14761   tatagcgtct tatcttgctg atataacaac agctaaaccg tatgcaccag gcaaatttga
14821   gaaaaagaca acttcagaag cattgaaaga tgtgttgagc gatacaggtt gggaagtttc
14881   tgaacaaacc gaatacgatg gcttacgtac tacgtcatgg acttcttatc aaactagata
14941   tgaagtttta aagcaattat gtacaaccta taaaatggtt ttagatttt atattgagct
15001   tagctctaat accgtcaaag gtagatatgt agtactcaaa agaaaaaca gcttattcaa
15061   aggtaaagaa attgaatatg gtaaagattt agtcgggtta actaggaaga ttgatatgtc
15121   agaaatcaaa acagcattaa ttgctgtggg acctgaaaat gacaaaggga agcgtttaga
15181   gctagttgtg acagatgacg aagcgcaaag tcaattcaac ctacctatgc gctatatttg
15241   ggggatatat gaaccacaat cagatgatca aaatatgaat gaaacacgat taagttcttt
15301   agccaaaaca gagttaaata aacgtaagtc ggcagttatg tcatatgaga ttacttctac
15361   tgatttggaa gttacgtatc cgcacgagat tatatcaatt ggcgatacag tcagagtaaa
15421   acatagagat tttaacccgc cattgtatgt agaggcagaa gttattgctg aagaatataa
15481   cataatttca gaaaatagca catatacatt cggtcaacct aaagagttca aagaatcaga
15541   attacgagaa gagtttaaca agcgattgaa cataatacat caaaagttaa acgataatat
15601   tagcaatatc aacactatag ttaaagatgt tgtagatggt gaattagaat actttgaacg
15661   caaaatacac aaaagtgata caccgccaga aaatccagtc aatgatatgc tttggtatga
15721   tacaagtaac cctgatgttg ctgtcttgcg tagatattgg aatggtcgat ggattgaagc
15781   aacaccaaat gatgttgaaa aattaggtgg tataacaaga gagaaagcgc tattcagtga
15841   attaaacaat attttattta atttatctat acaacacgct agtcttttgt cagaagctac
15901   agaattactg aatagcgagt acttagtaga taatgatttg aaagcggact acaagcaag
15961   tttagacgct gtgattgatg tttataatca aattaaaaat aatttagaat ctatgacacc
16021   cgaaactgca acgattggtc ggttggtaga tacacaagct ttattcttg agtatagaaa
16081   gaaattacaa gatgtttata cagatgtaga agatgtcaaa atcgccattt cagatagatt
16141   taaattatta cagtcacaat acactgatga aaaatataaa gaagcgttgg aaataatagc
16201   aacaaaattt ggtttaacgg tgaatgaaga tttgcagtta gtcggagaac ctaatgttgt
16261   taaatcagct attgaagcag ctagagaatc cacaaaagaa caattacgtg actatgtaaa
16321   aacatcggac tataaaacag acaaagacgg tattgttgaa cgtttagata ctgctgaagc
16381   tgagagaacg actttaaaag gtgaaatcaa agataaagtt acgttaaacg aatatcgaaa
16441   cggattggaa gaacaaaaac aatatactga tgaccagtta agtgatttgt ccaataatcc
16501   tgagattaaa gcaagtattg aacaagcaaa tcaagaagcg caagaagctt taaaatcata
16561   cattgatgct caagatgatc ttaaagagaa ggaatcgcaa gcgtatgctg atggtaaaat
```

TABLE 2-continued

>Bacteriophage 77, complete genome sequence, 41708 nucleotides

```
16621   ttcggaagaa gagcaacgcg ctatacaaga tgctcaagct aaacttgaag aggcaaaaca
16681   aaacgcagaa ctaaaggcta gaaacgctga aaagaaagct aatgcttata cagacaacaa
16741   ggtcaaagaa agcacagatg cacagaggaa acattgact cgctatggtt ctcaaattat
16801   acaaaatggt aaggaaatca aattaagaac tactaaagaa gagtttaatg caaccaatcg
16861   tacactttca aatatattaa acgagattgt tcaaaatgtt acagatggaa caacaatcag
16921   atatgatgat aacggagtgg ctcaagcttt gaatgtgggg ccacgtggta ttagattaaa
16981   tgctgacaaa attgatatta acggtaatag agaaataaac cttcttatcc aaaatatgcg
17041   agataaagta gataaaaccg atattgtcaa cagtcttaat ttatcaagag agggtcttga
17101   tatcaatgtt aatagaattg gaattaaagg cggtgacaat aacagatatg ttcaaataca
17161   gaatgattct attgaactag gtggtattgt gcaacgtact tggagaggga aacgttcaac
17221   agacgatatt tttacgcgac tgaaagacgg tcacctaaga tttagaaata acaccgctgg
17281   cggttcactt tatatgtcac attttggtat ttcgacttat attgatggtg aaggtgaaga
17341   cggtggttca tctggtacga ttcaatggtg ggataaaact tacagtgata gtggcatgaa
17401   tggtataaca atcaattcct atggtggtgt cgttgcacta acgtcagata taatcgggt
17461   tgttctggag tcttacgctt catcgaatat caaaagcaaa caggcaccgg tgtatttata
17521   tccaaacaca gacaaagtgc ctggattaaa ccgatttgca ttcacgctgt ctaatgcaga
17581   taatgcttac tcgagtgacg gttatattat gtttggttct gatgagaact atgattacgg
17641   tgcgggtatc aggttttcta aagaaagaaa taaaggtctt gttcaaattg ttaatggacg
17701   atatgcaaca ggtggagata caacaatcga agcagggtat ggcaaattta atatgctgaa
17761   acgacgtgat ggtaataggt atattcatat acagagtaca gacctactgt ctgtaggttc
17821   agatgatgca ggagatagga tagcttctaa ctcaatttat agacgtactt attcggcagc
17881   agctaatttg catattactt ctgctggcac aattgggcgt tcgacatcag cgcgtaaata
17941   caagttatct atcgaaaatc aatataacga tagagatgaa caactggaac attcaaaagc
18001   tattcttaac ttacctatta gaacgtggtt tgataaagct gagtctgaaa ttttagctag
18061   agagctgaga gaagatagaa aattatcgga agacacctat aaacttgata gatacgtagg
18121   tttgattgct gaagaggtgg agaatttagg attaaaagag tttgtcacgt atgatgacaa
18181   aggagaaatt gaaggtatag cgtatgatcg tctatggatt catcttatcc ctgttatcaa
18241   agaacaacaa ctaagaatca agaaattgga ggagtcaaag aatgcaggat aacaaacaag
18301   gattacaagc taatcctgaa tatacaattc attatttatc acaggaaatt atgaggttaa
18361   cacaagaaaa cgcgatgtta aaagcgtata caagaaaaa taagaaaat caacaatgtg
18421   ctgaggaaga gtaatcctta gcactatttt tatacaaaaa tttaaggagg tcatttaatt
18481   atggcaaaag aaattatcaa caatacagaa aggtttattt tagtacaaat cgacaaagaa
18541   ggtacagaac gtgtagtata tcaagatttc acaggaagtt ttacaacttc tgaaatggtt
18601   aaccatgctc aagattttaa atctgaagaa acgctaaga aaattgcgga gacgttaaat
18661   ttgttatatc aattaactaa caaaaaacaa cgtgtgaaag tagttaaaga agtagttgaa
18721   agatcagatt tatctccaga ggtaacagtt aacactgaaa cagtatgaaa agctatgagt
18781   tagatactca tagtctttat tcttttagaa agcgggtgta ctgaattggg gtggttcaaa
18841   aaacacgaac atgaatggcg catcagaagg ttagaagaga atgataaaac aatgctcagc
```

TABLE 2-continued

>Bacteriophage 77, complete genome sequence, 41708 nucleotides

```
18901  acactcaacg aaattaaatt aggtcaaaaa acccaagagc aagttaacat taaattagat
18961  aaaaccttag atgctattca aaaagaaaga gaaatagatg aaaagaataa gaaagaaaat
19021  gataagaaca tacgtgatat gaaaatgtgg gtgcttggtt tagttgggac aatatttggg
19081  tcgctaatta tagcattatt gcgtatgctt atgggcatat aagagaggtg attaccatgt
19141  tcggattaaa ttttggagct tcgctgtgga cgtgtttctg gtttggtaag tgtaagtaat
19201  agttaagagt cagtgcttcg gcactggctt tttattttgg ataaaaggag caaacaaatg
19261  gatgcaaaag taataacaag atacatcgta ttgatcttag cattagtaaa tcaattctta
19321  gcgaacaaag gtattagccc aattccagta gacgatgaaa ctatatcatc aataatactt
19381  actgtagtcg ctttatatac aacgtataaa gacaatccaa catctcaaga aggtaaatgg
19441  gcaaatcaaa aattaaagaa atataaagct gaaaataagt atagaaaagc aacagggcaa
19501  gcgccaatta aagaagtaat gacacctacg aatatgaacg acacaaatga tttagggtag
19561  gtggttgata tatgttaatg acaaaaaatc aagcagaaaa atggtttgac aattcattag
19621  ggaaacaatt caacccagat ggttggtatg gatttcagtg ttatgattac gccaatatgt
19681  tctttatgtt agcgacaggc gaaaggctgc aaggtttata tgcttataat atcccgtttg
19741  ataataaagc aaagattgaa aaatatggtc aaataattaa aaactatgac agcttttac
19801  cgcaaaagtt ggatattgtc gttttcccgt caaagtatgg tggcggagct ggacacgttg
19861  aaattgttga gagcgcaaat ttaaatactt tcacatcatt tggtcaaaac tggaacggta
19921  aaggttggac taatggcgtt gcgcaacctg gttggggtcc tgaaactgtg acaagacatg
19981  ttcattatta tgacaatcca atgtatttta ttaggttaaa cttccctaac aacttaagcg
20041  ttggcaataa agctaaaggt attattaagc aagcgactac aaaaaaagag gcagtaatta
20101  aacctaaaaa aattatgctt gtagccggtc atggttataa cgatcctgga gcagtaggaa
20161  acggaacaaa cgaacgcgat tttatacgta aatatataac gcctaatatc gctaagtatt
20221  taagacatgc aggacatgaa gttgcattat acgtggctc aagtcaatca caagatatgt
20281  atcaagatac tgcatacggt gttaatgtag gcaataaaaa agattatggc ttatattggg
20341  ttaaatcaca ggggtatgac attgttctag aaatacattt agacgcagca ggagaaagcg
20401  caagtggtgg gcatgttatt atctcaagtc aattcaatgc agatactatt gataaaagta
20461  tacaagatgt tattaaaaat aacttaggac aaataagagg tgtgacacct cgtaatgatt
20521  tactaaatgt taatgtatca gcagaaataa atataaatta tcgtttatcc gaattaggtt
20581  ttattactaa taaaaatgat atggattgga ttaagaaaaa ctatgacttg tattctaaat
20641  taatagccgg tgcgattcat ggtaagccta taggtggttt ggtagctggt aatgttaaaa
20701  catcagctaa aaacaaaaaa aatccaccag tgccagcagg ttatacactc gataagaata
20761  atgtccctta taaaaagaa caaggcaatt acacagtagc taatgttaaa ggtaataatg
20821  taagagacgg ttattcaact aattcaagaa ttacagggt attcccaac aacacaacaa
20881  ttacgtatga cggtgcatat tgtattaatg gttatagatg gattacttat attgctaata
20941  gtggacaacg tcgttatata gcgacaggag aggtagacaa ggcaggtaat agaataagta
21001  gttttggtaa gtttagcacg atttagtatt tacttagaat aaaaattttg ctacattaat
21061  tatagggaat cttacagtta ttaaataact atttggatgg atgttaatat tcctatacac
21121  tttttaacat ttctctcaag atttaaatgt agataacagg caggtacttc ggtacttgcc
21181  tattttttta tgttatagct agccttcggg ctagtttttt gttatgatgt gttacacatg
```

TABLE 2-continued

>Bacteriophage 77, complete genome sequence, 41708 nucleotides

```
21241  catcaactat ttacatctat ccttgttcac ccaagcatgt cactggatgt ttttcttgc
21301  gatagagagc atagttttca tactactccc cgtagtatat atgactttag cattcccgta
21361  taacagttta cggggtgctt ttatgttata attgctttta tatagtagga gtgaactata
21421  tagccgggca gaggccatgt atctgactgt tggtcccaca ggagacatct tccttgtcat
21481  cactcgatac atatatctta acaacataga aatgttacat tcgctataac cgtatcttaa
21541  tcgatacggt tatatttatt cccctacaac caacaaaacc acagatccta ttaatttagg
21601  attgtggtta ttttttgcgt ttttttgggg caaaaaaagg gcagattatt tgaaaaggg
21661  caaacgcttg tggaaaagct aaaaggttaa aaatgacaaa aaccttgata caacagtgtt
21721  tttggacgct cgtgtacgtt agagaatgac cggtttacca tcatacaagg gtgggattaa
21781  cttgtgttaa aaagccttta atatcagttg ttacaaagga tttgtagcgt ctttaaaaat
21841  aaaaagggc agaaaaggg cagatacctt ttagtacaca agttttcta attttgctc
21901  taactctctg tccattttct ctgttacatg tgtatacacc tttatagtcg ttttttcatc
21961  tgtatgtcct actcttttca taattgcttt taacgatata ttcatttccg ccaataaact
22021  tatgtgtgta tgccttagtg tgtgagtagt aacttttta tttatattta atgattctgc
22081  agctgaggac aatcgtttgt ttatcctact gccttgcata ggatttcctt ggcaagttgt
22141  gaatataaac cctctatcaa catagcttgg ttcccattgt tgcatctttt tattttctaa
22201  cattatttt ttcaatacat ttgctatcct tgaattgatg gcgattttc ttcttgaacc
22261  tgcggtctta gtagtatctt tgtgaccaaa tccagcatta catttgattc tgtgaatagt
22321  gccattaata gcgatcgttt tattttgag gtcaacatct ttaacttgga gagctaataa
22381  ctcacctatg cgcataccctg ttaaagcttg aacttctaca gccccagcaa ctaaaatacg
22441  agctctatac tgcatgttat tatcgttcag tataaaatcg cgtatctgta ttacctgttc
22501  catctctaaa tagttataca ttttcgcttc ttcttttct atatcttcta tcgtcttact
22561  cttctttggt agtgtgacgc tatttaatat gtgttcgttt ggataattgt aaaatttaac
22621  ggcgtattta atagcttctt tcatatgtcc aagttgacgc tttacctgat ttgcagaata
22681  tacgtttgat aatttgttaa taaatgtttg catgtacttt gtatcaattt tgtttaaaag
22741  taaattttga gaactgttct ttttgatgtt tttgattctt gttttcaaat tatcaagcgt
22801  cgttacttta aagccagatg tttttatatg atattcaagc cattcatcta ataacgcgtg
22861  aaaagtcaaa gtttttaatt cgcttgacga cttgttgttt agtttttctt ttattttttc
22921  ttctaaacga aacattgcct cttttttgcga ttgctttgta ttcttattca agacaacact
22981  tacacgtttc catttatctg tatacggatc tttgtatttc tcgtagtatc tatacttcgt
23041  ttcattgttc ttatttttaa atttttcaaa ccacatttta catccctcct caaaattggc
23101  aaaaaataat aagggtaggc gggctaccca tgaaaattgt ataaaaaag acgcctgtat
23161  aaaatacaga cgccacttat aattataaga ttacatggtt aattaccaaa aatggtaacg
23221  aatatatacg tgttttaaag gataaacctt taatatatta aaattatatc atcttatatc
23281  agggatctgc aatatatatt tattaattct atttatcagt aacataatat ccgaagaatc
23341  tattactgga tttttaattt tttgggtaa aacttttctt atgcgaaact tactaatcgg
23401  ctggaaagaa tttatgcaag cgtaactatt acctttaat ttttttacct tatcaattgc
23461  tgatactatg ttattaatgt ttctgtcaat tttatttaat ttattttcaa tttctaaact
```

TABLE 2-continued

>Bacteriophage 77, complete genome sequence, 41708 nucleotides

```
23521   atcagatata aattcaataa aataatcttt agtgatgaat tctgtgttgt tttttggta
23581   tttttatcg aaaacttctt ttaatatagc tgaattattt tgcgcgctaa ttaaatttaa
23641   aaacaatctt aaataatact cccatttcaa atcaaaattc atctttaaat acttttttgtt
23701   ttcttagag gataagggaa taacatttac tatatcctcc gtattagaat cattttttatt
23761   catcactatt gcaaagtgtg aattagaaaa ttctttatta acgtttatac cgaaatctac
23821   aaaaactatt tctccttgtt taaactttgg ataaaaacct ttatggtttt tttcacccttc
23881   aaatctcttg agtaaatagt gaatatctga atctaacttt ttaaattttg gatttccaga
23941   agttttttaat ttattaatgc gttttttctat attatgcgtc atcatttctc ctttattctc
24001   gctcacactc tcaccaccat tcaacgtcta cacttgtagg cgttttttga ttagtaaaat
24061   cataatgaat cttctttggt taacttatcg ccatctattt tttgtgaa&t aaattccaag
24121   tatttacgcg cattatgtga cgataaatct ttaggtaact cataagtgaa tggttgatta
24181   ccactagtta aaacttcata tactatagtt tcttttttta ttttgcaatt agttattttc
24241   attataaact cctttttaaac actgctgaaa tagacgtctt tttcaaataa gcatgattaa
24301   tactttaatt cttaatcca catatattta aaagtgaggt agtaggtaat aaatataaga
24361   cttaaagtta agattgcttt tttcatgtca atttctcctt tgtttatatt tatattaaag
24421   cgctaaatat acgttattaa tcacaataca actttgccca ttactttaat atcactaaac
24481   gaagcgactt tgatatcatc atacttcgga tttagagata ccaaattaat atagtcttcg
24541   catatatcta cacgcttgat aagacttact ccatctaata caacgagtgc aattgtacca
24601   tctttaatag aatcttcttt cttaataaaa gcgtatgttc cttgttttaa cataggttcc
24661   attgaatcac cattaactaa aatacaaaaa tcagcatttg atggcgtttc gtcttctttta
24721   aaaaatactt cttcatgcaa tatgtcatca tataattctt ctcctatgcc agcaccagtt
24781   gcaccacatg caatatacga tactagttta gactctttat attcatctat agaagtgact
24841   ttattctgtt catctaattg ctccatttgca tagttaagta cgttttcttg gcggggaggt
24901   gtgagttgag aaaatatgtt attgatttttt gacattatcg tttcatccttg acgttcttcg
24961   tcaggaactc gataagaatc tacatcatac cccataagcc acgcttcacc gacatttaaa
25021   gttttagata ataagaataa tttatgttgg tctggagaag accttccatt aacatactgg
25081   gataagtgac tttttgacat tttaatattc aattcttttt gaaagggttt cgacttttct
25141   agaatatcta cttgacgcaa gttcctatct ttcataattt gttttaatct ttcagaagtg
25201   ttttgcattg gtaatgcctc cttgaaattc attatatagg aagggaaata aaaatcaata
25261   caaaagttca acttttttaa ctttttgtgt tgacattgtt caaaattggg gttatagtta
25321   ttatagttca aatgtttgaa cttaggaggt gattatttga atactaatac aacttttgat
25381   ttttcgttat tgaacggtaa gatagtcgaa gtgtactcga cacaatttaa ctttgctata
25441   gctttaggtg tatcagaaag aactttgtct ttgaagttga acaacaaagt accatggaaa
25501   acaacagaca ttattaaagc ttgtaagtta ttgggaatac ctataaaaga tgttcacaaa
25561   tatttttta aacagaaagt tcaaatgttt gaacttaata agtaaaggag gcataacaca
25621   tgcaagaacg agaaaaggtt aataaaagta acacatcttc aaatgaagca tcaaaaccctt
25681   ttaggacaaa ttgaagctta cgacaaaacg cttaaagaaa taaagtacac tcgagacctt
25741   tacaacaaac acctaagcat gaacaacgaa gacgcattcg ctggtttgga aatggtagag
25801   gatgaaatta ctaaaaagct acgaagtgct atcaaagagt tccaaaaagt agtgaaagcg
```

TABLE 2-continued

>Bacteriophage 77, complete genome sequence, 41708 nucleotides

```
25861  ttagacaagc ttaacggtgt tgaaagcgat aacaaagtta ctgatttaac agagtggcgg
25921  aaagtgaatc agtaacattc acttcttaat ataaccacgc ttatcaacat ccacattgag
25981  cagatgtgag cgagagctgg cgatgatatg agccgcgttt aaatacattc gatagtcatt
26041  gcgataaccg tctgctgaat gtgggtgttg aggaaaaagg aggatactca aatgcaagca
26101  ttacaaacat ttaattttaa agagctacca gtaagaacag tagaaattga aaacgaacct
26161  tattttgtag gaaaagatat tgctgagatt ttaggatatg caagatcaaa caatgccatt
26221  agaaatcatg ttgatagcga ggacaagctg acgcaccaat ttagtgcatc aggtcaaaac
26281  agaaatatga tcattatcaa cgaatcagga ttatacagtc taatcttcga tgcttctaaa
26341  caaagcaaaa acgaaaaaat tagagaaacc gctagaaaat tcaaacgctg ggtaacatca
26401  gatgtcctac cagctattcg caaacacggt atatacgcaa cagacaatgt aattgaacaa
26461  acattaaaag atccagacta catcattaca gtgttgactg agtataagaa agaaaaagag
26521  caaaacttac ttttacaaca gcaagtagaa gttaacaaac caaaagtatt attcgctgac
26581  tcggtagctg gtagtgataa ttcaatactt gttggagaac tagcgaaaat acttaaacaa
26641  aacggtgttg atataggaca aaacagattg ttcaaatggt taagaaataa tggatatctc
26701  attaaaaaga gtggagaaag ttataactta ccaactcaaa agagtatgga tctaaaaatc
26761  ttggatatca aaaaacgaat aattaataat ccagatggtt caagtaaagt atcacgtaca
26821  ccaaaagtaa caggcaaagg acaacaatac tttgttaata agttttagg agaaaaacaa
26881  acatcttaaa aggaggaaca caatggaaca aatcacatta accaaagaag agttgaaaga
26941  aattatagca aaagaagtta gagaggctat aaatggcaag aaaccaatca gttcaggttc
27001  aattttcagt aaagtaagaa tcaataatga cgatttagaa gaaatcaata aaaaactcaa
27061  tttcgcaaaa gatttgtcgc taggaagatt gaggaagctc aatcatccga ttccgctaaa
27121  aaagtatcag catggcttcg aatcaattca tcaaaaagct tatgtacaag atgttcatga
27181  ccatattaga aaattaacat tatcaatttt tggagtgaca cttaattcag acttgagtga
27241  aagtgaatac aacctagcag caaaagttta tcgagaaatc aaaaactatt atttatacat
27301  ctatgaaaag agagtttcag aattaactat cgatgatttc gaataaagga ggaacaacaa
27361  atgttacaaa aatttagaat tgcgaaagaa aaaaataaat taaaactcaa attactcaag
27421  catgctagtt actgtttaga aagaaacaac aaccctgaac tgttgcgagc agttgcagag
27481  ttgttgaaaa aggttagcta aattcaacgg taaggatttg ccctgcctcc acacttagag
27541  tttgagatcc aacaaacaca taagttttag tagggtctag aaaaaatgtt tcgatttcct
27601  cttttgtaac agtttcaatt ccttcatatc ctggaaaaac aattttcttt aaatccgaaa
27661  catgtttttt tgaaccatcc tttaaagtaa ctagaagttt catacttatc acctccttag
27721  gttgataaca acattataca cgaaggagc ataaacaata tgcaagcatt acaaacaaat
27781  tcgaacatcg gagaaatgtt caatattcaa gaaaaagaaa atggagaaat cgcaatcagc
27841  ggtcgagaac ttcatcaagc attagaagtt aagacagcat ataaagattg gtttccaaga
27901  atgcttaaat acggatttga agaaaataca gattcacag ctatcgctca aaaaagagca
27961  acagctcaag gcaatatgac tcactatatt gaccacgcac tcacactaga cactgcaaaa
28021  gaaatcgcaa tgattcaacg tagtgaacct ggcaaacgtg caagacaata tttcatccaa
28081  gttgaaaaag catggaacag cccagaaatg attatgcaac gtgctttaaa aattgctaac
```

TABLE 2-continued

>Bacteriophage 77, complete genome sequence, 41708 nucleotides

| | | | | | |
|---|---|---|---|---|---|
| 28141 | aacacaatca | atcaattaga | aacaaagatt | gcacgtgaca | aaccaaaaat | tgtatttgca |
| 28201 | gatgcagtag | ctactactaa | gacatcaatt | ttagttggag | agttagcaaa | gatcattaaa |
| 28261 | caaaacggta | taaacatcgg | gcaacgcaga | ttgtttgagt | ggttacgtca | aaacggattc |
| 28321 | cttattaaac | gcaagggtgt | ggattataac | atgcctacac | agtattcaat | ggaacgtgag |
| 28381 | ttattcgaaa | ttaaagaaac | atcaatcaca | cattcggacg | gtcacacatc | aattagtaag |
| 28441 | acgccaaaag | taacaggtaa | aggacaacaa | tactttgtta | acaagttttt | aggagaaaaa |
| 28501 | caaacaactt | aataggagga | attacaaatg | aacgcactat | acaaaacaac | cctcctcatc |
| 28561 | acaatggcag | ttgtgacgtg | gaaggtttgg | aagattgaga | agcacactag | aaaacctgtg |
| 28621 | attagtagca | gggcgttgag | tgactatcta | aacaacaaat | ctttaaccat | accgaaagat |
| 28681 | gctgaaaatt | ctactgaatc | tgctcgtcgc | cttttgaagt | tcgccgaaca | aactattagc |
| 28741 | aaataacaac | attatacacg | aaaggaaaga | tagaaatgcc | aaaaatcata | gtaccaccaa |
| 28801 | caccagaaaa | cacatataga | ggcgaagaaa | aatttgtgaa | aaagttatac | gcaacaccta |
| 28861 | cacaaatcca | tcaattgttt | ggagtatgta | gaagtacagt | atacaactgg | ttgaaatatt |
| 28921 | accgcaaaga | taatttaggt | gtagaaaatt | tatacattga | ttattcacca | acaggcactc |
| 28981 | tgattaatat | ttctaaattg | gaagagtatt | tgatcagaaa | gcataaaaaa | tggtattagg |
| 29041 | aggatattaa | atgagcaaca | tttataaaag | ctacctagta | gcagtattat | gcttcacagt |
| 29101 | cttagcgatt | gtacttatgc | cgtttctata | cttcactaca | gcatggtcaa | ttgcgggatt |
| 29161 | cgcaagtatc | gcaacattca | tgtactacaa | agaatgcttt | ttcaaagaat | aaaaaaactg |
| 29221 | ctacttgttg | gagcaagtaa | cagtatcaaa | cacttaagaa | aaaattcatg | ttcaatataa |
| 29281 | aacgaaaaac | ggaggaagtc | aagatgtatt | acgaaatagg | cgaaatcata | cgcaaaaata |
| 29341 | ttcatgttaa | cggattcgat | tttaagctat | tcattttaaa | aggtcatatg | ggcatatcaa |
| 29401 | tacaagttaa | agatatgaac | aacgtaccaa | ttaaacatgc | ttatgtcgta | gatgagaatg |
| 29461 | acttagatat | ggcatcagac | ttatttaacc | aagcaataga | tgaatggatt | gaagagaaca |
| 29521 | cagacgaaca | ggacagacta | attaacttag | tcatgaaatg | gtaggaggtc | gctatgaagc |
| 29581 | agactgtaac | ttatatcatt | cgtcataggg | atatgccaat | ttatataact | aacaaaccaa |
| 29641 | ctgataacaa | ttcagatatt | agttactcca | caaatagaaa | tagagctagg | gagtttaacg |
| 29701 | gtatggaaga | agcgagtatc | aatatggatt | atcacaaagc | aatcaagaaa | acagtgacag |
| 29761 | aaactattga | gtacgaggag | gtagaacatg | actgaggaaa | aacaagaacc | acaagaaaaa |
| 29821 | gtaagcatac | tcaaaaaact | aaagataaat | aatatcgctg | agaaaaataa | aaggaaattc |
| 29881 | tataaatttg | cagtatacgg | aaaaattggc | tcaggaaaaa | ccacgtttgc | tacaagagat |
| 29941 | aaagacgctt | tcgtcattga | cattaacgaa | ggtggaacaa | cggttactga | cgaaggatca |
| 30001 | gacgtagaaa | tcgagaacta | tcaacacttt | gtttatgttg | taaattttt | acctcaaatt |
| 30061 | ttacaggaga | tgagagaaaa | cggacaagaa | atcaatgttg | tagttattga | aactattcaa |
| 30121 | aaacttagag | atatgacatt | gaatgatgtg | atgaaaaata | agtctaaaaa | accaacgttt |
| 30181 | aatgattggg | gagaagttgc | tgaacgaatt | gtcagtatgt | acagattaat | aggaaaactt |
| 30241 | caagaagaat | acaaattcca | ctttgttatt | acaggtcatg | aagtatcaa | caaagataaa |
| 30301 | gatgatgaag | gtagcactat | caaccctact | atcactattg | aagcgcaaga | acaaattaaa |
| 30361 | aaagctatta | cttctcaaag | tgatgtgtta | gctagggcaa | tgattgaaga | atttgatgat |
| 30421 | aacggagaaa | agaaagctag | atatattcta | aacgctgaac | cttctaatac | gtttgaaaca |

TABLE 2-continued

>Bacteriophage 77, complete genome sequence, 41708 nucleotides

```
30481   aagattagac attcaccttc aataacaatt aacaataaga aatttgcaaa tcctagcatt
30541   acgacgtag  tagaagcaat tagaaatgga aactaaaaat taattaaaag gacggtattt
30601   aattatgaaa atcacaggac aagcgcaatt tactaaagaa acaaatcaag aaaagttta
30661   taacggctca gcagggtttc aagctggaga attcacagtg aaagttaaaa atattgaatt
30721   caatgataga gaaaatagat atttcacaat cgtatttgaa aatgatgaag gcaaacaata
30781   taaacataat caatttgtac cgccgtataa atatgatttc caagaaaaac aattgattga
30841   attagttact cgattaggta ttaagttaaa tcttcctagc ttagattttg ataccaatga
30901   tcttattggt aagttttgtc acttggtatt gaaatggaaa ttcaatgaag atgaaggtaa
30961   gtattttacg gattttcat ttattaaacc ttacaaaag gcgatgatg ttgttaacaa
31021   acctattccg aagacagata agcaaaaagc tgaagaaaat aacggggcac aacaacaaac
31081   atcaatgtct caacaaagca atccatttga aagcagtggc caatttggat atgacgacca
31141   agatttagcg ttttaaggtg tggtttaaat gcaatacatt acaagatacc agaaagataa
31201   cgacggtact tattccgtcg ttgctactgg tgttgaactt gaacaaagtc acattgactt
31261   actagaaaac ggatatccac taaaagcaga agtagaggtt ccggacaata aaaaactatc
31321   tatagaacaa cgcaaaaaaa tattcgcaat gtgtagagat atagaacttc actgggcga
31381   accagtagaa tcaactagaa aattattaca aacagaattg gaaattatga aggttatga
31441   agaaatcagt ctgcgcgact gttctatgaa agttgcaagg gagttaatag aactgattat
31501   agcgtttatg tttcatcatc aaatacctat gagtgtagaa acgagtaagt tgttaagcga
31561   agataaagcg ttattatatt gggctacaat caaccgcaac tgtgtaatat gcggaaagcc
31621   tcacgcagac ctggcacatt atgaagcagt cggcagaggc atgaacagaa acaaaatgaa
31681   ccactatgac aaacatgtat tagcgttatg tcgcgaacat cacaacgagc aacatgcgat
31741   tggcgctaag tcgtttgatg ataaataccca cttgcatgac tcgtggataa aagttgatga
31801   gaggctcaat aaaatgttga aggagagaa aaaggaatga atagactaag aataataaaa
31861   atagcactcc taatcgtcat cttggcggaa gagattagaa atgctatgca tgctgtaaaa
31921   gtggagaaaa ttttaaaatc tccgtttagt taatacaggt ttttacaaaa gctttaccat
31981   aggcggacaa actaattgag cctttttttga tgtctattac ccagggggctg taatgtaact
32041   ttaatacttc aaattcaatg ccagaaagtt tacttattgt ttctaggttg tgtcctgact
32101   ttaacattct tttaacaaat tctaatcccg aaacaaatct ttgtttttct ataatcttat
32161   taaaagtgat taaaaactga ggagcataaa acttattata aattccttt tttgttaagt
32221   aagacatgtc aaaagtttca tttaaaaccc ctaaccttac taggttatta attgaaattt
32281   cggttgattc tatatctaac ggagagtctt ttattaacgt gtccgatata ttcataccgt
32341   cattctttgg gtttaaaacc gctctatatt taacggcagg atgtacttcg tgattcttta
32401   aatgttttaa aagaatagca tcatttgggg ataattgttt aattatttca acaaatgaat
32461   ggtgggttaa tgagttttt ctgtcatcca tagatgatgc tattagtttt gcgaacatat
32521   tacttaaagt ttttcacta atgtaaaact ttgaagcttc tagagcagga cctagaagag
32581   aaaattgtgg ttcttgtaaa ttattttag gtacagaaga tatttctttt ttaaattgtt
32641   ctttgaattt ttcaaattct acttctcttt gataaataac tttatccaca taaggtgga
32701   atttcccaaa gacaagttcc caagttttag agaatgtttc tacaggccct tttgatgcgc
```

TABLE 2-continued

>Bacteriophage 77, complete genome sequence, 41708 nucleotides

```
32761  cttcaataat tttatcaata cctttaccta aaataggatc cataattatt caccccaat
32821  ctaacgcaat agcgataata aaattatacc agaaaggaga atcaacatga ctgaccaacc
32881  aagttactac tcaataatta cagcaaatgt cagatacgat aaccgactta ctgacagcga
32941  aaagttactt tttgcagaaa taacatcttt aagtaacaaa tacggatact gcacagcaag
33001  taatggttac tttgcaactt tatacaacgt tgttaaggaa actatatctc gtagaatttc
33061  gaaccttacc aactttggtt atctaaaaat cgaaattatc aagaaggta atgaagttaa
33121  acaaaggaag atgtacccct tgacgcaaac gtcaatacct attgacgcaa aaatcaatac
33181  ccctattgat aatttcgtca ataccccat tgacgcaaat gtcaaagaga atattacaag
33241  tattaataat acaagtaata acaatataaa tagaatagat atattgtcgg caacccgac
33301  agcatcttct atacctata aagaaattat cgattactta acaaaaaag cgggcaagca
33361  ttttaaacac aatacagcta aaacaaaga ttttattaaa gcaagatgga atcaagattt
33421  taggttggag gattttaaaa aggtgattga tatcaaaaca gctgagtggc taaacacgga
33481  tagcgataaa taccttagac cagaaacact ttttggcagt aaatttgagg ggtacctcaa
33541  tcaaaaaata caaccaactg gcacggatca attggaacgc atgaagtacg acgaaagtta
33601  ttgggattag ggggatatta tgaaaccact attcagcgaa aagataaacg aaagcttgaa
33661  aaaatatcaa cctactcatg tcgaaaaagg attgaaatgt gagagatgtg aagtgaata
33721  cgacttatat aagtttgctc ctactaaaaa acacccgaat ggttacgagt ataagacgg
33781  ttgcaaatgt gaaatctatg aggaatataa gcgaaacaag caaoggaaga taaacaacat
33841  attcaatcaa tcaaacgtta atccgtcttt aagagatgca acagtcaaaa actacaagcc
33901  acaaaatgaa aaacaagtac acgctaaaca aacagcaata gagtacgtac aaggcttctc
33961  tacaaaagaa ccaaaatcat taatattgca aggttcatac ggaactggta aaagccacct
34021  agcatacgct atcgcaaaag cagtcaaagc taaagggcat acggttgctt ttatgcacat
34081  accaatgttg atggatcgta tcaaagcgac atacaacaaa aatgcagtag agactacaga
34141  cgagctagtc agattgctaa gtgatattga tttacttgta ctagatgata tgggtgtaga
34201  aaacacagag cacactttaa ataaactttt cagcattgtt gataacagag taggtaaaaa
34321  tataaattcg agaatgaaaa aaagagcaag aaaagtaaga gtaatcggag acgatttcag
34381  ggagcgagat gcatggtaac caaagaattt ttaaaaacta aacttgagtg ttcagatatg
34441  tacgctcaga aactcataga tgaggcacag ggcgatgaaa ataggttgta cgacctattt
34501  atccaaaaac ttgcagaacg tcatacacgc cccgctatcg tcgaatatta aggagtgtta
34561  aaaatgccga aagaaaaata ttacttatac cgagaagatg gcacagaaga tattaaggtc
34621  atcaagtata aagacaacgt aaatgaggtt tattcgctca caggagccca tttcagcgac
34681  gaaaagaaaa ttatgactga tagtgaccta aaacgattca aaggcgctca cgggcttcta
34741  tatgagcaag aattaggttt acaagcaacg atatttgata tttagaggtg gacgatgagt
34801  aaatacaacg ctaagaaagt tgagtacaaa ggaattgtat ttgatagcaa agtagagtgt
34861  gaatattacc aatatttaga aagtaatatg aatggcacca attatgatca tatcgaaata
34921  caaccgaaat tcgaattatt accaaaacta gataaacaac gaaagattga atatattgca
34981  gacttcgcgt tatatctcga tggcaaactg attgaagtta tcgacattaa aggtatgcca
35041  accgaagtag caaaacttaa agctaagatt ttcagacata aatacagaaa cataaaactc
35101  aattggatat gtaaagcgcc taagtataca ggtaaaacat ggattacgta cgaggaatta
```

TABLE 2-continued

| >Bacteriophage 77, complete genome sequence, 41708 nucleotides |

```
35161  attaaagcaa gacgagaacg caaaagagaa atgaagtgat ctaatgcaac aacaagcata
35221  tataaatgca acgattgata taaggatacc tacagaagtt gaatatcagc attttgatga
35281  tgtggataaa gaaaagaag cgctggcaga ttacttatat aacaatcctg acgaaatact
35341  agagtatgac aatttaaaaa ttagaaacgt aaatgtagag gtggaataaa tgggcagtgt
35401  tgtaatcatt aataataaac catataaatt taacaatttt gaaaaaagaa ataatggcaa
35461  agcgtgggat aaatgctgga attgtttcta aacgtgttag aggttgttgg gagttttcag
35521  aagctttaga cgcgccttat ggcatgcacc taaaagaata tagagaaatg aaacaaatgg
35581  aaaagattaa acaagcgaga ctcgaacgtg aattggaaag agagcgaaag aaagaggctg
35641  agctacgtaa gaagaagcca catttgttta atgtacctca aaaacattca cgtgatccgt
35701  actggttcga tgtcacttat aaccaaatgt tcaagaaatg gagtgaagca taatgagcat
35761  aatcagtaac agaaaagtag atatgaacaa aacgcaagac aacgttaagc aacctgcgca
35821  ttacacatac ggcgacattg aaattataga tttattgaa caagttacgc cacagtaccc
35881  accacaatta gcattcgcaa taggtaatgc aattaaatac ttgtctagag caccgttaaa
35941  gaatggtcat gaggatttag caaaggcgaa gttttacgtc gatagagtat ttgacttgtg
36001  ggagtgatga ccatgacaga tagcggacgt aaagaatact taaaacattt tttcggctct
36061  aagagatatc tgtatcagga taacgaacga gtggcacata tccatgtagt aaatggcact
36121  tattactttc acggtcatat cgtgccaggt tggcaaggtg tgaaaaagac atttgataca
36181  gcggaagagc ttgaaacata tataaagcaa agtgatttgg aatatgagga acagaagcaa
36241  ctaactttat ttaaaagg cggaaacaat gaaaatcaaa attgaaaaag aaatgaattt
36301  acctgaactt atccaatggg cttgggataa ccccaagtta tcaggtaata aagattcta
36361  ttcaaatgat gttgagcgca actgttttgt gactttcat gttgatagca tcttatgtad
36421  tgtgactgga tatgtatcaa ttaacgataa atttactgtt caagaggaga tataacaatg
36481  aaaatcaaag ttaaaaaaga aatgagatta gatgaattaa ttaaatgggc gcgagaaaat
36541  ccggatctat cacaaggaaa atatttttt tcaacaggat ttagtgatgg attcgttcgt
36601  tttcatccaa atacaaataa gtgttcgacg tcaagtttta ttccaattga tatcccctcc
36661  atagttgata ttgaaaaaga agtaacggaa gagactaagg ttgataggtt gattgaatta
36721  ttcgagattc aagaaggaga ctataactct acactatatg agaacactag tataaaagaa
36781  tgtttatatg gcagatgtgt gcctaccaaa gcattctaca tcttaaacga tgacctaact
36841  atgacgttaa tctggaaaga tggggagttg ctagtatgat gttgaaattt aaagcttggg
36901  ataaagataa aaaagttatg agtattattg acgaaatcga ttttaatagt gggtacattt
36961  tgatttcaac aggttataaa agtttcaatg aagtaaaact attacaatac acaggattta
37021  aagatgtgca cggtgtggag atttatgaag gggatattgt tcaagattgt tattcgagag
37081  aagtaagttt tatcgagttt aaagaaggag cctttttatat aacttttagc aatgtaactg
37141  aattactaag tgaaaatgac gatattattg aaattgttgg aaatattttt gaaaatgaga
37201  tgctattgga ggttatgaga tgacgttcac cttatcagat gaacaatata aaaatctttg
37261  tactaactct aacaagttat tagataaact tcacaaagca ttaaaagatc gtgaagagta
37321  caagaagcaa cgagatgagc ttattgggga tatagcgaag ttacgagatt gtaacaaaga
37381  tctagagaag aaagcaagcg catgggatag gtattgcaag agcgttgaaa aagatttaat
```

TABLE 2-continued

>Bacteriophage 77, complete genome sequence, 41708 nucleotides

| | | | | | |
|---|---|---|---|---|---|
| 37441 | aaacgaattc | ggtaacgatg | atgaaagagt | taaattcgga | atggaattaa acaataaaat |
| 37501 | ttttatggag | gatgacacaa | atgaataatc | gcgaaaaaat | cgaacagtcc gttattagtg |
| 37561 | ctagtgcgta | taacggtaat | gacacagagg | ggttgctaaa | agagattgag gacgtgtata |
| 37621 | agaaagcgca | agcgtttgat | gaaatacttg | agggaatgac | aaatgctatt caacattcag |
| 37681 | ttaaagaagg | tattgaactt | gatgaagcag | tagggattat | ggcaggtcaa gttgtctata |
| 37741 | aatatgagga | ggaataggaa | aatgactaac | acattacaag | taaaactatt atcaaaaaat |
| 37801 | gctagaatgc | ccgaacgaaa | tcataagacg | gatgcaggtt | atgacatatt ctcagctgaa |
| 37861 | actgtcgtac | tcgaaccaca | agaaaaagca | gtgatcaaaa | cagatgtagc tgtgagtata |
| 37921 | ccagagggct | atgtcggact | attaactagt | cgtagtggtg | taagtagtaa aacgtattta |
| 37981 | gtgattgaaa | caggcaagat | agacgcggga | tatcatggca | atttagggat taatatcaag |
| 38041 | aatgatgaag | aacgtgatgg | aatacccttt | ttatatgatg | atatagacgc tgaattagaa |
| 38101 | gatggattaa | taagcatttt | agatataaaa | ggtaactatg | tacaagatgg aagaggcata |
| 38161 | agaagagttt | accaaatcaa | caaaggcgat | aaactagctc | aattggttat cgtgcctata |
| 38221 | tggacaccgg | aactaaagca | agtggaggaa | ttcgaaagtg | tttcagaacg tggagcaaaa |
| 38281 | ggcttcggaa | gtagcggagt | gtaaagacat | cttagatcga | gttaaggagg ttttggggaa |
| 38341 | gtgacgcaat | acttagtcac | aacattcaaa | gattcaacag | gacgaccaca tgaacatatt |
| 38401 | actgtggcta | gagataatca | gacgtttaca | gttattgagg | cagagagtaa agaagaagcg |
| 38461 | aaagagaagt | acgaggcaca | agttaaaaga | gatgcagtta | ttaaagtggg tcagttgtat |
| 38521 | gaaaatataa | gggagtgtgg | gaaatgacgg | atgttaaaat | taaaactatt tcaggtggag |
| 38581 | tttattttgt | aaaaacagct | gaaccttttg | aaaaatatgt | tgaaagaatg acgagtttta |
| 38641 | atggttatat | ttacgcaagt | actataatca | agaaaccaac | gtatattaaa acagatacga |
| 38701 | ttgaatcaat | cacacttatt | gaggagcatg | ggaaatgaat | cagctgagaa ttttattaca |
| 38761 | tgacggtagt | agtttgatat | tacatgaaga | tgaattattt | aacgaaatag tatttgtttt |
| 38821 | ggacaatttt | agaaatgatg | atgactattt | aacgatagaa | aaagattatg gcagagaact |
| 38881 | tgtattgaac | aaaggttata | tagttgggat | caatgttgag | gaggcagatg atgattaaca |
| 38941 | tacctaaaat | gaaattcccg | aaaaagtaca | ctgaaataat | caaaaaatat aaaaataaag |
| 39001 | cacctgaaga | aaaggctaag | attgaagatg | attttattaa | agaaattaaa gataaagaca |
| 39061 | gtgaatttta | cagtcctacg | atggctaata | tgaatgaata | tgaattaagg gctatgttaa |
| 39121 | gaatgatgcc | tagtttaatt | gatactggag | atgacaatga | tgattaaaaa acttaaaaat |
| 39181 | atggatgggt | tcgacatctt | tattgttgga | atactgtcat | tattcggtat attcgcattg |
| 39241 | ctacttgtta | tcacattgcc | tatctataca | gtggctagtt | accaacacaa agaattacat |
| 39301 | caaggaacta | ttacagataa | atataacaag | agacaagata | aagaagacaa gttctatatt |
| 39361 | gtattagaca | acaaacaagt | cattgaaaat | tccgacttat | tattcaaaaa gaaatttgat |
| 39421 | agcgcagata | tacaagctag | gttaaaagta | ggcgataagg | tagaagttaa acaatcggt |
| 39481 | tatagaatac | actttttaaa | tttatatccg | gtcttatacg | aagtaaagaa ggtagataaa |
| 39541 | caatgattaa | acaaatacta | agactattat | tcttactagc | aatgtatgag ttaggtaagt |
| 39601 | atgtaactga | gcaagtgtat | attatgatga | cggctaatga | tgatgtagag gcgccgagtg |
| 39661 | attacgtctt | tcgagcggag | gtgagtgaat | aatgagaata | tttatttatg atttgatcgt |
| 39721 | tttgctgttt | gctttcttaa | tatccatata | tattattgat | gatggagtga taataaatgc |

TABLE 2-continued

>Bacteriophage 77, complete genome sequence, 41708 nucleotides

```
39781    attaggaatt tttggtatgt ataaaattat agattccttt tcagaaaata ttataaagag
39841    gtagataaaa atgaacgagc aaataatagg aagcatacat actttagcag gaggtgttgt
39901    gctttattca gttaaagaga tttttaggta ttttacagat tccaacttac aacgtaaaaa
39961    aatcaattta gaacaaatat atccgatata tttagattgt tttaaaaagg ctaaaaagat
40021    gattggagct tatattattc caacagaaca gcatgaattt ttagatttt ttgatattga
40081    agtctttaat aatttagata agcaaagtaa aaaagcgtat gaaaatgtta ttggatttag
40141    acaaatgatt aatttatcaa atagagttaa ggcaatggaa gattttaaga tgagtttcaa
40201    caatgaattt agtacaaatc agatttttt taatccttcc tctgttatgg aaacaattgc
40261    tattataaat gaatatcaaa aagatatatc ttatttaaaa aacataatta ataaaatgaa
40321    tgaaaataga gcttataatc atattgatag ttttatcact tcagagtacc gacgaaaaat
40381    aaacgattat aatctttatc ttgataaatt tgaagaacag tttagtcaaa agtttaaaat
40441    aaacagaact tcgataaaag aaagaattat tattaattta aacaagagga gatttaaatg
40501    atgtggatta ctatgactat tgtatttgct atattgctat tagtttgtat cagtattaat
40561    agtgatcgtg caagagagat acaagcactt agatatatga atgattatct acttgatgaa
40621    gtagttaaaa ctaaagggta caacggtta gaagaataca ggattgaatt gaagcgaatg
40681    aataacgata ttaaaagta atttatatta tcggaggtat tgcattgaat gataaagatt
40741    gagaaacacg atatcaaaaa gcttgaagaa tacattcagc acatcgataa ctatcgaaga
40801    gagttgaaga tgcgagaaca tgaattactt gaaagtcatg aaccagataa tgcgggagct
40861    ggcaaaagta atttgccggg taacccgatt gaacgatgtg caataaagaa gtttagtgat
40921    aacaggtaca atacattaag aaatatagtt aacggtgtag atagattgat aggtgaaagt
40981    gatgaggata cgcttgagtt attaaggttt agatattggg attgtcctat tggttgttat
41041    gaatgggaag atatagcaca ttactttggt acaagtaaga caagtatatt acgtagaagg
41101    aatgcactga tcgataagtt agcaaagtat attggttatg tgtagcggac ttttaccta
41161    tgtaagtccg cattaaaaca gtttattatg ttagtatcag attaatattt aaagttatta
41221    aatgctaata cgacgcatga acaagaggcg catcactatg tgatgtgtct tttatttat
41281    gaggtatgaa catgttcaaa ctaattgtaa atacattact acacatcaag tatagatgag
41341    tcttgatact acttaagtta tataaggtga acattatga tgactaaaga cgaacgtata
41401    cgattctata agtctaaaga atggcaaata acaagaaaaa gagtgctaga aagagataat
41461    tatgaatgtc aacaatgtaa gagagacggc aagttaacga catatgacaa agcaagcgt
41521    aagtcgttgg atgtagatca tatattatcg ctagaacatc atccggagtt tgctcatgac
41581    ttaaacaatt tagaaacact gtgtattaaa tgtcacaaca aaaagaaaa gagatttata
41641    aaaaagaaa ataaatggaa agacgaaaaa tggtaaatac ccccgggtca aaaaatcaa
41701    aagcgatc
```

| TABLE 3 | | TABLE 3-continued | |
|---|---|---|---|
| Name | Position | Name | Position |
| 1 77ORF005 | 19572 . . . 21026 | 3 77ORF007 | 21871 . . . 23076 |
| 2 77ORF006 | 3976 . . . 5196 | 4 77ORF008 | 2120 . . . 3307 |

TABLE 3-continued

| | Name | Position |
|---|---|---|
| 5 | 77ORF009 | 31946 ... 32803 |
| 6 | 77ORF010 | 26092 ... 26889 |
| 7 | 77ORF011 | 24441 ... 25208 |
| 8 | 77ORF012 | 29788 ... 30576 |
| 9 | 77ORF013 | 33620 ... 34399 |
| 10 | 77ORF014 | 27760 ... 28512 |
| 11 | 77ORF015 | 3291 ... 4028 |
| 12 | 77ORF016 | 32867 ... 33610 |
| 13 | 77ORF017 | 23269 ... 23982 |
| 14 | 77ORF018 | 31169 ... 31840 |
| 15 | 77ORF019 | 39851 ... 40501 |
| 16 | 77ORF020 | 6926 ... 7570 |
| 17 | 77ORF021 | 37762 ... 38304 |
| 18 | 77ORF022 | 30605 ... 31156 |
| 19 | 77ORF023 | 26903 ... 27346 |
| 20 | 77ORF024 | 10700 ... 11140 |
| 21 | 77ORF025 | 9707 ... 10147 |
| 22 | 77ORF026 | 40729 ... 41145 |
| 23 | 77ORF027 | 6518 ... 6925 |
| 24 | 77ORF028 | 34795 ... 35199 |
| 25 | 77ORF029 | 6117 ... 6521 |
| 26 | 77ORF030 | 36478 ... 36879 |
| 27 | 77ORF031 | 39151 ... 39546 |
| 28 | 77ORF032 | 33892 ... 34266 |
| 29 | 77ORF033 | 5758 ... 6120 |
| 30 | 77ORF034 | 7886 ... 8236 |
| 31 | 77ORF035 | 19258 ... 19560 |
| 32 | 77ORF036 | 36876 ... 37223 |
| 33 | 77ORF037 | 102 ... 446 |
| 34 | 77ORF038 | 34908 ... 35219 |
| 35 | 77ORF039 | 37220 ... 37528 |
| 36 | 77ORF040 | 41377 ... 41676 |
| 37 | 77ORF041 | 35454 ... 35753 |
| 38 | 77ORF042 | 5490 ... 5774 |
| 39 | 77ORF043 | 29304 ... 29564 |
| 40 | 77ORF044 | 18481 ... 18768 |
| 41 | 77ORF045 | 5216 ... 5500 |
| 42 | 77ORF046 | 25663 ... 25935 |
| 43 | 77ORF047 | 11159 ... 11425 |
| 44 | 77ORF048 | 28776 ... 29039 |
| 45 | 77ORF049 | 36013 ... 36255 |
| 46 | 77ORF050 | 35753 ... 36007 |
| 47 | 77ORF051 | 38931 ... 39167 |
| 48 | 77ORF052 | 1762 ... 2013 |
| 49 | 77ORF053 | 37521 ... 37757 |
| 50 | 77ORF054 | 22818 ... 23060 |
| 51 | 77ORF055 | 17546 ... 17788 |
| 52 | 77ORF058 | 18892 ... 19122 |
| 53 | 77ORF059 | 34564 ... 34785 |
| 54 | 77ORF064 | 29574 ... 29795 |
| 55 | 77ORF065 | 28528 ... 28746 |
| 56 | 77ORF066 | 27494 ... 27703 |
| 57 | 77ORF069 | 38341 ... 38547 |
| 58 | 77ORF070 | 36269 ... 36475 |
| 59 | 77ORF071 | 40498 ... 40701 |
| 60 | 77ORF072 | 38735 ... 38938 |
| 61 | 77ORF073 | 30945 ... 31148 |
| 62 | 77ORF074 | 38544 ... 38738 |
| 63 | 77ORF075 | 13673 ... 13870 |
| 64 | 77ORF077 | 25357 ... 25605 |
| 65 | 77ORF079 | 29089 ... 29280 |
| 66 | 77ORF080 | 35204 ... 35389 |
| 67 | 77ORF085 | 24060 ... 24242 |
| 68 | 77ORF092 | 39706 ... 39876 |
| 69 | 77ORF094 | 32226 ... 32393 |
| 70 | 77ORF096 | 13606 ... 13773 |
| 71 | 77ORF098 | 7092 ... 7256 |
| 72 | 77ORF102 | 29051 ... 29212 |
| 73 | 77ORF104 | 34393 ... 34551 |
| 74 | 77ORF109 | 18282 ... 18434 |
| 75 | 77ORF112 | 39543 ... 39692 |
| 76 | 77ORF117 | 27361 ... 27501 |
| 77 | 77ORF118 | 38390 ... 38530 |
| 78 | 77ORF120 | 36059 ... 36199 |
| 79 | 77ORF124 | 33699 ... 33833 |
| 80 | 77ORF128 | 14221 ... 14355 |
| 81 | 77ORF130 | 15675 ... 15806 |
| 82 | 77ORF133 | 8414 ... 8542 |
| 83 | 77ORF140 | 13113 ... 13235 |
| 84 | 77ORF147 | 7029 ... 7148 |
| 85 | 77ORF149 | 30668 ... 30787 |
| 86 | 77ORF151 | 31837 ... 31953 |
| 87 | 77ORF155 | 30278 ... 30391 |
| 88 | 77ORF157 | 4044 ... 4157 |
| 89 | 77ORF167 | 20692 ... 20799 |
| 90 | 77ORF175 | 35717 ... 35821 |
| 91 | 77ORF176 | 6836 ... 6940 |
| 92 | 77ORF178 | 35390 ... 35491 |
| 93 | 77ORF179 | 8318 ... 8419 |
| 94 | 77ORF182 | 29268 ... 29564 |

TABLE 4

```
77ORF017 sequence
23982   atgacgcataatatagaaaaacgcattaataaattaaaaacttct
1        M  T  H  N  I  E  K  R  I  N  K  L  K  T  S 23937   ggaaatccaaaatttaaaaagttagattcagatattcactattta
16       G  N  P  K  F  K  K  L  D  S  D  I  H  Y  L 23892   ctcaagagatttgaaggtgaaaaaaaccataaaggtttttatcca
31       L  K  R  F  E  G  E  K  N  H  K  G  F  Y  P 23847   aagtttaaacaaggagaaatagttttgtagatttcggtataaac
46       K  F  K  Q  G  E  I  V  F  V  D  F  G  I  N 23802   gttaataaagaattttctaattcacactttgcaatagtgatgaat
61       V  N  K  E  F  S  N  S  H  F  A  I  V  M  N 23757   aaaaatgattctaatacggaggatatagtaaatgttattccctta
76       K  N  D  S  N  T  E  D  I  V  N  V  I  P  L 23712   tcctctaaagaaaacaaaaagtatttaaagatgaattttgatttg
```

TABLE 4-continued

```
91      S  S  K  E  N  K  K  Y  L  K  M  N  F  D  L 23667   aaatgggagtattatttaagattgtttttaaatttaattagcgcg
106     K  W  E  Y  Y  L  R  L  F  L  N  L  I  S  A 23622   caaataattcagctatattaaaagaagttttcgataaaaaatac
121     Q  N  N  S  A  I  L  K  E  V  F  D  K  K  Y 23577   caaaaaaacaacacagaattcatcactaaagattattttattgaa
136     Q  K  N  N  T  E  F  I  T  K  D  Y  F  I  E 23532   tttatatctgatagtttagaaattgaaaataaattaaataaaatt
151     F  I  S  D  S  L  E  I  E  N  K  L  N  K  I 23487   gacagaaacattaataacatagtatcagcaattgataaggtaaaa
166     D  R  N  I  N  N  I  V  S  A  I  D  K  V  K 23442   aaattaaaaggtaatagttacgcttgcataaattctttccagccg
181     K  L  K  G  N  S  Y  A  C  I  N  S  F  Q  P 23397   attagtaagtttcgcataagaaaagttttaccccaaaaaattaaa
196     I  S  K  F  R  I  R  K  V  L  P  Q  K  I  K 23352   aatccagtaatagattcttcggatattatgttactgataaataga
211     N  P  V  I  D  S  S  D  I  M  L  L  I  N  R 23307   attaataataatatattgcagatccctgatataagatga  23269
226     I  N  N  N  I  L  Q  I  P  D  I  R  *
```

Physico-chemical parameters of ORF 77ORF017
1   MTHNIEKRIN KLKTSGNPKF KKLDSDIHYL LKRFEGEKNH KGFYPKFKQG
    EIVFVDFGIN

61  VNKEFSNSHF AIVMNKNDSN TEDIVNVIPL SSKENKKYLK MNFDLKWEYY
    LRLFLNLISA

121 QNNSAILKEV FDKKYQKNNT EFITKDYFIE FISDSLEIEN KLNKIDRNIN
    NIVSAIDKVK

181 KLKGNSYACI NSFQPISKFR IRKVLPQKIK NPVIDSSDIM LLINRINNNI
    LQIPDIR

| | |
|---|---|
| Number of amino acids: | 237 |
| Average molecular weight (Daltons): | 27887.38 |
| Mean amino acid weight (Daltons): | 117.67 |
| Monoisotopic molecular weight (Daltons): | 27869.83 |
| Mean amino acid monoisotopic weight (Daltons): | 117.59 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 5  | 2.11%  | 7.58% | Cys | C | 1  | 0.42%  | 1.66% |
| Asp | D | 14 | 5.91%  | 5.28% | Glu | E | 13 | 5.49%  | 6.37% |
| Phe | F | 16 | 6.75%  | 4.09% | Gly | G | 6  | 2.53%  | 6.84% |
| His | H | 4  | 1.69%  | 2.24% | Ile | I | 29 | 12.24% | 5.81% |
| Lys | K | 33 | 13.92% | 5.95% | Leu | L | 19 | 8.02%  | 9.42% |
| Met | M | 4  | 1.69%  | 2.37% | Asn | N | 30 | 12.66% | 4.45% |
| Pro | P | 7  | 2.95%  | 4.9%  | Gln | Q | 6  | 2.53%  | 3.97% |
| Arg | R | 8  | 3.38%  | 5.16% | Ser | S | 17 | 7.17%  | 7.12% |
| Thr | T | 5  | 2.11%  | 5.67% | Val | V | 11 | 4.64%  | 6.58% |
| Trp | W | 1  | 0.42%  | 1.23% | Tyr | Y | 8  | 3.38%  | 3.18% |

| | |
|---|---|
| Number of acidic (negative) amino acids (ED): | 27 / 11.39% |
| Number of basic (positive) amino acids (KR): | 41 / 17.30% |
| Total charge (KRED): | 68 / 28.69% |
| Net charge (KR-ED): | 14 / 5.91% |
| Theoretical pI: | 10.01 |
| Total linear charge density: | 0.30 |
| Average hydrophobicity: | -5.37 |
| Ratio of hydrophilicity to hydrophobicity: | 1.41 |

TABLE 4-continued

| | |
|---|---|
| Percentage of hydrophilic amino acid: | 57.81% |
| Percentage of hydrophobic amino acid: | 42.19% |
| Ratio of % hydrophilic to % hydrophobic: | 1.37 |

77ORF019 sequence

```
39851  atgaacgagcaaataataggaagcatatatactttagcaggaggt
1      M  N  E  Q  I  I  G  S  I  Y  T  L  A  G  G 39896  gttgtgctttattcagttaaagagatttttaggtatttttacagat
16     V  V  L  Y  S  V  K  E  I  F  R  Y  F  T  D 39941  tctaacttacaacgtaaaaaaatcaatttagaacaaatatatccg
31     S  N  L  Q  R  K  K  I  N  L  E  Q  I  Y  P 39986  atatatttagattgttttaaaaaggctaaaaagatgattggagct
46     I  Y  L  D  C  F  K  K  A  K  K  M  I  G  A 40031  tatattattccaacagaacagcatgaattttagattttttttgat
61     Y  I  I  P  T  E  Q  H  E  F  L  D  F  F  D 40076  attgaagtctttaataatttagataagcaaagtaaaaaagcgtat
76     I  E  V  F  N  N  L  D  K  Q  S  K  K  A  Y 40121  gaaaatgttattggatttagacaaatgattaatttatcaaataga
91     E  N  V  I  G  F  R  Q  M  I  N  L  S  N  R 40166  gttaaggcaatggaagattttaagatgagtttcaacaatgaattt
106    V  K  A  M  E  D  F  K  M  S  F  N  N  E  F 40211  agtacaaatcagattttttttaatccttcttttgttatggaaaca
121    S  T  N  Q  I  F  F  N  P  S  F  V  M  E  T 40256  attgctattataaatgaatatcaaaaagatatatcttatttaaaa
136    I  A  I  I  N  E  Y  Q  K  D  I  S  Y  L  K 40301  aatataattaataaaatgaatgaaaatagagcttataatcatatt
151    N  I  I  N  K  M  N  E  N  R  A  Y  N  H  I 40346  gatagtttatcacttcagagtaccgacgaaaaataaacgattat
166    D  S  F  I  T  S  E  Y  R  R  K  I  N  D  Y 40391  aatctttatcttgataaatttgaagaacagtttagtcaaaagttt
181    N  L  Y  L  D  K  F  E  E  Q  F  S  Q  K  F 40436  aaaataaacagaacttcgataaaagaaagaattattattaattta
196    K  I  N  R  T  S  I  K  E  R  I  I  I  N  L 40481  aacaagaggagatttaaatga  40501
211    N  K  R  R  F  K  *
```

Physico-chemical parameters of ORF 77ORF019

```
1    MNEQIIGSIY TLAGGVVLYS VKEIFRYFTD SNLQRKKINL EQIYPIYLDC
     FKKAKKMIGA

61   YIIPTEQREF LDFFDIEVFN NLDKQSKKAY ENVIGFRQMI NLSNRVKAME
     DFKMSFNNEF

121  STNQIFFNPS FVMETIAIIN EYQKDISYLK NIINKMNENR AYNHIDSFIT
     SEYRRKINDY

181  NLYLDKFEEQ FSQKFKINRT SIKERIIINL NKRRFK
```

| | |
|---|---|
| Number of amino acids: | 216 |
| Average molecular weight (Daltons): | 260 |
| | 26.06 |
| Mean amino acid weight (Daltons): | 120. |
| | 49 |
| Monoisotopic molecular weight (Daltons): | 260 |
| | 09.34 |
| Mean amino acid monoisotopic weight (Daltons): | 120. |
| | 41 |

Amino acid composition

| Acid | Symbol | Number | % | Average % an Swissprot | Acid | Symbol | Number | % | Average % in Swissprot |
|---|---|---|---|---|---|---|---|---|---|
| Ala | A | 7 | 3.24% | 7.58% | Cys | C | 1 | 0.46% | 1.66% |
| Asp | D | 10 | 4.63% | 5.28% | Glu | E | 16 | 7.41% | 6.37% |
| Phe | F | 19 | 8.80% | 4.09% | Gly | G | 5 | 2.31% | 6.84% |

TABLE 4-continued

| His | H | 2 | 0.93% | 2.24% | Ile | I | 28 | 12.96% | 5.81% |
|---|---|---|---|---|---|---|---|---|---|
| Lys | K | 22 | 10.19 | 5.95% | Leu | L | 12 | 5.56% | 9.42% |
| Met | M | 7 | 3.24% | 2.37% | Asn | N | 23 | 10.65 | 4.45% |
| Pro | P | 3 | 1.39% | 4.9% | Gln | Q | 10 | 4.63% | 3.97% |
| Arg | R | 11 | 5.09% | 5.16% | Ser | S | 13 | 6.02% | 7.12% |
| Thr | T | 7 | 3.24% | 5.67% | Val | V | 7 | 3.24% | 6.58% |
| Trp | W | 0 | 0.00% | 1.23% | Tyr | Y | 13 | 6.02% | 3.18% |

Number of acidic (negative) amino acids (ED): 26
12.04%
Number of basic (positive) amino acids (KR). 33
15.28%
Total charge (KRED): 59
27.31%
Net charge (KR - ED): 7
3.24%
Theoritical pI: 9.52
Total linear charge density: 0.28
Average hydrophobicity: -4.84
Ratio of hydrophilicity to hydrophobicity: 1.37
Percentage of hydrophllic amino acld: 54.17%
Percentage of hydrophobic amino acid: 45.83%
Ratio of % hydrophilic to % hydrophobic: 1.18

77ORF043 sequence
```
29304  atgtattacgaaataggcgaaatcatacgcaaaaatattcatgtt
1      M  Y  Y  E  I  G  E  I  I  R  K  N  I  H  V 29349  aacggattcgattttaagctattcattttaaaaggtcatatgggc
16     N  G  F  D  F  K  L  F  I  L  K  G  H  M  G 29394  atatcaatacaagttaaagatatgaacaacgtaccaattaaacat
31     I  S  I  Q  V  K  D  M  N  N  V  P  I  K  H 29439  gcttatgtcgtagatgagaatgacttagatatggcatcagactta
46     A  Y  V  V  D  E  N  D  L  D  M  A  S  D  L 29484  tttaaccaagcaatagatgaatggattgaagagaacacagacgaa
61     F  N  Q  A  I  D  E  W  I  E  E  N  T  D  E 29529  caggacagactaattaacttagtcatgaaatggtag   29564
76     Q  D  R  L  I  N  L  V  M  K  W  *
```

Physico-chemical parameters of ORF 77ORF043
1   MYYEIGEIIR KNIHVNGFDF KLFILKOHMG ISIQVKDMNN VPIKHAYVVD
    ENDLDMASDL

61  FNQAIDEWIE ENTDEQDRLI NLVMKW

Number of amino acids: 86
Average molecular weight (Daltons): 10186.68
Mean amino acid weight (Daltons): 118.45
Monoisotopic molecular weight (Daltons): 10180.02
Mean amino acid monoisotopic weight (Daltons): 118.37

| Acid | Symbol | Number | % | Average % in Swissprot | Acid | Symbol | Number | % | Average % in Swissprot |
|---|---|---|---|---|---|---|---|---|---|
| Ala | A | 3 | 3.49% | 7.58% | Cys | C | 0 | 0.00% | 1.66% |
| Asp | D | 9 | 10.47 | 5.28% | Glu | E | 7 | 8.14% | 6.37% |
| Phe | F | 4 | 4.65% | 4.09% | Gly | G | 4 | 4.65% | 6.84% |
| His | H | 3 | 3.49% | 2.24% | Ile | I | 11 | 12.79% | 5.81% |
| Lys | K | 6 | 6.98% | 5.95% | Leu | L | 6 | 6.98% | 9.42% |
| Met | M | 5 | 5.81% | 2.37% | Asn | N | 8 | 9.30% | 4.45% |
| Pro | P | 1 | 1.16% | 4.9% | Gln | Q | 3 | 3.49% | 3.97% |
| Arg | R | 2 | 2.33% | 5.16% | Ser | S | 2 | 2.33% | 7.12% |
| Thr | T | 1 | 1.16% | 5.67% | Val | V | 6 | 6.98% | 6.58% |
| Trp | W | 2 | 2.33% | 1.23% | Tyr | Y | 3 | 3.49% | 3.18% |

Number of acidic (negative) amino acids (ED): 16
18.60%
Number of basic (positive) amino acids (KR): 8
9.30%
Total charge (KRED): 24

TABLE 4-continued

| | |
|---|---|
| | 27.91% |
| Net charge (KR - ED): | -8 |
| | -9.30% |
| Theoritical pI: | 4.38 |
| Total linear charge density: | 0.30 |
| Average hydrophobicity: | -2.80 |
| Ratio of hydrophilicity to hydrophobicity: | 1.19 |
| Percentage of hydrophilic amino acid: | 48.84% |
| Percentage of hydrophobic amino acid: | 51.16% |
| Ratio of % hydrophilic to % hydrophobic: | 0.95 |

```
77ORF102 sequence
29051    atgagcaacatttataaaagctacctagtagcagtattatgcttc
1        M  S  N  I  Y  K  S  Y  L  V  A  V  L  C  F 29096    acagtcttagcgattgtacttatgccgtttctatacttcactaca
16       T  V  L  A  I  V  L  M  P  F  L  Y  F  T  T 29141    gcatggtcaattgcgggattcgcaagtatcgcaacattcatgtac
31       A  W  S  I  A  G  F  A  S  I  A  T  F  M  Y 29186    tacaaagaatgcttttcaaagaataa 29212
46       Y  K  E  C  F  F  K  E  *

Physico-chemical parameters of ORF 77ORF102
1    MSNIYKSYLV AVLCFTVLAI VLMPFLYFTT AWSIAOFASI ATPMYYKECF FKE
```

| | |
|---|---|
| Number of amino acids: | 53 |
| Average molecular weight (Daltons): | 6155.42 |
| Mean amino acid weight (Daltons): | 116.14 |
| Monoisotopic molecular weight (Daltons): | 6151.07 |
| Mean amino acid monoisotopic weight (Daltons): | 116.06 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 6 | 11.32% | 7.58% | Cys | C | 2 | 3.77% | 1.66% |
| Asp | D | 0 | 0.00% | 5.28% | Glu | E | 2 | 3.77% | 6.37% |
| Phe | F | 7 | 13.21 | 4.09% | Gly | G | 1 | 1.89% | 6.84% |
| His | H | 0 | 0.00% | 2.24% | Ile | I | 4 | 7.55% | 5.81% |
| Lys | K | 3 | 5.66% | 5.95% | Leu | L | 5 | 9.43% | 9.42% |
| Met | M | 3 | 5.66% | 2.37% | Asn | N | 1 | 1.89% | 4.45% |
| Pro | P | 1 | 1.89% | 4.9% | Gln | Q | 0 | 0.00% | 3.97% |
| Arg | R | 0 | 0.00% | 5.16% | Ser | S | 4 | 7.55% | 7.12% |
| Thr | T | 4 | 7.55% | 5.67% | Val | V | 4 | 7.55% | 6.58% |
| Trp | W | 1 | 1.89% | 1.23% | Tyr | Y | 5 | 9.43% | 3.18% |

| | | |
|---|---|---|
| Number of acidic (negative) amino acids (ED): | 2 | 3.77% |
| Number of basic (positive) amino acids (KR): | 3 | 5.66% |
| Total charge (KRED): | 5 | 9.43% |
| Net charge (KR - ED): | 1 | 1.89% |
| Theoretical pI: | 8.18 | |
| Total linear charge density: | 0.13 | |
| Average hydrophobicity: | 10.81 | |
| Ratio of hydrophilicity to hydrophobicity: | 0.40 | |
| Percentage of hydrophilic amino acid: | 28.30% | |
| Percentage of hydrophobic amino acid: | 71.70% | |
| Ratio of % hydrophilic to % hydrophobic: | 0.39 | |

```
77ORF104 sequence
34393    atggtaaccaaagaattttaaaaactaaacttgagtgttcagat
1        M  V  T  K  E  F  L  K  T  K  L  E  C  S  D 34438    atgtacgctcagaaactcatagatgaggcacagggcgatgaaaat
16       M  Y  A  Q  K  L  I  D  E  A  Q  G  D  E  N 34483    aggttgtacgacctatttatccaaaaacttgcagaacgtcataca
31       R  L  Y  D  L  F  I  Q  K  L  A  E  R  H  T 34528    cgccccgctatcgtcgaatattaa 34551
46       R  P  A  I  V  E  Y  *

Physico-chemical parameters of ORF 77ORF104
1    MVTKEFLKTK LECSDMYAQK LIDEAQGDEN RLYDLFIQKL AERHTRPAIV EY
```

TABLE 4-continued

| Number of amino acids: | 52 |
| Average molecular weight (Daltons): | 6193.13 |
| Mean amino acid weight (Daltons): | 119.10 |
| Monoisotopic molecular weight (Daltons): | 6189.12 |
| Mean amino acid monoisotopic weight (Daltons): | 119.02 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 4 | 7.69% | 7.58% | Cys | C | 1 | 1.92% | 1.66% |
| Asp | D | 4 | 7.69% | 5.28% | Glu | E | 6 | 11.54% | 6.37% |
| Phe | F | 2 | 3.85% | 4.09% | Gly | G | 1 | 1.92% | 6.84% |
| His | H | 1 | 1.92% | 2.24% | Ile | I | 3 | 5.77% | 5.81% |
| Lys | K | 5 | 9.62% | 5.95% | Leu | L | 6 | 11.54 | 9.42% |
| Met | M | 2 | 3.85% | 2.37% | Asn | N | 1 | 1.92% | 4.45% |
| Pro | P | 1 | 1.92% | 4.9% | Gln | Q | 3 | 5.77% | 3.97% |
| Arg | R | 3 | 5.77% | 5.16% | Ser | S | 1 | 1.92% | 7.12% |
| Thr | T | 3 | 5.77% | 5.67% | Val | V | 2 | 3.85% | 6.58% |
| Trp | W | 0 | 0.00% | 1.23% | Tyr | Y | 3 | 5.77% | 3.18% |

| Number of acidic (negative) amino acids (ED): | 10 |
| | 19.23% |
| Number of basic (positive) amino acids (KR): | 8 |
| | 15.38% |
| Total charge (KRED): | 18 |
| | 34.62% |
| Net charge (KR - ED): | -2 |
| | -3.85% |
| Theoritical pI: | 5.03 |
| Total linear charge density: | 0.38 |
| Average hydrophobicity: | -5.81 |
| Ratio of hydrophilicity to hydrophobicity: | 1.47 |
| Percentage of hydrophilic amino acid: | 53.85% |
| Percentage of hydrophobic amino acid: | 46.15% |
| Ratio of % hydrophilic to % hydrophobic: | 1.17 |

77ORF182 sequence

```
29268  atgttcaatataaaacgaaaaacggaggaagtcaagatgtattac
1       M  F  N  I  K  R  K  T  E  E  V  K  M  Y  Y 29313  gaaataggcgaaatcatacgcaaaaatattcatgttaacggattc
16      E  I  G  E  I  I  R  K  N  I  H  V  N  G  F 29356  gattttaagctattcattttaaaaggtcatatgggcatatcaata
31      D  F  K  L  F  I  L  K  G  H  M  G  I  S  I 29403  caagttaaagatatgaacaacgtaccaattaaacatgcttatgtc
46      Q  V  K  D  M  N  N  V  P  I  K  H  A  Y  V 29448  gtagatgagaatgacttagatatggcatcagacttattaaccaa
61      V  D  E  N  D  L  D  M  A  S  D  L  F  N  Q 29493  gcaatagatgaatggattgaagagaacacagacgaacaggacaga
76      A  I  D  E  W  I  E  E  N  T  D  E  Q  D  R 29538  ctaattaacttagtcatgaaatggtag 29564
91      L  I  N  L  V  M  K  W  *
```

Physico-chemical parameters of ORF 77ORF182

```
1   MFNIKRKTEE VKMYYEIGEI IRKNIHVNGF DFKLFILKGH MGISIQVKDM
    NNVPIKHSYV

61  VDENDLDMAS DLFNQAIDEW IEENTDEQDR LINLVMKW
```

| Number of amino acids: | 98 |
| Average molecular weight (Daltons): | 11691.50 |
| Mean amino acid weight (Daltons): | 119.30 |
| Monoisotopic molecular weight (Daltons): | 11683.84 |

TABLE 4-continued

Mean amino acid monoisotopic weight (Daltons): 119.22

Amino acid composition

| Acid | Symbol | Number | % | Average % in Swissprot | Acid | Symbol | Number | % | Average % in Swissprot |
|---|---|---|---|---|---|---|---|---|---|
| Ala | A | 3 | 3.06% | 7.58% | Cys | C | 0 | 0.00% | 1.66% |
| Asp | D | 9 | 9.18% | 5.28% | Glu | E | 9 | 9.18% | 6.37% |
| Phe | F | 5 | 5.10% | 4.09 | Gly | G | 4 | 4.08% | 6.84% |
| His | H | 3 | 3.06% | 2.24% | Ile | I | 12 | 12.24% | 5.81% |
| Lys | K | 9 | 9.18% | 5.95% | Leu | L | 6 | 6.12% | 9.42% |
| Met | M | 6 | 6.12% | 2.37% | Asn | N | 9 | 9.18% | 4.45% |
| Pro | P | 1 | 1.02% | 4.9% | Gln | Q | 3 | 3.06% | 3.97% |
| Arg | R | 3 | 3.06% | 5.16% | Ser | S | 2 | 2.04% | 7.12% |
| Thr | T | 2 | 2.04% | 5.67% | Val | V | 7 | 7.14% | 6.58% |
| Trp | W | 2 | 2.04% | 1.23% | Tyr | Y | 3 | 3.06% | 3.18% |

| | |
|---|---|
| Number of acidic (negative) amino acids (ED): | 18 |
| | 18.37% |
| Number of basic (positive) amino acids (KR): | 12 |
| | 12.24% |
| Total charge (KRED): | 30 |
| | 30.61% |
| Net charge (KR − ED): | −6 |
| | −6.12% |
| Theoritical pI: | 4.76 |
| Total linear charge density: | 0.33 |
| Average hydrophobicity: | −3.89 |
| Ratio of hydrophilicity to hydrophobicity: | 1.28 |
| Percentage of hydrophilic amino acid: | 51.02% |
| Percentage of hydrophobic amino acid: | 48.98% |
| Ratio of % hydrophilic to % hydrophobic: | 1.04 |

TABLE 5

BLASTP 2.0.8 [Jan-05-1999]

| Sequences producing significant alignments | Score (bits) | E Value |
|---|---|---|
| Query = sid\|100017\|lan\|77ORF017 Phage 77 ORF \|23269–23982\|-3 | | |
| (237 letters) | | |
| Database: nr | | |
| 393,678 sequences; 120,452,765 total letters | | |
| gi\|4493986\|emb\|CAB39045.1\|(AL034559) predicted using hexExon; . . . | 41 | 0.010 |
| gi\|730607\|sp\|P23250\|RPI1_YEAST NEGATIVE RAS PROTEIN REGULATOR P . . . | 38 | 0.053 |
| gi\|3097044\|emb\|CAA75299\| (Y15035) K1R [Cowpox virus] | 38 | 0.090 |
| gi\|2146245\|pir\|\|S73794 hypothetical protein H91_orf180 - Mycopl . . . | 38 | 0.090 |
| gi\|83910\|pir\|\|S04682 ribosomal protein var1 - yeast (Candida gl . . . | 37 | 0.15 |
| gi\|133135\|sp\|P21358\|RMAR_CANGA MITOCHONDRIAL RIBOSOMAL PROTEIN . . . | 37 | 0.15 |
| gi\|2128843\|pir\|\|H64475 hypothetical protein MJ1409 - Methanococ . . . | 36 | 0.20 |
| gi\|5107017\|gb\|AAD39926.1\|AF126285_2 (AF126285) RNA polymerase [ . . . | 36 | 0.35 |
| gi\|2146210\|pir\|\|S73342 hypothetical protein E07_orf166 - Mycopl . . . | 35 | 0.60 |
| Database: swissprot | | |
| 79,449 sequences: 28,874,452 total letters | | |
| sp\|P23250 RPI1_YEAST NEGATIVE RAS PROTEIN REGULATOR PROTEIN. | 38 | 0.014 |
| sp\|P21358 RMAR_CANGA MITOCHONDRIAL RIBOSOMAL PROTEIN VAR1. | 37 | 0.040 |
| sp\|Q21444 LDLC_CAEEL LDLC PROTEIN HOMOLOG. | 34 | 0.35 |
| sp\|P27240 RFAY_ECOLI LIPOPOLYSACCHARIDE CORE BIOSYNTHESIS PROT. | 33 | 0.46 |
| sp\|P53192 YGC0_YEAST HYPOTHETICAL 27.1 KD PROTEIN IN ALK1-CKB1. | 33 | 0.60 |
| sp\|P32908 SMC1_YEAST CHROMOSOME SEGREGATION PROTEIN SMC1 (DA-B. | 33 | 0.60 |
| sp\|P54683 TAGB_DICDI PRESTALK-SPECIFIC PROTEIN TAGB PRECURSOR. | 32 | 0.78 |
| sp\|Q03100 CYAA_DICDI ADENYLATE CYCLASE, AGGREGATION SPECIFIC (. | 32 | 0.78 |
| Query = sid\|100019\|lan\|77ORF019 Phage 77 ORF\|39851–40501\|2 | | |
| (216 letters) | | |
| Database: nr | | |
| 373,355 sequences; 114,214,446 total letters | | |
| gi\|3341966\|dbj\|BAA31932\| (AB009866) orf 59 [bacteriophage phi PVL] | 437 | e-122 |
| gi\|2689911 (AE000792) B. burgdorferi predicted coding region BB . . . | 38 | 0.058 |
| gi\|1171589\|emb\|CAA64574\| (X95275) frameshift [Plasmodium falcip . . . | 37 | 0.10 |
| gi\|4493986\|emb\|CAB39045.1\| (AL034559) predicted using hexExon; . . . | 36 | 0.23 |
| gi\|141257\|sp\|P18019\|YPI9_CLOPE HYPOTHETICAL 14.5 KD PROTEIN (OR . . . | 36 | 0.29 |
| gi\|133412\|sp\|P27059\|RPOB_ASTLO DNA-DIRECTED RNA POLYMERASE BETA . . . | 35 | 0.51 |
| gi\|3122231\|sp\|Q58851\|HISX_METJA HISTIDINOL DEHYDROGENASE (HDH) . . . | 35 | 0.51 |
| gi\|3649757\|emb\|CAB11106.1\| (Z98547) predicted using hexExon; MA . . . | 34 | 0.66 |

TABLE 5-continued

BLASTP 2.0.8 [Jan-05-1999]

| Sequences producing significant alignments | Score (bits) | E Value |
|---|---|---|
| gi\|2688313 (AE001146) sensory transduction histidine kinase, pu . . . | 34 | 0.87 |
| Database: swissprot | | |
| 79,449 seouences; 28,874,452 total letters | | |
| sp\|P18019 YPI9__CLOPE  HYPOTHETICAL 14.5 KD PROTEIN ORF9). | 36 | 0.079 |
| sp\|Q58851 HISX__METJA  HISTIDINOL DEHYDROGENASE (EC 1.1.1.23) (H. | 35 | 0.14 |
| sp\|P27059 RPOB__ASTLO  DNA-DIRECTED RNA POLYMERASE BETA CHAIN (E. | 35 | 0.14 |
| sp\|Q02224 CENE__HUMAN  CENTROMERIC PROTEIN E (CENP-E PROTEIN). | 34 | 0.31 |
| sp\|P04931 ARP__PLAFA  ASPARAGINE-RICH PROTEIN (AG319) (ARP) (FRA . . . | 33 | 0.53 |
| sp\|P18011 IPAB__SHIFL  62 KD MEMBRANE ANTIGEN. | 32 | 0.69 |
| sp\|P18709 VTA2__XENLA  VITELLOGENIN A2 PRECURSOR (VTG A2) (CONTA . . . | 32 | 0.90 |
| sp\|Q64409 CP3H__CAVPO  CYTOCHROME P450 3A17 (EC 1.14.14.1) (CYPI . . . | 32 | 0.90 |
| sp\|P21358 RMAR__CANGA  MITOCHONDRIAL RIBOSOMAL PROTEIN VAR1. | 32 | 0.90 |
| sp\|Q03945 IPAB__SHIDY  62 KD MEMBRANE ANTIGEN. | 32 | 1.2 |
| Query = sid\|100043\|lan\|77ORF043 Phage 77 ORF\|29304–29564\|3 | | |
| (86 letters) | | |
| Database: nr | | |
| 373,355 sequences; 114,214,446 total letters | | |
| gi\|3341947\|dbj\|BAA31913\| (AB009866) orf 39 [bacteriophage phi PVL] | 182 | 6e-46 |
| gi\|744518\|prf\|2014422A FKBP-rapamycin-associated protein (Homo . . . | 32 | 0.84 |
| gi\|1169736\|sp\|P42346\|FRAP__RAT FKBP-RAPAMYCIN ASSOCIATED PROTEIN . . . | 32 | 0.84 |
| gi\|1169735\|sp\|P42345\|FRAP__HUMAN FKBP-RAPAMYCIN ASSOCIATED PROTE . . . | 32 | 0.84 |
| gi\|3282239 (U88966) rapamycin associated protein FRAP2 (Homo sa . . . | 32 | 0.84 |
| gi\|3875402\|emb\|CAA98122\| (Z73906) cDNA EST EMBL:D64544 comes fr . . . | 31 | 2.5 |
| gi\|1084792\|pir\|\|S54091 hypothetical protein YPR070w - yeast (Sa . . . | 30 | 4.2 |
| Database: swissprot | | |
| 79,449 sequences; 114,214,446 total letters | | |
| sp\|P42345 FRAP__HUMAN FKBP-RAPAMYCIN ASSOCIATED PROTEIN (FRAP). | 32 | 0.24 |
| sp\|P42346 FRAP__RAT FKBP-RAPAMYCIN ASSOCIATED PROTEIN (FRAP) (R. | 32 | 0.24 |
| sp\|P34554 YNP1__CAEEL  HYPOTHETICAL 42.2 KD PROTEIN T05G5.1 IN C. | 28 | 3.5 |
| sp\|Q24118 LIO__DROME  LINOTTE PROTEIN. | 28 | 3.5 |
| sp\|P80034 ACH2__BOMMO  ANTICHYMOTRYPSIN II (ACHY-II). | 28 | 3.5 |
| sp\|P22922 A1AT__BOMMO  ANTITRYPSIN PRECURSOR (AT). | 28 | 3.5 |
| sp\|Q44363 TRAA__AGRT6  CONJUGAL TRANSFER PROTEIN TRAA. | 28 | 3.5 |
| sp\|P38255 YBU5__YEAST  HYPOTHETICAL 51.3 KD PROTEIN IN PHO5-VPS1. | 27 | 6.0 |
| sp\|P55822 SH3B__HUMAN  SH3BGR PROTEIN (21-GLUTAMIC ACID-RICH PRO. | 27 | 7.9 |
| sp\|Q58482 YA82__METJA  HYPOTHETICAL PROTEIN MJ1082 | 27 | 7.9 |
| sp\|P34252 YKK8__YEAST  HYPOTHETICAL 52.3 KD PROTEIN IN HAP4-AAT1. | 27 | 7.9 |
| Query = sid\|100102\|lan\|77ORF102 Phage 77 ORF\|29051–29212\|2 | | |
| (53 letters) | | |
| Database: nr | | |
| 373,355 sequences; 114,214,446 total letters | | |
| gi\|3341946\|dbj\|BAA31912\| (AB009866) orf 38 [bacteriophage phi PVL] | 96 | 3e-20 |
| gi\|4325288\|gb\|AAD17315\| (AF123593) voltage-dependent sodium cha . . . | 28 | 7.1 |
| gi\|2649684 (AE001040) A. fulgidus predicted coding region AF092 . . . | 28 | 9.3 |
| Database: swissprot | | |
| 79,449 sequences; 28,874,452 total letters | | |
| sp\|P42087 HUTM__BACSU  PUTATIVE HISTIDINE PERMRASE. | 26 | 7.1 |
| sp\|P04775 CIN2__RAT  SODIUM CHANNEL PROTEIN, BRAIN II ALPHA SUBU . . . | 26 | 9.2 |
| sp\|P42619 YQJF__ECOLI  HYPOTHETICAL 17.2 KD PROTEIN IN EXUR-TDCC . . . | 26 | 9.2 |
| Query = sid\|100104\|lan\|77ORF104 Phage 77 ORF\|34393–34551\|1 | | |
| (52 letters) | | |
| Database: nr | | |
| 373,355 sequences; 114,214,446 total letters | | |
| gi\|2315523 (AF016452) similar to the leucine-rich domains found . . . | 29 | 4.2 |
| gi\|4377168\|gb\|AAD18990\| (AE001666) CT711 hypothetical protein [ . . . | 29 | 5.4 |
| gi\|3882171\|dbj\|BAA34445\| (AB018268) KIAA0725 protein [Homo sapi . . . | 28 | 9.3 |
| Database: swissprot | | |
| 79,449 sequences; 28,874,452 total letters | | |
| sp\|P04879 RRPP__VSVIG  RNA POLYMERASE ALPHA SUBUNIT (EC 2.7.7.48. | 27 | 5.4 |
| sp\|P04880 RRPP__VSVIM  RNA POLYMERASE ALPHA SUBUNIT (EC 2.7.7.48. | 27 | 5.4 |
| sp\|Q13946 CN7A__HUMAN  HIGH-AFFINITY CAMP-SPECIFIC 3',5'-CYCLIC. | 26 | 7.1 |
| sp\|P35381 ATPA__DROME  ATP SYNTHASE ALPHA CHAIN, MITOCHONDRIAL P. | 26 | 9.3 |
| sp\|P54659 MVPB__DICDI  MAJOR VAULT PROTEIN BETA (MVP-BETA). | 26 | 9.3 |
| sp\|P40397 YHXC__BACSU  HYPOTHETICAL OXIDOREDUCTASE IN APRE-COMK. | 26 | 9.3 |
| Query = sid\|122748\|lan\|77ORF182 Phage 77 ORF\|29268–29564\|3 | | |
| (98 letters) | | |
| Database: nr | | |
| 393,678 sequences; 120,452,765 total letters | | |
| gi\|3341947\|dbj\|BAA31913.1\| (AB009866) orf 39 [bacteriophage phi . . . | 182 | 8e-46 |
| gi\|1084792\|pir\|\|S54091 hypothetical protein YPR070w - yeast (Sa . . . | 35 | 0.13 |
| gi\|1169736\|sp\|P42346\|FRAP__RAT FKBP-RAPAMYCIN ASSOCIATED PROTEIN . . . | 32 | 1.1 |
| gi\|744518\|prf\|2014422A FKBP-rapamycin-associated protein [Homo . . . | 32 | 1.1 |
| gi\|5051381\|emb\|CAB44736.1\| (AL049653) dJ647M16.2 (FK506 binding . . . | 32 | 1.1 |
| gi\|4826730\|ref\|NP__004949.1\|pFRAP1\| FK506 binding protein 12-rap . . . | 32 | 1.1 |

TABLE 5-continued

BLASTP 2.0.8 [Jan-05-1999]

| Sequences producing significant alignments | Score (bits) | E Value |
|---|---|---|
| gi\|3282239 (U88966) rapamycin associated protein FRAP2 [Homo sa . . . | 32 | 1.1 |
| Database:   swissprot | | |
|    79,909 sequences; 29,054,478 total letters | | |
| sp\|P42345 FRAP__HUMAN   FKBP-RAPAMYCIN ASSOCIATED PROTEIN (FRAP). | 32 | 0.29 |
| sp\|P42346 FRAP__RAT   FKBP-RAPAMYCIN ASSOCIATED PROTEIN (FRAP) (R. | 32 | 0.29 |
| sp\|P40557 YIA5__YEAST   PUTATIVE DISULFIDE ISOMERASE YIL005W PREC. | 29 | 3.3 |
| sp\|Q24118 LIO__DROME   LINOTTE PROTEIN. | 28 | 4.4 |
| sp\|Q44363 TRAA__AGRT6   CONJUGAL TRANSFER PROTEIN TRAA. | 28 | 4.4 |
| sp\|P80034 ACH2__BOMMO   ANTICHYMOTRYPSIN II (ACHY-II). | 28 | 4.4 |
| sp\|P34554 YNP1__CAEEL   HYPOTHETICAL 42.2 KD PROTEIN T05G5.1 IN C. | 28 | 4.4 |
| sp\|P22922 A1AT__BOMMO   ANTITRYPSIN PRECURSOR (AT). | 28 | 4.4 |

TABLE 6

| 1st position (5' end) | 2nd position | | | | 3rd position (3' end) |
|---|---|---|---|---|---|
| | U | C | A | G | |
| U | Phe | Ser | Tyr | Cys | U |
|   | Phe | Ser | Tyr | Cys | C |
|   | Leu | Ser | Stop | Stop | A |
|   | Leu | Ser | Stop | Trp | G |
| C | Leu | Pro | His | Arg | U |
|   | Leu | Pro | His | Arg | C |
|   | Leu | Pro | Gln | Arg | A |
|   | Leu | Pro | Gln | Arg | G |
| A | Ile | Thr | Asn | Ser | U |
|   | Ile | Thr | Asn | Ser | C |
|   | Ile | Thr | Lys | Arg | A |
|   | Met | Thr | Lys | Arg | G |
| G | Val | Ala | Asp | Gly | U |
|   | Val | Ala | Asp | Gly | C |
|   | Val | Ala | Glu | Gly | A |
|   | Val | Ala | Glu | Gly | G |

TABLE 7

Bacteriophage 3A, complete genome sequence

```
   1  caaacgctag caacgcggat aaatttttca tgaaaggggg tctttatatg aagttaacaa aaaaacagct
  71  aaaagaatat atagaagatt acaaaaaatc tgatgacata ttaattaatt tgtatataga aacatatgaa
 141  ttttattgtc ggttaagaga tgaacttaaa aatagtgatt taatgataga gcatacaaac aaggctggtg
 211  cgagcaatat tattaagaat ccattaagca tagaactgac aaaaacagtt caaacactaa ataacttact
 281  caagtctatg ggtttaactg cagcacaaag aaaaaagata gttcaagaag aaggtggatt cggtgactat
 351  taaagtttta aatgaaccett caccaaaact attaacaaca tggtatgcag agcaagtcac tcaagggaaa
 421  ataaaaacaa gcaaatatgt tagaaaagaa tgtgagagac atcttagata tctagaaaat ggaggtaaat
 491  gggtatttga tgaagaatta gcgcatcgtc ctattcgatt tatagaaaag ttttgtaaac cttccaaagg
 561  atctaaacgt caacttgtat tacagccatg gcaacatttt attatcggca gtttgtttgg ttgggttcat
 631  aaagaaacaa aactgcgcag gtttaaagaa gctttgatat ttatgggcg aaaaaatggt aaaacaacca
 701  ctatttctgg ggttgctaac tatgctgtat cacaagatgg agaaaatggt gcagaaattc atttgttagc
 771  aaacgtaatg aaacaagcta ggattctatt tgatgaatct aaggcgatga ttaaagctag cccaaagctt
 841  gataaaaatt tcagaacatt aagagatgaa atccattatg acgcaacgat atcaaaaatt atgccccaag
 911  catcagatag cgataagtta gatggattga atacacacat ggggattttt gatgaaattc atgaatttaa
 981  agactataaa ttgatttcag ttataaaaaa ctcaagagct gcaaggttac aacctcttct catctacatt
1051  acgacagcag ggtatcaatt agatggtcca cttgttgata tggtagaagc gggaagagac accttagatc
```

TABLE 7-continued

Bacteriophage 3A, complete genome sequence

```
1121  aaatcataga agacgaaaga acttttttatt atttagcatc tttggatgat gacgatgata ttaatgattc
1191  gtcgaactgg ataaaagcaa atcccaactt aggtgtctct ataaatttag atgagatgaa agaagagtgg
1261  gaaaaagcta agagaacacc agctgaacgt ggagatttta taaccaaaag gtttaatatc tttgctaata
1331  atgacgagat gagttttatt gattacccaa cactccaaaa aaataatgaa attgtttctt tagaagagct
1401  ggaaggcaga ccgtgcacga ttggttatga tttatcagaa acagaggact ttacagccgc gtgtgctact
1471  tttgcgttag ataatggtaa agttgcagtt ttatcgcatt catggattcc taagcacaaa gttgaatatt
1541  ctaacgaaaa aatacccta t agagaatggg aagaagatgg cttattaaca gtgcaagata agccttatat
1611  tgactaccaa gatgttttaa attggataat taagatgaat gagcattatg tagtagaaaa aattacttat
1681  gatagagcga acgcattcaa actaaatcaa gagttaaaaa attacgggtt tgaaacggaa gaaacaagac
1751  aaggagcttt gaccttgagc cctgcattga aggatttaaa agaaatgttt ttagatggga aataatatt
1821  taataataat cctttaatga aatggtatat caataatgtt cagttgaaac tagacagaaa cggaaactgg
1891  ttgccgtcta agcaaagcag atatcgtaaa atagatggct ttgcagcatt tttaaacaca tatacagata
1961  ttatgaataa agttgtttct gatagtggtg aaggaaacat agagtttatt agtattaaag acataatgcg
2031  ttaaggaggt gaatgttatc gcaaaagaga atattgtcac acgcataaag aaaaaattga tagacaattg
2101  gattgatcag tcaacttcta agctttatga ctttagccca tggaaaaata gatcttttg gggtgtaatt
2171  aataatacgc ttgaaactaa tgaaacgata ttttcagcta ttacaaagtt atctaattcg atggctagtt
2241  tgcccttgaa aatgtatgaa gattataaag tagttaatac agaagtatct gatttactta cagtgtcacc
2311  gaataattct ctgagcagtt ttgattttat taatcaaatt gaaacaatca gaatgaaaa aggtaatgca
2381  tatgtgctaa ttgaacgaga catctatcat caaccatcaa agcttttctt attaaatcca gatgttgttg
2451  aaatgttaat tgaaaaccaa tcacgtgaac tttattattc cattcatgct gcaactggaa ataaattgat
2521  tgttcataat atggacatgt tgcatttta a acacatcgtg gcatctaata tggtgcaagg cattagtccg
2591  attgatgtgt tgaagaatac aactgatttt gataatgcag taagaacctt taatcttaca gaaatgcaaa
2661  aacctgattc tttcatgctt aaatatggtt ccaatgtagg taaagaaaaa aggcagcaag tgttagaaga
2731  tttcaaacag tactatgaag aaaacggtgg aatattattc caagagcctg gtgttgaaat cgaaccgtta
2801  cctaaaaaat atgtctctga agatatagtg gcaagcgaga atttaacaag agaaagagta gctaacgttt
2871  ttcaattgcc ctcagtattc ttaaatgcaa gatcaaatac aaatttcgcg aaaaatgaag agttaaacag
2941  attttacttg cagcatacct tattgccaat cgtcaaacag tatgaagaag aatttaatcg gaaactactt
3011  actaaaacag acagagaaaa aaataggtat tttaaattta acgttaaatc ttatttaagg gctgatagtg
3081  caacacaagc agaagtgtac tttaaagcag ttcgtagtgg ttactacact ataaatgaca ttagagagtg
3151  ggaagattta ccaccagttg aaggtggaga taagccgcta ataagcggtg atttataccc aattgacacg
3221  ccacttgaat taagaaaatc tttgaaaggt ggtgataaaa atgtcaatga agctaagta ttttcaaatg
3291  aaaagaaaat caaaaagtaa aggtgaaata tttatttatg gtgatattgt aagtgataaa tggtttgaaa
3361  gtgatgtaac tgctacagat ttcaaaaata aactagatga actaggagac atcagtgaaa tagatgttca
3431  tataaattca tctggaggca gtgtatttga agggcatgca atatacaata tgctaaaaat gcatcctgca
3501  aaaattaata tctatgtcga tgccttagcg gcatcaattg ctagtgttat cgctatgagt ggtgacacta
3571  tttttatgca caaaaatagt ttttttaatga ttcataattc atgggttatg actgtaggta atgcagaaga
3641  gttaagaaag acagcggatt tacttgaaaa aacagatgct gttagtaatt cagcttattt agataaagca
3711  aaagatttag atcaagaaca cttaaaacag atgttagatg cagaaacttg gcttactgca gaagaagcct
3781  tgtctttcgg cttgatagat gaaattttag gagctaatga ataactgct agtatctcta aagagcaata
```

TABLE 7-continued

Bacteriophage 3A, complete genome sequence

```
3851  taagcgtttc gagaacgtcc cagaagattt aaagaaagat gtagacaaaa tcactaaaat cgatgatgta
3921  gatacgtttg aattggttga aacacctaaa gaaagtatgt cactagaaga aaaagaaaaa agagaaaaaa
3991  ttaaacgcga atgcgaaatt ttaaaaatga caatgagtta ttaggaggaa atgaaatgcc gacattatat
4061  gaattaaaac aatccttagg tatgattgga caacaattaa aaaataaaaa tgatgaattg agtcagaaag
4131  caacagaccc aaatattgat atggaagaca tcaaacaact agaaacagaa aaagcaggct tacaacaaag
4201  atttaacatt gttgaaagac aagtaaaaga cattgaagaa aaagaaaaag cgaaagttaa agacacagga
4271  gaagcttatc aatctttaaa tgatcatgag aagatggtta aagctaaggc agagttttat cgtcacgcga
4341  ttttaccaaa tgaatttgaa aaaccttcaa tggaggcaca acgtttatta cacgctttac caacaggtaa
4411  tgattcaggt ggtgataagc tcttaccaaa aacactttct aaagaaattg tttcagaacc atttgctaaa
4481  aaccaattac gtgaaaaagc tcgtctaact aacattaaag gtttagagat tccaagagtt tcatatactt
4551  tagacgatga tgacttcatt acagatgtag aaacagcaaa agaattaaaa ttaaaaggtg atacagttaa
4621  attcactact aataaattca aagtatttgc tgcaatttca gatactgtaa ttcatggatc agatgtagat
4691  ttagtaaact gggttgaaaa cgcactacaa tcaggtctag cagctaaaga acgtaaagat gccttagcag
4761  taagtcctaa atctggatta gatcacatgt cattttacaa tggatctgtt aaagaagttg agggagcaga
4831  catgtatgat gctattatta acgctttagc agatttacat gaagattacc gtgataacgc aacaatttat
4901  atgcgatatg cggattatgt caaaattatt agtgttcttt caaatggaac aacaaatttc tttgacacac
4971  cagcagaaaa agtatttggc aaaccagtag tatttacaga tgcagcagtt aaacctattg tgggagattt
5041  caattatttt ggaattaact atgatggaac aacttatgac actgataaag atgttaaaaa aggcgaatat
5111  ttgtttgtat taactgcatg gtatgatcag caacgtacat tagacagtgc attcagaatt gcaaaagcaa
5181  aagaaaatac aggttcatta cccagctaag ccccaaaagg ttaatgtaac agctaaggct aaatcagctg
5251  taatatcagc cgaataggggtgatgaaatg agtttagaag aaattaaatt gtggttgaga attgactata
5321  atttcgaaaa tgatttaatt gaaggtctca ttcaatcggc taagtctgaa ttactattaa gtggggttcc
5391  agattatgac aaagatgact tggaataccc gctttttgt acagcgatta gatatatcat tgcaagagat
5461  tatgaaagtc gtgggtactc aaatgaccaa tctagaagca aggtttttaa tgaaagggga ttgcaaaaaa
5531  tgattctgaa attaaaaaag tggtaggtga ttttttaaatg gaatttaatg aatttaaaga tcgcgcatat
5601  ttttttcaat atgtaaataa agggccgtat ccagatgaag aggaaaaaat gaagttgtat agttgctttt
5671  gtaaaatata taatccttct atgaaagata gagaaatttt aaaagcgact gaatcaaagt caggactaac
5741  cataattatg aggtcttcta aaattgaata tctaccacaa acaaatcact tagttaaaat tgacagaggc
5811  ttatattccg ataaattatt caacattaaa gaaataagaa ttgatacacc agatattggc tataatacag
5881  tggttttatc agaaaaatga gtgtagaaat taaagggata cctgaagtgt tgaagaaatt agaatcggta
5951  tacggtaaac aatcaatgca agctaagagt gatagagctt taatgaagc atctgaattt tttataaagg
6021  ctttaaagaa agaattcgag agttttaaag atacgggtgc tagcatagaa gaaatgacta atctaagcc
6091  ttatacaaaa gtaggaagtc aagaaagagc tgttttaatt gaatgggtag gccctatgaa tcgcaaaaac
6161  attattcact tgaatgaaca tggttataca agagatggaa aaaaatatac accaagaggt tttggagtta
6231  ttgcaaaaac attagctgct aatgaacgga agtatagaga aattataaaa aaggagttgg ccagataaat
6301  gaatatatta aacaccataa aagaaatttt attatctgat gcagagctcc aaacatatat aaattctaga
6371  atatactatt ataaagtcac tgaaaatgct gaaacttcca aaccttttgt tgttattaca cctatttatg
6441  atttaccttc agacttcatg tctgataaat atcttagtga agaatactta attcaaatag atgtagaatc
```

TABLE 7-continued

Bacteriophage 3A, complete genome sequence

| | |
|---|---|
| 6511 | ttcaaataat cagaaaacaa ttgatataac aaaacgaata agatatctgt tatatcaaca aaatttaatt |
| 6581 | caagcatcta gtcagttaga tgcttatttt gaagaaacta aacgttatgt gatgtcgaga cgttatcaag |
| 6651 | gcataccaaa aaatatatat tataaaaatc agcgcatcga ataggtgtgc tttttaattt ttaaggagga |
| 6721 | aataagcaat ggcagaagga caaggttctt ataaagtagg tttttaaaga ttatacgttg gagtttttaa |
| 6791 | cccagaagca acaaaagtag ttaaacgcat gacatgggaa gatgaaaaag gtggtacagt tgatctaaat |
| 6861 | atcacaggtt tagcaccaga tttagtagat atgtttgcat ctaacaaacg tgtttggatg aaaaaacaag |
| 6931 | gtactaatga agttaagtct gacatgagta ttttaatat tccaagtgaa gatctaaata cagttattgg |
| 7001 | tcgttctaaa gataaaatg gtacatcttg ggtaggagag aatacaagag caccatacgt aacagttatt |
| 7071 | ggagaatctg aagatggttt aacaggtcaa ccagtgtacg ttgcgctact taaaggtact tttagcttgg |
| 7141 | attcaattga atttaaaaca cgaggagaaa aagcagaagc accagagcca acaaaattaa ctggtgactg |
| 7211 | gatgaacaga aaagttgatg ttgatgtac tccacaaggt attgtatacg ggtatcatga aggtaaagaa |
| 7281 | ggagaagcag aattcttcaa aaaagtattc gttggataca cggacagtga agatcattca gaggattctg |
| 7351 | caagttcgtt acccagctaa cccccaaaat gttgaagtag cagttaattc aaaatctgca acagtttcag |
| 7421 | cagaataggg gctttcaaaa taaatcaaag gagaataatt tatgactaaa actttaaagg tttataaagg |
| 7491 | agacgacgtc gtagcttctg aacaaggtga aggcaaagtg tcagtaactt tatctaatt agaagcggat |
| 7561 | acaacttatc caaaggtac ttaccaagtg gcatgggaag aaaatggtaa agaatctagt aaagttgatg |
| 7631 | tacctcaatt caaaaccaat ccaattctag tctcaggcgt atcatttaca cccgaaacta atcaatcac |
| 7701 | ggtaaatgct gatgacaatg ttgaaccaaa cattgcacca agtacagcaa cgaataaaac gttgaaatat |
| 7771 | acaagtgaac atccagagtt tgttactgtt gatgagagaa caggagcaat tcacggtgta gctgagggaa |
| 7841 | cttcagttat cactgctacg tctactgacg gaagtgacaa gtctggacaa attacagtaa cagtaacaaa |
| 7911 | tggataatta tttgagacgc agaatatctg cgtcttttt atttgaataa aaggagctaa tacaatgatt |
| 7981 | aaatttgaaa ttaaagaccg taaaacagga aaaacagaga gctatacaaa agaagatgtg acaatgggcg |
| 8051 | aagcagaaaa atgctatgag tattagaat tagtaaatca agagaataaa aaagaagtac ctaacgcaac |
| 8121 | aaaaatgaga caaaagagc gacagttatt agtagattta tttaaagatg aaggattgac tgaagaagat |
| 8191 | gttttgaaca agatgagcac taaaacttat acaaaagcct tgaaagatat atttcgagaa atcaatggtg |
| 8261 | aagatgaaga agattcagaa actgaaccag aagagatggg aaagacagaa gaacaatctc aataaaagat |
| 8331 | atttttatcga acattaagaa aatacaacgt ttctgtatgg agcagtatgg gtggacatta actgaagtca |
| 8401 | gaaaacagcc gtatgtaaaa ctttagaaaa tacttaatga agagaataaa gaagagactg aagaaaaaca |
| 8471 | aagtgaacaa aaagtcatta caggtacgga tttaagaaaa ctttttggaa gctagaaagg aggttaatat |
| 8541 | gaatgaaaaa gtagaaggca tgaccttgga gctgaaatta gaccatttag gtgtccaaga aggcatgaag |
| 8611 | ggtttaaagc gacaattagg tgttgttaat agtgaaatga agctaatct gtcatcattt gataagtctg |
| 8681 | aaaaatcaat ggaaaagtat caggcgagaa ttaagggggtt aaatgataag cttaaagttc aaaaaaagat |
| 8751 | gtattctcaa gtagaagatg agcttaaaca agttaacgct aattatcaaa aagctaaatc tagtgtaaaa |
| 8821 | gatgttgaga aagcatattt aaagctagta gaagctaata aaaagaaaa attagctctt gataaatcta |
| 8891 | aagaagccct aaaatcttcg aatacagaac ttaaaaagc tgaaaatcaa tataaacgta caaatcaacg |
| 8961 | taaacaagat gcatatcaaa aacttaaaca gttgagagat gcagaacaaa agcttaagaa tagtaaccaa |
| 9031 | gctactactg cacaactaaa aagagcaagt gacgcagtac agaagcagtc cgctaagcat aaagcacttg |
| 9101 | ttgaacaata taaacaagaa ggcaatcaag ttcaaaaact aaaagtacaa aatgataatc tttcaaaatc |
| 9171 | aaacgaaaaa atagaaaatt cttacgctaa aactaatact aaattaaagc aaacagaaaa agaatttaat |

TABLE 7-continued

Bacteriophage 3A, complete genome sequence

```
 9241 gatttaaata atactattaa gaatcatagc gctaatgtcg caaaagctga aacagctgtt aacaaagaaa
 9311 aagctgcttt aaataattta gagcgttcaa tagataaagc ttcatccgaa atgaagactt ttaacaaaga
 9381 acaaatgata gctcaaagtc atttcggcaa acttgctagt caagcggatg tcatgtcaaa gaaatttagt
 9451 tctattggag ataaaatgac ttccctagga cgtacgatga cgatgggcgt atctacaccg attactttag
 9521 ggttaggtgc agcattaaaa acaagtgcag acttcgaagg gcaaatgtct cgagttggag cgattgcaca
 9591 agcaagcagt aaagacttaa aaagcatgtc taatcaagcg gttgacttag gcgctaaaac aagtaaaagt
 9661 gctaacgaag ttgctaaagg tatggaagaa ttggcagctt taggctttaa tgccaaacaa acaatggagg
 9731 ctatgccggg tgttatcagt gcagcagaag caagcggtgc agaaatggct acaactgcaa ctgtaatggc
 9801 atcagcaatt aattctttcg gtttaaaagc atctgatgca aaccatgttg ctgatttact tgcgagatca
 9871 gctaatgata gtgctgcaga tattcaatac atgggagatg cattaaaata tgcaggtact ccagcaaaag
 9941 cattaggagt ttcaatagag gacacttctg cagcaattga gtttttatct aactcagggt tagagggtc
10011 tcaagcaggt actgcattaa gagcttcgtt tattaggcta gctaatccaa gtaaaagtac agctaaggaa
10081 atgaaaaaat taggtattca tttgtctgat gctaaaggtc aatttgttgg catgggtgaa ttgattagac
10151 agttccaaga caacatgaaa ggcatgacga gagaacaaaa actagcaaca gtggctacaa tagttggcac
10221 tgaagcagca agtggatttt tagccttgat tgaagcgggt ccagataaaa ttaatagcta tagcaaatca
10291 ttgaagaact ctaatggtga agtaaaaaaa gcagctgatt tgatgaaaga caacctcaaa ggtgctctgg
10361 aacaattagg tggcgctttt gaatcgttag caattgaagt tggtaaagat ttaacgccta tgattagagc
10431 aggtgcggaa ggattaacaa aattagttga tggatttaca catcttcctg gttggtttag aaaggcttcg
10501 gtaggtttag cgatttttgg tgcatctatt ggccctgctg ttcttgctgg tggcttatta atacgtgcag
10571 ttggaagcgc ggctaaaggc tatgcatcat aaatagacg cattgctgaa aatacaatac tgtctaatac
10641 caattcaaaa gcaatgaaat ctttaggtct tcaaaccta tttcttggtt ctacaacagg aaaaacgtca
10711 aaaggcttta aaggattagc cggagctatg ttgtttaatt taaaacctat aaatgttttg aaaaattctg
10781 caaagctagc aattttaccg ttcaaacttt tgaaaaacgg tttaggatta gccgcaaaat ccttatttgc
10851 agtaagtgga ggcgcaagat ttgctggtgt agccttaaag ttttaacag gacctatagg tgctacaata
10921 actgctatta caattgcata taaagttttt aaaaccgcat atgatcgtgt ggaatggttc agaaacggta
10991 ttaacggttt aggagaaact ataaagtttt ttggtggcaa aattattggc ggtgctgtta ggaagctagg
11061 agagtttaaa aattatcttg gaagtatagg caaaagcttc aaagaaaagt tttcaaagga tatgaaagat
11131 ggttataaat ctttgagtga cgatgacctt ctgaaagtag gagtcaacaa gtttaaagga tttatgcaaa
11201 ccatgggcac agcttctaaa aaagcatctg atactgtaaa agtgttggg aaaggtgttt caaagaaac
11271 agaaaaagct ttagaaaaat acgtacacta ttctgaagag aacaacagaa tcatggaaaa agtacgttta
11341 aactcgggtc aaataacaga agacaaagca aaaaaacttt tgaaaattga agcggattta tctaataacc
11411 ttatagctga aatagaaaaa agaaataaaa aggaactcga aaaaactcaa gaacttattg ataagtatag
11481 tgcgttcgat gaacaagaaa agcaaaacat tttaactaga actaaagaaa aaaatgactt gcgaattaaa
11551 aaagagcaag aactcaatca gaaaatcaaa gaattgaaag aaaaagcttt aagtgatggt cagatttcag
11621 aaaatgaaag aaaagaaatt gaaaagcttg aaaatcaaag acgtgacatc actgttaaag aattgagtaa
11691 gactgaaaaa gagcaagagc gtatttagt aagaatgcaa agaaacagaa atgcttattc aatagacgaa
11761 gcgagcaaag caattaaaga agcagaaaaa gcaagaaaag caagaaaaaa agaagtggac aagcaatatg
11831 aagatgatgt cattgctata aaaaataacg tcaaccttc taagtctgaa aaagataaat tattagctat
```

TABLE 7-continued

Bacteriophage 3A, complete genome sequence

| | | | | | |
|---|---|---|---|---|---|
| 11901 | tgctgatcaa | agacataagg | atgaagtaag | aaaggcaaaa | tctaaaaaag atgctgtagt agacgttgtt |
| 11971 | aaaaagcaaa | ataaagatat | tgataaagag | atggatttat | ccagtggtcg tgtatataaa aatactgaaa |
| 12041 | agtggtggaa | tggccttaaa | agttggtggt | ctaacttcag | agaagaccaa aagaagaaaa gtgataagta |
| 12111 | cgctaaagaa | caagaagaaa | cagctcgtag | aaacagagaa | aatataaaga aatggtttgg aaatgcttgg |
| 12181 | gacggcgtaa | aaactaaaac | tggcgaagct | tttagtaaaa | tgggcagaaa tgctaatcat tttggcggcg |
| 12251 | aaatgaaaaa | aatgtggagt | ggaatcaaag | gaattccaag | caaattaagt tcaggttgga gctcagccaa |
| 12321 | aagttctgta | ggatatcaca | ctaaggctat | agctaatagt | actggtaaat ggtttggaaa agcttggcaa |
| 12391 | tctgttaaat | cgactacagg | aagtattcac | aatcaaacta | agcaaaagta ttcagatgcc tcagataaag |
| 12461 | cttgggcgca | ttcaaaatct | atttggaaag | ggacatcaaa | atggtttagc aatgcatata aaagtgcaaa |
| 12531 | gggctggcta | acggatatgg | ctaataaatc | gcgctcgaaa | tgggataata tttctagtac agcatggtcg |
| 12601 | aatgcaaaat | ccgtttgaaa | aggaacatcg | aaatggttta | gtaactcata caaatcttta aaaggttgga |
| 12671 | ctggagatat | gtattcaaga | gcccacgatc | gttttgatgc | aatttcaagt tcggcatggt ctaacgctaa |
| 12741 | atcagtattt | aatggttta | gaaaatggct | atcaagaaca | tatgaatgga ttagagatat tggtaaagac |
| 12811 | atgggaagag | ctgcggctga | tttaggtaaa | aatgttgcta | ataaagctat tggcggttta aatagcatga |
| 12881 | ttggcggtat | taataaaata | tctaaagcca | ttactgataa | aaatctcatc aagccaatac ctacattgtc |
| 12951 | tactggtact | ttagcaggaa | agggtgtagc | taccgataat | tcgggagcat taacgcaacc gacatttgct |
| 13021 | gtattaaatg | atagaggttc | tggaaacgcc | ccaggtggtg | gagttcaaga agtaattcac agggctgacg |
| 13091 | gaacattcca | tgcaccccaa | ggacgagatg | tggttgttcc | actaggagtt ggagatagtg taataaatgc |
| 13161 | caatgacact | ctgaagttac | agcggatggg | tgttttgcca | aaattccatg gtggtacgaa aaagaaagat |
| 13231 | tggctagacc | aacttaaagg | taatataggt | aaaaaagcag | gagaatttgg agctacagct aaaaacacag |
| 13301 | cgcataatat | caaaaaaggt | gcagaagaaa | tggttgaagc | agcaggcgat aaaatcaaag atggtgcatc |
| 13371 | ttggttaggc | gataaaatcg | gcgatgtgtg | ggattacgta | caacatccag ggaaactagt aaataaagta |
| 13441 | atgtcaggtt | taaatattaa | ttttggaggc | ggactaacgc | tacagtaaaa attgctaaag gcgcgtactc |
| 13511 | attgctcaaa | aagaaattaa | tagacaaagt | aaaatcgtgg | tttgaagatt ttggtggtgg aggcgatgga |
| 13581 | agctatctat | ttgaatatcc | aatctggcaa | agatttggac | gctacacagg tggacttaac tttaatgacg |
| 13651 | gtcgtcacta | tggtatagac | tttggtatgc | ctactggaac | aaacgtttat gccgttaaag gtggtatagc |
| 13721 | agataaggta | tggactgatt | acgtggcgg | taattctata | caaattaaga ccggtgctaa cgaatggaac |
| 13791 | tggtatatgc | atttatctaa | gcaattagca | agacaaggcc | aacgtattaa agctggtcaa ctgataggga |
| 13861 | aatcaggtgc | tacaggtaat | ttcgttagag | gagcacactt | acatttccaa ttgatgcaag ggtcacatcc |
| 13931 | agggaatgat | acagctaaag | atccagaaaa | atggttgaag | tcacttaaag gtagtggcgt tcgaagtggt |
| 14001 | tcaggtgtta | ataaggctgc | atctgcttgg | gcaggcgata | tacgtcgtgc agcaaaacga atgggtgtta |
| 14071 | atgttacttc | gggtgatgta | ggaaatatca | ttagcttgat | tcaacacgaa tcaggaggaa atgcaggtat |
| 14141 | aactcaatct | agttcgctta | gagacatcaa | cgttttacag | ggcaatccag caaaaggatt gcttcaatat |
| 14211 | atcccacaaa | catttagaca | ttatgctgtt | agaggtcaca | acaatatata tagtggttac gatcagttat |
| 14281 | tagcgttctt | taacaacaga | tattggcgct | cacagtttaa | cccaagaggt ggttggtctc caagtggtcc |
| 14351 | aagaagatat | gcgaatggtg | gtttgattac | aaagcatcaa | cttgctgaag tgggtgaagg agataaacag |
| 14421 | gagatggtta | tccctttaac | tagacgtaaa | cgagcaattc | aattaactga acaggttatg cgcatcatcg |
| 14491 | gtatggatgg | caagccaaat | aacatcactg | taaataatga | tacttctaca gttgaaaaat tgttgaaaca |
| 14561 | aattgttatg | ttaagtgata | aaggaaataa | attaacagat | gcattgattc aaactgtttc ttctcaggat |

TABLE 7-continued

Bacteriophage 3A, complete genome sequence

```
14631  aataacttag gttctaatga tgcaattaga ggtttagaaa aaatattgtc aaaacaaagt gggcatagag
14701  caaatgcaaa taattatatg ggaggtttga ctaattaatg caatcttttg taaaaatcat agatggttac
14771  aaggaagaag taataacaga ttttaatcag cttatatttt tagatgcaag ggctgaaagt ccaaacacca
14841  atgataacag tgtaactatt aacggagtga atggtatttt accgggcgca attagttttg cgccttttc
14911  attagtatta aggtttggct atgatggtat agatgttata gatttaaatt tatttgagca ttggtttaga
14981  tctgtgttta atcgcagaca tccttattat gttattactt ctcaaatgcc tggtgttaaa tatgcagtga
15051  atacagctaa tgttacatct aatttaaaag atggttcttc aactgaaatt gaagtaagtt taaatgttta
15121  taaagggtat tctgaatcag ttaattggac cgatagcgag ttcttattcg actctaattg gatgtttgaa
15191  aatggaattc ctcttgattt cacacctaaa tatactcata catcaaatca atttactatt tggaacggtt
15261  ctactgatac gataaatcca cgattcaagc acgatttgaa atattaatt aatttaaatg cgagtggagg
15331  atttgaactg gttaactata caacaggtga tattttaag tacaacaaaa gtatagataa aaacactgat
15401  tttgttttag atggtgtgta tgcatatcga gatataaata gagtgggaat tgatacaaat agaggcatta
15471  taacattagc gccaggtaaa aatgaattta agattaaagg agacatcagt gatattaaaa ctacatttaa
15541  gtttcctttt atttataggt aggtgattta atggattatc atgatcattt atcagtaatg gattttaatg
15611  aattgatttg tgaaaattta ctagatgtag attatggttc ttttaaagaa tattatgaac tgaatgaagc
15681  taggtacatc acttttacag tttatagaac tactcataat agttttgttt tcgatttact aatttgtgaa
15751  aacttcataa tttatcatgg tgaaaaatac acaattaagc agacagcgcc aaaggttgaa ggtgataaag
15821  tttttattga agttacggca tatcacataa tgtatgaatt tcaaaatcac tcagtggaat caaataagct
15891  tgatgacgac agtagcgaaa ctggtaaaac gccagaatac tctttagatg agtacttaag atatggattt
15961  gcaaatcaaa aaacttcggt caaaatgacc tataaaataa ttggaaattt taagcgaaaa gtaccgattg
16031  acgaattagg taacaaaaac ggcttagaat actgtaaaga agcggtagac ctatttggct gtataattta
16101  cccaaatgat acggagatat gtttttattc tcctgaaaca ttttatcaaa gaagcgagaa agtgattcga
16171  tatcaatata atactgatac tgtatctgca actgtcagta cattggaatt aagaacagct ataaaagttt
16241  ttggaaaaaa gtatacagct gaggaaaaga aaaattataa tcctattaga acaactgaca ttaaatattc
16311  aaatggtttt ataaaagaag gtacttatcg taccgcaaca attgggtcta agctactat taactttgat
16381  tgcaagtatg gtaatgaaac agttagattt acaataaaaa agggctctca aggtggaata tataagttga
16451  ttttagacgg caagcaaatt aagcaaattt cttgttttgc taagtcggtt cagtctgaaa caatagattt
16521  aataaaaaat attgataaag gcaagcacgt tttagaaatg atatttttag gagaagaccc caaaaataga
16591  attgatatat cttcaaataa aaaagctaag ccttgtatgt atgttggaac tgaaaaatca acagtcttaa
16661  atttaattgc tgacaactca ggtcgcaatc aatacaaagc aattgttgac tacgtcgcug atagtgcaaa
16731  gcagtttggg attcgatatg ctaatacgca aacaaatgaa gatatcgaaa cacaggataa gctgttagaa
16801  tttgcaaaaa agcaaataaa tgatactcct aagactgaat tagatgttaa ttatataggt tatgaaaaaa
16871  tagagccaag agatagcgta ttctttgttc atgaattaat gggatataac actgaattaa aggttgttaa
16941  acttgatagg tcacatccat ttgtaaacgc aatagatgaa gtgtctttca gcaatgaaat aaaggatatg
17011  gtacaaattc aacaagcgct taacagacga gttattgcac aagataatag atataactat caagcaaatc
17081  gtataaatca tttatacact agtactttga attctccttt cgagacaatg gatataggga gtgtattaat
17151  ataatggcaa cagaagaagt taaaatcaaa gcgctacttg aaaacgataa acagtacttt ccagctacac
17221  attggaaagc tataaatggg ataccttatg caggcagtag tgatattgat ggattgcctc aagacggtat
```

TABLE 7-continued

Bacteriophage 3A, complete genome sequence

```
17291  catttcggta gatgataaaa ataaattaga taatttaaaa ataggcgaag caggaattat tcaaaatagc
17361  attgtacaga aatccccaaa cggtaaattg tggaaaataa cagttgacga tagtgggaaa cttggtacag
17431  tgctatttta ttagaaagga aggtgcatta tggaaaattt gtatttaata aaggatttgg gagctttagc
17501  aggtcgagat tatagagcta aggaaataca aaacttacaa agaatagagc aatttgcgct tggcttgaca
17571  acagagttta agttgcatca gaaagctaaa acaattcaac acttcgctga gcaaatttat tataatggta
17641  gatcgcaagc agcagtaaac aaatctttac aaagtcaaat taacgcactt gttgtggcac cacgtaataa
17711  cagtgctaat gagattgttc aagctcgagt taatgtaaac ggcgaaacct tgacacatt aaaagaacat
17781  ttagacgatt gggaaaccca aactcaaatt aataaagagg aaactataag agaattaaat aagaccaaac
17851  aagaaattct tgatatcgag tatcgttttg aacctgataa gcaagaattt ttatttgtga cagaacttgc
17921  acctcttaca aatgcagtaa tgcaatcctt ctggtttgat aatagaacag gcatagtata catgacacaa
17991  gctagaaata atggctatat gctaagtcgt ctaagaccta atggtcaatt tatagacagc tcattgattg
18061  taggtggggg tcatggtaca cataacggtt atagatatat tgatgatgag ttatggattt atagtttat
18131  cttaaatggt aataatgaga atacattagt tcgtttcaag tatacgccta atgtggaaat tagctatggc
18201  aagtatggta tgcaagatgt atttacagga caccccagaaa aaccctacat caccccctgtc ataaatgaaa
18271  aagaaaataa aattctatac agaattgaga gacctagaag tcactgggaa cttgaaaact caatgaatta
18341  tatagagata agaagtttag acgatgttga taaaaatatt gataaagttt tgcataaaat cagtatccct
18411  atgagactaa caaacgaaac ccaaccaatg cagggtgtga cttttgatga aaaatacttg tattggtata
18481  caggagacag taatccaaat aatagaaact atttaacggc tttcgattta gaaacaggag aagaagcgta
18551  tcaggttaat gctgactatg gtggaacact agattcattt cctggcgaat ttgcggaagc agaaggtttg
18621  caaatatact atgacaaaga tagtggtaaa aaagctttga tgctaggtgt tactgtcggt ggtgatggaa
18691  atagaacaca tcgtattttc atgattgggc aaagaggtat tttagaaata cttcactcaa gaggcgttcc
18761  ttttatcatg agtgacacag gtggtagagt taaaccttta ccaatgaggc ctgataaact taagaatctt
18831  gggatgttaa cagagccagg tcttactat ttatacactg atcatacagt tcaaatcgat gatttcccat
18901  taccaagaga atggcgtgat gcaggttggt tcttggaagt taagccacca caaactggcg gtgatgtaat
18971  tcagatattg acgcgtaata gttatgcaag gaatatgatg acttttgaaa gggtgctttc tggaagaact
19041  ggagacattt cggactggaa ttatgtgcct aaaaatagtg gtaaatggga gagagtacct tcattcatca
19111  caaaaatgtc agatattaac atagtaggca tgtcgtttta tttaactacg gatgatacaa aacgttttac
19181  agattttcca actgaacgta aaggggtagc tggttggaac ttatatgtag aagcttcaaa cacaggtggc
19251  tttgttcata ggctagttcg taatagtgtt acagcatctg ctgagatact attgaaaaat tatgatagta
19321  aaacaagttc agggccatgg actttacacg aagggagaat tataagttaa tgagtaattt agagaaatct
19391  gtagctataa atttagaaaa cacagcgcat tatgaaaata tttcaaatct agatataact tttagaacag
19461  gagagagtga ttcttctgtt cttcttttta atatcactaa aaataatcaa ccgttattat tgagtgaaga
19531  aaatatcaaa gcacgaatag cgattcgagg taaaggagtc atggtagttg ctccactaga aatattagat
19601  ccatttaaag gtatttaaa atttcaatta cctaatgatg taattaaacg agatggaagt tatcaagctc
19671  aagtttcggt tgcagaatta ggtaattcag acgtggtagt tgtcgagaga actatcacat ttaacgttga
19741  aaaagtttg tttagcatga ttccatctga aacaaaatta cactatattg ttgaatttca ggaattagaa
19811  aaaactatta tggatcgtgc gaaagcaatg gacgaggcta taaaaaatgg tgaagattat gcgagtctga
19881  ttgaaaaagc taagaaaaa ggtctatcg atattcaaat agcaaaatct tcaagtatag atgaattaaa
19951  gcaacttgct aatagccata tatctgattt ggaaaataaa gcgcaagcat attcaagaac attcgatgag
```

TABLE 7-continued

Bacteriophage 3A, complete genome sequence

```
20021  caaaagcgat atatggatga gaaacatgaa gccttcaagc agtcagtgaa tagtggtggt ttagtcacaa
20091  gtggttctac ttcaaattgg caaaaagcta agattactaa agatgatggt aagataatgc agattactgg
20161  atttgatttt aataatccag aacaaagaat aggtgattca acccaattta tttatgtttc gcaagctata
20231  aattatccaa gaggtgttag tactaacggt actgtcgaat atttagtagt aacttcagat tacaagcgta
20301  tgacttatcg accgaacggt acaaataaag tgtttgttaa agaaaagaa gcgggttcat ggtctgagtg
20371  gtcagaatta gctattaatg attacaatac acctttttgaa actgttcaaa gtgcccaatc aaaagctaat
20441  atggccgaaa gtaacgctaa attatacgca gatgacaagt ttaataaaag gtattcggtt attttttgatg
20511  gaacagcaaa tggtgtgggc tctacattgt acttaaatga gagtttagac caattttattt tattaatttt
20581  ttatgggact tttccaggtg gtgactttac agagtttggc agtccttttg gaggaggaaa gatttcattg
20651  aatccctcaa atcttccaga tggtgatgga aatggtggag gtgtttatga gtttggatta actaaatcta
20721  gtcgtacatc tttaactata tcaaacgatg tctatttcga cttaggaagt caaagaggct ctggtgcgaa
20791  cgcaaataga gggacaatta acaaaattat aggagtgaga aaataatgca aatattagtt aacaagcgta
20861  atgagataat ttcatacgct atcattggtg gctttgaaga aggtattgat attgaaaatt taccagaaaa
20931  ttttctctcaa gtttttagac ctaaagcctt taaatattca atgggggaaa tagtttttaa cgaagattat
21001  tcagaagaaa aagatgactt gcatcaacag attgacagtg aagaacaaaa cacagtcgct tctgatgaca
21071  tcttacgaaa aatggttgct agtatgcaga acaagttgt tcaaagtaca agttatcga tgcaagttaa
21141  taagcaaaat gcactaatgg caaaacaact tgtgacactt aataaaaaat tagaagaggt taaggagag
21211  actgaaaatg cttaaattaa tttcaccaac attcgaagat attaaaacat ggtatcaatt gaagaatat
21281  agtaaagaag atatagcgtg gtatgtagat atggaagtta tagataaaga ggaatatgca attattacag
21351  gagaaaagta tccagaaaat ctagagtcat aggttataat cttatggctt tttaatttga ataaagtggg
21421  tggtgtaatg tttggattta ccaaacgaca cgaacaagat tggcgtttaa cgcgattaga agaaaatgat
21491  aagactatgt ttgaaaaatt cgacagaata gaagacagtc tgagaacgca agaaaaaatt tatgacaagt
21561  tagatagaaa tttcgaagaa ctaaggcgtg acaaagaaga agatgaaaaa ataaagaga aaaatgctaa
21631  aaatattaga gacatcaaga tgtggattct aggattaata gggacgattc taagtacatt tgttatagcc
21701  ttgttaaaaa ctattttttgg catttaaagg aggtgattac catgcttaag ggaattttag gatatagctt
21771  ttggtcgtgt ttctggttta gtaagtgtaa gtaatagtta agagtcagtg cttcggcact ggctttttat
21841  tttggaaaaa aggagcaaac aaatggatgc aaaagtaata acaagataca tcgtattgat cttagcatta
21911  gtaaatcaat tcttagcgaa caaaggtatt agcccgattc cagtagacga tgagaatata tcatcaataa
21981  tacttactgt tgttgcttta tatactacgt ataaagacaa tccaacatct caagaaggta atgggcaaa
22051  tcaaaagcta agaaatata agctgaaaaa caagtataga aaagcaacag ggcaagcgcc aattaaagaa
22121  gtaatgacac ctacgaatat gaacgacaca aatgatttag ggtaggtgtt gaccaatgtt gataacaaaa
22191  aaccaagcag aaaaatggtt tgataattca ttagggaagc agttcaatcc tgatttgttt tatggatttc
22261  agtgttacga ttcgcaaat atgttttta tgatagcaac aggcgaaagg ttacaaggtt tatacgctta
22331  taatattcca tttgataata aagcaaggat tgaaaaatac gggcaaataa ttaaaaacta tgatagcttt
22401  ttaccgcaaa agttggacat tgtcgttttc ccgtcaaagt atggtggcgg agctggacat gttgaaattg
22471  ttgagagcgc taatctaaac actttcacat cgtttggcca aaattggaat ggtaaaggtt ggacaaatgg
22541  cgttgcgcaa cctgttgggg gtcccgaaac cgttacaaga catgttcatt attacgatga cccaatgtat
22611  tttattagat taaatttccc agataaagta agtgttggag ataaagctaa aagcgttatt aagcaagcaa
```

TABLE 7-continued

Bacteriophage 3A, complete genome sequence

```
22681  ctgccaaaaa gcaagcagta attaaaccta aaaaaattat gcttgtagcc ggtcatggtt ataacgatcc
22751  tggagcagta ggaaacggaa caaacgaacg cgattttata cgtaaatata taacgccaaa tatcgctaag
22821  tatttaagac atgccggtca tgaagtcgca ttatatggtg gctcaagtca atcacaagac atgtatcaag
22891  atacagcata cggtgttaat gtaggtaata aaaaagatta tggcttatat tgggttaaat cacagggta
22961  tgacattgtt ctagaaatac atttagacgc agcaggagaa agcgcaagtg gtgggcatgt tattatctca
23031  agtcaattca atgcagatac tattgataaa agtatacaag atgttattaa aaataactta ggacaaataa
23101  gaggtgtaac acctcgtaac gatttactaa atgttaacgt atcagcagaa ataaatataa attatcgctt
23171  atctgaatta ggttttatca ctaataaaaa tgatatggat tggattaaga aaaactatga cttgtattct
23241  aaattaatag ccggtgcgat tcatggtaag cctatcggtg gtgtgatatc tagtgaggtt aaaacaccag
23311  ttaaaaacga aaagaatccg ccagtgccag caggttatac acccgataaa aataatgtac cgtataaaaa
23381  agaaactggt tattacacag ttgccaatgt taaaggtaat aacgtaaggg acggctattc aactaattca
23451  agaattactg gtgtattacc taataacgca acaatcaaat atgacggcgc atattgtatc aatggctata
23521  gatggattac ttatattgct aatagtggac aacgtcgtta tattgctaca ggagaggtag acaaggcagg
23591  taatagaata agcagttttg gtaagtttag tgcagtttga taattgtata tgatgaatct taggcaggta
23661  cttcggtact tgcctattat ttaaaattaa taaacagtta attttttacat gaatatatta aattttaaaa
23731  aaacaaacgt ttttagtata taaattattt tgtgttcgta ttgtgtgcta tgattaaaaa gttgttatgg
23801  tcaactatat cgtggtttta tgtttattat caatcaaaat ataaattatt tataatttgt ttggtaatga
23871  acgggttttt ttcgaaataa tagtaaaaaa acacatttgt agatatttta aactcggtaa atcttttaat
23941  aaatatttaa ttttattaaa agttaaaaag gtttaatata aaaatgtaat aaaatttata agaaaggaa
24011  atgatttta tggtcaaaaa aagactatta gctgcaacat tgtcgttagg aataatcact cctattgcta
24081  cttcgtttca tgaatctaaa gctgataaca atattgagaa tattggtgat ggcgctgagg tagtcaaaag
24151  aacagaagat acaagtagcg ataagtgggg ggtcacacaa atattcagt ttgattttgt taaagataaa
24221  aagtataaca aagacgcttt gattttaaaa atgcaaggtt ttatcaattc aaagactact tattacaatt
24291  acaaaaacac agatcatata aaagcaatga ggtggccttt ccaatacaat attggtctca aaacaaatga
24361  ccccaatgta gatttaataa attatctacc taaaaataaa atagattcag taaatgttag tcaaacatta
24431  ggttataaca taggtggtaa ttttaatagt ggtccatcaa caggaggtaa tggttcattt aattattcaa
24501  aaacaattag ttataataaa ataaaaagta ggtgataaga tgactcaatt tctagggcg cttcttctta
24571  caggagtttt aggttacata ccatataaat atctaacaat gataggttta gttagtgaaa aaaacaaggt
24641  tatcaatact cctgtattat tgatttttc tattgaaaca tgtttgatat ggttttatag ttttataatt
24711  tttaataatg ttgatttaaa aatttgaat ttaattcagt tgcttacagg tctaaaagca aatatttttgt
24781  ttctatttat ttttgtttta acagtgtttg tatttaatcc tttaattgtt aaatttatta tctggttaat
24851  taatataacc agaaagttta tgaaattgga ttgtataagc ttattagaca aagagacaa gttgtttaat
24921  aacaacggta aaccagtatt tatagttata aaagactttg aaaacagaat cattgaagag ggtgaactta
24991  aaacctataa ttcagctggt agcgatttcg atttactaga agttgagcga caagatttca aagtatctga
25061  tttaccgtca.aacgatgaat tgtatattaa acatacactt gtagaccta aacaacaaat taaattggat
25131  ttatattaa tgaatgaata ctaatcttt tcttagctt tttctgataa agtgctttt aattttcgc
25201  tggcgcccgg ctttcaaaa cttttgtta ttgggttact acgagtagct tcttgttttt tgttttatc
25271  cgccataaaa ttctcaccac cattcaacgt ctacacttgt aggcgttttt ttatttagta aagtcataat
25341  gaatcttctt tggttaactt atctccatct attttttgtg aaataaattc caagtattta cgcgcattat
```

TABLE 7-continued

Bacteriophage 3A, complete genome sequence

```
25411  gtgacgataa atctttaggt aactcataag tgaatggttg attaccacta gttaaaactt catatactat
25481  agtttctttt tttattttgc aattagttat tttcattata aacttccttt caaacactgc tgaaatagac
25551  gtcttttata ttaaagcgcc acacaggcgc tgttaatcac aatacaactt tgcccattac tttaatatta
25621  ctaaacgaag cgactttgat atcatcatac ttcggattta gagataccaa attaatatag tcttcgcata
25691  tatctacacg cttgataaga cttactccat ctaatacaac gagtgcaatt gtaccatctt aatagaatc
25761  ttctttctta ataaaagcgt atgttccttg ttttaacata ggttccattg aatcaccatt aactaaaata
25831  caaaaatcag catttgatgg cgtttcgtct tctttaaaaa atacttcttc atgcaatatg tcatcatata
25901  attcttctcc tatgccagca ccagttgcac cacatgcaat atacgatact agtttagact ctttatatcc
25971  atctatagaa gtgactttat tctgttcttc caattgttca tttgcatagt taagtacgtt ttcttggcgg
26041  ggaggtgtga gtttgttgta tatggaagtg atgtcgttat cgtctttgta tgtagtattt gattcactat
26111  acaaatcatt aatcttcaca ttgaagtact cagccaaaat tttggcagtt gataatcgag gttcttcctt
26181  ttcattttcc cattttgata tcttgccttt cgttaatttc attaagtcgg gatatttatt attaagatca
26251  gttgctaatt gttccatagt catattttta tttttttctt agcttcttta aaccttcacc aatacccata
26321  cgaaaccctc cttatataag ataatttcat tataaaagtt tcgaaaacga aacgcaagga aaatattatt
26391  gcaaaagttg ttgacatcga aacttttatg atgtattctt aaatcaagtt gttacaaacg aaacaaaagg
26461  aggggttca atgacaacta gtgtagcaga taaaccatac ttaaaaataa aaagcttgat tgcacttaaa
26531  ggaactaacc aaaaagaagt tgctaaagca atcggaatga gtagaagttt attgagtata aagataaatc
26601  gaattaatgg cagagatttt acaacttcag aagctaaaaa attagcagat catttaaatg ttaaagttga
26671  tgattttttt taaacttaaa gtttcgaaag tgacaactaa ataaaaataa ggaggacact atggaacaaa
26741  taacgttaac caaagaagag ttgaaagaaa ttatagcgaa agaagttaga aatgctataa aaggcgagaa
26811  accaatcagc tcaggtgcaa ttttcagtaa agtaagaatc aataatgacg atttagaaga atcaataaa
26881  aaactcaatt tcgcaaaaga tttgtcgcta ggaagattga ggaagctcaa tcatccgatt ccgctaaaaa
26951  agtatcagca tggcttcgaa tcaattcatc aaaaagctta tgtacaagat gttcatgacc atattagaaa
27021  attaacatta tcaatttttg gagtgacact taattcagac ttgagtgaaa gtgaatacaa cctagcagca
27091  aaaatttata gagatatcaa aaactattat ttatatatct atgaaaagag agtttcagaa ttaactatcg
27161  atgatttcga atgaaggagg aactacaaat gaaactacta agaaggctat tcaataaaaa acacgaaaac
27231  ttaattgacg tgtggcatgg aaatcaatgg ttaaaagtga agaaagcaa attaaaaaaa tataaagtgg
27301  tctcggatag agaaggtaag aaatatctaa ttaaataagc gcacttaatt agtgcaagta atcaagtgcg
27371  ctattgcctt acaatcctaa atcttttctg cttttttctt cttcttgtaa tcccaataac acagaagagt
27441  aaatgctgaa atagtcacga gcaacgctat cttttagcgaa tgcaattacg tcatcaccga cttcttgcca
27511  ttcgttatga atcttatgtc tatctagagc tctaggtaat agcgagattg taatatcgtg agcaattttc
27581  tctaaatcca taaatttcac ctccttccac tgggagataa ctaaattata taacaaaaca acttaaagga
27651  ggaacgacaa atgcaagctc aaaacaaaaa agtcatctat tactactatg acgaagaagg taataggcga
27721  ccattagata ttcaaattaa tgacggatat gaactgatgg tccgatctca tttcatcaac aacaccattg
27791  aagaaatacc atacgtaaat aataacttat atgccttggt tgatggttat gaattaagt tagattgaat
27861  ttttgagaaa gatattgaaa agctaatttc cccataagat taagagacat actggatgtt tgttaacga
27931  ctcttttaac ttcgttccaa gttttattgt ctctaatatt atcgagaaat tcatggccag accaagtgat
28001  gtcatcaata atccaagaaa cgaccctgcc ttcgatgaat ttcagatcgc aacaaataaa tttagcttct
```

TABLE 7-continued

| Bacteriophage 3A, complete genome sequence |
|---|

```
28071  tctaatttta aaagtgagta cattactgtt tcaaaatcat atttatcaaa aataatatta tcgttgaaat
28141  tatgtcgagt aagtggttca cctattttct tattagattc tatttctaag agcaagagtc taacgcaatc
28211  gtgattaagt ttcatcctat cacctccata acaggagtat agcagaaagg atcataaaca tcttaaaagg
28281  aggaataaca aatgaacatt caagaagcaa ctaagatagc tacaaaaaat cttgtctcta tgacacggaa
28351  agattggaaa gaaagtcatc gaactaagat attaccaaca aatgatagtt ttttacaatg catcatttca
28421  aatagcgatg ggacaaacct tatcagatat tggcaacctt cagccgatga cctcatggca aatgattggg
28491  aagttataaa cccaactaga gaccaggaat tattgaagca attttagaaa tgctatcaat gatacttttt
28561  aaattgtttt taaactcatt ttcaaagtaa acaacagtct tgtctgaaat tgttacatga taaatagtgt
28631  tactagcata cacgccgttt aggaacccag agttttttaag tttatttaaa tcgtattttta catcttcgaa
28701  atgtagtttt tgaaaatact ttgtatgtat atctttagca cttccaaaat tattgcaggt taatttaacc
28771  gaacctaact ttacacattc taaataatct ttgtagagta cggacaagat atattgttgg tctttagtaa
28841  gtgtatcaaa ttcatcagat atcaagggca tgttatcacc tccttaggtt gataacaaca ttatacacga
28911  aaggagcata aacaaatgaa cacaagatca gaaggattgc gtataggcgt cccacaagtt tctagcaaag
28981  ctgatgcttc ttcatcctat ttaacggaaa aggaacgtaa cttaggagcg gaaatattag agcttattaa
29051  aaaaagtgat tacagctact tagaaataaa caaagttttc tatgcattag atagagaact tcaatacagg
29121  gcgaataata acaaacttta acatttatct aaaggagtga tagagatgcc aaaaatcata ataccaccaa
29191  caccagaaaa cacatatcga ggcgaagaaa aatttgtgaa aaagttatac gcaacaccta cacaaatcca
29261  tcaattgttt ggagtatgta gaagtacagt atacaactgg ttgaaatatt accgtgaaga taatttaggt
29331  gtagaaaatt tatacattga ttattcagca acgggaacat tgattaatat ttctaaatta gaagagtatt
29401  tgatcagaaa gcataaaaaa tggtattagg aggattatca aatgagcgac acatataaaa gctacctatt
29471  agcagtgttg tgcttcacgg tcttagcgat tgtactcatg ccgtttctat acttcactac agcatggtca
29541  attgcgggat tcgcaagtat cgcaacattc atattttata aggaatactt ttatgaagaa taaagaaact
29611  gctacttgtt ggagcaagta acagtgcaag atgagcaatt gtcttaaata attatataag gagttattaa
29681  tatgaccttta caacaaaaaa tactatcaca ttttgcaaca tatgacaatt tcaattctga tgatgttgtt
29751  gaagttttttg ggatatctaa aacacatgca aaatccacac tttcaagact aagaaaaaa ggaaagattg
29821  aattggaaag ttggggtatc tggcgtgttg ttgaaccgca gttacattta actgttgtag aacgtaagaa
29891  agagatatta gaagaacaat tcgagttatt ggcaagatta aacgaacaaa gtgatgaccc tagagaaata
29961  gaagaacgca tcaagttaat gattcgttta gccaaccaat tttaaggagg agttaatcaa tggcaatatt
30031  agaaggtatt tttgaagaat taaaactatt aaataagaat ttacgtgtgc taaatactga actatcaact
30101  gtagattcat caattgtaca agagaaagtt aaagaagcac caatgccaaa agatgaaaca gctcaactgg
30171  aatcagttga agaagttaag gaaacttctg ctgatttaac taaagattat gttttatcag taggaaaaga
30241  gttccttaaa aaagcagata cttctgataa gaaagaattt agaaataaac ttaacgaact tggtgcggat
30311  aagctatcta ctatcaaaga agagcattat gaaaaaattg ttgattttat gaatgcgaga ataaatgcat
30381  gaagctagat cactcaaata gagctcatgc aaagcttagt gcaagtggag caaaacaatg gctaaactgt
30451  ccaccgagta ttaaggcaag tgaaggtatt gcagataaaa gttcagtttt tgctgaagaa ggtacattcg
30521  ctcatgagtt aagtgagtta tatttcagtc ttaaatatga aggcctaaca cagtttgagt ttaataaagc
30591  ttttcaaaat tataagcgaa atcaatatta cagtgaagag ttgcgcgaat atgttgaaga gtacgtagct
30661  aatgtagaag aaaaatataa cgaagctttg agtagagatg acgatgtaat agctttatttt gaaacaaaat
30731  tggatttagg taaatacgtc cctgaatctt ttggtactgg tgatgtcatt atattttcag gtggtgtact
```

TABLE 7-continued

Bacteriophage 3A, complete genome sequence

```
30801  tgaaattatt gaccttaaat acggtaaagg cattgaagtt tcagctatag ataatcctca acttagatta
30871  tatggcttgg gcgcatatga actgcttagt ttaatgtatg acattcatac agttcgcatg actatcatac
30941  aaccacgaat agataacttt tctactgaag agttaccaat atcaagatta cttcaatggg gaaccgattt
31011  tgttaaacca ttagccagac ttgcttataa cggtgaaggt gagtttaaag caggtagtca ttgtagattc
31081  tgtaagataa agcattcatg tagaacacgt gcagaataca tgcaaaatgt gcctcaaaag ccaccacatt
31151  tgttgagtga tgaagagatt gcagaacttt tatataaact gcctgacatc aaaaaatggg ctgatgaagt
31221  agaaaaatat gcactagatc aagcgaaaga aaatgataaa aactattctg gttggaagct tgtagaaggt
31291  cgctcgcgaa gaatgataac tgatacaaat gcaacgcttg aaaagttagt tgaagcaggt tataaacctg
31361  aagatattac agaaaccaag ttacttagca ttacgaattt agaaaaatta atcggcaaaa aagcattttc
31431  taaaattgca gaaggcttta tagaaaagcc acaaggtaaa ttaacacttg ctaccgagtc tgataaacga
31501  ccagctataa agcaatctgc tgaagatgat tttgacaaac tataaaaatt aaaaaggacg gtatataaac
31571  atgaaagcaa aagtattaaa taaaactaaa gtgattacag gaaaagtaag agcatcatat gcacatattt
31641  ttgaacctca cagtatgcaa gaagggcaag aagcaaagta ttcaatcagt ttaatcattc ctaaatcaga
31711  tacaagtacg ataaaagcca ttgaacaagc tatagaagct gctaaagaag aaggaaaagt tagtaagttt
31781  ggaggcaaag ttcctgcaaa tctgaaactt ccattacgtg atggagatac tgaaagagaa gatgatgtga
31851  attatcaaga cgcttatttt attaacgcat caagcaaaca agcacctggt attattgacc aaaacaaaat
31921  tagattaacg gattctgaaa ctattgtaag tggtgactat attagagctt caatcaattt atttccattc
31991  aacacaaatg gtaataaggg tatcgcagtt ggattgaaca acattcaact tgtagaaaaa ggcgaacctc
32061  ttggcggtgc aagtgcagca gaagatgatt tcgatgaatt agacactgat gatgaggatt tcttataagt
32131  caataggtgg ggttttttagc cccactttaa ttttaaagaa attgaggtgt caagaatttg aaatttatga
32201  atatagatat tgaaacatat agcagtaacg atatttcgaa atgtggtgtc tataaataca cagaagctga
32271  agatttcgaa atcttaatta tagcttattc aatagatggt ggaccgatta gtgcgattga catgactaaa
32341  gtagataatg agcctttcca cgctgattat gagacgtttta aaattgctct atttgaccct gctgtaaaaa
32411  agtatgcatt caatgctaat ttcgaaagaa cttgtcttgc taaacatttt aataaacaga tgccacctga
32481  agaatggatt tgcacaatgg ttaattcaat gcgtattggc ttacctgctt cgcttgataa agttggagaa
32551  gttttaagac tacaaaacca aaaagataaa gcaggtaaaa atttaattcg ttatttctct ataccttgta
32621  agccaacaaa agttaatgga ggaagaacaa gaaatttgcc tgaacatgat cttgaaaaat ggcaacaatt
32691  tatagattac tgtattcgag atgtagaagt agaaatgaca attgctaata aaattaaaga ctttccagta
32761  actgtaattg aacaagcata ttgggttttt gaccaacata taaacgacag aggtattaag cttttctaaat
32831  cattgatgtt aggagctaat gtgctcgata agcagagtaa agaagaattg cttaaacaag ctaaacatat
32901  aacaggttta gaaaatccta atagtcctac acagttattg gcttggttaa aggatgaaca aggattagat
32971  atacctaatt tacaaaagaa aacggttcag gattacttaa aagtagcaac aggaaaagct aaaaaaatgc
33041  tagaaattag attgcaaatg tctaaaacca gtgtgaaaaa atacaacaaa atgcatgaca tgatgtgcag
33111  tgatgaacgg gtaagaggtc tgtttcaatt ctacggtgcc ggtactggaa gatgggcagg tagaggtgta
33181  caacttcaga atttaacaaa gcattatatt tcagatactg aattagaaat agcaagagat cttattaaag
33251  aacaacgttt tgacgattta gatttattac tcaatgttca tcctcaagac ttattaagtc aattagttag
33321  gacgacattt actgctgaag aaggtaatga actagcagta agtgattttt ctgcaataga ggcaagagtc
33391  atagcatggt atgcaaaaga acaatggcgt ttagatgtgt tcaacacaca cggaaagata tatgaagcat
```

TABLE 7-continued

Bacteriophage 3A, complete genome sequence

```
33461  cggcttctca aatgtttaat gtaccggtag aaagcataac taaaggcgac cctctcagac aaaaaggaaa
33531  agtgtccgaa ttagcttag  gctatcaagg tggcgctgga gctttaaaag caatgggtgc attggaaatg
33601  ggcattgaag aaaacgagtt acaaggttta gttgatagtt ggcgtaacgc aaatcctaac atagttaatt
33671  tttggaaggc ttgccaagag gctgcaatta atactgtaaa atcccgaaag acgcatcata cacatggact
33741  tagattttat atgaaaaaag gttttctaat gattgaactg cctagtggaa gagctttagc ttatccaaaa
33811  gctttagttg gtgaaaatag ttggggtagt caagttgttg aatttatggg gttagatctt aaccgtaaat
33881  ggtcaaagtt aaaaacgtat ggtgggaagt tagtcgagaa tattgttcaa gcaactgcaa gggatttact
33951  tgcgatttct atagcaaggc ttgaagcatt aggttttaaa atagttggcc atgtccatga tgaagtaatt
34021  gtagaaatac ctagaggttc aaatggactt aaggaaatcg aaactatcat gaataagcct gttgattggg
34091  caaaaggatt gaatttgaat agtgacgggt ttacttctcc gttttatatg aaggattagg agtgtgattg
34181  catgcaacat caagcttata tcaatgcttc tgttgacatt agaattccta cagaagtcga aagtgttaat
34231  tacaatcaga ttgataaaga aaagaaaat  ttggcggact atttatttaa taatccaggt gaactattaa
34301  aatataacgt tataaatatt aaggttttag atttagaggt ggaatgatgg ctagaagaaa agttataaga
34371  gtgcgtatca aaggaaaact aatgacattg agagaagttt cagaaaaata tcacatatct ccagaacttc
34441  ttagatatag atacaaacat aaaatgcgcg gcgatgaatt attgtgtgga agaaaagact caaaatctaa
34511  agatgaagtt gaatatatgc agagtcaaat aaaagatgaa gaaaaagaga gagaaaaaat cagaaaaaaa
34581  gcgattttga acctatacca acgaaatgtg agagcggaat atgaagaaga agaaagaga  agattgagac
34651  catggctta  tgatggaacg ccacaaaaac attcacgtga tccgtactgg ttcgatgtca cttataacca
34721  aatgttcaag aaatggagtg aagcataatg agcgtaatca gtaacagaaa agtagatatg aacgaagcgc
34791  aagacaatgt taagcaacca gcgcactaca catacggcga cattgaaatt atagattta  tcgaacaggt
34861  tacggcacag tatccacctc aactagcatt cgcaataggt aatgcaataa aatacttgtc tagagcacct
34931  ttaaagaatg gtcatgagga tttagcaaag gcgaagtttt acgtccaaag agcttttgac ttgtgggagt
35001  gatgaccatg acagatagcg catgtaaaga atacttaaac caattttcg  gatctaagag atatctgtat
35071  caggataacg aacgagtggc acatatcat  gtagtgaatg gcacttatta ctttcacggg catatcgtac
35141  caggctggca aggcgtgaaa aagacatttg atacagcgga agagctcgaa acatatataa agcaacatgg
35211  tttggaatac gaggaacaga agcaactaac tttattttaa ggagataaa  atgatgaaaa tcaaagttga
35281  aaaaataatg aaaatagacg aattaattaa gtgggcgcga gaaaatccgg agctatcatt tggcagaaaa
35351  tattatacaa cagacaaaaa tgatgaaaac tttatttact tcggtgtttt taaaaattgt tttaaaataa
35421  gcgattttat attagttaat gctactttta gtgtcaaagt tgaagaagaa gtaaccgaag aaactaagtt
35491  tgataggttg tttgaagtgt acgagattca agaaggagtc tataaatctg catcatatga gaatgctagt
35561  ataaacgaac gtttaaaaaa tgacagaatt tttcttgcta agcattcta  catcttaaac gacgacctaa
35631  ctatgacgtt aatttggaaa gaaggagagt tgattaaata atggaacacg gttcaaaaga atattacgaa
35701  aagcaaagtg aatactggtt tgatgaagca agcaagtttt tgaagcaacg tgatgagctt attggagata
35771  tagctaagtt aagagagtgc aacaagagc  tggagaagaa agcaagtgca tgggataggt attgcaagag
35841  cgttgaaaaa gatttaataa acgaatttgg caagatggt  gaaagagtta aatttggaat ggaattaaac
35911  aataaaattt ttatggagga agacgcaaat gaataaccgc gaacaaatcg aacaatcagt tattagtgct
35981  agcgcgtata acggcaatga cacagaggga ttattaaaag agattgagga cgtgtataag aaagcgcaag
36051  cgtttgatga atacttgag  ggttttaccta atgctatgca agatgcaatc aaagaagata ttggtcttga
36121  tgaagcagta ggaattatga cgggtcaagt tgtctataaa tatgaggagg agcaggaaaa tgactaacat
```

TABLE 7-continued

Bacteriophage 3A, complete genome sequence

```
36191  attacaagtg aaactattat caaaagacgc tagaatgcca gaacgaaatc ataagacgga tgcaggttat
36261  gacatatttt cagctaaaac tgtcgtactt gagccacaag aaaaggcagt gatcaaaaca gatgtagctg
36331  taagcattcc agagggctat gtcggtttat taactagccg tagtggtgta agtagtaaaa cgcatttagt
36401  gattgaaaca ggcaagatag acgcgggata tcatggtaat ttagggatta atatcaagaa tgataatgaa
36471  acgttagaga gtgaggatat gagtaacttt ggtcggagtc cttctggtat agatggaaaa tacaccctac
36541  tacctgtaac agataaattt ttatgtatga atggtagtta tgtcataaat aaaggcgaca aactagctca
36611  attggttatc gtgcctatat ggacacctga actaaagcaa gtggaggaat tcgagagtgt ttcagaacgt
36681  ggagcaaaag gcttcggaag tagcggagtg taaagacata ttagatcgag tcaaggaggt tttggggaag
36751  tgagtgacat gttagaaata ttttcatag ggtttggtgt ttatctattt tgtcgcatag gtattatttt
36821  tctcaagagt aaaaagacta tacacacaaa cctatatgaa atgttgttga ttgctactat ctttgtgaca
36891  tctacatttg ctgataaaca tcaaaagacg catatcttaa tagcatttt agtaatgttt tttatgagta
36961  agctcaaaca agttcaaggg agctatgagg aatgacacaa tacctagtca caacatttaa agattcaaca
37031  ggacgtaagc atacacacat aactaaagct aagagcaatc aaaggtttac agttgttgat gcggagagta
37101  aagaagaagc gaaagagaag tacgaggcac aagttaaaag aaatgcagtt attaaattag gcagttgtt
37171  tgaaaatata agggagtgtg ggaaatgact aaacaaatac taagattatt attcttacta gcgatgtatg
37241  agctaggcaa gtatgtaact gagcaagtat atattatgat gacggcgtaat gatgatgcag aggcgccgag
37311  tgactttgaa aaaatcagag ctgaagtttc atggtaatag ctattatcat ttttgaatta attatattaa
37381  tgtgtttagc aatagcactg gaggtgttgt aaatatgtgg attgtcattt caattgtttt atctatattt
37451  ttattgatct tgttaagtag catttctcat aagatgaaaa ccatagaagc attggagtat atgaatgctt
37521  atctttttcaa gcagttagta aaaaataatg gtgttgaagg tatagaagat tatgaaaatg aagttgaacg
37591  aattagaaaa agatttaaaa gctaaagaga ggcgttggct tctctgttct atttaaaata atgaaaggag
37661  ccgaacatgt tagacaaagt cactcaaata gaaacaatta atatgatcg tgatgtttca tattcttatg
37731  ctgctagtcg tttatctaca cattggacta atcacaatat ggcttggtct gactttatgc agaagctagc
37801  acaaacagtt agaactaaag aagatttaac tgagtacaat aaaatgtcta agtctgaaca agccgatata
37871  aaagatgttg gcggatttgt cggtggttat ttaaaagaag gcaaacgacg tgctggtcaa gtcatgaatc
37941  gttcaatgtt aacacttgat atcgattatg ctgctcaaga tatgactgac atattatcta tgtttatga
38011  ttttgcatat tgtttatatt caacacataa gcatagagag ataagtccaa gactgcgttt agtgattcct
38081  ttaaaacgaa atgtaaatgc agatgagtat gaagctattg gcgtaaagt cgcagatatc gttggcatgg
38151  attacttcga tgatacaact tatcaaccac ataggttaat gtattggcct tcaactagta acgatgcgga
38221  attttctttt acctatgaag atttaccttt gttagaccca gataaaatat taaatgaata tgttgattgg
38291  actgacacat tagaatggcc aacgtcttca agggaagaga gtaagactaa aagattagca gataagcaag
38361  gcgacccaga agaaaagccg ggaattgttg gtgcatttg tagagcctat acgatagaag aagctataga
38431  aactttttatt cctgatttat acgaaaaaca ttctactaac cgttatacct atcatgaagg ttcaactgca
38501  ggtggattgg tgttatacga aaataacaag tttgcctatt ctcatcataa tacggatccc gtaagcggta
38571  tgcttgtgaa cagttttgat ttagtacgca tacacttata tggtgctcaa gatgaagacg ctaaaacaga
38641  tactccggtt aatcgactac ctagttataa agcaatgcag caaagagcgc aaaatgatga agttgttaaa
38711  aagcaattaa ttaacgacaa aatgtctgat gcaatgcagg attttcgatga aatagtaaat agcgatgatg
38781  catggtctga gacgttagaa attacttcga aaggtacttt caaagctagt atcccaaata tagaaattat
```

TABLE 7-continued

Bacteriophage 3A, complete genome sequence

```
38851  attgcgtaat gatccaaatt taaaaggaaa aatagcattt aatgaattta caaaacaaat tgaatgctta
38921  gggaaaatgc catgaataaa taattttaaa atacgtcaat ggcaagacgg tgatgatagc agtttaagaa
38991  gttatatcga aaagatttat gacatacacc attcaggcaa aacaaaagat gccattataa gcgtagcaat
39061  gcaaaatgcc tatcatccag taagagatta tctaaataaa atatcgtggg atggacataa acgtcttgaa
39131  aagttattta tcaaatactt aggtgttgaa gacactgaag tgaatagaac aactaccaaa aaggcattga
39201  ctgctggaat cgctcgagta atggagccag gatgtaaatt tgactatatg cttacacttt atggtcctca
39271  aggtgtaggt aaatctgctt tgctaaaaaa aataggtggt gcatggtttt ctgacagttt agtttctgtt
39341  actggtaagg aagcatatga ggcattacaa ggcgtttggt taatggaaat ggcagaactt gcagctacaa
39411  gaaaagctga agttgaagct attaagcatt tcatatctaa acaagttgac cggtttcgtg ttgcttatgg
39481  acattatatt gaagattttc caaggcaatg tattttcatt ggtacaacta ataaagttga tttcttaaga
39551  gatgaaactg gtggaagacg ttttggcca atgactgtaa atccagagag agttgaagtg aactggtcta
39621  aactaaccaa agaagagatc gaccaaatct gggcagaagc taaatactat tatgaacaag gagaagagtt
39691  gttccttaac cctgaactag aagaagaaat gcgttcaatc caagtaaac atactgagga atctccatat
39761  acaggtatta ttgatgaata tcttaacacg ccaatcccaa gcaattggga agacttaact atctttgaaa
39831  gaagacgatt ttatcaaggt gatgttgata tgttaccaac aggaaatgta gattacattg aaagagacaa
39901  ggtctgtgcg cttgaagtgt ttgttgaatg ttttggtaaa gataagggag atagtagagg atctatggaa
39973  attagaaaga tttctaacgt cttaagacaa ttagacaatt ggtctgtata tgaaggcaat aaaagtggga
40041  aaattcgatt tggaaaagat tatggtgtac agatagcgta tgtaagagat gaaagtttag aggatttaat
40111  ataagaaata ttgaataaat atacatttttt agatgttgta tcaaatgttg catcattttt tgagtgatgc
40181  aacacggtgg tgtaaaaagt aatcgtaggt gttgtatcat ttttggtgat gcaacattga tgcaacaaat
40251  gatacaacac ctctttccct tctcgctgta aggttcaacc ctgtttgttt ccaatgttgc atcaaattca
40321  ctataaagtt taaaaagtag tgttagggag taaagggta tagggtaac cctctaacag ctatttttaa
40391  aagtttggca agaattgatg caacatcgga acacaaatat aaattttgta tacaaggtga ataaatgaaa
40461  gaatcgacat tagaaaaata tttagtgaaa gagataacaa agttaaatgg attatgtttta aaatgggtcg
40531  cacctggaac aagaggtgta ccagatagaa ttattattat gccagaagga aaaacatatt ttgtagaaat
40601  gaagcaagaa aagggaaagt tacatccttt acaaaaatat gtgcatcggc aatttgaaaa cagagatcat
40671  acagtgtatg tgttatgaa taaagaacaa gtaaatactt ttataagaat ggtaggtgga acatttggcg
40741  attgatttca aaccacatag ctatcaaaag tatgcaatag ataaagtgat tgataatgag aaatacggtt
40811  tgttttttaga tatggggcta gggaaaacag tatcaacact tacagcattt agtgaattgc agttgttaga
40881  cactaaaaaa atgttagtca tagcacctaa acaagttgct aaagatacat gggttgatga agttgataag
40951  tggaaccatt taaatcatct gaaagtgtct ttagtcttag gaacacctaa agaaagaaat gatgcattaa
41021  acacagaggc tgatatctat gtaaccaata aagaaaatac taaatggtta tgtgatcaat ataaaaaaga
41091  atggccattt gacatggttg taattgatga actgtctaca tttaaaagtc ctaagagtca aaggtttaaa
41161  tctattaaaa agaaattacc actcattaat agatttatag gattaacagg aacacctagt ccaaatagtt
41231  tacaggattt atgggctcaa gtttatttga tagacagagg cgaaagactt gagtcttcat tcagtcgtta
41301  tcgagaaagg tactttaaac caacacatca agttagcgaa catgttttta actgggagct aagagacgga
41371  tctgaagaaa agatatatga acgaatagaa gatatatgtt taagcatgaa agcgaaagat tatctggata
41441  tgcctgacag agttgatact aaacaaacag tagtcttatc tgaaaaagaa agaaaagtat atgaagaatt
41511  agaaaaaaac tatatttttag aatcggaaga agaaggaaca gttgtagctc agaatggggc atcattaagt
```

TABLE 7-continued

Bacteriophage 3A, complete genome sequence

```
41581  caaaaactac ttcaactatc taacggtgca gtttatacag atgatgaaga tgtaagactt atacatgata
41651  agaagttaga taagttagag gaaattatag aggagtctca aggccaacca atattattgt tttataactt
41721  caaacatgat aaagaaagaa tacttcaaag gtttaaggaa gcaaccacat tagaggattc aaactataaa
41791  gaacgttgga atagtggaga cattaagctg cttatagcac atccagcaag tgcagggcat ggattaaact
41861  tacaacaagg tgggcacatt attgtttggt ttggacttac atggtcattg gaattatacc aacaagcaaa
41931  tgcaagatta tatagacaag gacaaaatca tacgactatt attcatcaca tcatgaccga taacacaata
42001  gatcaaagag tatataaagc tttacaaaat aaagaactaa cgcaagaaga attgatgaaa gctattaaag
42071  caagaatagc taagcataag taatggaggt ataagatggg aaaggcgtca tatgatatta agccaggaac
42141  atttaaatat attgaatcag aaatatataa tttaaatgag aacaagaaag agataaatag attgagaatg
42211  gagatactta acccaacgaa agaactagac accaacattg tgtatggacc gttacaaaaa ggagagccag
42281  ttagaacaac tgagttaatg gcgacaaggt tattgactaa taagatgtta cgtaacttag aagagatggt
42351  tgaagcagtt gaaagtgagt acttaaagtt acctgaagat cataagaaag taataaggtt aaagtattgg
42421  aataaagata agaagctaaa gatagaacaa ataggggatg cttgtcacat gcatcgcaat acagttacta
42491  caatacgaaa gaactttgtt aaagcgatag cgtatcatgc aggtatcaaa taacattgtg caaagattgt
42561  gcaaaaggcc tacaaatctg tagtaatatg atagtatcgg aaagatgtat aaagttatct gaaagttata
42631  cgacataaat acatgaggca catcgctaag cggtgtgtct tttgttatgc aatcaaagag gtgtaagaga
42701  tgaccaagca taataacatt tataagcatg gtcgtaagtc atatcaatac gattggttct atcattcaaa
42771  agcatggaag aagttaagag agatagcatt agatagagat aattatcttt gtcaaatgtg tttacgcgaa
42841  gatattataa cagatgcaaa gattgtgcat cacattattt atgttgatga agattttaac aaagctttag
42911  acttagataa tctaatgtca gtttgttata gctgtcataa caaaattcat gcaaatgata atgacaaaag
42981  taatcttaag aaaattagag ttctaaaaat ttaaataaaa aaattattta ataaaatttt tatgcccccc
43051  tgcccatcgg cttaaaatgt tttttcgccg ggtaccggag aggcc
```

TABLE 8

Bacteriophage 3A ORFs list

| SID | LAN | FRA | POS | a.a. | RBS sequence | STA | STO |
|---|---|---|---|---|---|---|---|
| 100379 | 3AORF001 | 1 | 8515 ... 13488 | 1657 | acaggtacggatttaagaaaactt | ttg | taa |
| 100380 | 3AORF002 | 2 | 37667 ... 40114 | 815 | ttttaaaataatgaaaggagccgaac | atg | taa |
| 100381 | 3AORF003 | 1 | 32188 ... 34149 | 653 | ttaaagaaattgaggtgtcaagaat | ttg | tag |
| 100382 | 3AORF004 | 3 | 17457 ... 19370 | 637 | gctattttattagaaaggaaggtgc | att | taa |
| 100383 | 3AORF005 | 1 | 334 ... 2034 | 566 | agaaaaaagatagttcaagaagaag | gtg | taa |
| 100384 | 3AORF006 | 1 | 15571 ... 17154 | 527 | cttttatttataggtaggtgattta | atg | taa |
| 100385 | 3AORF007 | 2 | 19337 ... 20836 | 499 | atgatagtaaaacaagttcagggcc | atg | taa |
| 100386 | 3AORF008 | 3 | 22176 ... 23630 | 484 | aatgatttagggtaggtgttgacca | atg | tga |
| 100387 | 3AORF009 | 1 | 40726 ... 42093 | 455 | gtaaatacttttataagaatggtag | gtg | taa |
| 100388 | 3AORF010 | 3 | 13491 ... 14738 | 415 | gaggcggactaacgctacagtaaaa | att | taa |
| 100389 | 3AORF011 | 2 | 2039 ... 3277 | 412 | attaagacataatgcgttaaggag | gtg | taa |
| 100390 | 3AORF012 | 2 | 4001 ... 5209 | 402 | aaaaagagaaaaaattaaacgcga | atg | taa |
| 100391 | 3AORF013 | 1 | 30379 ... 31545 | 388 | attttatgaatgcgagaataaatgc | atg | taa |
| 100392 | 3AORF014 | 2 | 14738 ... 15562 | 274 | attatatgggaggtttgactaatta | atg | tag |
| 100393 | 3AORF015 | 3 | 3249 ... 4034 | 261 | cttgaattaagaaaatctttgaaag | gtg | tag |
| 100394 | 3AORF016 | -2 | 25587 ... 26273 | 228 | aagaagctaagaaaaaataaaaat | atg | tga |
| 100395 | 3AORF017 | 3 | 6729 ... 7370 | 213 | ttaattttttaaggaggaaataagca | atg | taa |
| 100396 | 3AORF018 | 3 | 24540 ... 25154 | 204 | aataaaataaaaagtaggtgataag | atg | taa |
| 100397 | 3AORF019 | 2 | 31565 ... 32128 | 187 | ctataaaaattaaaaaggacggtat | ata | taa |
| 100398 | 3AORF020 | 3 | 36150 ... 36713 | 187 | gcagtaggaattatgacgggtcaag | ttg | taa |
| 100399 | 3AORF021 | 2 | 24011 ... 24535 | 174 | gtaataaaatttataagaaaggaa | atg | tga |
| 100400 | 3AORF022 | -2 | 12423 ... 12938 | 171 | taaagtaccagtagacaatgtaggt | att | tga |
| 100401 | 3AORF023 | 1 | 7462 ... 7917 | 151 | aaaataaatcaaaggagaataattt | atg | taa |

TABLE 8-continued

Bacteriophage 3A ORFs list

| SID | LAN | FRA | POS | a.a. | RBS sequence | STA | STO |
|---|---|---|---|---|---|---|---|
| 100402 | 3AORF024 | 1 | 26731 . . . 27174 | 147 | actaaataaaaataaggaggacact | atg | tga |
| 100403 | 3AORF025 | 1 | 42106 . . . 42543 | 145 | taagcataagtaatggaggtataag | atg | taa |
| 100404 | 3AORF026 | 2 | 35255 . . . 35671 | 138 | aagcaactaactttattttaaggag | ata | taa |
| 100405 | 3AORF027 | 2 | 5888 . . . 6298 | 136 | atattggctataatacagtggtttt | atc | taa |
| 100406 | 3AORF028 | −3 | 27845 . . . 28255 | 136 | cctttaagatgtttatgatcctttt | ctg | taa |
| 100407 | 3AORF029 | 3 | 34344 . . . 34748 | 134 | ttaaggttttagatttagaggtgga | atg | taa |
| 100408 | 3AORF030 | 2 | 6299 . . . 6694 | 131 | tataaaaaaggagttggccagataa | atg | tag |
| 100409 | 3AORF031 | 1 | 20833 . . . 21225 | 130 | ttaacaaaattataggagtgagaaa | ata | taa |
| 100410 | 3AORF032 | −2 | 39984 . . . 40361 | 125 | aaatagctgttagagggttacccct | ata | tag |
| 100411 | 3AORF033 | 1 | 7957 . . . 8325 | 122 | gaatatctgcgtcttttttatttga | ata | taa |
| 100412 | 3AORF034 | −2 | 28506 . . . 28871 | 121 | gttatcaacctaaggaggtgataac | atg | tag |
| 100413 | 3AORF035 | −2 | 10671 . . . 11036 | 121 | tcctagcttcctaacagcaccgcca | ata | tga |
| 100414 | 3AORF036 | 2 | 30020 . . . 30382 | 120 | accaattttaaggaggagttaatca | atg | tga |
| 100415 | 3AORF037 | 2 | 21818 . . . 22165 | 115 | aagtgtaagtaatagttaagagtca | gtg | tag |
| 100416 | 3AORF038 | −2 | 42003 . . . 42347 | 114 | gtactcactttcaactgcttcaacc | atc | tga |
| 100417 | 3AORF039 | 2 | 21386 . . . 21727 | 113 | tccagaaaatctagagtcataggtt | ata | taa |
| 100418 | 3AORF040 | −3 | 29654 . . . 29995 | 113 | ttgattaactcctccttaaaattgg | ttg | taa |
| 100419 | 3AORF041 | −1 | 4333 . . . 4671 | 112 | tactaaatctacatctgatccatga | att | tga |
| 100420 | 3AORF042 | 3 | 5568 . . . 5900 | 110 | taaaaaagtggtaggtgattttttaa | atg | tga |
| 100421 | 3AORF043 | 1 | 25690 . . . 26019 | 109 | taccaaattaatatagtcttcgcat | ata | tag |
| 100422 | 3AORF044 | 3 | 29676 . . . 30005 | 109 | gtcttaaataattatataaggagtt | att | taa |
| 100423 | 3AORF045 | 3 | 30 . . . 353 | 107 | cgctagcaacgcggataaattttc | atg | taa |
| 100424 | 3AORF046 | 3 | 27894 . . . 28214 | 106 | aagatattgaaaagctaatttcccc | ata | tga |
| 100425 | 3AORF047 | −2 | 11907 . . . 12227 | 106 | ttcgccgccaaaatgattagcattt | ctg | tga |
| 100426 | 3AORF048 | −3 | 40343 . . . 40663 | 106 | ccataacacatacactgtatgatct | ctg | taa |
| 100427 | 3AORF049 | −3 | 6749 . . . 7069 | 106 | tgttaaaccatcttcagattctcca | ata | taa |
| 100428 | 3AORF050 | 1 | 42700 . . . 43014 | 104 | ttatgcaatcaaagaggtgtaagag | atg | taa |
| 100429 | 3AORF051 | −2 | 13077 . . . 13388 | 103 | ttgtacgtaatcccacacatcgccg | att | tga |
| 100430 | 3AORF052 | −3 | 3722 . . . 4024 | 100 | gcatttcatttcctcctaataactc | att | taa |
| 100431 | 3AORF053 | 3 | 17145 . . . 17444 | 99 | tcgagacaatggatatagggagtgt | att | tag |
| 100432 | 3AORF054 | −1 | 19915 . . . 20211 | 98 | ataatttatagcttgcgaaacataa | ata | tga |
| 100433 | 3AORF055 | −1 | 42436 . . . 42729 | 97 | aatcgtattgatatgacttacgacc | atg | tag |
| 100434 | 3AORF056 | 3 | 40455 . . . 40745 | 96 | taaattttgtatacaaggtaataaa | atg | taa |
| 100435 | 3AORF057 | −1 | 38665 . . . 38952 | 95 | atcatcaccgtcttgccattgacgt | att | taa |
| 100436 | 3AORF058 | −1 | 21265 . . . 21549 | 94 | gaaatttctatctaacttgtcataa | att | tga |
| 100437 | 3AORF059 | −2 | 10278 . . . 10562 | 94 | tttagccgcgcttccaactgcacgt | att | tag |
| 100438 | 3AORF060 | 1 | 5276 . . . 5556 | 92 | atatcagccgaatagggggtgatgaa | atg | tag |
| 100439 | 3AORF061 | 1 | 35668 . . . 35946 | 92 | tttggaaagaaggagagttgattaa | ata | taa |
| 100440 | 3AORF062 | 2 | 35912 . . . 36187 | 91 | gttaaatttggaatggaattaaaca | ata | taa |
| 100441 | 3AORF063 | 3 | 36720 . . . 36995 | 91 | cggaagtagcggagtgtaaagacat | att | tga |
| 100442 | 3AORF064 | −2 | 35694 . . . 35969 | 91 | ccgttatacgcgctagcactaataa | ctg | taa |
| 100443 | 3AORF065 | −2 | 32697 . . . 32972 | 91 | aaccgttttcttttgtaaattaggt | ata | taa |
| 100444 | 3AORF066 | 3 | 29157 . . . 29429 | 90 | caaacttttaacatttatctaaagga | gtg | tag |
| 100445 | 3AORF067 | −2 | 26661 . . . 26930 | 89 | atactttttttagcgggaatcggatga | ttg | taa |
| 100446 | 3AORF068 | −2 | 9624 . . . 9893 | 89 | ttttaatgcatctcccatgtattga | ata | tga |
| 100447 | 3AORF069 | −2 | 13847 . . . 14110 | 87 | tgcatttcctcctgattcgtgttga | atc | tga |
| 100448 | 3AORF070 | 1 | 34993 . . . 35250 | 85 | tttacgtccaaagagcttttgactt | gtg | taa |
| 100449 | 3AORF071 | 2 | 34745 . . . 35002 | 85 | aaatgttcaagaaatggagtgaagc | ata | tga |
| 100450 | 3AORF072 | −1 | 27379 . . . 27636 | 85 | ttttgtcgttcctccttttaagttgtt | ttg | taa |
| 100451 | 3AORF073 | 2 | 37367 . . . 37615 | 82 | tggtaatagctattatcattttga | att | taa |
| 100452 | 3AORF074 | −2 | 23466 . . . 23714 | 82 | cgtttgtttttttaaaatttaatat | att | taa |
| 100453 | 3AORF075 | −3 | 2471 . . . 2719 | 82 | agtactgtttgaaatcttctaacac | ttg | tga |
| 100454 | 3AORF076 | 1 | 26047 . . . 26292 | 81 | aagtacgttttcttggcggggaggt | gtg | tag |
| 100455 | 3AORF077 | 2 | 28292 . . . 28537 | 81 | aacatcttaaaaggaggaataacaa | atg | tag |
| 100456 | 3AORF078 | −1 | 5836 . . . 6075 | 79 | ttttgtataaggcttagatttagtc | att | taa |
| 100457 | 3AORF079 | −2 | 5460 . . . 5699 | 79 | attcagtcgcttttaaaatttctct | atc | taa |
| 100458 | 3AORF080 | −2 | 31350 . . . 31586 | 78 | cctgtaatcacttagttttattta | ata | taa |
| 100459 | 3AORF081 | −3 | 8252 . . . 8488 | 78 | aagttttcttaaatccgtacctgta | ata | tga |
| 100460 | 3AORF082 | −1 | 35905 . . . 36138 | 77 | atatttatagacaacttgacccgtc | ata | taa |
| 100461 | 3AORF083 | −1 | 34039 . . . 34272 | 77 | atagttcacctggattattaaataa | ata | taa |
| 100462 | 3AORF084 | −1 | 12007 . . . 12240 | 77 | acatttttttcatttcgccgccaaa | atg | taa |
| 100463 | 3AORF085 | 2 | 32367 . . . 32597 | 76 | cttacaaggtatagagaaataacga | att | taa |
| 100464 | 3AORF086 | −2 | 30618 . . . 30848 | 76 | atataatctaagttgaggattatct | ata | taa |
| 100465 | 3AORF087 | −3 | 24746 . . . 24973 | 75 | ataggttttaagttcaccctcttca | atg | tga |
| 100466 | 3AORF088 | −3 | 12980 . . . 13204 | 74 | tctttctttttcgtaccaccatgga | att | tag |
| 100467 | 3AORF089 | 3 | 4290 . . . 4508 | 72 | acaggagaagcttatcaatctttaa | atg | taa |
| 100468 | 3AORF090 | 3 | 28926 . . . 29141 | 71 | ttatacacgaaaggagcataaacaa | atg | taa |
| 100469 | 3AORF091 | −2 | 13587 . . . 13802 | 71 | cttgtcttgctaattgctagataa | atg | tag |
| 100470 | 3AORF092 | 2 | 26471 . . . 26683 | 70 | aaacgaaacaaaaggaggggggttca | atg | taa |
| 100471 | 3AORF093 | −1 | 2524 . . . 2736 | 70 | tccaccgttttcttcatagtactgt | ttg | tga |
| 100472 | 3AORF094 | −3 | 25334 . . . 25546 | 70 | tggcgctttaatataaaagacgtct | att | taa |
| 100473 | 3AORF095 | 3 | 8316 . . . 8525 | 69 | aagagatgggaaagacagaagaaca | atc | tag |
| 100474 | 3AORF096 | 2 | 36992 . . . 37198 | 68 | aacaagttcagggagctatgagga | atg | tga |
| 100475 | 3AORF097 | −1 | 32593 . . . 32799 | 68 | aaagcttaatacctctgtcgtttat | atg | taa |
| 100476 | 3AORF098 | −1 | 15346 . . . 15552 | 68 | aatccattaaatcacctacctataa | ata | tag |

TABLE 8-continued

Bacteriophage 3A ORFs list

| SID | LAN | FRA | POS | a.a. | RBS sequence | STA | STO |
|---|---|---|---|---|---|---|---|
| 100477 | 3AORF099 | 1 | 7225 ... 7428 | 67 | actggtgactggatgaacagaaaag | ttg | tag |
| 100478 | 3AORF100 | −2 | 22620 ... 22823 | 67 | cgacttcatgaccggcatgtcttaa | ata | taa |
| 100479 | 3AORF101 | −1 | 40060 ... 40260 | 66 | aaccttacagcgagaagggaaagag | gtg | taa |
| 100480 | 3AORF102 | −1 | 35035 ... 35235 | 66 | ttctatctccttaaaataaagttag | ttg | taa |
| 100481 | 3AORF103 | −2 | 1149 ... 1349 | 66 | attttttggagtgttgggtaatca | ata | taa |
| 100482 | 3AORF104 | 1 | 27661 ... 27858 | 65 | aaacaacttaaaggaggaacgacaa | atg | tga |
| 100483 | 3AORF105 | −2 | 9420 ... 9617 | 65 | gcctaagtcaaccgcttgattagac | atg | tga |
| 100484 | 3AORF106 | −2 | 23244 ... 23438 | 64 | caccagtaattcttgaattagttga | ata | taa |
| 100485 | 3AORF107 | 2 | 11966 ... 12157 | 63 | tctaaaaagatgctgtagtagacg | ttg | taa |
| 100486 | 3AORF108 | −3 | 35054 ... 35245 | 63 | ttttcatcatttctatctcttaaa | ata | tag |
| 100487 | 3AORF109 | −3 | 16010 ... 16201 | 63 | gttcttaattccaatgtactgacag | ttg | taa |
| 100488 | 3AORF110 | −1 | 6184 ... 6372 | 62 | attttcagtgactttataatagtat | att | taa |
| 100489 | 3AORF111 | −2 | 16500 ... 16688 | 62 | gtagtcaacaattgctttgtattga | ttg | tga |
| 100490 | 3AORF112 | −2 | 8502 ... 8690 | 62 | cttaattctcgcctgatactttcc | att | taa |
| 100491 | 3AORF113 | 1 | 34162 ... 34347 | 61 | tatgaaggattaggagtgtgattgc | atg | tga |
| 100492 | 3AORF114 | 2 | 12356 ... 12541 | 61 | ggatatcacactaaggctatagcta | atg | tga |
| 100493 | 3AORF115 | −2 | 7635 ... 7820 | 61 | tgaagttccctcagctacaccgtga | att | tga |
| 100494 | 3AORF116 | −1 | 26434 ... 26613 | 59 | tttagcttctgaagttgtaaaatct | ctg | tga |
| 100495 | 3AORF117 | −3 | 17804 ... 17983 | 59 | atagccattatttctagcttgtgtc | atg | tga |
| 100496 | 3AORF118 | 2 | 27899 ... 28075 | 58 | attgaaaagctaatttcccataag | att | taa |
| 100497 | 3AORF119 | −1 | 39268 ... 39444 | 58 | acgaaaccggtcaacttgtttagat | atg | taa |
| 100498 | 3AORF120 | −2 | 37152 ... 37328 | 58 | tagctattaccatgaaacttcagct | ctg | taa |
| 100499 | 3AORF121 | −2 | 18900 ... 19076 | 58 | aaggtactctctcccatttaccact | att | taa |
| 100500 | 3AORF122 | −1 | 21550 ... 21723 | 57 | taagcatggtaatcacctcctttaa | atg | taa |
| 100501 | 3AORF123 | −3 | 33062 ... 33235 | 57 | aaacgttgttctttaataagatctc | ttg | tag |
| 100502 | 3AORF124 | 2 | 21212 ... 21382 | 56 | aaattagaagaggttaaaggagaga | ctg | tag |
| 100503 | 3AORF125 | −1 | 22051 ... 22221 | 56 | aaatcaggattgaactgcttcccta | atg | tga |
| 100504 | 3AORF126 | −2 | 7821 ... 7991 | 56 | tgttttttcctgttttacggtctta | att | tga |
| 100505 | 3AORF127 | −3 | 34712 ... 34882 | 56 | ttgcattaccctattgcgaatgctag | ttg | taa |
| 100506 | 3AORF128 | −3 | 24056 ... 24226 | 56 | tttttaaaatcaaagcgtctttgtt | ata | taa |
| 100507 | 3AORF129 | −3 | 4940 ... 5110 | 56 | cataccatgcagttaatacaaacaa | ata | tga |
| 100508 | 3AORF130 | 3 | 27171 ... 27338 | 55 | cagaattaactatcgatgatttcga | atg | taa |
| 100509 | 3AORF131 | −1 | 40387 ... 40554 | 55 | ccttctggcataataataattctat | ctg | taa |
| 100510 | 3AORF132 | −2 | 1860 ... 2027 | 55 | gcgataacattcacctcctaacgc | att | tga |
| 100511 | 3AORF133 | −3 | 42317 ... 42484 | 55 | acaaagttctttcgtattgtagtaa | ctg | tag |
| 100512 | 3AORF134 | 2 | 12671 ... 12835 | 54 | tcatacaaatctttaaaaggttgga | ctg | tag |
| 100513 | 3AORF135 | −1 | 39484 ... 39648 | 54 | ataatagtatttagcttctgcccag | atg | taa |
| 100514 | 3AORF136 | 1 | 29710 ... 29871 | 53 | accttacaacaaaaaatactatcac | att | taa |
| 100515 | 3AORF137 | 1 | 37186 ... 37347 | 53 | ggcagttgtttgaaaatataaggga | gtg | taa |
| 100516 | 3AORF138 | 2 | 20996 ... 21157 | 53 | aatggggaaatagttttaacgaag | att | taa |
| 100517 | 3AORF139 | 3 | 15114 ... 35275 | 53 | tcaactgaaattgaagtaagttaa | atg | taa |
| 100518 | 3AORF140 | 3 | 29442 ... 29603 | 53 | aaaatggtattaggaggattatcaa | atg | taa |
| 100519 | 3AORF141 | −1 | 39883 ... 40044 | 53 | tacaccataatcttttccaaatcga | att | taa |
| 100520 | 3AORF142 | −1 | 20416 ... 20577 | 53 | accacctggaaaagtcccataaaaa | att | tga |
| 100521 | 3AORF143 | −1 | 1942 ... 2103 | 53 | ataaagcttagaagttgactgatca | atc | taa |
| 100522 | 3AORF144 | −3 | 39380 ... 39541 | 53 | ttccaccagtttcatctcttaagaa | atc | taa |
| 100523 | 3AORF145 | 3 | 20388 ... 20546 | 52 | tctgagtggtcagaattagctatta | atg | taa |
| 100524 | 3AORF146 | −2 | 2358 ... 2516 | 52 | aacatgtccatatttatgaacaatca | att | tga |
| 100525 | 3AORF147 | −3 | 5606 ... 5764 | 52 | gtgatttgtttgtggtagatattca | att | tga |
| 100526 | 3AORF148 | 2 | 34145 ... 34300 | 51 | tttacttctccgttttatatgaagg | att | taa |
| 100527 | 3AORF149 | −1 | 7918 ... 8073 | 51 | tattctcttgatttactaattctaa | ata | taa |
| 100528 | 3AORF150 | −2 | 11745 ... 11900 | 51 | ttctcttctatgtctttgatcagca | ata | taa |
| 100529 | 3AORF151 | −3 | 7097 ... 7252 | 51 | tttaccttcatgataccgtataca | ata | tga |
| 100530 | 3AORF152 | 1 | 21652 ... 21804 | 50 | ctaaaaatattagagacatcaagat | gtg | tga |
| 100531 | 3AORF153 | 2 | 5381 ... 5533 | 50 | tcggctaagtctgaattactattaa | gtg | tga |
| 100532 | 3AORF154 | −1 | 39670 ... 39822 | 50 | ttgataaaatcgtcttctttcaaag | ata | taa |
| 100533 | 3AORF155 | −1 | 38233 ... 38385 | 50 | ataggctctacaaaatgcaccaaca | att | tag |
| 100534 | 3AORF156 | −1 | 33040 ... 33192 | 50 | tatctgaaatataatgctttgttaa | att | tag |
| 100535 | 3AORF157 | −2 | 10119 ... 10271 | 50 | cttcaatgtttgctatagctatta | att | tga |
| 100536 | 3AORF158 | −3 | 36074 ... 36226 | 50 | atccgtcttatgatttcgttctggc | att | taa |
| 100537 | 3AORF159 | −3 | 18338 ... 18490 | 50 | taaatagtttctattatttggatta | ctg | taa |
| 100538 | 3AORF160 | 3 | 39399 ... 39548 | 49 | gtttggttaatggaaatggcagaac | atg | taa |
| 100539 | 3AORF161 | −2 | 8976 ... 9125 | 49 | ttgtacttttagttttgaacttga | ttg | tga |
| 100540 | 3AORF162 | −3 | 31199 ... 31348 | 49 | tctgtaatatcttcaggttttataac | ctg | tag |
| 100541 | 3AORF163 | −3 | 14459 ... 14608 | 49 | attatcctgagaagaaacagtttga | atc | tga |
| 100542 | 3AORF164 | 3 | 25182 ... 25328 | 48 | ttttttcttagcttttttctgataaa | gtg | tag |
| 100543 | 3AORF165 | 3 | 28353 ... 28499 | 48 | aatcttgtctctatgacacggaaag | att | taa |
| 100544 | 3AORF166 | −1 | 8899 ... 9045 | 48 | gtactgcgtcacttgctcttttag | ttg | taa |
| 100545 | 3AORF167 | −2 | 411 ... 557 | 48 | taatacaagttgacgtttagatcct | ttg | tga |
| 100546 | 3AORF168 | −3 | 25973 ... 26119 | 48 | gctgagtacttcaatgtgaagatta | atg | tag |
| 100547 | 3AORF169 | −3 | 25151 ... 25297 | 48 | aaaaaaacgcctacaagtgtagacg | ttg | tag |
| 100548 | 3AORF170 | −3 | 24995 ... 25141 | 48 | taagaaaaaagattagtattcattc | att | tag |
| 100549 | 3AORF171 | 1 | 23437 ... 23580 | 47 | aaaggtaataacgtaagggacggct | att | tag |
| 100550 | 3AORF172 | 2 | 32414 ... 32557 | 47 | ctatttgaccctgctgtaaaaaagt | atg | taa |
| 100551 | 3AORF173 | −1 | 38005 ... 38148 | 47 | ataagttgtatcatcgaagtaatcc | atg | taa |

TABLE 8-continued

Bacteriophage 3A ORFs list

| SID | LAN | FRA | POS | a.a. | RBS sequence | STA | STO |
|---|---|---|---|---|---|---|---|
| 100552 | 3AORF174 | −1 | 4123 ... 4266 | 47 | attttaaagattgataagcttctcct | gtg | tga |
| 100553 | 3AORF175 | −1 | 3124 ... 3267 | 47 | ttcatttgaaaatacttagctttca | ttg | tag |
| 100554 | 3AORF176 | −1 | 580 ... 723 | 47 | cattttctccatcttgtgatacagc | ata | taa |
| 100555 | 3AORF177 | −2 | 39819 ... 39962 | 47 | ttagaaatcttctaatttccatag | atc | tag |
| 100556 | 3AORF178 | −2 | 38466 ... 38609 | 47 | ttagcgtcttcatcttgagccaccat | ata | tag |
| 100557 | 3AORF179 | −2 | 33927 ... 34070 | 47 | ttttgcccaatcaacaggcttattc | atg | tga |
| 100558 | 3AORF180 | −2 | 33555 ... 33698 | 47 | cgtctttcgggatttacagtatta | att | tga |
| 100559 | 3AORF181 | −2 | 29538 ... 29681 | 47 | atagtattttttgttgtaaggtcat | att | tga |
| 100560 | 3AORF182 | −3 | 17099 ... 17242 | 47 | aatatcactactgcctgcataaggt | atc | tag |
| 100561 | 3AORF183 | 2 | 23750 ... 23890 | 46 | ttaaaaaaacaaacgttttagtat | ata | taa |
| 100562 | 3AORF184 | −1 | 31648 ... 31788 | 46 | tggaagtttcagatttgcaggaact | ttg | tga |
| 100563 | 3AORF185 | −1 | 30565 ... 30705 | 46 | attttgtttcaaataaagctattac | ata | taa |
| 100564 | 3AORF186 | −1 | 16951 ... 17091 | 46 | gagaattcaaagtactagtgtataa | atg | tga |
| 100565 | 3AORF187 | −1 | 7153 ... 7293 | 46 | tatccaacgaatacttttttgaaga | att | taa |
| 100566 | 3AORF188 | −1 | 1237 ... 1377 | 46 | ccagctcttctaaagaaacaatttc | att | taa |
| 100567 | 3AORF189 | −2 | 33309 ... 33449 | 46 | catttgagaagccgatgcttcatat | atc | tga |
| 100568 | 3AORF190 | −2 | 7197 ... 7337 | 46 | gtaacgaacttgcagaatcctctga | atg | taa |
| 100569 | 3AORF191 | −3 | 41459 ... 41599 | 46 | tcatctgtataaactgcaccgttag | ata | tag |
| 100570 | 3AORF192 | 3 | 4863 ... 5000 | 45 | gatgctattattaacgctttagcag | att | tag |
| 100571 | 3AORF193 | 3 | 25965 ... 26102 | 45 | tatacgatactagtttagactcttt | ata | tga |
| 100572 | 3AORF194 | −1 | 37069 ... 37206 | 45 | ctagtaagaataataatcttagtat | ttg | tga |
| 100573 | 3AORF195 | −1 | 11749 ... 11886 | 45 | tttgatcagcaatagctaataattt | atc | tga |
| 100574 | 3AORF196 | −2 | 40764 ... 40901 | 45 | atctttagcaacttgttaggtgct | atg | tga |
| 100575 | 3AORF197 | −2 | 31989 ... 32126 | 45 | ggctaaaaacccccacctattgactt | ata | tga |
| 100576 | 3AORF198 | −3 | 36431 ... 36568 | 45 | tttatttatgacataactaccattc | ata | tga |
| 100577 | 3AORF199 | −3 | 33515 ... 33652 | 45 | ttccaaaaattaactatgttaggat | ttg | tga |
| 100578 | 3AORF200 | −3 | 21233 ... 21370 | 45 | ataagattataacctatgactctag | att | tga |
| 100579 | 3AORF201 | 1 | 23293 ... 23427 | 44 | aagcctatcggtggtgtgatatcta | gtg | taa |
| 100580 | 3AORF202 | −1 | 39088 ... 39222 | 44 | atagtcaaatttacatcctggctcc | att | taa |
| 100581 | 3AORF203 | −1 | 16309 ... 16443 | 44 | tttgcttgccgtctaaaatcaactt | ata | tga |
| 100582 | 3AORF204 | 1 | 23845 ... 23976 | 43 | atgtttattatcaatcaaaatataa | att | taa |
| 100583 | 3AORF205 | 1 | 29500 ... 29631 | 43 | gtgttgtgcttcacggtcttagcga | ttg | taa |
| 100584 | 3AORF206 | 2 | 16667 ... 16798 | 43 | gaaaaatcaacagtcttaaatttaa | ttg | tag |
| 100585 | 3AORF207 | −1 | 35386 ... 35517 | 43 | tgcagatttatagactccttcttga | atc | tag |
| 100586 | 3AORF208 | −1 | 30013 ... 30144 | 43 | cagttgagctgtttcatcttttggc | att | taa |
| 100587 | 3AORF209 | −1 | 28366 ... 28497 | 43 | taattcctggtctctagttgggttt | ata | tga |
| 100588 | 3AORF210 | −1 | 15739 ... 15870 | 43 | catcaagcttatttgattccactga | gtg | tag |
| 100589 | 3AORF211 | −1 | 7693 ... 7824 | 43 | taactgaagttccctcagctacacc | gtg | tga |
| 100590 | 3AORF212 | −2 | 4314 ... 4445 | 43 | ggttctgaaacaatttctttagaaa | gtg | tag |
| 100591 | 3AORF213 | −2 | 4011 ... 4142 | 43 | tgtttgatgtcttccatatcaatat | ttg | taa |
| 100592 | 3AORF214 | −2 | 1722 ... 1853 | 43 | tctgtctagtttcaactgaaccatta | ttg | taa |
| 100593 | 3AORF215 | −3 | 16616 ... 16747 | 43 | tcttcatttgtttgcgtattagcat | atc | tag |
| 100594 | 3AORF216 | −3 | 15833 ... 15964 | 43 | gtcattttgaccgaagttttttgat | ttg | tag |
| 100595 | 3AORF217 | 3 | 6363 ... 6491 | 42 | gatgcagagctccaaacatatataa | att | taa |
| 100596 | 3AORF218 | −1 | 32146 ... 32274 | 42 | aataagctataattaagatttcgaa | atc | taa |
| 100597 | 3AORF219 | −1 | 29800 ... 29928 | 42 | ctagggtcatcactttgttcgttta | atc | taa |
| 100598 | 3AORF220 | −1 | 18409 ... 18537 | 42 | gcattaacctgatacgcttcttctc | ctg | tag |
| 100599 | 3AORF221 | −1 | 13234 ... 13362 | 42 | ttttatcgcctaaccaagatgcacc | atc | tag |
| 100600 | 3AORF222 | −1 | 12313 ... 12441 | 42 | cccaagcttatctgaggcatctga | ata | tga |
| 100601 | 3AORF223 | −1 | 4915 ... 5043 | 42 | tccatcatagttaattccaaaataa | ttg | tag |
| 100602 | 3AORF224 | −1 | 2125 ... 2253 | 42 | attaactacttatataatcttcatac | att | taa |
| 100603 | 3AORF225 | −2 | 26298 ... 26426 | 42 | tcgtttgtaacaacttgatttaaga | ata | taa |
| 100604 | 3AORF226 | −2 | 17184 ... 17312 | 42 | cgcctattttaaattatctaattt | att | tag |
| 100605 | 3AORF227 | −2 | 1425 ... 1553 | 42 | atcttcttcccattctctatagggt | att | tag |
| 100606 | 3AORF228 | −3 | 31055 ... 31183 | 42 | catttttgatgtcaggcagtttat | ata | taa |
| 100607 | 3AORF229 | −3 | 22592 ... 22720 | 42 | gttataaccatgaccggctacaagc | ata | taa |
| 100608 | 3AORF230 | −1 | 27883 ... 28008 | 41 | gaaggcagggtcgtttcttggatta | ttg | tag |
| 100609 | 3AORF231 | −1 | 29968 ... 30113 | 41 | gcttcttaactttctcttgtacaa | ttg | tag |
| 100610 | 3AORP232 | −2 | 22485 ... 22610 | 41 | tatctgggaaatttaatctaataaa | ata | tag |
| 100611 | 3AORF233 | −2 | 9264 ... 9389 | 41 | aagtttgccgaaatgactttgagct | atc | tga |
| 100612 | 3AORF234 | −3 | 23033 ... 23158 | 41 | acctaattcagataagcgataattt | ata | tga |
| 100613 | 3AORF235 | 1 | 25558 ... 25680 | 40 | aacactgctgaaatagacgtcttt | att | tag |
| 100614 | 3AORF236 | 1 | 34420 ... 34542 | 40 | acattgagagaagtttcagaaaaat | atc | tag |
| 100615 | 3AORF237 | 3 | 38442 ... 38564 | 40 | gaagagctatagaaactttttattc | ctg | tag |
| 100616 | 3AORF238 | −1 | 33628 ... 33750 | 40 | caatcattagaaaaccttttttcat | ata | taa |
| 100617 | 3AORF239 | −1 | 29248 ... 29370 | 40 | tcttctaatttagaaatattaatca | atg | tag |
| 100618 | 3AORF240 | −2 | 18156 ... 18278 | 40 | gtctctcaattctgtatagaatttt | att | tag |
| 100619 | 3AORF241 | −2 | 8088 ... 8210 | 40 | tttcaaggcttttgtataagtttta | gtg | tga |
| 100620 | 3AORF242 | −3 | 39149 ... 39271 | 40 | ttagcaaagcagatttacctacacc | ttg | taa |
| 100621 | 3AORF243 | −3 | 23558 ... 23680 | 40 | aaaattaactgtttattaatttaa | ata | taa |
| 100622 | 3AORF244 | −3 | 1697 ... 1819 | 40 | catttcattaaaggattattattaa | ata | taa |
| 100623 | 3AORF245 | 1 | 19015 ... 19134 | 39 | agttatgcaaggaatatgatgactt | ttg | tag |
| 100624 | 3AORF246 | 1 | 22504 ... 22623 | 39 | gctaatctaaacactttcacatcgt | ttg | taa |
| 100625 | 3AORF247 | −1 | 40567 ... 40686 | 39 | aaagtatttacttgttctttattcc | ata | taa |
| 100626 | 3AORF248 | −1 | 23956 ... 24075 | 39 | tttagattcatgaaacgaagtagca | ata | taa |

TABLE 8-continued

Bacteriophage 3A ORFs list

| SID | LAN | FRA | POS | a.a. | RBS sequence | STA | STO |
|---|---|---|---|---|---|---|---|
| 100627 | 3AORF249 | −1 | 11113 ... 11232 | 39 | cacctttccccaacacttttacagt | atc | tga |
| 100628 | 3AORF250 | −1 | 8719 ... 8838 | 39 | ttttattagcttctactagctttaa | ata | taa |
| 100629 | 3AORF251 | −2 | 16899 ... 17018 | 39 | aactcgtctgttaagcgcttgttga | att | tga |
| 100630 | 3AORF252 | −3 | 37025 ... 37144 | 39 | acaactgccctaatttaataactgc | att | taa |
| 100631 | 3AORF253 | −3 | 29138 ... 29257 | 39 | tctacatactccaaacaattgatgg | att | taa |
| 100632 | 3AORF254 | −3 | 15476 ... 15595 | 39 | caaatcaattcattaaaatccatta | ctg | taa |
| 100633 | 3AORF255 | 1 | 13552 ... 13668 | 38 | ttaatagacaaagtaaaatcgtggt | ttg | tag |
| 100634 | 3AORF256 | 2 | 12545 ... 12661 | 38 | aaaagtgcaaagggctggctaacgg | ata | taa |
| 100635 | 3AORF257 | 2 | 41870 ... 41986 | 38 | gggcatggattaaacttacaacaag | gtg | tga |
| 100636 | 3AORF258 | 3 | 10827 ... 10943 | 38 | tcaaacttttgaaaaacggtttagg | att | taa |
| 100637 | 3AORF259 | −1 | 34570 ... 34686 | 38 | gtgacatcgaaccagtacggatcac | gtg | tga |
| 100638 | 3AORF260 | −1 | 32389 ... 32505 | 38 | aagcaggtaagccaatacgcattga | att | tag |
| 100639 | 3AORF261 | −1 | 23630 ... 23946 | 38 | cctttttaactttaataaaattaa | ata | tga |
| 100640 | 3AORF262 | −1 | 8158 ... 8274 | 38 | ccatctcttctggttcagtttctga | atc | taa |
| 100641 | 3AORF263 | −2 | 14001 ... 14117 | 38 | ttatacctgcatttcctcctgattc | gtg | tga |
| 100642 | 3AORF264 | −2 | 294 ... 410 | 38 | tttgcttgttttttattttcccttga | gtg | tga |
| 100643 | 3AORF265 | −3 | 42683 ... 42799 | 38 | tgacaaagataattatctctatcta | atg | tga |
| 100644 | 3AORF266 | −3 | 31979 ... 32095 | 38 | aatcctcatcatcagtgtctaattc | atc | taa |
| 100645 | 3AORF267 | −3 | 26306 ... 26422 | 38 | ttgtaacaacttgatttaagaatac | atc | tga |
| 100646 | 3AORF268 | −3 | 16490 ... 16606 | 38 | tacatacaaggcttagcttttttat | ttg | tag |
| 100647 | 3AORF269 | −3 | 9872 ... 9988 | 38 | tgagaccctctaaccctgagttag | ata | tag |
| 100648 | 3AORF270 | 1 | 21829 ... 21942 | 37 | atagttaagagtcagtgcttcggca | ctg | tag |
| 100649 | 3AORF271 | 2 | 29468 ... 29581 | 37 | tgagcgacacatataaaagctacct | att | taa |
| 100650 | 3AORF272 | 3 | 2955 ... 3068 | 37 | gagttaaacagattttacttgcagc | ata | taa |
| 100651 | 3AORF273 | 3 | 5010 ... 5123 | 37 | ttttggcaaaccagtagtatttacag | atg | taa |
| 100652 | 3AORF274 | 3 | 19956 ... 20069 | 37 | tcaagtatagatgaattaaagcaac | ttg | tga |
| 100653 | 3AORF275 | 3 | 39882 ... 39995 | 37 | gatatgttaccaacaggaaatgtag | att | taa |
| 100654 | 3AORF276 | −1 | 27211 ... 27324 | 37 | attaagtgcgcttatttaattagat | att | tga |
| 100655 | 3AORF277 | −1 | 13516 ... 13629 | 37 | cgaccgtcattaaagttaagtccac | ctg | tga |
| 100656 | 3AORF278 | −1 | 11893 ... 12006 | 37 | ttttatatacacgaccactggataa | atc | taa |
| 100657 | 3AORF279 | −2 | 17535 ... 17648 | 37 | ttttgtaaagatttgtttactgctgc | ttg | taa |
| 100658 | 3AORF280 | −2 | 6474 ... 6587 | 37 | tcaaaataagcatctaactgactag | atg | taa |
| 100659 | 3AORF281 | −2 | 759 ... 872 | 37 | ttttgatatcgttgcgtcataatgg | att | tga |
| 100660 | 3AORF282 | −3 | 36608 ... 36721 | 37 | cccaaaacctccttgactcgatcta | ata | tga |
| 100661 | 3AORF283 | −3 | 14960 ... 15073 | 37 | tttcagttgaagaaccatctttaa | att | taa |
| 100662 | 3AORF284 | 1 | 18859 ... 18969 | 36 | atgttaacagagccaggtctttact | att | taa |
| 100663 | 3AORF285 | 2 | 8237 ... 8347 | 36 | aaaacttatacaaaagccttgaaag | ata | taa |
| 100664 | 3AORF286 | 3 | 5157 ... 5267 | 36 | tatgatcagcaacgtacattagaca | gtg | tag |
| 100665 | 3AORF287 | 3 | 38610 ... 38720 | 36 | tttgatttagtacgcatacacttat | atg | taa |
| 100666 | 3AORF288 | −1 | 36454 ... 36564 | 36 | tttatgacataactaccattcatac | ata | tga |
| 100667 | 3AORF289 | −1 | 30217 ... 30327 | 36 | aacaattttttcataatgctcttct | ttg | taa |
| 100668 | 3AORF290 | −1 | 16678 ... 16788 | 36 | gctttttttgcaaattctaacagctt | atc | tga |
| 100669 | 3AORF291 | −2 | 14310 ... 14420 | 36 | gtctagttaaagggataaccatctc | ctg | tga |
| 100670 | 3AORF292 | −2 | 11457 ... 11567 | 36 | ttctttcaattctttgattttctga | ttg | tga |
| 100671 | 3AORF293 | −3 | 29462 ... 29572 | 36 | ttcataaaagtattcctttataaaat | atg | tag |
| 100672 | 3AORF294 | −3 | 22388 ... 22498 | 36 | accattccaattttggccaaacgat | gtg | tag |
| 100673 | 3AORF295 | −3 | 18629 ... 18739 | 36 | aaaaggaacgcctcttgagtgaagt | att | tag |
| 100674 | 3AORF296 | −3 | 6332 ... 6442 | 36 | tatcagacatgaagtctgaaggtaa | atc | taa |
| 100675 | 3AORF297 | 1 | 13984 ... 14091 | 35 | aaatggttgaagtcacttaaaggta | gtg | tag |
| 100676 | 3AORF298 | 1 | 40174 ... 40281 | 35 | tatcaaatgttgcatcattttttga | atg | tag |
| 100677 | 3AORF299 | 2 | 1481 ... 1588 | 35 | gccgcgtgtgctactttttgcgttag | ata | taa |
| 100678 | 3AORF300 | 2 | 40451 ... 40558 | 35 | aatataaattttgtatacaaggtga | ata | tag |
| 100679 | 3AORF301 | 3 | 25479 ... 25586 | 35 | accactagttaaaacttcatatact | ata | taa |
| 100680 | 3AORF302 | 3 | 32106 ... 32213 | 35 | gaagatgatttcgatgaattagaca | ctg | taa |
| 100681 | 3AORF303 | 3 | 36024 ... 36131 | 35 | gacacagagggattattaaaagaga | ttg | tag |
| 100682 | 3AORF304 | −1 | 37762 ... 37869 | 35 | accgacaaatccgccaacatctttt | ata | tga |
| 100683 | 3AORF305 | −1 | 24088 ... 24195 | 35 | ttatctttaacaaaatcaaactga | ata | tga |
| 100684 | 3AORF306 | −1 | 19507 ... 19614 | 35 | atcattaggtaattgaaattttaaa | ata | tga |
| 100685 | 3AORF307 | −1 | 16081 ... 16188 | 35 | atgtactgacagttgcagatacagt | atc | tag |
| 100686 | 3AORF308 | −1 | 11398 ... 11505 | 35 | tttctttagttctagttaaaatgtt | ttg | taa |
| 100687 | 3AORF309 | −2 | 33003 ... 33110 | 35 | aaacagacctcttacccgttcatca | ctg | taa |
| 100688 | 3AORF310 | −2 | 24894 ... 25001 | 35 | gtaaatcgaaatcgctaccagctga | att | taa |
| 100689 | 3AORF311 | −2 | 22005 ... 22112 | 35 | ttcgtaggtgtcattacttctttaa | ttg | tag |
| 100690 | 3AORF312 | −2 | 21711 ... 21818 | 35 | aaaataaaagccagtgccgaagca | ctg | tag |
| 100691 | 3AORF313 | −2 | 17901 ... 18008 | 35 | cattaggtcttagacgacttagcat | ata | taa |
| 100692 | 3AORF314 | −2 | 16710 ... 16817 | 35 | taattcagtcttaggagtatcattt | att | tag |
| 100693 | 3AORF315 | −2 | 15990 ... 16097 | 35 | acatatctccgtatcatttgggtaa | att | tag |
| 100694 | 3AORF316 | −2 | 2862 ... 2969 | 35 | aattcttcttcatactgtttgacga | ttg | tag |
| 100695 | 3AORF317 | −3 | 40217 ... 40324 | 35 | tccctaacactactttttaaacttt | ata | tga |
| 100696 | 3AORF318 | −3 | 37535 ... 37642 | 35 | tgttcggctccttttcattattttaa | ata | taa |
| 100697 | 3AORF319 | −3 | 34421 ... 34528 | 35 | ttcttcatcttttatttgactctgc | ata | tga |
| 100698 | 3AORF320 | −3 | 28262 ... 28369 | 35 | catttgttggtaatatcttagttcg | atg | tga |
| 100699 | 3AORF321 | 1 | 23989 ... 24093 | 34 | taaaaaggtttaatataaaaatgta | ata | tga |
| 100700 | 3AORF322 | 1 | 34660 ... 34764 | 34 | aagagaagattgagaccatggcttt | atg | taa |
| 100701 | 3AORF323 | 3 | 30105 ... 30209 | 34 | ctaaatactgaactatcaactgtag | att | taa |

TABLE 8-continued

Bacteriophage 3A ORFs list

| SID | LAN | FRA | POS | a.a. | RBS sequence | STA | STO |
|---|---|---|---|---|---|---|---|
| 100702 | 3AORF324 | 3 | 30258 . . . 30362 | 34 | ggaaaagagttccttaaaaaagcag | ata | tga |
| 100703 | 3AORF325 | 3 | 40236 . . . 40340 | 34 | gttgtatcattttggtgatgcaac | att | tag |
| 100704 | 3AORF326 | −1 | 36964 . . . 37068 | 34 | cgcatcaacaactgtaaacctttga | ttg | tga |
| 100705 | 3AORF327 | −1 | 35242 . . . 35346 | 34 | attttgtctgttgtataatatttt | ctg | taa |
| 100706 | 3AORF328 | −1 | 21916 . . . 22020 | 34 | ccatttaccttcttgagatgttgga | ttg | tga |
| 100707 | 3AORF329 | −1 | 18820 . . . 18924 | 34 | ggtggcttaacttccaagaaccaac | ctg | taa |
| 100708 | 3AORF330 | −1 | 15631 . . . 15735 | 34 | ttatgaagttttcacaaattagtaa | atc | tag |
| 100709 | 3AORF331 | −2 | 37998 . . . 38102 | 34 | ttacgcccaatagcttcatactcat | ctg | tag |
| 100710 | 3AORF332 | −2 | 7359 . . . 7463 | 34 | ttttataaaccttttaaagttttagtc | ata | taa |
| 100711 | 3AORF333 | −3 | 24584 . . . 24688 | 34 | aaaaattataaaactataaaaccat | atc | taa |
| 100712 | 3AORF334 | −3 | 24269 . . . 24373 | 34 | tattttaggtagataatttattaa | atc | tga |
| 100713 | 3AORF335 | −3 | 14273 . . . 14377 | 34 | cacttcagcaagttgatgctttgta | atc | tga |
| 100714 | 3AORF336 | 2 | 7559 . . . 7660 | 33 | gtaacttatctaatttagaagcgg | ata | tag |
| 100715 | 3AORF337 | 2 | 13277 . . . 13378 | 33 | aatataggtaaaaaagcaggagaat | ttg | tag |
| 100716 | 3AORF338 | 3 | 9501 . . . 9602 | 33 | taggacgtacgatgacgatgggcgt | atc | taa |
| 100717 | 3AORF339 | 3 | 27348 . . . 27449 | 33 | atatctaattaaataagcgcactta | att | tga |
| 100718 | 3AORF340 | −1 | 37372 . . . 37473 | 33 | ttctatggttttcatcttatgagaa | atg | taa |
| 100719 | 3AORF341 | −1 | 33421 . . . 33522 | 33 | aagctaattcggacactttcctttt | ttg | taa |
| 100720 | 3AORP342 | −1 | 29047 . . . 29148 | 33 | ttttggcatctctatcactcctttag | ata | taa |
| 100721 | 3AORF343 | −1 | 7549 . . . 7650 | 33 | atgatacgcctgagactagaattgg | att | taa |
| 100722 | 3AORF344 | −1 | 7297 . . . 7398 | 33 | ctgctgaaactgttgcagattttga | att | tga |
| 100723 | 3AORF345 | −2 | 23850 . . . 23951 | 33 | ttaaaccttttaacttttaataaa | att | taa |
| 100724 | 3AORF346 | −2 | 20607 . . . 20708 | 33 | aaagatgtacgactagatttagtta | atc | taa |
| 100725 | 3AORF347 | −2 | 14175 . . . 14276 | 33 | atctgttgttaaagaacgctaataa | ctg | taa |
| 100726 | 3AOR7348 | −2 | 6984 . . . 7085 | 33 | cgtacactggttgacctgttaaacc | atc | tag |
| 100727 | 3AORF349 | −2 | 6882 . . . 6983 | 33 | tagaacgaccaataactgtatttag | atc | taa |
| 100728 | 3AORF350 | −3 | 40748 . . . 40849 | 33 | aactgcaattcactaaatgctgtaa | gtg | tga |
| 100729 | 3AORP351 | −3 | 38345 . . . 38446 | 33 | ggttagtagaatgtttcgtataa | atc | taa |
| 100730 | 3AORF352 | −3 | 38081 . . . 38182 | 33 | tagttgaaggccaatacattaacct | atg | taa |
| 100731 | 3AORF353 | −3 | 35432 . . . 35533 | 33 | tagcattctcatatgatgcagattt | ata | taa |
| 100732 | 3AORF354 | −3 | 34952 . . . 35053 | 33 | ttatcctgatacagatatctcttag | atc | taa |

TABLE 9

Bacteriophage 96, complete genome sequence

```
   1  catagttata ggcttttcag ctatatacca agataagatt tatcccgccg tctccataaa aatatgcttg
  71  gaaaccttga tttaatgggg ttttaatcta gcaagtgtca aatatgtgtc aagaaaataa ttttctgaca
 141  cgttgacctt gctcttttt atgttcatca agtaagtgag agtaggtgtc taaagttata gatatattat
 211  aatggcctaa tcttttgcta atatattcaa taggtatacc tttagaaagt aggaaagatg tatgcgtgtg
 281  tcttaatgaa taaggtgtta ttgtagtatc atttagtcct atttgactct tagcatggtt aaatgacttt
 351  ttaacggcat tatgactcaa tttaaacaac ttattatctg tacgttttgg taatttgat aatttagctt
 421  taatatgttg tatatccttt tttggtacct ccacaagtct gtccgcgtta actgttttg ttccacgaag
 491  atgtattgta ccctcttttt cgtttagatc gataggcaac atattaatta catcgctgta tcttgcacca
 561  gtgatagcta ggatgaataa aaaaatataa ctcgattcgt ctctagattt aaagtattct atcaattgca
 631  agtattgttc tatggtgatg aatttagagt gttcgtcttt tgatttttt gtaccacgaa tatctatttg
 701  atagctaggg tctttcttta aatagccctc atatactgca tctctgaagc attgtgataa acaactgttt
 771  aatttacgaa ccgtttcatt agtacgacct cgaccgaatt cgttcaaaaa cttttgatac tccgaacgtt
 841  tgatgttttt tattaaaaaa tcactcccga aatattcgtt aaataatttt aatgaacgtt gataccaata
 911  gaattgttgt gaagcgacat gttttcttat ttttgaatct aaccaatcat tgtaatattc ttcaaacttt
 981  ttattttcat ctaaattgtt tccatcatcc aaatctctaa gcagttgttg agcagcgttg gttgcctcag
1051  ctttagtttt gaatcctgac tttctttct ttcctgattt gaaagacgga tgttttacgt cgtactgcca
1121  agatgctgtt gctttattct tccttttgt aattgtaaat gacgccattt tactttcct cctcaaaatt
1191  ggcaaaaaat aataagggta ggcgagctac ccgaaatttt attgttgaac aactattgct tcacttcttg
1261  cttttcctac ttctttcta aaactatcat atgattgatt agggtgtgtt aacgacattc ctggaccacc
1331  tccagcatgt tggtttttgt ccggattatt ttccatttct tcagtggctc ttttagcatt taaatattct
1401  tcgtaactag gttcgttttgg gtcgcgtggt tgtgcttgtt gtccattatt ggtagctgga agattcttct
1471  gtacctgttg cttagatgtg ttattggttt gttgattgtt gttaatgttt gtgttgttct cgttgtttac
1541  ttgattattg ttatcgtttt gattactatt ttctttttc gcttctgctt tatcttttagt ttctttcttt
1611  ttgtctttgt tctctttctt tgtttcggtt ttcttgcttt cctctttctt atcgccgtcg ttgctaccgc
1681  atgcacctaa cactaacgca ctagctaata ataaaactaa taatctttttc atgttttaca ctccttttatt
1751  tgctatttgt tttaataaat ctatgatttc attgttttgt tctatgattt tgttttcatt tttaagatgt
1821  tcgtctaaca tctctattaa gacgaaattt tgatttatca tttcgtaagt aaacatttga cctgtgttgt
1891  taggattaga aaacgaacta ctgaaacgcg ttgaaaagct atctataaat tgaccaactt tattttttaa
1961  taacatatct ttaccgctct cagacattgt atttagttcg cgcttattta agttttttc tataattttg
2031  tattttgttt cctgatttct ttcgatttct tctacttcaa aagggatatt gttattaaat tttcgataa
2101  tatcacgttt ttcagaaact gacatacgat caaatacttg ttttgacct ttatttaact tccctcgaat
2171  ttttccggca gtccaagact cttaactgt taacttatca ttaggaactt gattcatctt ttatatgact
2241  ccttttctca tatttcttta tatttaaaaa ctctcaacgg ctcaaatgta atcgaatact cgccatagtg
2311  agttccaata ccgtatatct tcttatattg ttctattgcc tccaatatgt attcttcgct taattgtaga
2381  tactcagaca actcatacaa gttacgtacg ccataattgt aagctctac aatttcgcgt aacgggactg
2451  ctgagataaa gccgtgtcgt cttgcgtaat tttcgaactt gcgattgttg aatttcgatt gatctaaaat
```

TABLE 9-continued

Bacteriophage 96, complete genome sequence

| | | | | | |
|---|---|---|---|---|---|
| 2521 | gttgccatac | gtcaacttgt | ggtgggcaag | ttcttcatat | aatacttcta | atttgttcct | ttcggataag |
| 2591 | gaaggtctaa | taaaaatttc | tccttcttga | taccaaccat | cgaatcctcg | aggtactctt | tgtgtttctt |
| 2661 | tcacttcaac | ttcacatttc | ataagcaatt | cttcgtattt | tcccatgcgc | caaaccccctt | tggtgtctta |
| 2731 | tttctttcta | tctctaaccc | attgcataaa | attttcgatt | tcttcccatt | cttcgggagt | aaattcatct |
| 2801 | ttatttgcat | gaccggctat | agtttcttga | tgaatacttc | tttcttctgt | aattctcgat | ttaggtacat |
| 2871 | taaagtaatc | tgctaattgt | tggacttttg | atattctagg | atatttaagt | tctttaagcc | agttagagat |
| 2941 | tgttgattga | cttacccccga | ttgcttcaga | caattctact | tgactaatgt | tgttctcttt | cataagttgt |
| 3011 | tctaagttct | ctgataaaat | tttttctagca | ctcttatatt | ccataatttt | ctcctttagt | attacttaat |
| 3081 | gtaatactaa | tttaccataa | gtaatatcac | ttttcaatac | aaaatattac | ttttttgaaa | taaatatcac |
| 3151 | tttaggtgtt | gacatattac | tttaagtgat | agtatagttg | taaatgtcaa | cgggaggtga | tacgaaatgc |
| 3221 | cagaaaattt | taaagagttc | tctgtaaagg | tctggagaac | taattcgaat | atgacacaac | aagatgtcgc |
| 3291 | tgataaatta | ggcgttacta | aacaatctgt | aataagatgg | gaaaagatg | acgcagaatt | aaaaggctta |
| 3361 | caattgtatg | ctttagccaa | attattcaac | acagaagttg | attatataaa | ggctaaaaaa | atttaacatt |
| 3431 | aatatcactt | taagtgataa | aggaggaaac | tgaaatgcaa | gaattacaaa | catttaattt | tgaagaatta |
| 3501 | ccagtaagga | aaattgaagt | ggaaggagaa | cccttctttt | taggtaagga | tgttgctgaa | attttagggt |
| 3571 | atgcacgagc | agataacgcc | atacgcaatc | atgttgatag | tgaagatagg | ctgatgcacc | aaattagtgc |
| 3641 | gtcaggtcaa | aacagaaata | tgatcatcat | caacgaatct | ggattataca | gtttaatctt | tgacgcttct |
| 3711 | aaacaaagta | aaaacgaaaa | cattagagaa | accgctagga | aattcaaacg | ctgggtaact | tcggaagttt |
| 3781 | taccgacgtt | aagaaaaact | ggtgcttacc | aagtacctag | tgacccaatg | caagcattga | gattaatgtt |
| 3851 | tgaagctaca | gaagaaacaa | aacaagaaat | taaaaacgtg | aaagatgatg | ttattgattt | gaaagaaaat |
| 3921 | caaaaactgg | atgcgggaga | ctacaatttc | ttaactagaa | caatcaatca | aagagtagct | catatacaaa |
| 3991 | gactacatgc | gataacaaac | caaaaacaac | gtagcgaatt | attcagggat | attaattcag | aagtgaaaaa |
| 4061 | gatgactggt | gcgagttcaa | gaacgaacgt | aagacaaaaa | catttcgacg | atgtaattga | aatgattgct |
| 4131 | aattggttcc | cgtcacaagc | tactttatac | agaatcaagc | aaattgaaat | gaaattttaa | aacgaaatat |
| 4201 | aggagaggct | gaatatgaa | tacatcggat | atgcagacgc | aaatgcgttt | gtaaaaataa | gtgcatttc |
| 4271 | aaaagatgat | ctagagaaaa | aagtctactc | gaacaaagag | tttcaaaaag | aatgcatgta | cagatttggt |
| 4341 | cgaggacaaa | agcgttatat | aaaaattgac | aaagctattc | aatttatcgg | taccaattta | atgattaatg |
| 4411 | aatacgaatt | ataggaggag | ttatcaaatg | agtaaaactt | ataaaagcta | cctagtagca | gtactatgct |
| 4481 | tcacagtctt | agcgattgta | cttatgccgt | ttctatactt | cactacagcg | tggtcaattg | caggattcgc |
| 4551 | aagtatcgca | acattcatat | actacaaaga | atacttttat | gaagaataaa | aaaactgcta | cttgcgtcaa |
| 4621 | caagtaacag | tgacaaacat | ttatcaaaat | atacaactta | attaaatcaa | aatatacgga | ggtagtcaac |
| 4691 | tatggctgaa | aatattaaaa | ctgaacaaca | ttattacact | aaagatttct | caggatacag | aaatgaagaa |
| 4761 | gataacttg | tagcaaatca | agaattgaca | gtaacaatca | cattgaacga | gtacagaaaa | cttattgaaa |
| 4831 | taaaggctgt | taaagataaa | gaagaagata | cttacagagg | taagtatttt | gcggaagaaa | gaaaaaacga |
| 4901 | aaaattggaa | aaagaaaata | taaaactaaa | aaacaaaatt | tatgaattac | aaaacgaaga | agataacgag |
| 4971 | gaggacgaag | aagacaagga | ggacgagaac | gatgtattac | aaaattggtg | agataaaaaa | caaaattata |
| 5041 | agctttaacg | ggtttgaatt | taaagtgtct | gtgatgaaga | gacatgacgg | tatcagtata | caaatcaagg |
| 5111 | atatgaataa | tgttccactt | aaatcgtttc | atgtcataga | tttaagcgaa | ctatatattg | cgacggatgc |
| 5181 | aatgcgtgac | gttataaacg | aatggattga | aaataacaca | gatgaacagg | acaaactaat | taacttagtc |
| 5251 | atgaaatggt | aggaggtatg | aaaagtgaat | gatttacaag | agagagaatt | agaaacattc | gaacaagacg |
| 5321 | accgattcaa | agtaactgat | ctagacagtg | ctaactgggt | ttttaagaaa | ctggatgcaa | tcacaactaa |
| 5391 | agagaatgaa | atcaacgatt | tagcaaataa | agaaattgaa | cgcataaacg | aatggaaaga | taagaagta |
| 5461 | gaaaaattac | agagtggcaa | agaatattta | caaagccttg | taattgaata | ttacagaata | caaaaagaac |
| 5531 | aagatagcaa | attcaagttg | aatacacctt | acggaaaagt | gacagccaga | aaaggttcaa | aagtcattca |
| 5601 | agttagcaat | gagcaagaag | tcattaaaca | acttgagcaa | cgaggttttg | acaactatgt | aaaagtaact |
| 5671 | aaaaaactta | gccaatcaga | cattaagaaa | gatttcaatg | taactgaaaa | cggcacattg | attgacgcaa |
| 5741 | acggcgaagt | tttagagggt | gctagcattg | tggagaaacc | aacgtcatac | acggtaaagg | tgggagaata |
| 5811 | gatgactgaa | aaaactaatc | aagatgtcga | tattttaacg | caactaggtg | taaaagacat | cagcaaacaa |
| 5881 | aatgcaaaca | agttttataa | atttgcgata | tacggcaagt | tcggtactgg | taaaactacg | tttttaacaa |
| 5951 | aagataacaa | taccttagta | ctagatataa | atgaggacgg | aacaacggta | acagaagatg | gggcagttgt |
| 6021 | gcagattaag | aattataagc | attttagtgc | agtgattaaa | atgctgccta | aaattattga | acaactaaga |
| 6091 | gaaaacggaa | aacaaattga | tgttgtagtg | attgaaacaa | tccaaaagtt | acgtgatatc | actatggacg |
| 6161 | acatcatgga | cggtaaaatca | aagaaaccga | catttaatga | ttggggcgag | tgtgctacac | gcattgtaag |
| 6231 | tatttatcgt | tatatttcta | aattacaaga | acattatcaa | tttcatcttg | ctataagcgg | acacgagggc |
| 6301 | attaacaaag | acaaagatga | tgagggaagt | actatcaatc | caacaatcac | gatagaggca | caagaccaaa |
| 6371 | taaaaaaagc | agtcatcagt | caatctgacg | tgttagcaag | atgacaata | gaagaacatg | agcaagacgg |
| 6441 | cgaaaaaact | tatcaatatg | tacttaacgc | tgaaccatca | aatttattcg | agacaaagat | aagcacactca |
| 6511 | agcaacatca | aaattaacaa | caaacgtttc | attaatccaa | gtattaacga | tgttgtacaa | gcaattagaa |
| 6581 | atggtaatta | aaaattaatt | aaaaggacgg | tataaaaatt.atgaaaatca | ctggtagaac | acaatacatt |
| 6651 | caagaaacta | atcaagaggc | attcatgaaa | ggtggggact | ttttaggagc | tggagaattt | acagtaaaag |
| 6721 | ttgcaaatgt | cgagtttaac | gacacagaaa | acagatactt | cacgattgtt | tttgaaaaca | acgaaggtaa |
| 6791 | acaatacaaa | cacaaccaat | tcgtcccacc | attccaacaa | gattatcaag | aaaaacaata | tatcgagtta |
| 6861 | cttagtagat | taggaattaa | attgaactta | ccagatttaa | cttttgacac | agatcaatta | attaacaaaa |
| 6931 | tcggaactat | tgtacttaaa | aataaattta | acgaggaaca | aggcaacttat | tttgtaagac | tctcatatgt |
| 7001 | aaaagtttgg | aataaagacg | atgaagtagt | taataaccaa | gaacctaaaa | ctgatgagat | gaaacaaaaa |
| 7071 | gaacagcaag | caaatggtaa | acagacacct | atgagtcaac | aatcaaaccc | attcgctaat | gctaatggtc |
| 7141 | caatagaaat | caatgatgat | gatttaccgt | tctaggacgt | ggtttaaatg | caatacatta | caagatacca |
| 7211 | gaaagacaat | gacggtactt | attccgtcgt | tgctactggt | gttgaacttg | aacaaagtca | cattgattta |
| 7281 | ctagaaaacg | gatatccgct | aaaagcagaa | gtagaggttc | cggacaataa | aaactatct | atagaacaac |
| 7351 | gcaaaaaat | attcgcaatg | tgtagagata | tagaacttca | ctggggcgaa | ccagtagaat | caactacaac |
| 7421 | attattacaa | acagaattgg | aaattatgaa | aggttatgaa | gaaatcagtc | tgcgtgactg | ttcaatgaaa |
| 7491 | gttgcgagag | agttaataga | actgattata | tcgtttatgt | tcatcatca | aatacctatg | agtgtagaa |
| 7561 | cgagtaagtt | gttaagcgaa | gataaagcgt | tattatattg | ggctacaatc | aaccgcaact | gtgtaatatg |
| 7631 | cggaaagcct | cacgcagacc | tggcacatta | tgaagcagtc | ggcagaggta | tgaacagaaa | caagatgaat |
| 7701 | cactacgaca | aacatgtgtt | agcactgtgt | agacaacatc | ataatgaaca | gcacgcaatt | ggtgttaagt |
| 7771 | cgtttgatga | taaatatcaa | ttgcatgact | cgtggataaa | agttgatgag | aggctcaata | aaatgttgaa |
| 7841 | aggagagaaa | aatgaataag | ttactaatag | atgactatcc | gatacaagta | ttaccgaaat | tagctgaatt |

TABLE 9-continued

Bacteriophage 96, complete genome sequence

```
 7911 aatagggtta aacgaagcaa tagtattgca acaaattcat tattggctaa acaactcaaa acataaatac
 7981 gatgcaaaaa cttggatttt taattcttat ccagaatggc aaaacaatt tccattttgg agcgagagaa
 8051 ctataa&a&g gacatttggg agtttagaaa aacaaaattt attgcatgta ggtaactaca acaaggctgg
 8121 attttgaccgt acaaaatggt attcaatcaa ttatgaaaca ttaaacaaac tagtggcacg accatcggga
 8191 caaaatggcc cgacgatgag gacaaattgg cacgatgcaa gaggacaaaa tgacccgacc aataccatag
 8261 actacacaga gactaacaaa catagagaga cagacgacgt ctcaaagtca tttaagtata ttagtaccaa
 8331 tttagaaatt atacaaaacc ctttaaaagc agaacagtta gaacacgaaa ttaaatcatt taagcaagat
 8401 cagttcgaaa tagtaaaagt cgctaccgat tactgcaaag aaaacaacaa aggtctgaat tacttactaa
 8471 ctgtattaaa gaactggaat aaagaaggcg tttcagataa agaaagtgct gaaaacaaat tgaaacctcg
 8541 taactctaaa aaagaaacta ctgatgatgt catagcacaa atggaaaaag aattgagtga tgactaatgc
 8611 cgatgagcaa aacacaagca ttagaaatta ttaaaaaagt taggtacgta tacaacatcg attttgataa
 8681 accaaagtta gaaatgtgga ttgatgtatt aagtcaaaac ggggattatc aaccaactgt aaaagctgta
 8751 gatggatata tcaacagtaa caacccgtac ccgcctaacc taccagcaat catgcgtaag gcacctaaaa
 8821 aagtatctat tgagccggta gacaacgaaa ccgctacaca ccaatggaaa atgcagaatg accccgaata
 8891 tgtcagacaa agaaaaatag cgctagataa cttcatgaat aagttggcag aatttgggg cgataacgaa
 8961 tgaattacgg tcaatttgaa attgaaagca caataatcgc tacgctactt aaacaaccgg acgtactaga
 9031 aaagataaga gttaaagatt acatgtttac gaacgaaaag tttaaaacct ttttcaatta tgtaatggac
 9101 gtcggaaaga tagatcatca agaaatctat ttaaaagcaa ctaaagataa agagttttta gatgcagata
 9171 ctataactaa actttacaac tccgatttca ttggatacgg attcttttgaa cgttatcaac aagaattatt
 9241 ggaaagttat caaatcaaca aagcgaaaga attggtaact gagttcaaac aacaacctac gaaccaaaat
 9311 tttaataact tgattgatga actcaaggat ttaaaaacaa ttactaacag aaaagaagac ggaaccaaga
 9381 agtttgttga ggagtttgtc gatgagttat acagcgatag ccctaagaag caaattaaga cgggttataa
 9451 gctcatggat tacaaaatag ggggattgga gccgtcgcaa ttaatcgtca tcgcagcgcg tccctcagtg
 9521 ggtaagacag gttttgcatt aaacatgatg ctgaacatag cacaaaatgg atacaaaaca tctttctttta
 9591 gtctcgaaac aactggcaca tcagtattga aacgtatgtt atcaacaatt actggtattg agttaacaaa
 9661 gataaaagaa atcaggaact taacgccgga tgacttaaca aagttaacga atgcgatgga taaaatcatg
 9731 aaattaggca tcgatatttc tgataaaagt aatatcacac cgcaagatgt gcgagcgcaa gcaatgaggc
 9801 attcagacag gcaacaagtt atttttatag attatcttca actgatggat actgatgcga aagttgatag
 9871 acgtgtagca gtagaaaaga tatcacgtga cttaaagata atcgctaacg agacaggcgc aatcatcgta
 9941 ctactttcac aactgaatcg tggtgtcgag tctagacagg ataaaagacc aatgctatcg gacatgaaag
10011 aatcaggcgg aatagaagca gatgcgagtt tagcgatgct actttaccgt gatgattatt ataaccgtga
10081 cgaagatgac agtatcactg gcaaatctat tgttgaatgt aacatagcca aaaacaaaga cggcgaaacc
10151 ggaataattg aatttgagta ttacaagaag actcagaggt ttttcacatg aatataatgc aattcaaaag
10221 cttattgaaa tcgatgtatg aagagacaaa gcaaagcgac ccgattgtag caaatgtata tatcgagact
10291 ggttgggcgg tcaatagatt gttggacaat aacgagttat cgccttttcga tgattacgac agagttgaaa
10361 agaaaatcat gaatgaaatc aactggaaga aaacacacat taaggagtgt taaaaaatgc cgaaagaaaa
10431 atattactta taccgagaag atggcacgga agatattaag gtcatcaagt ataaagacaa cgtaaatgaa
10501 gtttattcgc tcacaggagc ccatttcagc gacgaaaaga aaattatgac tgatagtgac ctaaaacgat
10571 ttaaaggcgc tcacgggctt ctatatgagc aagagctagg attgcaagca acgatatttg atatttagag
10641 gtggcacaat gagtaaaatac aatgctaaga aagttgagta caaggaatt gtatttgata gcaaagtaga
10711 gtgcgaatat taccaatatt tagaaagtaa tatgaatggc actaactatg atcgtatcga aatacaaccg
10781 aaatttgaat tacaacctaa attcgggaaa caaagaccga ttacgtatat agccgatttc tctttgtgga
10851 aggaagggaa actggttgaa gttatagacg ttaaaggtaa ggcgactgaa gttgccaaca tcaaagcgaa
10921 gatattcaga tatcagtata gagatgtgaa tttaacgtgg atatgtaaag cgcctaaata cacaggtcaa
10991 gaatgatgg tatatgagga cttagtgaaa gtcagacgta aaagaaaag agaaatgaag tgatctaatg
11061 caacaacaag catatataaa cgcaacaatt gatataagaa tacctacaga agttgaatat cagcattacg
11131 atgatgtgga taaagaaaaa gatacgctgg caaagcgctt agatgacaat ccggacgaat tactaaagta
11201 tgcaacaata acaataagac atgcatatat agaggtggaa taaatgaagt tgaacgaagt attcgcaact
11271 aatttaaggg taatcatggc tagagataac gtaagtgtcc aagatttgca caatgaaact ggcgtatcaa
11341 gatcaactat tagtggatat aaaaacggaa aagctgagat ggttaactta aatgtattag ataaaattggc
11411 agatgctcta ggtgttaatg taagtgaact atttactaga aatcacaaca cgcacaaatt agaggattgg
11481 attaaaaaag taaatgtata gaggtggaat aaatgagtgat cgtaaagatt aacggtaaac catataaatt
11551 taccgaacat gaaatgaat tgataaaaaa gaacggttta actccaggaa tggttgcaaa aagagtacga
11621 ggtggctggg cgttgttaga agccttacat gcaccttatg gtatgcgctt agctgagtat aaagaaattg
11691 tgttatccaa aatcatggag cgagagagca aagagcgtga aatggttagg caacgacgta aagaggctga
11761 actacgtaag aagaagccac atttgttttaa tgtgcctcaa aaacattcct gtgatccgta ctgttcgat
11831 gtcacttata accaaatgtt caagaaatgg agtgaagcat aatgacgata atcagtaaca gaaaagtaga
11901 tatgaacaaa acgcaagaca atgttaaaca accggcgcat tacacatacg gcaacattga aattatagat
11971 tttatcgaac aggttacggc acagtatcca cctcaactag cattcgcaat aggtaatgca atcaaatact
12041 tgtctagagc accgttaaag aatggtcatg aggatttagc aaaggcgaag ttttacgtcc aaaagctttt
12111 tgacttgtgg gagggttaac gatggcaacg caaaaacaag ttgattacgt aatgtcatta caggaacaat
12181 tgggattaga agactgtgaa aaatatacag acgaacaagt taaagctatg agtcataaag aagttagcaa
12251 tgtgattgaa aactataaga caagcatatg ggatgaagag ctatataacg aatgcatgtc gtttggtctg
12321 cctaattgtt aaaaggagtg atgaccatga acgatagcgc acgcaaagaa tacttaaacc aatttttcag
12391 ctctaagaga tatctgtatc aagacaacga gcgagtggca catatccatg tagtaaatga cacttattca
12461 tttcacggac attataaaac gatgtttaaa ggcgtgaaaa agacatttga tactgctgaa gagctcgaaa
12531 tatatataaa gcaacatgat ttggaatatg aggaacagaa gcaaccaact ttattttaga ggagatggaa
12601 ataatggcaa agattaaaag aaaaaagaag atgacgctac tcgaactggt ggaatgggca tggaacaatc
12671 ctgaacaagt tgaaagtaaa gtgtttcaat cagatagaat gggcacgctt ggagaatgta gcgaagtaca
12741 tttttcaact gatgggcatg ggtttttatac aaaagtagta acagataaag atattttac tgtagaaatc
12811 acagaggaag tcactgaaga tactgagttt gattgtctag tagaactaaa cgatattgaa ggttttgaaa
12881 tatatgaaaa tgattcaatc agagagttga tagacggtac ttccagacg tttttatatac taaacgaaga
12951 taaaactatg acattaattt ggaaagtgg gggagttgta gtatgatgca aacctataaa gtatgtcttt
13021 gtatcaagtt ctttgcatct aaatgtgatt ataaattaaa gaaacattat ttcgtgaaaa gtacgaatga
13091 ggaaaaagcc acgaacatgg tattaaaact gattcgtaaa aagctcccgt tcgaaactgc aagcatagaa
13161 gtcgaaaaag tggaggcaat ataatgatac aaccaacaag agaagaatta attaatttca tgaaaaaaca
13231 tggagctgaa aatgttgact ctatcactga tgagcaaagt gcaataagac acttagagc tcaatcaaaa
```

TABLE 9-continued

Bacteriophage 96, complete genome sequence

```
13301  gtttttaaag acgaacgtga tgagtacaag aagcaacgag atgagcttat cgaggatata gctaagttaa
13371  gaaaacgtaa cgaagagctg gagaacatgt ggcgcacagt caaaaatgaa ttgcttggaa gatacgaaca
13441  ttactgtttt aaaattagag aactacaccc tgagagcaaa gcgaacagga taggagctct ctatatagga
13511  ggtaaaagca ctgcagatat tatactgtcg cgaatggaag aactagacgg aacaaatgag ttctacgaat
13581  ttttagggca aatggaggca gacacaaatg aataaccgtg aacaaataga acaatcagtg atcagtacta
13651  gtgcgtataa cggtaatgac acagaggggt tactaaaaga gattgaggac gtgtataaga aagcgcaagc
13721  gtttgatgaa atacttgagg gaatgacaaa tgctattcaa cattcagtta aagaaggtat tgaacttgat
13791  gaagcagtag gggttatggc aggtcaagtt gtctataaat atgaggagga gcaggaaaat gagtattagt
13861  gtaggagata aagtatataa ccatgaaaca aacgaaagtc tagagattgt gcaattggtc ggagatatta
13931  gagatacaca ttataaactg tctgatgatt cagttattag cattatagat ttgattacta aaccaattta
14001  tctaattaag ggggacgagt gagtggaatg gaaacgatta aaaaatgtgg tgccgcaccc agttatcaaa
14071  aataaaaatt taaagtcggt atacgtaaca aaagtaaatg tgaaagaggt tcaaaaagaa ttaggtttct
14141  ttgaaatttt taatgaagaa gtgttattaa ctggattttt atcatttcaa aggataccta tttacattat
14211  ttggattaat cctaaatctc ataagacgcc tagatattac tttgctaacg agcatgagat tgaaagatat
14281  tttgaatttt tggaggacga gtaaatgctt gaaatcatcg accaacgtga tgcattgcta gaagaaaagt
14351  atttaaacga cgactggtgg tacgagctag attattggtt gaataaacgc aagtcagaaa atgaacagat
14421  tgatattgat agagtgctta aatttattga ggaattaaaa cgataggaga taacgaataa atgaataatt
14491  taacagtaga tcaattaaaa gaactttttac aaatacaaaa ggagttcgac gatagaatac cgactagaaa
14561  tttaaatgac acagtagcta gtatgattat tgaatttgcg gagtgggtta acacacttga gttttttaaa
14631  aattggaaga aacaaccagg taagccatta gatacacaat tagatgagat tgctgattac ttagctttca
14701  gtttgcaatt aactctgact attgttgatg aagaagattt ggaagagact actgaggtta tggttgattt
14771  gattgaaaat gaagttactt tacctaaact acattcagtt tattttgttc atgtaatgca tacactaaca
14841  gaacaatttg taaaaggtat tgataatgat attgtacaag ttttaataat gcctttttg tacgccaata
14911  cttactatac aatcgaccaa ctcattgacg catacaaaaa gaaaatgaaa aggaaccacg aaagacaaga
14981  tggaacagca gacgcaggaa aaggatacgt gtaaagacat cttagatcga gtcaaggagg ttttggggaa
15051  gtgacgcaat acttagtcac aacattcaaa gattcaacag gacaaccaca tgaacatttt actgctgcta
15121  gagataatca gacgtttaca gttgttgagg cggagagtaa agaaggaggcg aaagagaagt acgagaaaca
15191  agttaagata aggagagatg gagatgccaa agaaaacggt aacgattgat gtagatgaaa acttattagt
15261  agtagctagt aatgaaatat cagaactatt atatgaatat gacagtgagt taatgtcagc tgatgaagat
15331  ggcgataata gagatatcga aaaaaaaaga gacgcattaa aacaagctat acaaattatc gataaattaa
15401  catgtcgagg aggcagacga tgattaacat acctaaaatg aaattcccga aaaagtacac tgaaataatc
15471  aagaaatata aaaataaaac acctgaagaa aaagctaaga ttgaagatga tttcattaaa gaaattaatg
15541  ataaagacag tgaattttac agtcctatga tggctaatat gaatgaacat gaattaaggg ctatgttaag
15611  aatgatgcct agtttaattg atactggaga tggcaatgat gattaaaaaa cttaaaaata tggattggtt
15681  cgatatcttt attgctgata tactgcgatt attcggcgta atcgcactga tgcttgttgt catatcgcct
15751  atctatacag tggctagtta ccaaaacaaa gaagtatatc aagggacaat tacagataaa tataacaaga
15821  gacaagataa agaagacaag ttctatattg tgttagacaa caagcaagtc atcgaaaact ctgacttact
15891  attcaaaaag aaatttgata gcgcagacat acaagctagg ttaaaagtag gcgacaaagt agaagttaaa
15961  acgattggtt atagaataca ctttttaaat ttatatccgg tcttataccga agtaaagaag gtagataaat
16031  aatgattaaa caaatattaa gactattatt cttactagcg atgtatgagc taggtaagta tgtaactgag
16101  aaagtatata ttatgacgac ggctaatgat gatgtagagg cgccgagtga cttcgcaaag ttgagcgatc
16171  agtctgattt gatgagggcg gaggtgtcag agtagatgta tagcaaagag tcaattgtta atatgatagg
16241  cacacataaa atgaagtgta atgtattagc tgatgtaata ccggaatatg atagcaattc aattgcacag
16311  tatggcatac aagcaacgtt gccgaaacca caagggggaaa actcaagtaa agttgaagat gttgttgtga
16381  ggcttgagag agcaaataaa aggtatgctc agatgttaaa agaggttgag ttttataaatc aatcgcaaca
16451  gagattggga cacgttgact tttgcttctt agagttattg aagaaaggtt ataacaggga tgcgattatc
16521  aagaagatgc ctaactctaa attaaataga aacaacttct tagcgcgccg tgatgagtta gcagaaaaga
16591  tttatctact acagtgacga aaatgacaaa aatgacagaa atgacgaaaa tgacactatt tttaaactgt
16661  gaattaattt tatataattg attttgtaaga attatcttaa gacgtgggt aatagccaca ttagatgttc
16731  tcatcgatgt gattgagaag tgacaaacat ataaagatg atatgttacg ctattaatca cctactacct
16801  gcctatatgg tgggtagttt aattcttgca ttttgagtca taactatttt cctcctttca catttattga
16871  acgtagctcc tgcacaagat gtaggggcat ttttttatatt taaataacta gagtaattaa cgtaaaggcg
16941  tgtgatacag tgaaaacaat tgattaaatt aacaccgaag caagaaaagt ttgtgctagg actcatagag
17011  ggcaagagcc aacggaaagc atatattgac gcagggtatt cgactaaagg taagagtggg gaatatctag
17081  ataaagaagc gagtacactt tttaaaaatc ggaaggtttc cggaaggtac gaaaaattgc gtcaagaagt
17151  agctgaacaa tcaaaatgga cacgccaaaa ggccttttgaa gaatatgagt ggctaaagaa tgtagctaag
17221  aatgacattg aaatagaggg agtgaagaaa gcgacagctg atgcattcct cgctagttta gatggtatga
17291  atagaatgac gttaggtaac gaagttttag ctaaaaagaa aatagaaact gaaattaaga tgcttgagaa
17361  gaagattgaa caaatagata aaggtgacag tggaacagaa gataaaatca aacaacttca cgacgcaata
17431  acggaagtga tcgtcaatga ataaacttaa atctttatat acggacaaac aaattgaaat attgaagcaa
17501  acgcaaaaac aagattggtt tatgttaatt aatcacggac caaagcgtac aggtaaaaca atattaaaca
17571  atgacttatt tttacgtgag ttaatgcgtg tgcgaaagat agcagacgaa gaaggaattg agacacctca
17641  atatatactt gctggtgcaa cattaggtac gattcaaaaa aacgtactaa tagagttaac taacaaatat
17711  ggcattgagt ttaattttga taaatataat tcattcatgt tattttggcgt tcaagtggtt cagacaggtc
17781  acagtaaagt aagtggtata ggagctatac gtggtatgac atcgtttggt gcatatatca atgaagcgtc
17851  gttagcgcat gaagaggtgt ttgacgagat taagtcacgt tgtagtggaa ctggtgcaag aatattggta
17921  gataccaacc ctgaccatcc cgagcattgg ttgttgaaag attatattga aaatacagat cctaaagcag
17991  gtatactgag tcaccaattt aagctcgatg acaataactt tcttaatgat agatataaag agtctattaa
18061  ggcttcaaca ccatcaggta tgttctatga acgtaaatatc acgtaaatatc atgtcctcag tgacggtgta
18131  gtatatgccg actttgattt gaatgagaat acgattaaag cagatgaact ggacgacata cctatcaaag
18201  aatactttgc tggtgtcgac tgggggttacg agcactatgg atctattgtg ttaataggac gaggtatata
18271  tggtaaacttt tatttttattg aggagcacgc acaccaattt aagttttattg atgattgggt ggtattgca
18341  aaagatattg taagtagata tggcaatatt aatttttact gcgatactgc acgacctgaa tacatcactg
18411  aatttagaag acatagatta cgtgcaatta acgctgataa aagtaaacta tcgggtgtgg aggaagttgc
18481  taagttgttc aaacaaaaca agttacttgt tctttatgat aatatgagta ggtttaagca agaggtattt
18551  aaatatgttt ggcacccta aaacggagag ccctataaaag aatttgatga cgtgttggac tcgttaagat
18621  atgccatata cacacatact aaaccctgaac gattaaggag ggggaaatga cattgtataa gttaatagat
```

TABLE 9-continued

Bacteriophage 96, complete genome sequence

```
18691 gatattgaag cacaaggaat attgcctaag catattgagg ctctaataga gtcacataaa gacgatagag
18761 agagaatggt taatctctat aatagataca agacacatat tgactatgta ccaatattca aacgtcgacc
18831 aattgaagaa aaagaagatt ttgaaactgg tggaaatgta aggcgattag acgtgtctgt taataacaaa
18901 cttaacaact cttttgacag cgaaattgtt gatacacgtg ttggttattt acatggtgtt cctgttactt
18971 atgatttaga tgaaaacgca gaaaaaaacg aaaagttgaa aaagtttata accaactttg ccattagaaa
19041 tagtgttgat gatgaggatt ctgaaatagg taaaatggca gcaatttgcg gatatggtgc taggttagca
19111 tatattgata cgaatggtga tattaggatt aagaatatag atccctataa tgttattttt gttggcgaca
19181 atattttaga acctacatac tcattgcgct acttttatga aaaagatgat gataatggca ctgattatgt
19251 gtacgcagag ttttacgata atgcttatta ttatgtattt cgaggagaag gtattgacgc tttgcaagaa
19321 gttggacgat atgaacattt atttgattac aatccattgt ttggtgtacc taacaacaaa gagatgatag
19391 gagatgctga aaaggttatt cacttaattg acgcatatga tttaacaatg agcgatgcat caagtgagat
19461 tagtcagaca cgtttagcat accttgtgtt acgcggtatg ggtatgagtg aagaaatgat tcaagaaaca
19531 caaaagagtg gcgcatttga gttgttcgac aaagatatgg acgttaaata cttaacaaaa gatgtaaatg
19601 acacaatgat tgagaaccat ttagatcgaa tcgaaaagaa tatcatgcgt tttgcaaagt cagtaaactt
19671 taattctgac gagtttaacg gaaatgtacc tatcattgga atgaaactta aacttatggc tttagagaac
19741 aagtgtatga cgtttgagcg taagatgaca gctatgttga ggtatcaatt caaagttatt ttatctgcat
19811 taaagcgtaa agggtacaac ttggatgatg atagttattt aaacctgata tttaagttca ctcgtaacat
19881 tccagttaat aagttagaag aatcacaagt gctaattaac ctgaaggagc aagtttcaga acgaacaagg
19951 ttaggacaat cacaactagt tgatgatgtt gattacgaat tagacgaaat ggaaaaagaa agtcttgaat
20021 ttaatgacaa attacctgac atagatgaag gtgacgcaaa tgacaaatcc caaaataacc aatcagaatg
20091 atattgatga gtatatcgag ggtttaatct ctaaagcaga aaaaccaata gaacaactat ttgctaatcg
20161 acttaaagag ataaaacaaa tcatcgcaga tatgtttgag aaatatcaaa atgatgatgt gtatgttaca
20231 tggactgaat tcaataaata caacaggctc aataaggagt taactcgtat aggtacaatg ttgacttatg
20301 actataggca agtagctaag atgattcaga agtcacaaga agatgcttat atagaaaaat tccttatgag
20371 ccttttattta tatgaaatgg cgagtcaaac atctatgcag tttgatgttc cgagtaaaga ggtaatcaaa
20441 tcagctattg aacaacctat tgagttcatt cgtttaatgc caacactaca aaaacatcgt gatgaagtat
20511 tgaaaaagat acgtatgcac attacacaag gtattatgag tggagagggt tactctaaga tagctaaagc
20581 aatacgtgat gatgtcggca tgtctaaagc tcaatcattg cgtgtggctc gtacagaagc aggcagagca
20651 atgtcacaag ctggacttga tagcgcaatg gttgctaaag ataacggttt gaatatgaag aaacgttggc
20721 atgctactaa agatacacga acacgtgata ctcatcgtca tttagatggg gaatcagtgg aaatagatca
20791 gaattttaaa tcaagtgggt gtgttgggca ggcgcccaag ctatttattg gtgtaaacag tgccgaaagag
20861 aatattaatt gtcgttgcaa attactttat tatattgatg aaaatgaatt gccaactgta atgagagcac
20931 gtaaagacga tggtaaaaat gaagttatcc cattcatgac ttatcgtgag tgggagaaat ataagcgaaa
21001 aggtggtaat tgatatggat tttaaaataa aagtaaatgt tgatactggc gaagctatag aaaagttaga
21071 acgcattaaa tccttgtacg aagagataat agagttacaa aacgaaaaag ttgttgtaaa cgtaacagtt
21141 aaaaatgaag ctgatttaga tatggttaaa acatctatta gcgaagaaaa tgctaaaaat aatgatttca
21211 cacttttttta gttgtctctt tgctactcga ccttagcatg tcgttaaact gcttttttatt atgcacttt
21281 cggactgtta gggtacgcga agggcaaaaa ggagttttga tatatgaata tcgaagaagt taagtctttt
21351 tttgaagaac acaaagacga taaagaagta aaagattatc taaagggact taagacggtg tctgttgatg
21421 acgttaaagg ctttttagat acagaagaag gtaaacgatt cattcaaacct gaattagatc gttatcattc
21491 gaaaggatta gaatcatgga aagagaaaaa tcttgaggat ctaatcgaac aagaagtacg gaagcgtaat
21561 cctgagcaat cagaagaaca aaaacgtatt agtgctcttg aacaagagtt agaaaaacgc gacgcagagg
21631 caaaacgtga gaagttaaga agtaacgcgc taggtaaagc gcaggaacta aatttaccaa catccttagt
21701 tgatagattt ttaggcgatt ctgatgaaga tactgagcaa aacttaaaag ctttaaaaga aacctttgac
21771 aagtatgttc aaaaaggcgt tgagtctaaa tttaaatcga gtgtgaagaga tgttaaagaa tcacgaaatc
21841 aagatttaga cccttcaaat gtaaagtcca ttgaagaaat ggcgaaagaa atcaatatta gaaataaag
21911 tgaggtaata aaatatgcga actccaacat acacgccagg caatgttatt ttatcggatt ttaaaaacgg
21981 cgttattcca gcagaacaag gtactttaat catgaaagac attatggcta attcagcaat tatgaaatta
22051 gctaaaaatg agccaatgac agcacaaaag aaaaaaattta cttacttagc aaaaggtgta ggcgcctact
22121 gggtatcaga aacggaacgt attcaaactt ctaagcctga atatgcgcaa gcagaaatgg aagctaagaa
22191 aattggtgta attattccgt tatcaaaaga gtttcttaaa tggactgcaa aagatttctt taatgaggtt
22261 aaacctctaa ttgcagaggc attttacaaa gcgtttgacc aagctgttat cttttggtact aaatcacctt
22331 acaacacttc aactagtggt aaaccgcttg ttgaaggcgc agaagagaaa ggtaacgttg ttacagatac
22401 taataattta tacgtagacc tttcggcatt aatggctact attgaagatg aagagttaga tccaaacgga
22471 gtattaacta cacgttcatt cagaagtaaa atgcgtaatg ctttagatgc taatgacaga ccattatttg
22541 atgctaacgg gaacgagatt atgggattac cactatctta tactggacgg gatgtatacg acaaaaaagaa
22611 atcgttagca ctaatgggtg attgggatta cgcacgttac ggtatccttac aaggtattga gtatgcaatt
22681 tctgaaatgg ccacgttaac gacgttacaa gcatcagatg cttctggcca accagtatca ttatttgaac
22751 gtgatatgtt cgctttacgt gcgacgatgc atattgcata catgaacgtt aaaccagaag cgttcgcaac
22821 gcttaaacca actgaatagg aggagatatg atggctaatc ctgcagaaga gattaaggta aaaaaagaca
23891 atatgactat tactgttaca aagaaggcat ttgactctta ttacagtctt gtcggttaca aagaggttaa
22961 atcacgtcgt actacgtctg ataagagcga gtgataaaaa tgactcttta tgaagatgtt aaactttttac
23031 tcaagaaaaa tggagtgaaa gttaaaagtg atgaagaaga aatatttaag atggaagttg acggaatact
23101 agaagatgtt agggatataa caaacaatga tttttatgaaa gatggtcaag tcatttatcc ttactcaatc
23171 aaaagtatg tcgcagatgt cctagagtat tatcaacgac ctgaagttaa aaagaattta aagtcaagaa
23241 gtatggggac agtgtcgtac acttataacg atggtgtccc tgattacatt agtgaagtat taaacaggta
23311 taaacgagca aagtttcatc cgtttaaacc aataaggtag aggtgttgtt tgtgtttaac ccatacgacg
23381 aattccctca cactattttct attggaagta tcaaaaaagt aggagagtat ccaattatac aagagcgctt
23451 tgtaagcgat aaaacaatta aaggatttat ggatacgcct actacactg aacaactaaa atttcatcaa
23521 atgtcacaag aatatgacag aaacctatat gtaccttatg acttgccaat atctaaaaac aatttatttg
23591 agtatgaggg tagaatcttt agtattgaag gtgattctgt agatcagggc ggacaacatg aaattaagtt
23661 actacgactt aagcaggtgc catatgcaaa aagttaagta cggtgctgat agcatggttg ttgaattgga
23731 taagttcgat aagaaaatag aagagtgggt taaaaaggt attgctaaaa caacgacgaa gatttacaac
23801 actgctgtag cattagctcc tgttgactta ggttttttag aagaaagtat tgactttaaa tatttcgatg
23871 gtgggttatc cagtgttata agtgtcggcg cagattatgc aatatacgtt gaatacggta ctgtatata
23941 tgctactggt cctggtggta gtcgtgctac aaagattccg tggagtttta aggtgatga cggcgaatgg
24011 tacaccacat atggtcaagc gccacagcca ttttggaacc ctgcaattga cgcaggacgc aagacattcg
```

TABLE 9-continued

Bacteriophage 96, complete genome sequence

```
24081  agcagtattt ttcatagagg tggttaaata tgtgggtatc agttgagcct gaacttacaa atcaaatata
24151  taaaagatta atctcagacc ctaacattaa caaactagtt gatgataggg tttttgacgt tgttcaagat
24221  gacgctgttt acccatatat tgttgtgggt gaatcaaacg tcactaacaa cgaatctagc gcaacaatga
24291  gagaaacagt cggtattgtc atacatgtgc attcacagtt cgctacacaa tacgaggcta agctcatttt
24361  aagcgcgata ggttatgtgc ttaacagacc tatagaaata gataattacg agtttcaatt tagccgtatc
24431  gatagtcaag cagtattccc tgatatagac aggtttacta agcatggcac gatacggctt ttatttaagt
24501  acagacataa aaagaaaaac gaaggagtgt attaaatggc gcaaaaaaac tatttagcag ttgtacgtcc
24571  agctgaaact gacttagatc cagtagaatc tttattatta gctgacttac aagaaggtgg acatacgatt
24641  gaaaatgatt tagctgaaat agtacgagcc ggtaaaacgg actattctcc caatgcaatg tcagaatcat
24711  ttaaattaac aattggtaat gtgcctggag ataaaggaat tgaagcagtg aaacacgctg tacaaacagg
24781  tggacagttg cgtatatggc tttatgagcg taataaacgt gcagacggta aacatcacgg aatgtttggt
24851  tatgttgttc cagaatcatt tgaaatgtca tttgatgatg aaagtgacaa aatcgaacta tcattaaaag
24921  ttaaatggaa tacagcagaa ggtgctgaag ataacttgcc gaaagagtgg tttgaagctg caggtgcgcc
24991  tacagttgaa tacgaaaaat tcggcgaaaa agtcggaaca ttcgagacgc aaaagaaagc tagtgttgta
25061  tctgattcac acacggaaga ccattctatg taaactaata gatcaagggg gcgtaagctc cctatttttt
25131  tataaaaaaa ttgaaaagag gtatatattt tgactgaatt taatccaatt acaacattaa aaattaatga
25201  cggagaaaaa gattacgaag tagaagcaaa agtaacattt gcatttgacc gaaaagctga aaaattctca
25271  gaagatagcg aagatgggag aaaaggagca atgccaggat tcaatgttat ctttaacggt ttgctagaat
25341  ctagaaacaa agcgatttta caattttggg aatgtgctac tgcttattta aaaaacccac caactcgaga
25411  acaattagaa aaagcaattg atgatttcat cactgaaaac gaggatactt tgccgttatt acaagggct
25481  ttggacaaac ttaacaatag tggtttttc aagagggaga gtcgctcgta ctggatgaca ttgaacaaag
25551  caccgaatat ggccaaaagc gaggacaaag aaatgacgaa agcaggcata gaaatgatga aagagaatta
25621  caaggaaatc atgggcgcag aaccttacac gattactcaa aaataaggca actgacagct agatatttag
25691  gatatatccc tgaacatgaa ttgttagcac taacacctgc tgaatgcgt gattggctta ttggtggtca
25761  ggataggtac ctagatcaaa gacaattatt aattgaacaa gcgcaagcta acggcttagt acaagcttct
25831  aagaggctaa ctagtatgat tcgtgacatt gagaaacaac gttacgaaat aagagaacct ggtagctatg
25901  ctcgtgtaca aaaagctaga ttagaagaag aaaaaagaag acgtagaagc ttcaaagaag gtacaagaaa
25971  attccttgaa tcgaaaggag gttagccttt ggatactcat tttatgcaa agattatggc caatattaga
26041  gatttccaaa gcaacgtaag gaaagctcaa cgattagcaa agacgtctgt accaaacgaa attgaaacag
26111  atgtaaaagc agatatttca agattccaaa gagctttaca acgcgctaaa tcaatggctc aacgatggcg
26181  agagcattct gttaaattat tcatgaaaac agatgagtat aaagcgaatt tagaacgcgc taaagctcaa
26251  gtagagcgat ttaaacaaca taaagtagat ttgaaactaa gtaacactga attaatggcc aaatataatg
26321  caactaaagc tactgtcgaa gcttggagaa aacatgttgt taagttggat ttagatgcaa accccgctaa
26391  aatggcggtt aaagggttta aagaagattt aatagatctt agcaggcata gttttgatat tgattccagc
26461  agatggaaat taggaaataa attcacaaaa gaatttcaata agtcgaaagg agcagttaaa cgttctttcg
26531  gaagaattgg tcagattatg agaaaagaag taaatggaac aagtgatatt tggggtaasc ttaacaactc
26601  attgaaagat tacggcgaga aaatggacgc cttagctact aaaaatccgaa cttttcggtac tatcttcgcg
26671  caacaggtca aaggcttaat gattgctagt atacaagcat tgataccagt gattgccgga ttagtacctg
26741  caataatgac agtacttaat gcggttgtg tattaggtgg tggcgttta ggtttagttg gcgcattctc
26811  tgtcgcaggt cttggagttg ttggctttgg tgcaatggct attagcgctc ttaaaatggt tgaagatgga
26881  acattggcag taacaaaaga agttcaaaac tttagagatg cgagcgatca gttaaaaact acatggcgtg
26951  atattgttaa agagaatcaa gcaagtatct ttaatgcgat gtcagcaggt atcagaggcg ttacaagtgc
27021  gatgtctcaa ttaaaaccat tcttatcga agtatctatg ctagttgaag caaacgcacg cgagtttgag
27091  aattgggtta aacattccga aacagctaag aaagcgtttg aagcattgaa tagcataggt ggcgcaatct
27161  tcggagattt attgaacgct gcaggacgat ttggcgacgg attagttaac attttcactc aattaatgcc
27231  gttgttcaaa tttgtgtctc aaggactaca gaacatgtct atagcttttc aaaattgggc taatagtgta
27301  gctggtcaga atgctattaa agcgtttatt gactacacta ccactaactt acctaagatt ggtcagatat
27371  ttggtaatgt gttcgctggt attggtaatt taatgattgc ttttgcacaa aacagttcca acattttga
27441  ttggttggtt aaattaactt ctcaatttag agcatggtca gaacaagtag gacaatcaca agggtttaaa
27511  gactttatca gttatgttca agagaatggt cctactatta tgcagttaat cggtaatatc gtaaaagcat
27581  tagttgcttt tggtactgca atggctccta tagctagtaa attgttagac tttatcacta atctagctgg
27651  atttatcgct aaactattcg aaacacaccc agctatagca caagttgctg gcgttatggg tatttaggc
27721  ggtgtatttt gggctttaat ggctccgatt gttgctataa gtagtgtact tacaaatgtg tttggtttga
27791  gcttattcag cgtcactgaa aagattttag acttcgttag aacatcaagt ttagttactg gagctacgga
27861  agcattaata ggtgcattcg gttcgatttc agcaccatt ttagcagttg ttgcagtaat tggtgcattc
27931  attggtgtcc tcgtttattt atggaaaaca aacgagaact ttagaaatac tattactgaa gcgtgaaacg
28001  gtgttaaaac ggcagttcct ggtgcgattc aaggtgtagt cggctggtta actgaattgt ggggcaaaat
28071  ccaatctacc ttacaaccga taatgcctat attgcaagta ttaggacaaa tattcatgca agttttaggt
28141  gttttggtaa taggcatcat tacaaacgtt atgaatatca tacaaggttt gtggacttta attacaattg
28211  cgttccaagc cataggaaca gtgatatccg tagcagtcca aatcatagta ggtttgttca ctgctttaat
28281  tcagttgctt actggcgact tctcaggtgc ttgggagact attaaaacta cggttaccaa tgtgcttgat
28351  acgatttggc aatacatgca atcagttgg gagtcaatta tcggcttttt aactggcgta atgaatcgaa
26421  cactttctat gtttggtaca agttggtcac agatatggag tacaatcact aattttgtta gcagtatttg
28491  gaacactgtt acaagttggt tcagtcgagt ggcttcgagt gtagctgaaa aaatggggca agcactaaac
28561  tttattatca caaaaggttc tgaatgggtt tctaacattt ggaatacagt tacaagtttc gcgagtaaag
28631  tagctgatgg gtttaaaaga gttgtctcaa atgtaggtga cggtgatgagt gatgcacttg gtaagattaa
28701  aagtttcttc agtgatttct taaatgccgg agcggaatta atcggcaaag tagctgaggg tgtagccaaa
28771  tctgcgcaca aagtagtcag cgcggtaggc gatgcgattt catcagcttg ggactctgta acttcattcg
28841  taagtggaca cggtggaggt agtagcttag gtaaaggttt agcggtatca caagcaaaag taattgctac
28911  agactttggc agtgccttta ataaagagct atcctctact ttgacagata gtatagtaaa tcctgtaagt
28981  acttctatag acagacacat gactagcgat gttcaacata gcttaaaaga aataaataga cctattgtga
29051  atgtaacgat tagaaatgag ggcgaccttg atttaattaa atcacgcatt gatgacatga acgctataga
29121  cggaagtttc aacttattat aagggaggtt tgttagttga tagcgacga tataagta ataaggaatg
29191  gttcacagta tcgcgtcagt gacaatcctt tcacttataa tcacttggaa gtagttgaat ataacgttac
29261  aggcgcagga tatcatcgta actattctga tatagagggt attgatggta gatttcataa ttacgctaaa
29331  gaagaactta aaaaagtaga gcttaagata aggtataaag tacctaaaat tgcttatgct tcacatttaa
29401  agtcagacgt ccaagcacta tttgctggac gttttttattt aagggaatta gctacaccag acaattcaat
```

TABLE 9-continued

Bacteriophage 96, complete genome sequence

```
29471  taagtatgag catatattag atataccaaa agacaaacaa gcatttgagc ttgattatgt tgatggacga
29541  caactttttg taggactagt aagtgaagtt tcttttgaca caacacaaac atcagggaaa ttttctttgt
29611  cgtttgaaac aaccgaacta ccatactttg aaagtgtcgg ttatagtact gatcttgaaa gtaataacga
29681  ccctgaaaaa tggtcggtac ctgatagatt gcctacaaac gaaggtgata agaggcgtca aatgacattt
29751  tacaacacta actcaggaga agtttattat aacggtgatg ttcctttaac acagtttaat cagtttaatg
29821  ttgttgaaat agagttagct gaagatgtta aagctaatga taaggatgga ttcactttct atacagataa
29891  aggaaatatc tcagttatta aggaagttga tttaaaagcc ggagataaaa taatcttcga cggtaaacat
29961  acctatagag gttatttaaa tatagattct tttaataaaa ctttagaaca accggtttta tatccagcct
30031  ggaatcgatt caagtctaat aaagtaatga aacaaattac atttagacac aaattatatt ttagataagg
30101  agtagcctat gccaatttta ttaaaaagtc tacagggtgt agggcacgct attaatgtta gtacaaaggt
30171  aagtaaaaag ctaaatgaag atagttcttt ggatctaact attatcgaga acgcgagtac gtttgacgca
30241  ataggtgcta taactaaaat gtggacgatc actcatgttg aaggtgaaga tgatttcaac gaatatgtaa
30311  ttgtcatact tgataagtct actattggcg aaaaaataag gcttgatatc aaagctaggc aaaaagaact
30381  tgatgacctt aacaattcta ggatttacca agagtataac gaaagtttta caggcgttga gttcttcaat
30451  actgtctttta aaggaacggg ttataagtat gtattacatc caaaagtaga tgcatcctaaa ttcgaggat
30521  taggcaaagg agatacacga ttagaaatct ttaaaaaagg acttgagcgt tatcatctcg aatatgaata
30591  cgatgcaaag actaaaacgt ttcatttgta tgatgaatta tctaagtttg ccaattatta cattaaagct
30661  ggtgtgaatg ctgataacgt caaaatacaa gaagatgcat ctaaatgtta tacctttatt aaaggttatg
30731  gtgattttga tggacaacag acttttgcag aagcgggact acaaattgaa ttcactcatc cattagcaca
30801  attgataggt aaaagagaag cgccaccgct tgttgatgga cgtattaaaa aagaagatag tttaaaaaaa
30871  gcaatggagt tattgataaa gaaaagtgtc actgcttcta tttccttaga cttttgtagcg ttacgtgaac
30941  atttcccaga agctaaccct aaaataggtg atgttgttag agtggtggat tctgccatag gatataacga
31011  cttagtgaga atagtcgaaa tcactacaca tagagatgcg tacaataata tcactaagca agatgtagta
31081  ttaggagact ttacaaggcg taatcgttat aacaaagcag ttcatgatgc tgcaaattat gttaaaagcg
31151  taaaatctac aaaatccgac ccatctaaag aactaaaagc attaaacgca aaagttaacg caagtttatc
31221  tataaaataat gaattggtta agcagaatga aaaaataaac gctaaagtcg ataagatgaa tactaaaaca
31291  gttacaactg ctaatgtgtac gatcatgtac gactttacta gtcaatcaag tataagaaac atcaaatcaa
31361  ttggaacgat tggcgactct gtagctagag ggtcgcacgc aaaaactaat ttcacagaaa tgttaggcaa
31431  gaaattgaaa gctaaaacga ctaatcttgc aagaggtggc gcaacaatg caacagttcc aataggtaaa
31501  gaagcggtag aaaacagcat ttatagacaa gcagagcaaa taagaggaga cctaatcata ttacaaggca
31571  ctgatgatga ctggttacac ggttattggg caggcgtacc gatggcact gataaaacgg atacaaaaac
31641  gttttacggt gcctttttgtt ctgcaattga agttattaga aagaataatc cagattcaaa aatactagtg
31711  atgacagcta caagacaatg ccctatgagt ggtacaacaa tacgccgtaa agacacggac aaaaacaaac
31781  tagggttaac acttgaggac tatgtaaacg ctcaaatatt agcttgtagt gagttagatg taccagtgtt
31851  tgacgcatat cacacagatt actttaagcc atacaatcca gcttttagga aagcgagcat ggaggacggc
31921  ttacacccta acgaaaaagg tcacgaggtt attatgtacg agttaatcaa ggattattac agttttttacg
31991  actaaaggag gcaaccaatg gcttacggat taattacaag tttacattca atgacaggtc ggaaaatagt
32061  tgctcaacat gagtataact atcgcttgtt agatgaaggt atgagcaaac ttgagaaaat gtttatatac
32131  catcaaaaag aagaaatata cgcacactca gcgaaacaaa ttaaatactt gaatgacagt gttgaagatt
32201  atttaacgta tttaaatagc cgttttagca atatgattct aggccataac ggcgacggta tcaatgaagt
32271  aaaagacgcg cgtattgata atacaggtta tggtcataag acattgcaag atcgtttgta tcatgattat
32341  tcaacactag atgctttcac taaaaaggtt gagaaagctg tagatgaaca ctataaagaa tatcgagcga
32411  cagaataccg attcgaacca aaagagcaag aaccggaatt tatcactgat ttatcgccat atacaaatgc
32481  agtaatgcaa tcatttttggg tagaccctag aacgaaaatt atttatatga cgcaagctcg tccaggtaat
32551  cattacatgt tatctagatt gaagcccaac ggacaattta ttgatagatt gcttgttaaa aacggcggtc
32621  acgtacaca caatgcgtat agatacattg atggagaatt atggatttat tcagctgtat tggacagtaa
32691  caaaaacaac aagtttgtac gttttccaata tagaactgga gaataactt atggtaatga aatgcaagat
32761  gtcatgccga atatatttaa cgacagatat acgtcagcga tttataatcc tatagaaaat ttaatgattt
32831  tcagacgtga atataaagct tctgaaagac aagctaagaa ttcattgaat ttcattgaag taagaagtgc
32901  tgacgatatt gataaagta tagacaaagt attgtatcaa atggatatac ctatggaata cacttcgatt
32971  acacaaccta tgcaaggtat cacttatgat gcaggtatct tatattggta tacaggtgat tcgaatacag
33041  ccaaccctaa ctacttacaa ggtttcgata taaaaacaaa agaattgtta tttaaacgac gtatcgtatat
33111  tggcggtgtg aataataact ttaaaggaga cttccaagaa gctgagggtc tagatatgtattacgatcta
33181  gaaacaggac gtaaagcact tttaataggg gtaactattg gacctggtaa taacagacat cactcaattt
33251  attctatcgg ccaaagaggt gttaaccaat tcttaaaaaa cattgcacct caagtatcga tgactgattc
33321  aggtggacgt gttaaaccgt taccaataca gaacccagca tatctaagtg atattacgga agttggtcat
33391  tactatatct atacgcaaga cacacaaaat gcattagatt tcccgttacc gaaagcgttt agagatgcag
33461  ggtggttctt ggatgtactg cctggacact ataatggtgc tctaagacaa gtacttacca gaaacagcac
33531  aggtagaaat atgcttaaat tcgaacgtgt cattgacatt ttcaataaga aaaacaacgg agcatggaat
33601  ttctgtccgc aaaacgccgg ttattgggaa catatcccta agagtattac aaaattatca gatttaaaaa
33671  tcgttggttt agatttctat atcactactg aagaatcaaa acgatttact gattttccta aagacttttaa
33741  aggtattgca ggttggatat tagaagtaaa atcgaataca ccaggtaaca caacacaagt attaagacgt
33811  aataacttcc cgtctgcaca tcaattttta gttagaaact ttggtactgg tggcgttggt aaatggagtt
33881  tattcgaagg aaaggtggtt gaataatgat agtagataat tttcgaaag acgataactt aatcgagtta
33951  caaacaacat cacaatataa tccaattatt gacacaaaca tcagttttcta tgaatcagat agaggaactg
34021  gtgttttaaa ttttgcagta actaagaata acagaccgtt atctataagt tctgaacatg ttaaaacatc
34091  tatcgtgtta aaaaccgatg attataacgt agatagaggc gcttatattt cagacgaatt aacgatagta
34361  gacgcaatta atgggcgttt gcagtatgtg ataccgaatg aattttttaaa acattcaggc aaggtgcatg
34231  ctcaggcatt cttacacaa aacgggagta ataatgttgt tgttgaacgt caatttagct tcaatattga
34301  aaatgattta gttagtgggt ttgatggtat aacaaagctt gttttatatca aatctattca agatactatc
34371  gaagcagtcg gtaaagactt taaccaatta aagcaagata tggatgatac aaaacgtta atagcaaaag
34441  tgaatgatag tgcgacaaaa ggcattcaac aaatcgaaat caagcaaaac gaagctatac aagctattac
34511  tgcgacgcaa actagtgcaa cacaagctgt tacagctgaa gtcgataaaa tagttgaaaa aggacaagcg
34581  attttttgaac gtgttaacga agttgaacaa caaatcaatg gcgctgacct tgttaaaggt aattcaacaa
34651  caaattggca aaagtctaaa cttacagatg attacggtaa agcaattgaa tcgtatgagc agtccataga
34721  tagcgtttta agcgcagtta acacatctag gattattcat attactaatg caacagatgc gccagaaaag
34791  acggatatag gcacgttaga gaagcctgga caagatggtg ttgatgacgg ttcttcgttc gatgaatcaa
```

TABLE 9-continued

Bacteriophage 96, complete genome sequence

```
34861  cttatacatc aagcaaatct ggtgtgttag ttgtttatgt tgttgataat aatactgctc gtgcaacatg
34931  gtacccagac gattcaaacg atgagtacac aaaatacaaa atctacggca catggtaccc gttttataaa
35001  aagaatgatg gaaacttaac taagcaatttt gttgaagaaa cgtctaacaa cgctttaaat caagctaagc
35071  agtatgtaga tgataaattc ggaacaacga gctggcaaca acataagatg acagaggcga atggtcaatc
35141  aattcaagtt aacttaaata atgcgcaagg cgatttggga tatttaactg ctggtaatta ctatgcaaca
35211  agagtgccgg atttaccagg tagtgttgaa agttatgagg gttatttatc ggtattcgtt aaagacgata
35281  caaacaagct atttaacttc acgccttata actctaaaaa gatttacaca cgatcaatca caaacgcag
35351  acttgagcaa cagtggacag ttcctaatga acataagtca acggtattgt tcgacggtgg agcaaatggt
35421  gtaggtacaa caatcaatct aaccgaacca tacacaaact attctatttt attagtaagt ggaacttatc
35491  caggtggcgt tattgaggga ttcggactaa ccacattacc taatgcaatt caattaagta aagcgaatgt
35561  agttgactca gacggtaacg gtggcggtat ttatgagtgt ttactatcca aaacaagtag cactactta
35631  agaatcgata acgatgtgta ctttgattta ggtaaaacat caggttctgg agcgaatgcc aacaaagtta
35701  ctataactaa aattatgggg tggaaataat gaaatcaca gtaaatgata aaaatgaagt tatcggatac
35771  gttaatactg gcggtttacg caatagttta gatgtagacg ataacaatgt gtctatcaaa ttcaaagaag
35841  agttcgaacc tagaaagttc gtttttcacta acggcgaaat taaatacaat agcaatttcg aaaaagaaga
35911  cgtaccgaat gcatcaaacc aacaaagtgc gtcagattta agtgatgagg aacttcgcgg aatggttgca
35981  agtatgcaaa tgcagatgac gcaagtgaac atgttgacaa tgcaattgac gcaacaaaac gctatgttaa
36051  cacaacagtt gaccgaactg aaaactaaca aacaaatacc tgaggggac gtttaaatga tgaagatgat
36121  ttatccaact tttaaagaca ttaaaacttt ttatgtgtgg ggttgctata aaaatgagca aattaagtgg
36191  tacgtagaca tgggtgtaat cgacaaagaa gaatatgcat tgatcactgg tgaaaaatat ccagaggcaa
36261  aagatgaaaa gtcacaggtg taatg;ttga ggctttttaa tttaacacaa gtaggtggc gtaatgtttg
36331  gatttaccaa acggcacgaa catgaatggc gaattagaag attagaagag aatgataaaa caatgcttag
36401  cactctcaat gagattaaat taggtcaaaa aactcaagag caagttaaca ttaaattaga taaaacttta
36471  gatgctatcc agagggaaag acagatagac gaaaaaaata agaaagaaaa cgacaaaaat atacgcgata
36541  tgaaaatgtg gattctcggt ttgataggga ctatcttcag tacgattgtc atagctttac taagaactat
36611  ttttggtatt taaaggaggt gattaccatg cttaaaggga ttttaggata tagcttctgg gcgtgcttct
36681  ggttttggtaa atgtaaataa cagttaagag tcagtgcttc ggcactggct tttatttg attgaaatga
36751  ggtgcataca tgggattacc taacccaaag actagaaagc ctacagctag tgaagtggtg gagtgggcaa
36921  agtcgaatat tggtaagagg attaatatag Btaattatcg gggcagtcaa tgttgggata cacctaactt
36891  tatttttaaa agatattggg gttttgtaac atgggcaat gctaaggata tggctaatta cagatatcct
36961  aagggttttcc gattctatcg ttattcatct ggatttgtac cggaacctgg agacatcgca gtttggcacc
37031  ctggcaacgg aataggttcg gacggacaca ccgcaatagt agtaggacca tctaataaaa gttattttta
37101  tagcgttgac caaaactggg ttaattctaa tagttggaca ggttctccag gaagattagt aagacaccct
37171  tatgtaagtg ttacaggctt tgttaggcct ccatactcaa aagatactag caaacctagt agtactgata
37241  caagttcagc atcaaaagcc aatgactcaa caattactgg cgaacgcaag aaaccgcaat ttaaagaagt
37311  taaaacagta aaatacactg cttacagcaa tgttttagat aagaagagc acttcattga tcatatagtt
37381  gtaatgggtg atgaacgctc agacattcaa ggattatata taaagaatc aatgcatatg cgttctgtag
37451  acgaactgta tacgcaaaga aataagttta taagcgatta tgaaataccg catttatatg tcgatagaga
37521  ggctacatgg cttgctagac caaccaattt tgatgaccg cgtcagtcca attggctagt tattgaagta
37591  tgtggtggtc aaacagatag caaacgacaa ttcttattga atcaaatacca agcgttaata cgtggtgttt
37661  ggttattgtc agggattgat aaaaacttat ctgaaacgac gttaaaagta gaccctaata tttggcgtag
37731  tatgaaagat ttaattaatt acgacttgat taagcaaggt ataccggata acgcaaagta tgagcaagtt
37801  aaaaagaaaa tgcttgagac atacattaaa cgagatatat tgacacgaga aaatataaaa gaagtaacga
37871  caaaaacaac aataagaatt agtgataaaa catcagttga cagtgcgtcc acacgaggcc ctactccatc
37941  agacgaaaaa ccaagcatcg ttactgaaac aagtccattc acattccagc aagcactgga tagacaaatg
38011  tctagggta acccgaaaaa atctcataca tggggctggg ctaatgcaac acgagcacaa acgagctcgg
38081  caatgaatgt taagcgaata tgggaaagta acacgcaatg ctatcaaatg cttaattttag gcaagtatca
38151  aggcatttca gttagtgcgc ttaacaaaat acttaaggca aaggaaacgc tcgacggaca aggcaaagca
38221  ttcgcggaag cttgtaagaa aaacaacatt aacgaaattt atttgatcgc gcacgctttc ttagaaaagtg
38291  gatacggaac aagtaacttc gctagtggta gatacggtgc atataattac ttcggtattg gtgcattcga
38361  caacgaccct gattatgcaa tgacgttttgc taaaaataaa ggttggacat ctccagcaaa agcaatcatg
38431  ggcggtgcta gcttcgtaag aaaggattac atcaataaag gtcaaaacac attgtaccga attagatgga
38501  atcctaagaa tccagctacc caccaatacg ctactgctat agagtggtgc caacatcaag caagtacaat
38571  cgctaagtta tataaacaaa tcggcttaaa aggtatctac ttcacaaggg ataaatataa ataaagaggt
38641  gtgtaaatgt acaaaataaa agatgttgaa acgagaataa aaaatgatgg tgttgactta ggtgacattg
38711  gctgtcgatt ttacactgaa gatgaaaata caagagtagt atcaatgaca aacaaggtcg
38781  tatcgatcta aaagcacatg gcttaacacc tagattacat ttgtttatgt aagatggctc tatattcaaa
38851  aatgagcccc ttattatcga cgatgttgta aaagggttcc ttacctacaa aatacctaaa aaggttatca
38921  aacacgctgg ttatgttcgc tgtaagctgt ttttagagaa agaagaagaa aaaatacatg tcgcaaactt
38991  ttcttttcaat atcgttgata gtggtattga atctgctgta gcaaaagaaa tcgatgttaa attggtagat
39061  gatgctatta cgagaatttt aaaagataac gcgacagatt tattgagcaa agactttaaa gagaaaatag
39131  ataaagatgt catttcttac atcgaaaaga atgaaagtag atttaaaggt gcgaaaggtg ataaaggcga
39201  accgggacaa cctggtgcga aaggtgatac aggtaaaaa ggagaacaag gcgcacccgg taaaacggt
39271  actgtagtat caatcaaatcc tgacactaaa gatgtggcaaa ttgatggtaa agatacagat atcaaagcag
39341  aaacctgagtt attggacaaa atcaatatcg caaatgttga agggttagaa gataaattgc aagaagttaa
39411  aaaaatcaaa gatacaactc tcaacgactc taaaacgtat acggattcaa aaattgctga actagttgat
39481  agcgcgcctg aatctatgaa tacattaaga gaattagcag aagcaataca aacaactct atttcagaaa
39551  gtgtattgca acagattggc tcaaagttta gtacagaaga tttgaggaa ttcaaacaaa cactaaacga
39621  tttatatgct ccaaaaaatc ataatcatga tgagcgtgat gtttttgtcat ctcaagcttt tactaaacaa
39691  caagcggata atttatatca actaaaaagc gcatctcaac cgacggttaa aatttggaca ggaacagaaa
39761  atgaatataa ctatatatat caaaaagacc ctaatacact ttacttaatt aaggggtgat ttttatgaa
39831  ggtaatttta aaatgtaaa gaagtttatt tacgaaggtg aagaatatac aaaagtatat gctggaaata
39901  tccaagtatg gaaaaagcct tcatctttg taataaaacc cttacctaaa aataaatatc cggatagcat
39971  agaagaatca acagcaaaat ggacaataaa tggagttgaa cctaataaaa gttatcaggt gacaatagaa
40041  aatgtacgta gcggtataat gagggggtttcg caaactaatt taggttcaag tgatttagga atatcaggag
40111  tcaatagcgg agttgcaagt aaaaatatca actttagtaa tccttcaggg atgttgtatg tcactataag
40181  tgatgtttat tcaggatctc caacattgac cattgaataa ttttaaacga ctaattttt agtcgttttt
```

TABLE 9-continued

Bacteriophage 96, complete genome sequence

```
40251  tattttggat aaaaggagca acaaatgga tgcaaaagta ataacaagat acatcgtatt gatcttagca
40321  ttagtaaatc aattcttagc gaacaaaggt attagcccga ttccagtaga cgatgagact atatcatcaa
40391  taatacttac tgttgttgct ttatatacta cgtataaaga caatccaaca tctcaagaag gtaaatgggc
40461  aaatcaaaag ctaaagaaat ataaagctga aaacaagtat agaaaagcaa cagggcaagc gccaattaaa
40531  gaagtaatga cacctacgaa tatgaacgac acaaatgatt tagggtaggt gttgaccaat gttgataaca
40601  aaaaaccaag cagaaaaatg gtttgataat tcattaggga agcagttcaa tcctgatttg ttttatggat
40671  ttcagtgtta cgattacgca aatatgtttt ttatgatagc aacaggcgaa aggttacaag gtttatacgc
40741  ttataatatt ccatttgata ataaagcaag gattgaaaaa tacgggcaaa taattaaaaa ctatgatagc
40811  tttttaccgc aaaagttgga tattgtcgtt ttcccgtcaa agtatggtgg cggagctgga catgttgaaa
40881  ttgttgagag cgcaaattta aacactttca catcatatgg gcaaaattgg aatggtaaag gttggacaaa
40951  tggcgttgcg caacctggtt ggggtcctga aactgttaca agacatgttc attattacga tgacccaatg
41021  tattttatta gattaaattt cccagataaa gtaagtgttg gagataaagc taaaagcgtt attaagcaag
41091  caactgccaa aaagcaagca gtaattaaac ctaaaaaaat tatgcttgta gccggtcatg gttataacga
41161  tcctggagca gtaggaaacg gaacaaacga acgcgatttt atccgtaaat atataacgcc aaatatcgct
41231  aagtatttaa gacatgcagg tcatgaagtt gcattatatg gtggctcaag tcaatcacaa gacatgtatc
41301  aagatactgc atacggtgtt aatgtaggaa.ataataaga ttatggatta tattgggtta aatcacaggg
41371  gtatgacatt gttctagaga ttcatttaga cgcagcagga gaaaatgcaa gtggtgggca tgttattatc
41441  tcaagtcaat tcaatgcgga tactattgat aaaagtatac aagtatgttat taaaaataac ttaggacaaa
41511  taagaggtgt aacacctcgt aatgatttac tgaacgttaa tgtatcagca gaaataaata tcaattatcg
41581  tttatctgaa ttaggtttta ttactaataa aaaagatatg gattggatta agaagaatta tgacttgtat
41651  tctaaattaa tagctggtgc gattcatggt aagcctatag gtggtttggt agctggtaat gttaaaacat
41721  cagctaaaaa ccaaaaaaat ccaccagtgc cagcaggtta tacacttgat aagaataatg tgcctataaa
41791  aaaagagact ggtaattaca cagttgccaa tgttaaaggt aataacgtaa gggacggcta ttcaactaat
41861  tcaagaatta caggtgtatt acctaataac gcaacaatca aatatgacgg cgcatattgc atcaatgggt
41931  atagatggat tacttatatt gctaatagtg gacaacgtcg ctatattgcg acaggagagg tagataaagc
42001  aggtaatagg ataagtagtt ttggtaagtt tagcacgatt tagtatttac ttagaataaa aattttgcta
42071  cattaattat agggaatctt acagttatta aataacttatt tggatggatg ttaatattcc tatacacttt
42141  ttaacattac tctcaagatt taaatgtaga taacaggcag gtactacggt acttgcctat ttttttgtta
42211  taatgtaatt acattaccag taaccaatct ggcttaaaac cacatttccg gtagccaatc cggctatgca
42281  gaggacttac ttgcgtaaag tagtaagaag ctgactgcat atttaaacca cccatactag ttgctgggtg
42351  gttgttttt atgttatatt ataaatgatc aaaccacacc acctaatttt ttaggagtgt ggttattttt
42421  tatgcaaaaa aaacgaaaaa aagttcataa aaagtattgc atatcacgtt taaccgtgtt ataataaggt
42491  ataccagttg agaggaggat aaaagtgtt agaaattttt aaactatag cagaaatcgc cttttataca
42561  atgtcagcaa ttgccatagc gaaaacattg aaaaaagacg ataagtaagt agacaagccc gaaagggctg
42631  tctatatata aattctaaca ctaaaatact atgaaaacaa tttacattat tttaatcatt cttatttgga
42701  taaacgtgtt tttaggcaac gatataagta aaagtgttgt tgcactgctt actactttac tgcttatcaa
42771  tttatggaag agggataaaa atgacagcaa taaaagaaat aattgaatca atagaaaagt tattcgaaaa
42841  agaaacggga tataaaattg ctaaaaattc cggattacca tatcaaactg tgcaagattt aagaaatgga
42911  aaaacatctt tatcagatgc cagatttaga acgataataa agttatacga gtatcaaaga tcgcttgaaa
42981  acgaagaaga taaataaaag gagccaaaaa tatgttttgtt acaaaagaag aatttaaaac tttgaatgta
43051  aaagaagtat ttgaatcagg taaaaacttt ataaaaatta cagatgcaag acatgcaata tattgggtaa
43121  atgatagata cgtagtactt gaccataaaa aaggcgattt gtacccgcaa aaagcatacc caaatatat
43191  caaaagaaaa ttagtaagtt aaataattag aaaaccacgt cttaattgac gtggttattt tttaggtttg
43261  cgcgtgtcaa atacgtgtca atttagttct atttctttag ttttcttttct aaacttaatt gcttgtaaac
43331  cgcatagtta taggcttttc agctatatac caagataaga tttatcccgc cgtctccata aaaatatgct
43401  tggaaacctt gatttaatgg ggttttaatc tagcaagtgt caaatatgtg tcaagaaaat aattttctga
43471  cacgttgacc ttgctctttt ttatgttcat caagtaagtg agagtaggtg tctaaagtta tagatatatt
43541  ataatggcct aatcttttgc taatatattc aatagg
```

TABLE 10

Bacteriophage 96 ORFs list

| SID | LAN | FRA | POS | a.a. | RBS sequence | STA | STO |
|---|---|---|---|---|---|---|---|
| 100733 | 96ORF001 | 1 | 25999 ... 29142 | 1047 | ccttgaatcgaaaggaggttagcct | ttg | taa |
| 100734 | 96ORF002 | 1 | 32008 ... 33906 | 632 | tttttacgactaaaggaggcaacca | atg | taa |
| 100735 | 96ORF003 | 1 | 30109 ... 31995 | 628 | ttatattttagataaggagtagcct | atg | taa |
| 100736 | 96ORF004 | 1 | 36760 ... 38634 | 624 | attttgattgaaatgaggtgcatac | atg | taa |
| 100737 | 96ORF005 | 3 | 33903 ... 35729 | 608 | gtttattcgaaggaaaggtggttga | ata | taa |
| 100738 | 96ORF006 | 2 | 40589 ... 42043 | 484 | aatgatttagggtaggtgttgacca | atg | tag |
| 100739 | 96ORF007 | 1 | 18652 ... 20091 | 479 | tatacacactactaaacctgaacg | att | tga |
| 100740 | 96ORF008 | 2 | 8960 ... 10201 | 413 | tggcagaatttgggggcgataacga | atg | tga |
| 100741 | 96ORF009 | 2 | 17447 ... 18670 | 407 | gacgcaataacggaagtgatcgtca | atg | tga |
| 100742 | 96ORF010 | 1 | 38647 ... 39819 | 390 | taaatataaataaagaggtgtgata | atg | tga |
| 100743 | 96ORF011 | -1 | 119 ... 1195 | 358 | gtagctcgcctacccttattatttt | ttg | tga |
| 100744 | 96ORF012 | 2 | 20045 ... 21013 | 322 | tttaatgacaaattacctgacatag | atg | tga |
| 100745 | 96ORF013 | 3 | 29157 ... 30098 | 313 | acttattataagggaggtttgttag | ttg | taa |
| 100746 | 96ORF014 | 1 | 21925 ... 22839 | 304 | agaaaataaagttaggtaataaaat | atg | tag |
| 100747 | 96ORF015 | 1 | 5812 ... 6591 | 259 | atacacggtaaaggtgggagaataa | atg | taa |
| 100748 | 96ORF016 | 1 | 7852 ... 8607 | 251 | aataaaatgttgaaaggagagaaaa | atg | taa |
| 100749 | 96ORF017 | 3 | 3444 ... 4190 | 248 | aaatttaacattaatatcactttaa | gtg | taa |
| 100750 | 96ORF018 | -3 | 28281 ... 29000 | 239 | taagctatgttgaacatcgctagtc | atg | tga |
| 100751 | 96ORF019 | 3 | 7188 ... 7859 | 223 | tttaccgttctaggacgtggtttaa | atg | taa |

TABLE 10-continued

Bacteriophage 96 ORFs list

| SID | LAN | FRA | POS | a.a. | RBS sequence | STA | STO |
|---|---|---|---|---|---|---|---|
| 100752 | 96ORF020 | 3 | 21324 ... 21908 | 194 | gaagggcaaaaaggagttttgatat | atg | taa |
| 100753 | 96ORF021 | 3 | 6612 ... 7175 | 187 | attaaaaattaattaaaaggacggt | ata | tag |
| 100754 | 96ORF022 | 2 | 24536 ... 25093 | 185 | aaagaaaaacgaaggagtgtattaa | atg | taa |
| 100755 | 96ORF023 | 1 | 5275 ... 5511 | 178 | catgaaatggtaggaggtatgaaaa | gtg | taa |
| 100756 | 96ORF024 | 3 | 14481 ... 15014 | 177 | taaaacgataggagataacgaataa | atg | taa |
| 100757 | 96ORF025 | 2 | 25157 ... 25666 | 169 | ataaaaaaattgaaaagaggtatat | att | taa |
| 100758 | 96ORF026 | -3 | 15084 ... 15590 | 168 | tcattcttaacatagcccttaattc | atg | tga |
| 100759 | 96ORF027 | -1 | 1229 ... 1732 | 167 | aatagcaaataaaggagtgtaaaac | atg | taa |
| 100760 | 96ORF028 | 1 | 16960 ... 17454 | 164 | aaggcgtgtgatacagtgaaaacaa | ttg | taa |
| 100761 | 96ORF029 | -1 | 1736 ... 2227 | 163 | tatgagaaaaggagtcatataaaag | atg | taa |
| 100762 | 96ORF030 | 1 | 25531 ... 25995 | 154 | ttttcaagagggagagtcgctcgta | ctg | tag |
| 100763 | 96ORF031 | 2 | 23633 ... 24097 | 154 | tttagtattgaaggtgattctgtag | atc | taa |
| 100764 | 96ORF032 | -2 | 2248 ... 2706 | 152 | ataagacaccaaaggggtttggcgc | atg | tga |
| 100765 | 96ORF033 | -3 | 39147 ... 39605 | 152 | agcatataaatcgtttagtgtttgt | ttg | taa |
| 100766 | 96ORF034 | 2 | 13181 ... 13615 | 144 | tagaagtcgaaaaagtggaggcaat | ata | taa |
| 100767 | 96ORF035 | 2 | 10628 ... 11053 | 141 | gagctaggattgcaagcaacgatat | ttg | tga |
| 100768 | 96ORF036 | 2 | 24110 ... 24535 | 141 | gtattttcatagaggtggttaaat | atg | taa |
| 100769 | 96ORF037 | 1 | 12583 ... 12996 | 137 | atgaggaacagaagcaaccaacttt | att | tga |
| 100770 | 96ORF038 | 1 | 15628 ... 16032 | 134 | atgttaagaatgatgcctagtttaa | ttg | taa |
| 100771 | 96ORF039 | 3 | 39816 ... 40220 | 134 | ctaatacactttacttaattaaggg | gtg | taa |
| 100772 | 96ORF040 | -3 | 27528 ... 27932 | 134 | ttttccataaataaacgaggacacca | atg | tga |
| 100773 | 96ORF041 | 3 | 16206 ... 16607 | 133 | gatgagggcggaggtgtcagagtag | atg | tga |
| 100774 | 96ORF042 | 2 | 35720 ... 36106 | 128 | aagttactataactaaaattatggg | gtg | taa |
| 100775 | 96ORF043 | -2 | 35713 ... 36081 | 122 | ttaaacgtccccctcagtatttgtt | ttg | taa |
| 100776 | 96ORF044 | -2 | 9460 ... 9828 | 122 | agtatccatcagttgaagataatct | ata | taa |
| 100777 | 96ORF045 | -3 | 5139 ... 5504 | 121 | ttcttttgtattctgtaatattca | att | tga |
| 100778 | 96ORF046 | 2 | 11513 ... 11872 | 119 | aagtaaatgtatagaggtggaataa | atg | taa |
| 100779 | 96ORF047 | 2 | 22991 ... 23350 | 119 | gtcgtactacgtctgataagagcga | gtg | tag |
| 100780 | 96ORF048 | 3 | 8607 ... 8963 | 118 | tggaaaaagaattgagtgatgacta | atg | taa |
| 100781 | 96ORF049 | 1 | 23353 ... 23697 | 114 | atccgtttaaaccaataaggtagag | gtg | taa |
| 100782 | 96ORF050 | -2 | 2728 ... 3072 | 114 | tggtaaattagtattacattaagta | ata | taa |
| 100783 | 96ORF051 | 3 | 4692 ... 5021 | 109 | tcaaaatatacggaggtagtcaact | atg | tga |
| 100784 | 96ORF052 | -1 | 20882 ... 21211 | 109 | gtagcaaagagacaactaaaaaagt | gtg | taa |
| 100785 | 96ORF053 | 1 | 40252 ... 40578 | 108 | acgactaattttttagtcgttttt | att | tag |
| 100786 | 96ORF054 | 1 | 4942 ... 5262 | 106 | aatataaaactaaaaaacaaaattt | atg | tag |
| 100787 | 96ORF055 | -2 | 4840 ... 5151 | 103 | ccgtcgcaatatatagttcgcttaa | atc | taa |
| 100788 | 96ORF056 | 3 | 36324 ... 36623 | 99 | aatttaacacaaagtaggtggcgta | atg | taa |
| 100789 | 96ORF057 | 2 | 1394 ... 1590 | 98 | cttcagtggctctttagcatttaa | ata | taa |
| 100790 | 96ORF058 | -3 | 26247 ... 26537 | 96 | tacttcttttctcataatctgacca | att | tga |
| 100791 | 96ORF059 | -1 | 21485 ... 21772 | 95 | agactcaacgccttttgaacatac | ttg | tga |
| 100792 | 96ORF060 | -3 | 22647 ... 22931 | 94 | cctctttgtaaccgacaagactgta | atg | taa |
| 100793 | 96ORF061 | 1 | 14023 ... 14304 | 93 | ttatctaattaagggggacgagtga | gtg | taa |
| 100794 | 96ORF062 | -2 | 38281 ... 38559 | 92 | tatataactagcgattgtacttgc | ttg | taa |
| 100795 | 96ORF063 | -3 | 30786 ... 31064 | 92 | gtctcctaatactacatcttgctta | gtg | tga |
| 100796 | 96ORF064 | -2 | 30205 ... 30480 | 91 | atgcatctacttttggatgtaatac | ata | tag |
| 110797 | 9EORF065 | 1 | 2617 ... 2886 | 89 | aaggtctaataaaaatttctcctte | ttg | taa |
| 100798 | 96ORF066 | 3 | 28056 ... 28325 | 89 | aaggtgtagtcggctggttaactga | att | taa |
| 100799 | 96ORF067 | -3 | 17142 ... 17411 | 89 | ttccgttattgcgtcgtgaagttgt | ttg | tga |
| 100800 | 96ORF068 | 2 | 12326 ... 12589 | 87 | aatgcatgtcgtttggtctgcctaa | ttg | tag |
| 100801 | 96ORF069 | 2 | 42734 ... 42997 | 87 | ttttaggcaacgatataagtaaaa | gtg | taa |
| 100802 | 96ORF070 | 1 | 11869 ... 12129 | 86 | aaatgttcaagaaatggagtgaagc | ata | taa |
| 100803 | 96ORF071 | 3 | 15396 ... 15656 | 86 | aacaagctatacaaattatcgataa | att | taa |
| 100804 | 96ORF072 | -3 | 37749 ... 38009 | 86 | agattttttcgggttacccctagac | att | taa |
| 100805 | 96ORF073 | 3 | 11244 ... 11501 | 85 | acatgcatatatagaggtggaataa | atg | tag |
| 100806 | 96ORF074 | -3 | 42936 ... 43193 | 85 | aattatttaacttactaattttctt | ttg | taa |
| 100807 | 96ORF075 | -3 | 26610 ... 26867 | 85 | tactgccaatgttccatcttcaacc | att | taa |
| 100808 | 96ORF076 | -1 | 11126 ... 11380 | 84 | tttatctaatacatttaagttaacc | atc | taa |
| 100809 | 96ORF077 | -2 | 16537 ... 16791 | 84 | tacccaccatataggcaggtagtag | gtg | tag |
| 100810 | 96ORF078 | -3 | 19521 ... 19775 | 84 | aataactttgaattgatacctcaac | ata | tga |
| 100811 | 96ORF079 | 3 | 13608 ... 13859 | 83 | ttagggcaaatggaggcagacacaa | atg | tag |
| 100812 | 96ORF080 | -3 | 28029 ... 28280 | 83 | tgagaagtcgccagtaagcaactga | att | tga |
| 100813 | 96ORF081 | 3 | 20973 ... 21221 | 82 | aatgaagttatcccattcatgactt | atc | tag |
| 100814 | 96ORF082 | -1 | 8729 ... 8974 | 81 | cgattattgtgctttcaatttcaaa | ttg | taa |
| 100815 | 96ORF083 | -3 | 3147 ... 3392 | 81 | tttagcctttatataatcaacttct | gtg | tga |
| 100816 | 96ORF084 | 3 | 1611 ... 1853 | 80 | tgctttatctttagtttctttcttt | ttg | tga |
| 100817 | 96ORF085 | -2 | 29470 ... 29709 | 79 | ctcttatcaccttcgttttgtaggca | atc | taa |
| 100818 | 96ORF086 | 1 | 35188 ... 35424 | 78 | gcgcaaggcgatttgggatatttaa | ctg | tga |
| 100819 | 96ORF087 | -2 | 13039 ... 13275 | 78 | ttttgattgagctctaaagtgtctt | att | tag |
| 100820 | 96ORF088 | 3 | 24930 ... 25163 | 77 | gaactatcattaaaagttaaatgga | ata | tga |
| 100821 | 96ORF089 | -3 | 22329 ... 22562 | 77 | tccagtataagatagtggtaatccc | ata | taa |
| 100822 | 96ORF090 | -3 | 16803 ... 17036 | 77 | acctttagtcgaataccctgcgtca | ata | taa |
| 100823 | 96ORF091 | -1 | 22559 ... 22789 | 76 | aacgcttctggtttaacgttcatgt | atg | taa |
| 100824 | 96ORF092 | 3 | 18360 ... 18587 | 75 | attgcaaaagatattgtaagtagat | atg | taa |
| 100825 | 96ORF093 | -2 | 25384 ... 25608 | 74 | catgatttccttgtaattctcttc | atc | taa |
| 100826 | 96ORF094 | 1 | 10417 ... 10638 | 73 | aacacacattaaggagtgttaaaaa | atg | tag |

TABLE 10-continued

Bacteriophage 96 ORFs list

| SID | LAN | FRA | POS | a.a. | RBS sequence | STA | STO |
|---|---|---|---|---|---|---|---|
| 100827 | 96ORF095 | 3 | 12963 ... 13184 | 73 | tactaaacgaagataaaactatgac | att | taa |
| 100828 | 96ORF096 | 1 | 42994 ... 43212 | 72 | gatcgcttgaaaacgaagaagataa | ata | taa |
| 100829 | 96ORF097 | -1 | 36047 ... 36265 | 72 | tcaagcattacacctgtgactttc | atc | taa |
| 100830 | 96ORF098 | -2 | 36766 ... 36984 | 72 | caggttccggtacaaatccagatga | ata | taa |
| 100831 | 96ORF099 | -2 | 34765 ... 34983 | 72 | tcattcttttataaaacgggtacc | atg | tag |
| 100832 | 96ORF100 | 1 | 10198 ... 10413 | 71 | acaagaagactcagaggttttcac | atg | taa |
| 100833 | 96ORF101 | 1 | 15208 ... 15423 | 71 | gagaaacaagttaagataaggagag | atg | tga |
| 100834 | 96ORF102 | 3 | 4209 ... 4424 | 71 | attttaaaacgaaatataggagagg | ctg | tag |
| 100835 | 96ORF103 | 3 | 11673 ... 11888 | 71 | catgcaccttatggtatgcgcttag | ctg | taa |
| 100836 | 96ORF104 | 3 | 12117 ... 12332 | 71 | tttacgtccaaagagcttttgactt | gtg | taa |
| 100837 | 96ORF105 | 3 | 23892 ... 24107 | 71 | gatggtgggttatccagtgttataa | gtg | taa |
| 100838 | 96ORF106 | -3 | 34428 ... 34643 | 71 | tagacttttgccaatttgttgttga | att | taa |
| 100839 | 96ORF107 | -3 | 24495 ... 24710 | 71 | ggcacattaccaattgttaatttaa | atg | taa |
| 100840 | 96ORF108 | -1 | 23876 ... 24088 | 70 | acatatttaaccacctctatgaaaa | ata | taa |
| 100841 | 96ORF109 | -2 | 17317 ... 17529 | 70 | acctgtacgctttgctccgtgatta | att | taa |
| 100842 | 96ORF110 | -3 | 38931 ... 39143 | 70 | actttcattcttttcgatgtaagaa | atg | taa |
| 100843 | 96ORF111 | -3 | 21855 ... 22067 | 70 | agtaaatttttcttttgtgctgtc | att | tga |
| 100844 | 96ORF112 | 1 | 3217 ... 3426 | 69 | aaatgtcaacgggaggtgatacgaa | atg | taa |
| 100845 | 96ORF113 | -1 | 25469 ... 25678 | 69 | tcagggatatatcctaaatatctag | ctg | taa |
| 100846 | 96ORF114 | -2 | 9838 ... 10047 | 69 | ataataatcatcacggtaaagtagc | atc | tga |
| 100847 | 96ORF115 | 1 | 13819 ... 14022 | 67 | gcagtaggggttatggcaggtcaag | ttg | tga |
| 100848 | 96ORF116 | -1 | 41033 ... 41236 | 67 | caacttcatgacctgcatgtcttaa | ata | taa |
| 100849 | 96ORF117 | -3 | 24711 ... 24914 | 67 | tctgctgtattccatttaactttta | atg | taa |
| 100850 | 96ORF118 | -1 | 12374 ... 12574 | 66 | tccatctcctctaaaataaagttgg | ttg | taa |
| 100851 | 96ORF119 | -1 | 3980 ... 4180 | 66 | ctcctatatttcgttttaaaatttc | att | taa |
| 100852 | 96ORF120 | -3 | 6033 ... 6233 | 66 | ttgtaatttagaaatataacgataa | ata | taa |
| 100853 | 96ORF121 | -2 | 37939 ... 38136 | 65 | ctgaaatgccttgatacttgcctaa | att | tga |
| 100854 | 96ORF122 | 2 | 37892 ... 38086 | 64 | acgacaaaaacaacaataagaatta | gtg | tga |
| 100855 | 96ORF123 | -3 | 29193 ... 29387 | 64 | ggacgtctgactttaaatgtgaagc | ata | taa |
| 100856 | 96ORF124 | 1 | 4408 ... 4599 | 63 | ttttatcggtaccaatttaatgatta | atg | taa |
| 100857 | 96ORF125 | -1 | 7787 ... 7978 | 63 | ttaaaaatccaagttttgccatcgt | att | tga |
| 100858 | 96ORF126 | -3 | 27027 ... 27218 | 63 | aaatttgaacaacggcattaattga | gtg | tga |
| 100859 | 96ORF127 | 3 | 15051 ... 15239 | 62 | atcgagtcaaggaggttttggggaa | gtg | tga |
| 100860 | 96ORF128 | -1 | 6914 ... 7102 | 62 | agcgaatgggtttgattgttgactc | ata | tga |
| 100861 | 96ORF129 | -3 | 31332 ... 31520 | 62 | tcttatttgctctgcttgtctataa | atg | tga |
| 100862 | 96ORF130 | -3 | 30084 ... 30272 | 62 | gaaatcatcttcaccttcaacatga | gtg | taa |
| 100863 | 96ORF131 | 3 | 11058 ... 11243 | 61 | agaaaaagagaaatgaagtgatcta | atg | taa |
| 100864 | 96ORF132 | -1 | 36434 ... 36619 | 61 | taagcatggtaatcacctcctttaa | ata | tga |
| 100865 | 96ORF133 | -1 | 35591 ... 35776 | 61 | ctaaactattgcgtaaaccgccagt | att | taa |
| 100866 | 96ORF134 | -2 | 9250 ... 9435 | 61 | atccatgagcttataacccgtctta | att | tga |
| 100867 | 96ORF135 | 1 | 29563 ... 29745 | 60 | cgacaacttttgtaggactagtaa | gtg | tga |
| 100868 | 96ORF136 | -3 | 12486 ... 12668 | 60 | cactttacttcaacttgttcagga | ttg | taa |
| 100869 | 96ORF137 | -1 | 14501 ... 14680 | 59 | caaactgaaagctaagtaatcagca | atc | tga |
| 100870 | 96ORF138 | -2 | 23326 ... 23505 | 59 | cttgtgacatttgatgaaatttag | ttg | tga |
| 100871 | 96ORF139 | -3 | 42672 ... 42851 | 59 | aatccggaattttagcaattttat | atc | taa |
| 100872 | 96ORF140 | -3 | 31137 ... 31316 | 59 | acttgattgactagtaaagtcgtac | atg | taa |
| 100873 | 96ORF141 | -3 | 18969 ... 19148 | 59 | aacaaaataacattataggatct | ata | tga |
| 100874 | 96ORF142 | -3 | 4740 ... 4919 | 59 | cataaattttgttttttagtttat | att | tga |
| 100875 | 96ORF143 | 2 | 36107 ... 36283 | 58 | aacaaatactgagggggacgtttaa | atg | taa |
| 110876 | 96ORF144 | 3 | 16029 ... 16205 | 58 | tatacgaagtaaagaaggtagataa | ata | tag |
| 100877 | 96ORF145 | -3 | 29013 ... 29189 | 58 | tgtcactgacgcgatactgtgaacc | att | tga |
| 100878 | 96ORF146 | -3 | 14883 ... 15059 | 58 | aatctttgaatgttgtgactaagta | ttg | taa |
| 100879 | 96ORF147 | -1 | 18251 ... 18424 | 57 | tatcagcgttaattgcacgtaatct | atg | taa |
| 100880 | 96ORF148 | -1 | 13583 ... 13756 | 57 | aataccttctttaactgaatgttga | ata | taa |
| 100881 | 96ORF149 | -2 | 10756 ... 10929 | 57 | taaattcacatctctatactgatat | ctg | tag |
| 100882 | 96ORF150 | 2 | 14171 ... 14341 | 56 | attttaatgaagaagtgttattaa | ctg | tag |
| 100883 | 96ORF151 | 2 | 19217 ... 19387 | 56 | cctacatactcattgcgctactttt | atg | tga |
| 100884 | 96ORF152 | -1 | 12614 ... 12784 | 56 | atttctacagtaaaaatatctttat | ctg | taa |
| 100885 | 96ORF153 | -2 | 11836 ... 12006 | 56 | ttgcattaccctattgcgaatgctag | ttg | taa |
| 100886 | 96ORF154 | -2 | 4165 ... 4335 | 56 | atataacgcttttgtcctcgaccaa | atc | tga |
| 100887 | 96ORF155 | -3 | 40464 ... 40634 | 56 | aaatcaggattgaactgcttccta | atg | tga |
| 100888 | 96ORF156 | 3 | 423 ... 590 | 55 | tggtaattttgataatttagcttta | ata | taa |
| 100889 | 96ORF157 | -1 | 41879 ... 42046 | 55 | gtagcaaaattttattctaagtaa | ata | taa |
| 100890 | 96ORF158 | -2 | 36166 ... 36333 | 55 | cattcatgttcgtgccgtttggtaa | atc | tag |
| 100891 | 96ORF159 | -2 | 16228 ... 16395 | 55 | tttaacatctgagcataccttttat | ttg | taa |
| 100892 | 96ORF160 | 3 | 1038 ... 1202 | 54 | atctctaagcagttgttgagcagcg | ttg | taa |
| 100893 | 96ORF161 | -1 | 19193 ... 19357 | 54 | tctttgttgttaggtacaccaaaca | atg | tag |
| 100894 | 96ORF162 | -1 | 18074 ... 18238 | 54 | ctcgtcctattaacacaatagatcc | ata | taa |
| 100895 | 96ORF163 | -1 | 15386 ... 15550 | 54 | agccatcataggactgtaaaattca | ctg | taa |
| 100896 | 96ORF164 | -1 | 10049 ... 10213 | 54 | tacatcgatttcaataagcttttga | att | tag |
| 100897 | 96ORF165 | -2 | 18514 ... 18678 | 54 | gtgcttcaatatcatctattaactt | ata | taa |
| 100898 | 96ORF166 | -2 | 11104 ... 11268 | 54 | ctagccatgattacccttaaattag | ttg | tag |
| 100899 | 96ORF167 | -3 | 13764 ... 13928 | 54 | agacagtttataatgtgtatctcta | ata | tga |
| 100900 | 96ORF168 | 1 | 14305 ... 14466 | 53 | ttttgaattttggaggacgagtaa | atg | tag |
| 100901 | 96ORF169 | -1 | 17885 ... 18046 | 53 | gtgttgaagccttaatagactcttt | ata | tga |

TABLE 10-continued

Bacteriophage 96 ORFs list

| SID | LAN | FRA | POS | a.a. | RBS sequence | STA | STO |
|---|---|---|---|---|---|---|---|
| 100902 | 96ORF170 | −1 | 10790 . . . 10951 | 53 | taggcgctttacatatccacgttaa | att | taa |
| 100903 | 96ORF171 | −3 | 12765 . . . 12926 | 53 | atcttcgtttagtatataaaacgct | ctg | taa |
| 100904 | 96ORF172 | 3 | 23836 . . . 22994 | 52 | cgttcgcaacgcttaaaccaactga | ata | tga |
| 100905 | 96ORF173 | −1 | 15956 . . . 16114 | 52 | ctctacatcatcattagccgtcgtc | ata | taa |
| 100906 | 96ORF174 | −1 | 10571 . . . 10729 | 52 | tagtgccattcatattactttctaa | ata | taa |
| 100907 | 96ORF175 | −1 | 3440 . . . 3598 | 52 | cagcctatcttcactatcaacatga | ttg | taa |
| 100908 | 96ORF176 | −3 | 37170 . . . 37328 | 52 | tttatctaaaacattgctgtaagca | gtg | taa |
| 100909 | 96ORF177 | −3 | 6693 . . . 6851 | 52 | ttcctaatctactaagtaactcgat | ata | taa |
| 100910 | 96ORF178 | −3 | 5655 . . . 5813 | 52 | gacatcttgattagttttttcagtc | atc | tag |
| 100911 | 96ORF179 | 1 | 34564 . . . 34719 | 51 | gttacagctgaagtcgataaaatag | ttg | tag |
| 100912 | 96ORF180 | 1 | 42661 . . . 42816 | 51 | atataaattctaacactaaaatact | atg | tga |
| 100913 | 96ORF181 | −2 | 37741 . . . 37896 | 51 | tggacgcactgtcaactgatgtttt | atc | taa |
| 100914 | 96ORF182 | −2 | 25039 . . . 25194 | 51 | ttcgtaatcttttctccgtcatta | att | tga |
| 100915 | 96ORF183 | −2 | 4534 . . . 4689 | 51 | tcagttttaatattttcagccatag | ttg | tga |
| 100916 | 96ORF184 | 1 | 6721 . . . 6873 | 50 | ggagctggagaatttacagtaaaag | ttg | tag |
| 100917 | 96ORF185 | 2 | 36548 . . . 36700 | 50 | acaaaaatatacgcgatatgaaaat | gtg | taa |
| 100918 | 96ORF186 | −1 | 40025 . . . 40177 | 50 | tggagatcctgaataaacatcactt | ata | tga |
| 100919 | 96ORF187 | −1 | 34466 . . . 34618 | 50 | attacctttaacaaggtcagcgcca | ttg | tga |
| 100920 | 96ORF188 | −1 | 33842 . . . 33994 | 50 | agttcctctatctgattcatagaaa | ctg | taa |
| 100921 | 96ORF189 | −1 | 24914 . . . 25066 | 50 | acatagaatggtcttccgtgtgtga | atc | taa |
| 100922 | 96ORF190 | −2 | 20395 . . . 20547 | 50 | tatcttagagtaaccctctccactc | ata | tga |
| 100923 | 96ORF191 | 3 | 24768 . . . 24917 | 49 | aaaggaattgaagcagtgaaacacg | ctg | taa |
| 100924 | 96ORF192 | −1 | 16169 . . . 16318 | 49 | ttgtggtttcggcaacgttgcttgt | atg | tga |
| 100925 | 96ORF193 | −2 | 39100 . . . 39249 | 49 | cagtaccgttttaccgggtgcgcc | ttg | taa |
| 100926 | 96ORF194 | −2 | 25921 . . . 26070 | 49 | ttggtacagacgtctttgctaatcg | ttg | taa |
| 100927 | 96ORF195 | −2 | 17779 . . . 17928 | 49 | caaccaatgctcgggatggtcaggg | ttg | tga |
| 100928 | 96ORF196 | −2 | 14182 . . . 14331 | 49 | ttaaatactttcttctagcaatgc | atc | tga |
| 100929 | 96ORF197 | −2 | 7609 . . . 7758 | 49 | ttatcatcaaacgacttaacaccaa | ttg | tga |
| 100930 | 96ORF198 | −2 | 1537 . . . 1686 | 49 | ttattagctagtgcgttagtgttag | gtg | taa |
| 100931 | 96ORF199 | −3 | 7719 . . . 7868 | 49 | taatacttgtatcggatagtcatct | att | taa |
| 100932 | 96ORF200 | 2 | 22271 . . . 22417 | 48 | ttctttaatgaggttaaacctctaa | ttg | tag |
| 100933 | 96ORF201 | 2 | 30353 . . . 30499 | 48 | tctactattggcgaaaaaataaggc | ttg | tag |
| 100934 | 96ORF202 | 2 | 32591 . . . 32737 | 48 | agattgaagcccaacggacaattta | ttg | taa |
| 100935 | 96ORF203 | 2 | 39131 . . . 39277 | 48 | agcaaagactttaaagagaaaatag | ata | tag |
| 100936 | 96ORF204 | −2 | 36985 . . . 37131 | 48 | atcttcctggagaacctgtccaact | att | tga |
| 100937 | 96ORF205 | −3 | 38721 . . . 38867 | 48 | aaggaaccctttacaacatcgtcg | ata | taa |
| 100938 | 96ORF206 | −3 | 35880 . . . 36026 | 48 | gttaacatagcgttttgttgcgtca | att | taa |
| 100939 | 96ORF207 | −3 | 11550 . . . 11696 | 48 | ttgctctctcgctccatgattttgg | ata | taa |
| 100940 | 96ORW208 | 2 | 37178 . . . 37321 | 47 | agattagtaagacacccttatgtaa | gtg | taa |
| 100941 | 96ORW209 | 2 | 42341 . . . 42484 | 47 | tgcatatttaaaccaccccatactag | ttg | taa |
| 100942 | 96ORF210 | 3 | 41850 . . . 41993 | 47 | aaaggtaataacgtaagggacggct | att | tag |
| 100943 | 96ORF211 | −1 | 6662 . . . 6805 | 47 | ttgttggaatggtgggacgaattgg | ttg | tga |
| 100944 | 96ORF212 | −2 | 25213 . . . 25356 | 47 | agtagcacattcccaaaattgtaaa | atc | taa |
| 100945 | 96ORF213 | −3 | 42219 . . . 42362 | 47 | gtggtttgatcatttataatataac | ata | taa |
| 100946 | 96ORF214 | 3 | 27834 . . . 27974 | 46 | aaaagatttagacttcgttagaac | atc | tag |
| 100947 | 9GORF215 | 3 | 35811 . . . 35951 | 46 | ttacgcaatagtttagatgtgaacg | ata | taa |
| 100948 | 96ORF216 | −1 | 5402 . . . 5542 | 46 | tttccgtaaggtgtattcaacttga | att | tga |
| 100949 | 96ORF217 | −2 | 24229 . . . 24369 | 46 | tataggtctgttaagcacataacct | atc | taa |
| 100950 | 96ORF218 | −2 | 6253 . . . 6393 | 46 | ttgtcattcttgctaacacgtcaga | ttg | taa |
| 100951 | 96ORF219 | 1 | 883 . . . 1020 | 45 | aaatcactcccgaaatattcgttaa | atg | taa |
| 100952 | 96ORF220 | 2 | 32936 . . . 33073 | 45 | gataaaggtatagacaaagtattgt | atc | taa |
| 100953 | 96ORF221 | 3 | 41703 . . . 41840 | 45 | ggtaagcctataggtggtttggtag | ctg | taa |
| 100954 | 96ORF222 | −1 | 39860 . . . 39997 | 45 | acttttattaggttcaactccattt | att | taa |
| 100955 | 96ORF223 | −1 | 24716 . . . 24853 | 45 | acatttcaaatgattctggaacaat | atg | taa |
| 100956 | 96ORF224 | −2 | 26794 . . . 26931 | 45 | caatatcacgccatgtagttttaa | ctg | taa |
| 100957 | 96ORF225 | −2 | 19201 . . . 19338 | 45 | caaacaatggattgtaatcaaataa | atg | tga |
| 100958 | 96ORF226 | −2 | 15709 . . . 15846 | 45 | tgacttgcttgttgtctaacacaat | ata | taa |
| 100959 | 96ORF227 | −3 | 36711 . . . 36848 | 45 | acattgactgccccgataattatct | ata | tga |
| 100960 | 96ORF228 | 3 | 2325 . . . 2459 | 44 | tcgccatagtgagttccaataccgt | ata | taa |
| 100961 | 96ORW229 | −1 | 39612 . . . 38746 | 44 | ttgtcattgatacctattcttatag | atg | tga |
| 100962 | 96ORF230 | −1 | 31733 . . . 31867 | 44 | gctggattgtatggcttaaagtaat | ctg | tag |
| 100963 | 96ORF231 | −2 | 12076 . . . 12210 | 44 | tgactcatagcttaacttgttcgt | ctg | tag |
| 100964 | 96ORF232 | −3 | 31644 . . . 31778 | 44 | atagtcctcaagtgttaaccctagt | ttg | taa |
| 100965 | 96ORF233 | −3 | 23988 . . . 24122 | 44 | attttgatttgtaagttcaggctcaa | ctg | taa |
| 100966 | 96ORF234 | −3 | 17529 . . . 17663 | 44 | agtacgttttttgaatcgtaccta | atg | taa |
| 100967 | 96ORF235 | 1 | 7153 . . . 7284 | 43 | aatgctaatggtccaatagaaatca | atg | tag |
| 100968 | 96ORF236 | 2 | 2681 . . . 2812 | 43 | ttctttcacttcaacttcacatttc | ata | taa |
| 100969 | 96ORF237 | 2 | 4496 . . . 4627 | 43 | gtactatgcttcacagtcttagcga | ttg | taa |
| 100970 | 96ORF238 | −1 | 41720 . . . 41851 | 43 | cacctgtaattcttgaattagttga | ata | tga |
| 100971 | 96ORF239 | −1 | 35324 . . . 35455 | 43 | acttactaataaaatagaatagttt | gtg | taa |
| 100972 | 96ORF240 | −1 | 8570 . . . 8701 | 43 | atcccgttttgacttaatacatca | atc | tga |
| 100973 | 96ORF241 | −2 | 33502 . . . 33633 | 43 | ataattttgtaatactcttagggat | atg | tag |
| 100974 | 96ORF242 | −2 | 23662 . . . 23793 | 43 | agctaatgctacagcagtgttgtaa | atc | tag |
| 100975 | 96ORF243 | −3 | 32391 . . . 32522 | 43 | acctggacgagcttgcgtcatataa | ata | tag |
| 100976 | 96ORF244 | −3 | 30273 . . . 30404 | 43 | aaaactttcgttatactcttggtaa | atc | tga |

TABLE 10-continued

Bacteriophage 96 ORFs list

| SID | LAN | FRA | POS | a.a. | RBS sequence | STA | STO |
|---|---|---|---|---|---|---|---|
| 100977 | 96ORF245 | −3 | 5895 . . . 6026 | 43 | tgcactaaaatgcttataattctta | atc | taa |
| 100978 | 96ORF246 | −3 | 2679 . . . 2810 | 43 | attcatcaagaaactatagccggtc | atg | tga |
| 100979 | 96ORF247 | 1 | 34891 . . . 35019 | 42 | acatcaagcaaatctggtgtgttag | ttg | taa |
| 100980 | 96ORF248 | 2 | 30668 . . . 30796 | 42 | aattattacattaaagctggtgtga | atg | tag |
| 100981 | 96ORF249 | 2 | 31838 . . 31966 | 42 | caaatattagcttgtagtgagttag | atg | taa |
| 100982 | 96ORF250 | 2 | 33539 . . . 33667 | 42 | cttaccagaaacagcacaggtagaa | ata | taa |
| 100983 | 96ORF251 | −1 | 20486 . . . 20614 | 42 | cttctgtacgagccacacgcaatga | ttg | tag |
| 100984 | 96ORF252 | −1 | 15128 . . . 15256 | 42 | gatatttcattactagctactacta | ata | tga |
| 100985 | 96ORF253 | −2 | 41446 . . .41574 | 42 | aaaacctaattcagataaacgataa | ttg | tga |
| 100986 | 96ORF254 | −2 | 41005 . . . 41133 | 42 | gttataaccatgaccggctacaagc | ata | taa |
| 100987 | 96ORF255 | −2 | 23008 . . . 23136 | 42 | aggataaatgacttgaccatctttc | ata | taa |
| 100989 | 96ORF256 | −2 | 14794 . . . 14922 | 42 | ttgtatgcgtcaatgagttggtcga | ttg | tag |
| 100989 | 96ORF257 | −2 | 8503 . . . 8631 | 42 | tacctaactttttaataatttcta | atg | tga |
| 100990 | 96ORF258 | −3 | 22143 . . . 22271 | 42 | aaacgcttttgtaaaatgcctctgca | att | tga |
| 100991 | 96ORF259 | −3 | 38639 . . . 18767 | 42 | cttgtatctattatagagattaacc | att | tag |
| 100992 | 96ORF260 | −3 | 15624 . . . 15752 | 42 | gttttggtaactagccactgtatag | ata | taa |
| 100993 | 96ORF261 | 2 | 18746 . . . 18871 | 41 | catattgaggctctaatagagtcac | ata | taa |
| 100994 | 96ORF262 | −1 | 13067 . . . 13192 | 41 | aattaattaattcttctcttgttgg | ttg | taa |
| 100995 | 96ORF263 | −2 | 18742 . . . 18867 | 41 | taacagacacgtctaatcgccttac | att | tga |
| 100996 | 96ORF264 | −2 | 18376 . . . 18501 | 41 | catattatcataaagaacaagtaac | ttg | taa |
| 100997 | 96ORF265 | −2 | 367 . . . 492 | 41 | ctaaacgaaaaagagggtacaatac | atc | taa |
| 100998 | 96ORF266 | −3 | 32802 . . . 32927 | 41 | aggtatatccatttgatacaatact | ttg | taa |
| 100999 | 96ORF267 | −3 | 10194 . . . 10319 | 41 | atcatcgaaaggcgataactcgtta | ttg | tga |
| 101000 | 96ORF268 | 1 | 1159 . . . 1281 | 40 | ttattcttccttttgtaattgtaa | atg | taa |
| 101001 | 96ORF269 | 2 | 10373 . . . 10495 | 40 | gacagagttgaaaagaaaatcatga | atg | taa |
| 101002 | 96ORF270 | 2 | 15734 . . . 15856 | 40 | ttattcggcgtaatcgcactgatgc | ttg | tag |
| 101003 | 96ORF271 | −1 | 43451 . . . 43573 | 40 | c c tNo shine-dalgarno sequence | att | tga |
| 101004 | 96ORF272 | −1 | 36959 . . . 37081 | 40 | acgctataaaaataacttttattag | atg | tag |
| 101005 | 96ORF273 | −1 | 35798 . . . 35920 | 40 | ctgacgcactttgttggtttgatgc | att | taa |
| 101006 | 96ORF274 | −1 | 8147 . . . 8269 | 40 | tctgtctctcatgtttgttagtct | ctg | tga |
| 101007 | 96ORF275 | −2 | 43066 . . . 43188 | 40 | tttaacttactaatttctttttgat | ata | tga |
| 101008 | 96ORF276 | −2 | 42535 . . . 42657 | 40 | aaataatgtaattgttttcatagt | att | tag |
| 101009 | 96ORF277 | −2 | 30628 . . . 30750 | 40 | tttgtagtcccgcttctgcaaaagt | ctg | taa |
| 101010 | 96ORF278 | −2 | 13291 . . . 13413 | 40 | ttcgtatcttccaagcaattcattt | ttg | tga |
| 101011 | 96ORF279 | −2 | 3172 . . . 3294 | 40 | cagattgtttagtaacgcctaattt | atc | taa |
| 101012 | 96ORF280 | −3 | 18804 . . . 18926 | 40 | taaataaccaacacgtgtatcaaca | att | tag |
| 101013 | 96ORF281 | −3 | 15843 . . . 15965 | 40 | atttaaaaagtgtattctataacca | atc | taa |
| 101014 | 96ORF282 | −3 | 8460 . . . 8582 | 40 | ttagtcatcactcaattcttttcc | att | taa |
| 101015 | 96ORF283 | −3 | 7593 . . . 7715 | 40 | gatgttgtctacacagtgctaacac | atg | taa |
| 101016 | 96ORF284 | −3 | 6453 . . . 6575 | 40 | aattaattttaattaccatttcta | att | tga |
| 101017 | 96ORF285 | 1 | 15082 . . . 15201 | 39 | caatacttagtcacaacattcaaag | att | taa |
| 101018 | 96ORF286 | 1 | 34444 . . . 34563 | 39 | acacaaacgttaatagcaaaagtga | atg | tag |
| 101019 | 96ORF287 | 2 | 27920 . . . 28039 | 39 | cctattttagcagttgttgcagtaa | ttg | tag |
| 101020 | 96ORF288 | 2 | 28415 . . . 28534 | 39 | atcggcttttaactggcgtaatga | atc | tag |
| 101021 | 96ORF289 | 2 | 38147 . . . 38266 | 39 | tatcaaatgcttaatttaggcaagt | atc | tga |
| 101022 | 96ORF290 | 3 | 40917 . . . 41036 | 39 | gcaaatttaaacactttcacatcat | atg | taa |
| 101023 | 96ORF291 | −2 | 38815 . . . 38934 | 39 | tctctaaaaacagcttacagcgaac | ata | taa |
| 101024 | 96ORF292 | −2 | 32671 . . . 32790 | 39 | ctataggattataaatcgctgacgt | ata | tga |
| 101025 | 96ORF293 | −2 | 31216 . . . 31335 | 39 | ttgatttgatgtttcttatacttga | ttg | tag |
| 101026 | 96ORF294 | −2 | 21589 . . . 21708 | 39 | gtatcttcatcagaatcgcctaaaa | atc | taa |
| 101027 | 96ORF295 | −2 | 18976 . . . 19095 | 39 | tatcaatatgctaacctagcacc | ata | taa |
| 101028 | 96ORF296 | −2 | 11482 . . . 11601 | 39 | gccacctcgtactcttttgcaacc | att | taa |
| 101029 | 96ORF297 | −3 | 12933 . . . 13052 | 39 | tcacgaaataatgtttctttaattt | ata | taa |
| 101030 | 96ORF298 | −3 | 8262 . . . 8381 | 39 | gaactgatcttgcttaaatgattta | att | tag |
| 101031 | 96ORF299 | −3 | 6993 . . . 7112 | 39 | cattagcattagcgaatgggtttga | ttg | tga |
| 101032 | 96ORF300 | 2 | 23516 . . . 23632 | 38 | actacatctgaacaactaaaatttc | atc | tag |
| 101033 | 96ORF301 | 2 | 25943 . . . 26059 | 38 | agattagaagaagaaaaaagaagac | gtg | taa |
| 101034 | 96ORF302 | 2 | 36929 . . . 37045 | 38 | tattggggttttgtaacatggggca | atg | tag |
| 101035 | 96ORF303 | 3 | 4476 . . . 4592 | 38 | ataaaagctacctagtagcagtact | atg | taa |
| 101036 | 96ORF304 | 3 | 20586 . . . 20702 | 38 | tactctaagatagctaaagcaatac | gtg | tga |
| 101037 | 96ORF305 | 3 | 28356 . . . 28472 | 38 | cggttaccaatgtgcttgatgcgat | atg | taa |
| 101038 | 96ORF306 | −1 | 24359 . . . 24475 | 38 | acttaaataaaagccgtatcgtgcc | atg | taa |
| 101039 | 96ORF307 | −1 | 20147 . . . 20263 | 38 | ttgtacctatacgagttaactcctt | att | tag |
| 101040 | 96ORF308 | −2 | 38158 . . . 38274 | 38 | ttccgtatccactttctaagaaagc | gtg | tga |
| 101041 | 96ORF309 | −2 | 35149 . . . 35265 | 38 | agcttgtttgtatcgtctttaacga | ata | taa |
| 101042 | 96ORF310 | −2 | 31423 . . . 31539 | 38 | gtaatatgattaggtctcctccttat | ttg | taa |
| 101043 | 96ORF311 | −2 | 10438 . . . 10554 | 38 | cgcctttaaatcgttttaggtcact | atc | taa |
| 101044 | 96ORF312 | −2 | 1390 . . . 1506 | 38 | gagaacaacacaaacattaacaaca | atc | taa |
| 101045 | 96ORF313 | −3 | 33051 . . . 33167 | 38 | acgtcctgtttctagatcgtaatac | ata | tag |
| 101046 | 96ORF314 | −3 | 25194 . . . 25310 | 38 | agcaaaccgttaaagataacattga | atc | taa |
| 101047 | 96ORF315 | −3 | 6273 . . . 6389 | 38 | cattcttgctaacacgtcagattga | ctg | tga |
| 101048 | 96ORF316 | −3 | 4281 . . . 4397 | 38 | ataattcgtattcattaatcattaa | att | tag |
| 101049 | 96ORF317 | 1 | 2260 . . . 2373 | 37 | atgactccttttctcatatttcttt | ata | taa |
| 101050 | 96ORF318 | 2 | 21230 . . . 21343 | 37 | atttcacactttttagttgtctct | ttg | taa |

TABLE 10-continued

Bacteriophage 96 ORFs list

| SID | LAN | FRA | POS | a.a. | RBS sequence | STA | STO |
|---|---|---|---|---|---|---|---|
| 101051 | 96ORF319 | 3 | 18018 . . . 18131 | 37 | atactgagtcaccaatttaagctcg | atg | tag |
| 101052 | 96ORF320 | 3 | 36972 . . . 37085 | 37 | attacagatatcctaagggtttccg | att | taa |
| 101053 | 96ORF321 | −1 | 36302 . . . 36415 | 37 | ctcttgagtttttgacctaattta | atc | taa |
| 101054 | 96ORF322 | −1 | 32606 . . . 32719 | 37 | ccataagttatttctccagttctat | att | taa |
| 101055 | 96ORF323 | −1 | 11453 . . . 11566 | 37 | ttaaaccgttcttttttatcaattc | att | tga |
| 101056 | 96ORF324 | −1 | 7268 . . . 7381 | 37 | tactggttcgccccagtgaagttct | ata | tga |
| 101057 | 96ORF325 | −2 | 32347 . . . 32460 | 37 | ttactgcatttgtatatggcgataa | atc | tag |
| 101058 | 96ORF326 | −2 | 24682 . . . 24795 | 37 | acgtttattacgctcataaagccat | ata | tag |
| 101059 | 96ORF327 | −2 | 23905 . . . 24018 | 37 | aaatggctgtggcgcttgaccatat | gtg | taa |
| 101060 | 96ORF328 | −2 | 21460 . . . 21573 | 37 | agagcactaatacgttttgttctt | ctg | tga |
| 101061 | 96ORF329 | −2 | 21208 . . . 21321 | 37 | gacttaacttcttcgatattcatat | atc | tga |
| 101062 | 96ORF330 | −2 | 18085 . . . 18198 | 37 | ccagtcgacaccagcaaagtattct | ttg | tag |
| 101063 | 96ORF331 | −2 | 8170 . . . 8283 | 37 | actttgagacgtcgtctgtctctct | atg | tag |
| 101064 | 96ORF332 | −2 | 5971 . . . 6084 | 37 | caatttgttttccgttttctcttag | ttg | tag |
| 101065 | 96ORF333 | −3 | 37632 . . . 37745 | 37 | accttgcttaatcaagtcgtaatta | att | tga |
| 101066 | 96ORF334 | −3 | 29628 . . . 29741 | 37 | ctgagttagtgttgtaaaatgtcat | ttg | tag |
| 101067 | 96ORF335 | −3 | 7164 . . . 7277 | 37 | ttagcggatatccgttttctagtaa | atc | tag |
| 101068 | 96ORF336 | 1 | 22903 . . . 23013 | 36 | gtaaaaaagacaatatgactatta | ctg | tga |
| 101069 | 96ORF337 | 1 | 43258 . . . 43368 | 36 | taattgacgtggttattttttaggt | ttg | taa |
| 101070 | 96ORF338 | 2 | 12668 . . . 12778 | 36 | gaactggtggaatgggcatggaaca | atc | tag |
| 101071 | 96ORF339 | 2 | 28292 . . . 28402 | 36 | ttcactgcttaattcagttgctta | ctg | taa |
| 101072 | 96ORF340 | 2 | 35396 . . . 35506 | 36 | ttcctaatgaacataagtcaacggt | att | tga |
| 101073 | 96ORF341 | 3 | 25428 . . . 25538 | 36 | actcgagaacaattagaaaaagcaa | ttg | tga |
| 101074 | 96ORF342 | −1 | 40913 . . . 41023 | 36 | tatctgggaaatttaatctaataaa | ata | tga |
| 101075 | 96ORF343 | −1 | 39173 . . . 39283 | 36 | tgccacatttagtgtcaggattga | ttg | tag |
| 101076 | 96ORF344 | −1 | 37580 . . . 37690 | 36 | gggtctacctttaacgtcgtttcag | ata | taa |
| 101077 | 96ORF345 | −1 | 31556 . . . 31666 | 36 | ggattattctttctaataacttcaa | ttg | tga |
| 101078 | 96ORF346 | −1 | 29972 . . . 30082 | 36 | ggctactcctatctaaaatataat | ttg | taa |
| 101079 | 96ORF347 | −1 | 28787 . . . 28897 | 36 | ctgccaaagtctgtagcaattactt | ttg | taa |
| 101080 | 96ORF348 | −1 | 21839 . . . 21949 | 36 | ttaaaatccgataaaataacattgc | ctg | tga |
| 101081 | 96ORF349 | −1 | 3647 . . . 3757 | 36 | taaaacttccgaagttacccagcgt | ttg | tga |
| 101082 | 96ORF350 | −2 | 40801 . . . 40911 | 36 | accattccaattttgcccatatgat | gtg | tag |
| 101083 | 96ORF351 | −2 | 38953 . . . 39063 | 36 | tatcttttaaaattctcgtaatagc | atc | taa |
| 101084 | 96ORF352 | −2 | 31585 . . . 31695 | 36 | tagctgtcatcactagtattttga | atc | taa |
| 101085 | 96ORF353 | −2 | 24550 . . . 24660 | 36 | atagtccgttttaccgcctcgtact | att | tag |
| 101086 | 96ORF354 | −2 | 20083 . . . 20193 | 36 | atcatcatttgatatttctcaaac | ata | tga |
| 101087 | 96ORF355 | −2 | 991 . . . 1101 | 36 | gcatcttggcagtacgacgtaaaac | atc | tag |
| 101088 | 96ORF356 | −3 | 38148 . . . 38258 | 36 | taagaaagcgtgcgcgatcaaataa | att | tga |
| 101089 | 96ORF357 | −3 | 8790 . . . 8900 | 36 | tgaagttatctagcgctattttct | ttg | tag |
| 101090 | 96ORF358 | −3 | 4458 . . . 4568 | 36 | ttcataaaagtattctttgtagtat | atg | tag |
| 101091 | 96ORF359 | 1 | 4666 . . . 4773 | 35 | ttatcaaaatatacaacttaattaa | atc | tga |
| 101092 | 96ORF360 | 1 | 11569 . . . 11676 | 35 | ataaatttaccgaacatgaaaatga | att | tga |
| 101093 | 96ORF361 | 2 | 6122 . . . 6229 | 35 | ggaaaacaaattgatgttgtagtga | ttg | taa |
| 101094 | 96ORF362 | −1 | 40418 . . . 40525 | 35 | ttcgtaggtgtcattacttctttaa | ttg | tag |
| 101095 | 96ORF363 | −1 | 34358 . . . 34465 | 35 | gttttgcttgatttcgatttgttga | atg | tga |
| 101096 | 96ORF364 | −1 | 20654 . . . 20761 | 35 | ctatttccactgattcccccatctaa | atc | tga |
| 101097 | 96ORF365 | −1 | 8423 . . . 8530 | 35 | tcttttttagagttacgaggtttca | att | tag |
| 101098 | 96ORF366 | −1 | 2402 . . . 2509 | 35 | tgacgtatggcaacatttagatca | atc | taa |
| 101099 | 96ORF367 | −2 | 36607 . . . 36714 | 35 | aaaataaaagccagtgccgaagca | ctg | tag |
| 101100 | 96ORF368 | −2 | 27061 . . . 27168 | 35 | caaatcgtcctgcagcgttcaataa | atc | tag |
| 101101 | 96ORF369 | −2 | 26470 . . . 26577 | 35 | atgagttgttaagtttaccccaaat | atc | taa |
| 101102 | 96ORF370 | −2 | 10327 . . . 10434 | 35 | ccgtgccatcttctcggtataagta | ata | taa |
| 101103 | 96ORF371 | −2 | 8650 . . . 8757 | 35 | gggtacgggttgttactgttgatat | atc | taa |
| 101104 | 96ORF372 | −3 | 14382 . . . 14489 | 35 | gttcttttaattgatctactgttaa | att | taa |
| 101105 | 96ORF373 | −3 | 8151 . . . 8258 | 35 | atgttgttagtctctgtgtagtct | atg | taa |
| 101106 | 96ORF374 | −3 | 5007 . . . 5114 | 35 | aaacgatttaagtggaacattattc | ata | taa |
| 101107 | 96ORF375 | 2 | 30563 . . . 30667 | 34 | cgattagaaatctttaaaaaggac | ttg | tga |
| 101108 | 96ORF376 | −1 | 19916 . . . 20020 | 34 | tctatgtcaggtaatttgtcattaa | att | taa |
| 101109 | 96ORF377 | −1 | 9236 . . . 9340 | 34 | cttttctgttagtaattgttttaa | atc | taa |
| 101110 | 96ORF378 | −1 | 9026 . . . 9130 | 34 | actctttatctttagttgctttaa | ata | tag |
| 101111 | 96ORF379 | −2 | 28447 . . . 28551 | 34 | cttttgtgataataaagtttagtgc | ttg | tga |
| 101112 | 96ORF380 | −3 | 40329 . . . 40433 | 34 | ccatttaccttcttcgagatgttgga | ttg | tga |
| 101113 | 96ORF381 | −3 | 39801 . . . 39905 | 34 | caaaagatgaaggctttttccatac | ttg | tga |
| 101114 | 96ORF382 | −3 | 33831 . . . 33935 | 34 | atgttgtttgtaactcgattaagtt | atc | tga |
| 101115 | 96ORF383 | −3 | 33687 . . . 33791 | 34 | gttattacgtcttaatacttgtgtt | gtg | tag |
| 101116 | 96ORF384 | −3 | 13530 . . . 13634 | 34 | tatacgcactagtactgatcactga | ttg | taa |
| 101117 | 96ORF385 | −3 | 3843 . . . 3947 | 34 | tttgattgattgttctagttaagaa | att | tag |
| 101118 | 96ORF386 | 1 | 12256 . . . 12357 | 33 | agtcataaagaagttagcaatgtga | ttg | tag |
| 101119 | 96ORF387 | 2 | 2207 . . . 2308 | 33 | tccaagactctttaactgttaactt | atc | tag |
| 101120 | 96ORF388 | 2 | 2519 . . . 2620 | 33 | attgttgaatttcgattgatctaaa | atg | tga |
| 101121 | 96ORF389 | 2 | 22517 . . . 22618 | 33 | agaagtaaatgcgtaatgctttag | ttg | taa |
| 101122 | 96ORF390 | 2 | 27302 . . . 27403 | 33 | ttccaaaattgggctaatagtgtag | ctg | taa |
| 101123 | 96ORF391 | 2 | 32384 . . . 32485 | 33 | actaaaaggttgagaaagctagg | atg | taa |
| 101124 | 96ORF392 | 2 | 39287 . . . 39388 | 33 | aaaaacggtactgtagtatcaatca | atc | tag |
| 101125 | 96ORF393 | 3 | 18153 . . . 18254 | 33 | gtagtatatgccgactttgatttga | atg | taa |

TABLE 10-continued

Bacteriophage 96 ORFs list

| SID | LAN | FRA | POS | a.a. | RBS sequence | STA | STO |
|---|---|---|---|---|---|---|---|
| 101126 | 96ORF394 | 3 | 24189 ... 24290 | 33 | tcagaccctaacattaacaaactag | ttg | tga |
| 101127 | 96ORF395 | −1 | 15266 ... 15367 | 33 | tcgataatttgtatagcttgtttta | atg | tag |
| 101128 | 96ORF396 | −2 | 32239 ... 32340 | 33 | ttttagtgaaagcatctagtgttga | ata | tag |
| 101129 | 96ORF397 | −2 | 16123 ... 16224 | 33 | ttatgtgtgcctatcatattaacaa | ttg | tag |
| 101130 | 96ORF398 | −2 | 13648 ... 13749 | 33 | tctttaactgaatgttgaatagcat | ttg | tag |
| 101131 | 96ORF399 | −2 | 10987 ... 11088 | 33 | acttctgtaggtattcttatatcaa | ttg | tga |
| 101132 | 96ORF400 | −2 | 3382 ... 3483 | 33 | cttactggtaattcttcaaaattaa | atg | taa |
| 101133 | 96ORF401 | −3 | 40794 ... 40895 | 33 | ccatatgatgtgaaagtgtttaaat | ttg | taa |
| 101134 | 96ORF402 | −3 | 39978 ... 40079 | 33 | atattcctaaatcacttgaacctaa | att | tga |
| 101135 | 96ORF403 | −3 | 38607 ... 38708 | 33 | atcttcagtgtaaaatcgacagcca | atg | tag |
| 101136 | 96ORF404 | −3 | 21288 ... 21389 | 33 | cagacaccgtcttaagtccctttag | ata | taa |

TABLE 11

SEQUENCE INFORMATION FOR PHAGES MATCHING WITH TABLE 1

M32695
    Bacteriophage PM2 nuclease cleavage site
    gi|166145|gb|M32695|BM2NCS [166145]
    (View GenBank report, FASTA report, ASN.1 report, Graphical view, 1 MEDLINE link, or 1 nucleotide neighbor)
M32693
    Bacteriophage PM2 Hind III fragment 4
    gi|166144|gb|M32693|BM24HIND3 [166144]
    (View GenBank report, FASTA report, ASN.1 report, Graphical view, 1 MEDLINE link, or 1 nucleotide neighbor)
M32693
    Bacteriophage PM2 Hind III fragment 4
    gi|166144|gb|M32693|BM24HIND3 [166144]
    (View GenBank report, FASTA report, ASN.1 report, Graphical view, 1 MEDLINE link, or 1 nucleotide neighbor)
M32694
    Bacteriophage PM2 Hind III fragment 3
    gi|166143|gb|M32694|BM23HIND3 [166143]
    (View GenBank report, FASTA report, ASN.1 report, Graphical view, or 1 MEDLINE link)
M26134
    Bacteriophage PM2 structural protein gene containing purine/pyrimidine rich
    regions and anti-Z-DNA-IgG binding regions, complete cds
    gi|289360|gb|M26134|BM2PROTIV [289360]
    (View GenBank report, FASTA report, ASN.1 report, Graphical view, 1 MEDLINE link, or 1 protein link)
J02452
    bacteriophage fi 3′-terminal region ma
    gi|215409|gb|J02452|PFITR3 [215409]
    (View GenBank report, FASTA report, ASN.1 report, Graphical view, or 1 MEDLINE link)
AF020798
    Bacteriophage Chp1 genome DNA, complete sequence
    gi|217761|dbj|D00624|BCP1 [217761]
    (View GenBank report, FASTA report, ASN.1 report, Graphical view, 1 MEDLINE link, 12 protein links, or 1 genome link)
X72793
    *Clostridium botulinum* C phage BONT/C1, ANTP-139, ANTP-33, ANTP-17, ANTP-70
    genes and ORF-22
    gi|516171|emb|X72793|CBCBONT [516171]
    (View GenBank report, FASTA report, ASN.1 report, Graphical view, 1 MEDLINE link, 6 protein links, or 4 nucleotide neighbors)
X51464
    *Clostridium botulinum* D Phage C3 gene for exoenzyme C3
    gi|14907|emb|X51464|CBDPE3 [14907]
    (View GenBank report, FASTA report, ASN.1 report, Graphical view, 1 MEDLINE link, 1 protein link, or 2 nucleotide neighbors)
D90210
    Bacteriophage c-st (from *C. botulinum*) C1-tox gene for *botulinum* C1 neurotoxin
    gi|217780|dbj|D90210|CSTC1TOX [217780]
    (View GenBank report, FASTA report, ASN.1 report, Graphical view, 1 MEDLINE link, or 1 protein link)
S49407
    type D neurotoxin [bacteriophage d-16 phi, host = *C. botulinum*, type D, CB16, Genomic, 4087 nt]
    gi|260238|gb|S49407|S49407 [260238]
    (View GenBank report, FASTA report, ASN.1 report, Graphical view, 1 MEDLINE link, or 1 protein link)
X53370
    Bacteriophage phi29 temperature sensitive mutant TS2(98) DNA polymerase gene
    gi|15733|emb|X53370|POTS298 [15733]
    (View GenBank report, FASTA report, ASN.1 report, Graphical view, 1 MEDLINE link, 1 protein link, or 7 nucleotide neighbors)
X53371
    Bacteriophage phi29 temperature sensitive mutant TS2(24) DNA polymerase gene
    gi|15731|emb|X53371|POTS224 [15731]
    (View GenBank report, FASTA report, ASN.1 report, Graphical view, 1 MEDLINE link, 1 protein link, or 7 nucleotide neighbors)

TABLE 11-continued

SEQUENCE INFORMATION FOR PHAGES MATCHING WITH TABLE 1

X05973
    Bacteriophage phi29 prohead RNA
    gi|15680|emb|X05973|POP29PRO [15680]
    (View GenBank report, FASTA report, ASN.1 report, Graphical view, 2 MEDLINE links, or 4 nucleotide neighbors)
V01155
    Left end of bacteriophage phi-29 coding for 15 potential proteins Among
    these are the terminal protein and the proteins encoded by the genes 1, 2 (sus), 3, and (probably) 4
    gi|15659|emb|V01155|POP29B [15659]
    (View GenBank report, FASTA report, ASN.1 report, Graphical view, 1 MEDLINE link, 16 protein links, or 16 nucleotide neighbors)
X73097
    Bacteriophage phi-29 left origin of replication
    gi|312194|emb|X73097|BP29ORIL [312194]
    (View GenBank report, FASTA report, ASN.1 report, Graphical view, 1 MEDLINE link, or 5 nucleotide neighbors)
M14430
    Bacteriophage phi-29 gene-17 gene, complete cds
    gi|215321|gb|M14430|P29G17A [215321]
    (View GenBank report, FASTA report, ASN.1 report, Graphical view, 1 MEDLINE link, 6 protein links, or 8 nucleotide neighbors)
M14431
    Bacteriophage phi-29 gene-16 gene, complete cds
    gi|215319|gb|M14431|P29G16A [215319]
    (View GenBank report, FASTA report, ASN.1 report, Graphical view, 1 MEDLINE link, 2 protein links, or 7 nucleotide neighbors)
M20693
    Bacteriophage phi-29 DNA, 3' end
    gi|215343|gb|M20693|P29REPINB [215343]
    (View GenBank report, FASTA report, ASN.1 report, Graphical view, 1 MEDLINE link, or 4 nucleotide neighbors)
M21016
    Bacteriophage phi-29 DNA, 5' end
    gi|215342|gb|M21016|P29REPINA [215342]
    (View GenBank report, FASTA report, ASN.1 report, Graphical view, 1 MEDLINE link, or 1 nucleotide neighbor)
M12456
    Bacteriophage phi-29 genes 9, 10 and 11 encoding p9 tail, incomplete, p10
    connector, complete, and p11 lower collar, incomplete, respectively
    gi|215338|gb|M12456|P29P9 [215338]
    (View GenBank report, FASTA report, ASN.1 report, Graphical view, 1 MEDLINE link, 3 protein links, or 2 nucleotide neighbors)
M14782
    Bacillus phage phi-29 head morphogenesis, major head protein, head fiber
    protein, tail protein, upper collar protein, lower collar protein, pre-neck
    appendage protein, morphogenesis(13), lysis, morphogenesis(15), encapsidation genes, complete cds
    gi|215323|gb|M14782|P29LATE2 [215323]
    (View GenBank report, FASTA report, ASN.1 report, Graphical view, 1 MEDLINE link, 11 protein links, or 11 nucleotide neighbors)
M26968
    Bacteriophage phi-29 (from *Bacillus subtilis*) proteins p1 delta-1 genes, complete cds, and the sus1(629) mutation
    gi|341558|gb|M26968|P29P1D1A [341558]
    (View GenBank report, FASTA report, ASN.1 report, Graphical view, 1 MEDLINE link, 2 protein links, or 1 nucleotide neighbor)
J02448
    Bacteriophage f1, complete genome
    gi|166201|gb|J02448|F1CCG [166201]
    (View GenBank report, FASTA report, ASN.1 report, Graphical view, 1 MEDLINE link, 10 protein links, 205 nucleotide neighbors,
    or 1 genome link)
M24832
    Bacteriophage f2 coat protein gene, partial cds
    gi|166228|gb|M24832|F2CRNACA [166228]
    (View GenBank report, FASTA report, ASN.1 report, Graphical view, 1 MEDLINE link, 1 protein link, or 4 nucleotide neighbors)
J02451
    Bacteriophage fd, strain 478, complete genome
    gi|215394|gb|J02451|PFDCG [215394]
    (View GenBank report, FASTA report, ASN.1 report, Graphical view, 5 MEDLINE links, 10 protein links, 204 nucleotide neighbors,
    or 1 genome link)
M34834
    Bacteriophage fr replicase gene, 5' end
    gi|166139|gb|M34834|BFRREGRA [166139]
    (View GenBank report, FASTA report, ASN.1 report, Graphical view, 1 protein link, or 9 nucleotide neighbors)
M38325
    Bacteriophage fr replicase gene, 5' end
    gi|166137|gb|M38325|BFRREGR [166137]
    (View GenBank report, FASTA report, ASN.1 report, Graphical view, 1 protein link, or 9 nucleotide neighbors)
M35063
    Bacteriophage fr coat protein replicase cistron (R region) RNA
    gi|166134|gb|M35063|BFRRCRRA [166134]
    (View GenBank report, FASTA report, ASN.1 report, Graphical view, 1 protein link, or 3 nucleotide neighbors
S66567
    alpha-atrial natriuretic factor/coat protein=fusion polypeptide [human,
    bacteriophage fr, expression vector pFAN15, PlasmidSyntheticRecombinant, 510 nt]
    gi|435742|gb|S66567|S66567 [435742]
    (View GenBank report, FASTA report, ASN.1 report, Graphical view, 1 MEDLINE link, 1 protein link, or 15 nucleotide neighbors)

TABLE 11-continued

SEQUENCE INFORMATION FOR PHAGES MATCHING WITH TABLE 1

X15031
    Bacteriophage fr RNA genome
    gi|15071|emb|X15031|LEBFRX [15071]
    (View GenBank report, FASTA report, ASN.1 report, Graphical view, 1 MEDLINE link, 4 protein links, 9 nucleotide neighbors, or 1 genome link)
U51233
    *Mus musculus* neutralizing anti-RNA-bacteriophage fr immunoglobulin variable
    region light chain (IgM) mRNA, partial cds
    gi|1277150|gb|U51233|MMU51233 [1277150]
    (View GenBank report, FASTA report, ASN.1 report, Graphical view, 1 protein link, or 1669 nucleotide neighbors)
U51232
    *Mus musculus* neutralizing anti-RNA-bacteriophage fr immunoglobulin variable region heavy chain (IgM) mRNA, partial cds
    gi|1277148|gb|U51232|MMU51232 [1277148]
    (View GenBank report, FASTA report, ASN.1 report, Graphical view, 1 protein link, or 1073 nucleotide neighbors)
U02303
    Bacteriophage If1, complete genome
    gi|3676280|gb|U02303|B2U02303 [3676280]
    (View GenBank report, FASTA report, ASN.1 report, Graphical view, 10 protein links, or 1 genome link)
V00604
    Phage M13 genome
    gi|14959|emb|V00604|INM13X [14959]
    (View GenBank report, FASTA report, ASN.1 report, Graphical view, 1 MEDLINE link, 10 protein links, or 205 nucleotide neighbors)
A32252
    Synthetic bacteriophage M13 protein III probe
    gi|1567340|emb|A32252|A32252 [1567340]
    (View GenBank report, FASTA report, ASN.1 report, or Graphical view)
A32251
    Synthetic bacteriophage M13 protein III probe
    gi|1567339|emb|A32251|A32251 [1567339]
    (View GenBank report, FASTA report, ASN.1 report, or Graphical view)
M12465
    Bacteriophage M13 mp10 mutations in lac operon
    gi|215210|gb|M12465|M13LACMUT [215210]
    (View GenBank report, FASTA report, ASN.1 report, Graphical view, 1 MEDLINE link, or 215 nucleotide neighbors)
M24177
    Synthetic Bacteriophage M13 (clone M13.SV.B12) SV40 early promoter region DNA
    gi|209416|gb|M24177|SYNSVB12 [209416]
    (View GenBank report, FASTA report, ASN.1 report, Graphical view, 1 MEDLINE link, or 1 nucleotide neighbor)
M24176
    Synthetic Bacteriophage M13 (clone M13.SV.B11) SV40 early promoter region DNA
    gi|209415|gb|M24176|SYNSVB11 [209415]
    (View GenBank report, FASTA report, ASN.1 report, Graphical view, 1 MEDLINE link, or 1 nucleotide neighbor)
M24175
    Synthetic Bacteriophage M13 (clone M13.SV.8) SV40 early promoter region DNA
    gi|208806|gb|M24175|SYNM13SV8 [208806]
    (View GenBank report, FASTA report, ASN.1 report, Graphical view, 1 MEDLINE link, or 242 nucleotide neighbors)
M19979
    Synthetic hybrids; recombinant DNA from bacteriophage M13 and plasmid pHV33
    gi|207813|gb|M19979|SYN33M13M [207813]
    (View GenBank report, FASTA report, ASN.1 report, Graphical view, 1 MEDLINE link, or 617 nucleotide neighbors)
M19565
    Synthetic hybrids; recombinant DNA from bacteriophage M13 and plasmid pHV33
    gi|207808|gb|M19565|SYN33M13H [207808]
    (View GenBank report, FASTA report, ASN.1 report, Graphical view, 1 MEDLINE link, or 567 nucleotide neighbors)
M19564
    Synthetic hybrids; recombinant DNA from bacteriophage M13 and plasmid pHV33
    gi|207807|gb|M19564|SYN33M13G [207807]
    (View GenBank report, FASTA report, ASN.1 report, Graphical view, 1 MEDLINE link, or 12 nucleotide neighbors)
M19563
    Synthetic hybrids; recombinant DNA from bacteriophage M13 and plasmid pHV33
    gi|207806|gb|M19563|SYN33M13F [207806]
    (View GenBank report, FASTA report, ASN.1 report, Graphical view, 1 MEDLINE link, or 262 nucleotide neighbors)
M19561
    Synthetic hybrids; recombinant DNA from bacteriophage M13 and plasmid pHV33
    gi|207804|gb|M19561|SYN33M13D [207804]
    (View GenBank report, FASTA report, ASN.1 report, Graphical view, 1 MEDLINE link, or 27 nucleotide neighbors)
M19560
    Synthetic hybrids; recombinant DNA from bacteriophage M13 and plasmid pHV33
    gi|207803|gb|M19560|SYN33M13C [207803]
    (View GenBank report, FASTA report, ASN.1 report, Graphical view, or 1 MEDLINE link)
M19559
    Synthetic hybrids; recombinant DNA from bacteriophage M13 and plasmid pHV33
    gi|207802|gb|M19559|SYN33M13B [207802]
    (View GenBank report, FASTA report, ASN.1 report, Graphical view, 1 MEDLINE link, or 227 nucleotide neighbors)

TABLE 11-continued

SEQUENCE INFORMATION FOR PHAGES MATCHING WITH TABLE 1

M10568
    Bacteriophage M13 replicative form II, replication origin, specific nick location
    gi|215220|gb|M10568|M13ORIB [215220]
    (View GenBank report, FASTA report, ASN.1 report, Graphical view, 1 MEDLINE link, or 650 nucleotide neighbors)
M10910
    Bacteriophage M13 gene II regulatory region and M13sj1 mutant
    gi|215209|gb|M10910|M13IIREG [215209]
    (View GenBank report, FASTA report, ASN.1 report, Graphical view, 1 MEDLINE link, or 72 nucleotide neighbors)
M38295
    Bacteriophage M13 HaeIII restriction fragment DNA
    gi|215208|gb|M38295|M13HAEIII [215208]
    (View GenBank report, FASTA report, ASN.1 report, Graphical view, or 67 nucleotide neighbors)
E02067
    DNA encoding a part of Bacteriophage M13 tg 127
    gi|2170311|dbj|E02067|E02067 [2170311]
    (View GenBank report, FASTA report, ASN.1 report, or Graphical view)
J02467
    Bacteriophage MS2, complete genome
    gi|215232|gb|J02467|MS2CG [215232]
    (View GenBank report, FASTA report, ASN.1 report, Graphical view, 8 MEDLINE links, 4 protein links, 20 nucleotide neighbors,
    or 1 genome link)
AJ004950
    Bacteriophage P1 ban gene
    gi|3688226|emb|AJ011592|BP1011592 [3688226]
    (View GenBank report, FASTA report, ASN.1 report, Graphical view, or 1 protein link)
U88974
    Bacteriophage P1 structural lytic transglycosylase (orf47), pep44b (orf44b),
    pep44a (orf44a), and pep43 (orf43) genes, complete cds; and pep42 (orf42) gene, partial cds
    gi|2661099|gb|AF035607|AF035607 [2661099]
    (View GenBank report, FASTA report, ASN.1 report, Graphical view, 5 protein links, or 1 nucleotide neighbor)
AJ000741
    Bacteriophage P1 darA operon
    gi|2462938|emb|AJ000741|BPAJ7641 [2462938]
    (View GenBank report, FASTA report, ASN.1 report, Graphical view, 1 MEDLINE link, 10 protein links, or 31 nucleotide neighbors)
X01828
    Bacteriophage P1 recombinase gene cin
    gi|15133|emb|X01828|MYP1CIN [15133]
    (View GenBank report, FASTA report, ASN.1 report, Graphical view, 1 MEDLINE link, 1 protein link, or 3 nucleotide neighbors)
X98146
    Bacteriophage P1 DNA sequence around the Op88 operator
    gi|1359513|emb|X98146|BP1OP88OP [1359513]
    (View GenBank report, FASTA report, ASN.1 report, Graphical view, or 1 nucleotide neighbor)
S61175
    immI operon: icd=cell division repressor, anti=antirepressor {promoters
    P51a, P51b} [bacteriophage P1, Genomic, 728 nt]
    gi|385908|gb|S61175|S61175 [385908]
    (View GenBank report, FASTA report, ASN.1 report, Graphical view, 1 MEDLINE link, or 3 nucleotide neighbors)
X87824
    Bacteriophage P1 gene 26
    gi|861164|emb|X87824|XXBP1G26 [861164]
    (View GenBank report, FASTA report, ASN.1 report, Graphical view, or 1 protein link)
X15638
    Phage P1 DNA for lytic replicon containing promoter P53 and two open reading frames
    gi|15735|emb|X15638|PP1LREP [15735]
    (View GenBank report, FASTA report, ASN.1 report, Graphical view, 1 MEDLINE link, 3 protein links, or 24 nucleotide neighbors)
X17512
    Bacteriophage P1 DNA for immunity region immI
    gi|15479|emb|X17512|P1IMMUNTY [15479]
    (View GenBank report, FASTA report, ASN.1 report, Graphical view, 2 MEDLINE links, or 4 nucleotide neighbors)
X16005
    Bacteriophage P1 c1 gene for P1c1 repressor protein
    gi|15477|emb|X16005|P1C1 [15477]
    (View GenBank report, FASTA report, ASN.1 report, Graphical view, 1 MEDLINE link, 1 protein link, or 3 nucleotide neighbors)
X03453
    Bacteriophage P1 cre gene for recombinase protein
    gi|15135|emb|X03453|MYP1CRE [15135]
    (View GenBank report, FASTA report, ASN.1 report, Graphical view, 1 MEDLINE link, 2 protein links, or 12 nucleotide neighbors)
X06561
    Bacteriophage P1 c1 gene 5'-region
    gi|15128|emb|X06561|MYP1C1 [15128]
    (View GenBank report, FASTA report, ASN.1 report, Graphical view, 1 MEDLINE link, 4 protein links, or 6 nucleotide neighbors)
V01534
    Bacteriophage P1 genome fragment (IS2 insertion spot). This regions contains
    four unidentified reading frames and is known as insertion hot spot for IS2 insertion sequences
    gi|15118|emb|V01534|MYOVP1 [15118]
    (View GenBank report, FASTA report, ASN.1 report, Graphical view, 1 MEDLINE link, 4 protein links, or 3 nucleotide neighbors)

TABLE 11-continued

SEQUENCE INFORMATION FOR PHAGES MATCHING WITH TABLE 1

X56951
    Bacteriophage P1 gene10
    gi|406728|emb|X56951|BPP1GP10 [406728]
    (View GenBank report, FASTA report, ASN.1 report, Graphical view, 2 MEDLINE links, 3 protein links, or 1 nucleotide neighbor)
K02380
    Bacteriophage P1 replication region including repA, parA, and parB genes and
    incA, incB, and incC incompatibility determinants
    gi|215652|gb|K02380|PP1REP [215652]
    (View GenBank report, FASTA report, ASN.1 report, Graphical view, 5 MEDLINE links, 4 protein links, or 8 nucleotide neighbors)
X87674
    Bacteriophage P1 lydA & lydB genes
    gi|974763|emb|X87674|BACP1LYD [974763]
    (View GenBank report, FASTA report, ASN.1 report, Graphical view, 1 MEDLINE link, 2 protein links, or 2 nucleotide neighbors)
X87673
    Bacteriophage P1 gene 17
    gi|974761|emb|X87673|BACP117 [974761]
    (View GenBank report, FASTA report, ASN.1 report, Graphical view, 1 MEDLINE link, 1 protein link, or 1 nucleotide neighbor)
M16618
    Bacteriophage P1 c1 repressor binding sites
    gi|215600|gb|M16618|PP1C1 [215600]
    (View GenBank report, FASTA report, ASN.1 report, Graphical view, 1 MEDLINE link, 2 protein links, or 3 nucleotide neighbors)
SEG_PP1CIN
    Bacteriophage P1 cin gene encoding recombinase, cixL recombination site, and 5' end of C invertible element
    gi|215607|gb||SEG_PP1CIN [215607]
    (View GenBank report, FASTA report, ASN.1 report, Graphical view, 1 MEDLINE link, 1 protein link, or 4 nucleotide neighbors)
K03173
    Bacteriophage P1 C invertible element, right end, and cixR recombination site
    gi|215606|gb|K03173|PP1CIN2 [215606]
    (View GenBank report, FASTA report, ASN.1 report, or Graphical view)
215605
    Bacteriophage P1 cin gene encoding recombinase, cixL recombination site, and 5' end of C invertible element
    gi|215605|lcl|X01828 [215605]
    (View GenBank report, FASTA report, ASN.1 report, or Graphical view)
M25470
    Bacteriophage P1 tail fiber protein gene, complete cds
    gi|341349|gb|M25470|PP1TFPR [341349]
    (View GenBank report, FASTA report, ASN.1 report, Graphical view, 1 MEDLINE link, 3 protein links, or 3 nucleotide neighbors)
M34382
    Bacteriophage P1 sim region proteins, complete cds
    gi|215661|gb|M34382|PP1SIM [215661]
    (View GenBank report, FASTA report, ASN.1 report, Graphical view, 1 MEDLINE link, or 2 protein links)
M81956
    Bacteriophage P1 R protein (R) gene, complete cds
    gi|215658|gb|M81956|PP1RP [215658]
    (View GenBank report, FASTA report, ASN.1 report, Graphical view, 1 MEDLINE link, 2 protein links, or 4 nucleotide neighbors)
M37080
    Bacteriophage P1 mini-P1 plasmid origin of replication
    gi|215657|gb|M37080|PP1REPOR [215657]
    (View GenBank report, FASTA report, ASN.1 report, Graphical view, 1 MEDLINE link, or 46 nucleotide neighbors)
M27041
    Bacteriophage P1 ref gene, complete cds
    gi|215650|gb|M27041|PP1REF [215650]
    (View GenBank report, FASTA report, ASN.1 report, Graphical view, 1 MEDLINE link, 1 protein link, or 1 nucleotide neighbor)
L01408
    Bacteriophage P1 partition protein (parB) gene, 3' end
    gi|215642|gb|L01408|PP1PARB [215642]
    (View GenBank report, FASTA report, ASN.1 report, Graphical view, 1 protein link, or 41 nucleotide neighbors)
SEG_PP1PAR
    Bacteriophage miniplasmid P1 parA gene, 5' end
    gi|215639|gb||SEG_PP1PAR [215639]
    (View GenBank report, FASTA report, ASN.1 report, Graphical view, 1 MEDLINE link, 2 protein links, or 48 nucleotide neighbors)
M36425
    Bacteriophage miniplasmid P1 parB gene, 3' end
    gi|215638|gb|M36425|PP1PAR2 [215638]
    (View GenBank report, FASTA report, ASN.1 report, or Graphical view)
M36424
    Bacteriophage miniplasmid P1 parA gene, 5' end
    gi|215637|gb|M36424|PP1PAR1 [215637]
    (View GenBank report, FASTA report, ASN.1 report, or Graphical view)
M11129
    Bacteriophage P1 miniplasmid origin of replication region
    gi|215632|gb|M11129|PP1ORIM [215632]
    (View GenBank report, FASTA report, ASN.1 report, Graphical view, 1 MEDLINE link, 1 protein link, or 43 nucleotide neighbors)
M25414
    Bacteriophage P1 c1 repressor binding site, operator 88 (Op88)
    gi|215631|gb|M25414|PP1OP88A [215631]
    (View GenBank report, FASTA report, ASN.1 report, Graphical view, 1 MEDLINE link, or 3 nucleotide neighbors)

TABLE 11-continued

SEQUENCE INFORMATION FOR PHAGES MATCHING WITH TABLE 1

M25413
    Bacteriophage P1 c1 repressor binding site, operator 68 (Op68)
    gi|215630|gb|M25413|PP1OP68A [215630]
    (View GenBank report, FASTA report, ASN.1 report, Graphical view, or 1 MEDLINE link)
M25412
    Bacteriophage P1 c1 repressor binding site, operator 21 (Op21)
    gi|215629|gb|M25412|PP1OP21A [215629]
    (View GenBank report, FASTA report, ASN.1 report, Graphical view, 1 MEDLINE link, or 1 nucleotide neighbor)
M10510
    Bacteriophage P1 recombination site loxR
    gi|215628|gb|M10510|PP1LOXR [215628]
    (View GenBank report, FASTA report, ASN.1 report, Graphical view, 1 MEDLINE link, or 1 nucleotide neighbor)
M10287
    Bacteriophage P1 loxP X loxP recombination site
    gi|215627|gb|M10287|PP1LOXPX [215627]
    (View GenBank report, FASTA report, ASN.1 report, Graphical view, 1 MEDLINE link, or 13 nucleotide neighbors)
M10494
    Bacteriophage P1 recombination site loxP
    gi|215626|gb|M10494|PP1LOXP [215626]
    (View GenBank report, FASTA report, ASN.1 report, Graphical view, 1 MEDLINE link, or 134 nucleotide neighbors)
M10511
    Bacteriophage P1 recombination site loxL
    gi|215625|gb|M10511|PP1LOXL [215625]
    (View GenBank report, FASTA report, ASN.1 report, Graphical view, 1 MEDLINE link, or 1 nucleotide neighbor)
M10512
    Bacteriophage P1 recombination site loxB
    gi|215624|gb|M10512|PP1LOXB [215624]
    (View GenBank report, FASTA report, ASN.1 report, Graphical view, or 1 MEDLINE link)
M10145
    Bacteriophage P1 genome fragment with recombination site loxP
    gi|215623|gb|M10145|PP1CREX [215623]
    (View GenBank report, FASTA report, ASN.1 report, Graphical view, 1 MEDLINE link, or 21 nucleotide neighbors)
M13327
    Bacteriophage P1 Cin recombinase activated cross over site, junction IV, clone pSHI326
    gi|215622|gb|M13327|PP1CN26IV [215622]
    (View GenBank report, FASTA report, ASN.1 report, Graphical view, 1 MEDLINE link, or 7 nucleotide neighbors)
M13325
    Bacteriophage P1 Cin recombinase activated cross over site, junction II, clone pSHI326
    gi|215621|gb|M13325|PP1CN26II [215621]
    (View GenBank report, FASTA report, ASN.1 report, Graphical view, 1 MEDLINE link, or 1401 nucleotide neighbors)
M13323
    Bacteriophage P1 Cin recombinase activated cross over site, junction IV, clone pSHI325
    gi|215620|gb|M13323|PP1CN25IV [215620]
    (View GenBank report, FASTA report, ASN.1 report, Graphical view, 1 MEDLINE link, or 7 nucleotide neighbors)
M13321
    Bacteriophage P1 Cin recombinase activated cross over site, junction II, clone pSHI325
    gi|215619|gb|M13321|PP1CN25II [215619]
    (View GenBank report, FASTA report, ASN.1 report, Graphical view, 1 MEDLINE link, or 1058 nucleotide neighbors)
M13324
    Bacteriophage P1 Cin recombinase activated cross over site, junction I, clone pSHI326
    gi|215618|gb|M13324|PP1CIR26I [215618]
    (View GenBank report, FASTA report, ASN.1 report, Graphical view, 1 MEDLINE link, or 7 nucleotide neighbors)
M13319
    Bacteriophage P1 Cin recombinase activated cross over site, right junction, clone pSHI327
    gi|215617|gb|M13319|PP1CIN27R [215617]
    (View GenBank report, FASTA report, ASN.1 report, Graphical view, 1 MEDLINE link, or 7 nucleotide neighbors)
M13320
    Bacteriophage P1 Cin recombinase activated cross over site, junction I, clone pSHI325
    gi|215616|gb|M13320|PP1CIN25I [215616]
    (View GenBank report, FASTA report, ASN.1 report, Graphical view, 1 MEDLINE link, or 7 nucleotide neighbors)
M13318
    Bacteriophage P1 Cin recombinase activated cross over site, left junction, clone pSHI324
    gi|215615|gb|M13318|PP1CIN24L [215615]
    (View GenBank report, FASTA report, ASN.1 report, Graphical view, 1 MEDLINE link, or 1370 nucleotide neighbors)
M13317
    Bacteriophage P1 Cin recombinase activated cross over site, right junction, clone pSHI323
    gi|215614|gb|M13317|PP1CIN23M [215614]
    (View GenBank report, FASTA report, ASN.1 report, Graphical view, 1 MEDLINE link, or 1055 nucleotide neighbors)
M13316
    Bacteriophage P1 Cin recombinase activated cross over site, left junction, clone pSHI323
    gi|215613|gb|M13316|PP1CIN23L [215613]
    (View GenBank report, FASTA report, ASN.1 report, Graphical view, 1 MEDLINE link, or 7 nucleotide neighbors)
M13315
    Bacteriophage P1 Cin recombinase activated cross over site, right junction, clone pSHI322
    gi|215612|gb|M13315|PP1CIN22R [215612]
    (View GenBank report, FASTA report, ASN.1 report, Graphical view, 1 MEDLINE link, or 7 nucleotide neighbors)

TABLE 11-continued

SEQUENCE INFORMATION FOR PHAGES MATCHING WITH TABLE 1

M13314
    Bacteriophage P1 Cin recombinase activated cross over site, left junction, clone pSHI322
    gi|215611|gb|M13314|PP1CIN22L [215611]
    (View GenBank report, FASTA report, ASN.1 report, Graphical view, 1 MEDLINE link, or 1401 nucleotide neighbors)
M13313
    Bacteriophage P1 Cin recombinase activated cross over site, right junction, clone pSHI321
    gi|215610|gb|M13313|PP1CIN21R [215610]
    (View GenBank report, FASTA report, ASN.1 report, Graphical view, 1 MEDLINE link, or 7 nucleotide neighbors)
M13312
    Bacteriophage P1 Cin recombinase activated cross over site, left junction, clone pSHI321
    gi|215609|gb|M13312|PP1CIN21L [215609]
    (View GenBank report, FASTA report, ASN.1 report, Graphical view, 1 MEDLINE link, or 1058 nucleotide neighbors)
M16568
    Bacteriophage P1 c4 repressor gene, complete cds
    gi|215603|gb|M16568|PP1C4 [215603]
    (View GenBank report, FASTA report, ASN.1 report, Graphical view, 1 MEDLINE link, 1 protein link, or 4 nucleotide neighbors)
M13326
    Bacteriophage P1 Cin recombinase activated cross over site, junction III, clone pSHI326
    gi|215602|gb|M13326|PP1C26III [215602]
    (View GenBank report, FASTA report, ASN.1 report, Graphical view, 1 MEDLINE link, or 1192 nucleotide neighbors)
M13322
    Bacteriophage P1 Cin recombinase activated cross over site, junction III, clone pSHI325
    gi|215601|gb|M13322|PP1C25III [215601]
    (View GenBank report, FASTA report, ASN.1 report, Graphical view, 1 MEDLINE link, or 1231 nucleotide neighbors)
J05651
    Bacteriophage P1 modulator protein (bof) gene, complete cds
    gi|215598|gb|J05651|PP1BOFY1 [215598]
    (View GenBank report, FASTA report, ASN.1 report, Graphical view, 1 MEDLINE link, 1 protein link, or 3 nucleotide neighbors)
M33224
    Bacteriophage P1 regulatory protein (bof) gene, complete cds
    gi|215596|gb|M33224|PP1BOFFO [215596]
    (View GenBank report, FASTA report, ASN.1 report, Graphical view, 1 MEDLINE link, 1 protein link, or 3 nucleotide neighbors)
M10288
    *E.coli*/bacteriophage P1 loxR recombination site
    gi|146647|gb|M10288|ECOLOXR [146647]
    (View GenBank report, FASTA report, ASN.1 report, Graphical view, 1 MEDLINE link, or 3 nucleotide neighbors)
M10289
    *E.coli*/bacteriophage P1 loxL recombination site
    gi|146646|gb|M10289|ECOLOXL [146646]
    (View GenBank report, FASTA report, ASN.1 report, Graphical view, 1 MEDLINE link, or 2 nucleotide neighbors)
M10290
    *E.coli* loxB site, which can recombine with bacteriophage P1 loxP site
    gi|146645|gb|M10290|ECOLOXB [146645]
    (View GenBank report, FASTA report, ASN.1 report, Graphical view, 1 MEDLINE link, or 2 nucleotide neighbors)
M10287
    Bacteriophage P1 loxP X loxP recombination site
    gi|215627|gb|M10287|PP1LOXPX [215627]
    (View GenBank report, FASTA report, ASN.1 report, Graphical view, 1 MEDLINE link, or 13 nucleotide neighbors)
M74046
    Bacteriophage P1 pacA and pacB genes, complete cds
    gi|215634|gb|M74046|PP1PACAB [215634]
    (View GenBank report, FASTA report, ASN.1 report, Graphical view, 1 MEDLINE link, or 2 protein links)
M95666
    Bacteriophage P1 gene 10, doc and phd genes, complete cds
    gi|463276|gb|M95666|PP1PHDDOC [463276]
    (View GenBank report, FASTA report, ASN.1 report, Graphical view, 2 MEDLINE links, 4 protein links, or 1 nucleotide neighbor)
M25604
    Bacteriophage Q-beta mutated autonomously replicating sequence MDV1 RNA fragment
    gi|556359|gb|M25604|PQBARSMUT [556359]
    (View GenBank report, FASTA report, ASN.1 report, Graphical view, 1 MEDLINE link, or 8 nucleotide neighbors)
V00643
    first half of the phage Q-beta gene for coat protein
    gi|15088|emb|V00643|LEQBET [15088]
    (View GenBank report, FASTA report, ASN.1 report, Graphical view, 1 MEDLINE link, 1 protein link, or 4 nucleotide neighbors)
M25167
    Bacteriophage Q-beta RNA fragment recovered from replicase binding complex
    gi|556362|gb|M25167|PQBREPLICB [556362]
    (View GenBank report, FASTA report, ASN.1 report, Graphical view, 1 MEDLINE link, or 2 nucleotide neighbors)
M24876
    Bacteriophage Q-beta replicase RNA, 5' end
    gi|556360|gb|M24876|PQBREPLICA [556360]
    (View GenBank report, FASTA report, ASN.1 report, Graphical view, 1 MEDLINE link, 1 protein link, or 4 nucleotide neighbors)

TABLE 11-continued

SEQUENCE INFORMATION FOR PHAGES MATCHING WITH TABLE 1

M25444
    Synthetic bacteriophage Q-beta DNA
    gi|209118|gb|M25444|SYNPQBTERM [209118]
    (View GenBank report, FASTA report, ASN.1 report, Graphical view, 1 MEDLINE link, or 8 nucleotide neighbors)
M25463
    Bacteriophage Q-beta self-replicating microvariant (+) RNA
    gi|532489|gb|M25463|PQBMVSRRNA [532489]
    (View GenBank report, FASTA report, ASN.1 report, Graphical view, or 1 MEDLINE link)
M25014
    Bacteriophage Q-beta RNA replicase gene, 5' end, and maturation protein gene, 3' end
    gi|294316|gb|M25014|PQBREPLC [294316]
    (View GenBank report, FASTA report, ASN.1 report, Graphical view, 1 MEDLINE link, 2 protein links, or 2 nucleotide neighbors)
M25065
    Bacteriophage Q-beta RNA sequence with putative stem loop
    gi|294315|gb|M25065|PQBLOOP [294315]
    (View GenBank report, FASTA report, ASN.1 report, Graphical view, 1 MEDLINE link, or 3 nucleotide neighbors)
M10265
    Bacteriophage Q-beta RNA molecule with the ability to replicate extracellularly
    gi|215726|gb|M10265|PQBRNA [215726]
    (View GenBank report, FASTA report, ASN.1 report, Graphical view, 1 MEDLINE link, or 8 nucleotide neighbors)
M24815
    Bacteriophage Q-beta specified replicase subunit RNA,
    gi|215725|gb|M24815|PQBREPL [215725]
    (View GenBank report, FASTA report, ASN.1 report, Graphical view, 1 MEDLINE link, or 4 nucleotide neighbors)
M25461
    Bacteriophage Q-beta plus-strand RNA, 5' terminus
    gi|215724|gb|M25461|PQBPS5E [215724]
    (View GenBank report, FASTA report, ASN.1 report, or Graphical view)
M25462
    Bacteriophage Q-beta plus-strand RNA, 3' terminus
    gi|215723|gb|M25462|PQBPS3E [215723]
    (View GenBank report, FASTA report, ASN.1 report, Graphical view, or 8 nucleotide neighbors)
M24871
    Bacteriophage Q-beta nanovariant WSIII RNA
    gi|215722|gb|M24871|PQBNVWSIC [215722]
    (View GenBank report, FASTA report, ASN.1 report, Graphical view, 1 MEDLINE link, or 2 nucleotide neighbors)
M24870
    Bacteriophage Q-beta nanovariant WSII RNA
    gi|215721|gb|M24870|PQBNVWSIB [215721]
    (View GenBank report, FASTA report, ASN.1 report, Graphical view, 1 MEDLINE link, or 2 nucleotide neighbors)
M24869
    Bacteriophage Q-beta nanovariant WSI RNA
    gi|215720|gb|M24869|PQBNVWSIA [215720]
    (View GenBank report, FASTA report, ASN.1 report, Graphical view, 1 MEDLINE link, or 2 nucleotide neighbors)
M10495
    Coliphage Q-beta MDV-1(+) RNA
    gi|215719|gb|M10495|PQBMDV1A [215719]
    (View GenBank report, FASTA report, ASN.1 report, Graphical view, 1 MEDLINE link, or 10 nucleotide neighbors)
J02484
    bacteriophage qbeta coat protein cistron first half
    gi|215717|gb|J02484|PQBCP5 [215717]
    (View GenBank report, FASTA report, ASN.1 report, Graphical view, 1 MEDLINE link, 1 protein link, or 4 nucleotide neighbors)
M57754
    Bacteriophage Q-beta minus strand RNA, 5' terminus
    gi|215716|gb|M57754|PQBBMS5E [215716]
    (View GenBank report, FASTA report, ASN.1 report, Graphical view, or 8 nucleotide neighbors)
M24297
    Bacteriophage Q-beta 5'-terminal region of the minus strand
    gi|215715|gb|M24297|PQB5END [215715]
    (View GenBank report, FASTA report, ASN.1 report, Graphical view, 1 MEDLINE link, or 8 nucleotide neighbors)
M10695
    Bacteriophage Q-beta, MDV-1 RNA
    gi|215714|gb|M10695|PQB1IR [215714]
    (View GenBank report, FASTA report, ASN.1 report, Graphical view, 2 MEDLINE links, or 12 nucleotide neighbors)
M24827
    Bacteriophage R17 A protein gene, 5' end
    gi|216078|gb|M24827|R17RNACIS [216078]
    (View GenBank report, FASTA report, ASN.1 report, Graphical view, 1 MEDLINE link, or 5 nucleotide neighbors)
M24829
    Bacteriophage R17 coat protein gene, 5' end
    gi|216075|gb|M24829|R17CP5 [216075]
    (View GenBank report, FASTA report, ASN.1 report, Graphical view, 1 MEDLINE link, or 5 nucleotide neighbors)
J02488
    bacteriophage r17 rna synthetase initiation site
    gi|216080|gb|J02488|R17RNASYN [216080]
    (View GenBank report, FASTA report, ASN.1 report, Graphical view, 3 MEDLINE links, 2 protein links, or 6 nucleotide neighbors)

TABLE 11-continued

SEQUENCE INFORMATION FOR PHAGES MATCHING WITH TABLE 1

J02487
    bacteriophage r17 coat protein initiation site
    gi|216073|gb|J02487|R17COATP [216073]
    (View GenBank report, FASTA report, ASN.1 report, Graphical view, or 1 MEDLINE link)
J02486
    bacteriophage r17 a protein initiation site
    gi|216071|gb|J02486|R17APROT [216071]
    (View GenBank report, FASTA report, ASN.1 report, Graphical view, or 1 MEDLINE link)
M24826
    Bacteriophage R17 coat protein RNA fragment
    gi|216077|gb|M24826|R17CPRAA [216077]
    (View GenBank report, FASTA report, ASN.1 report, Graphical view, 1 MEDLINE link, or 7 nucleotide neighbors)
M24296
    Bacteriophage R17 3'-terminal fragment A RNA
    gi|216070|gb|M24296|R173TFA [216070]
    (View GenBank report, FASTA report, ASN.1 report, Graphical view, 1 MEDLINE link, or 9 nucleotide neighbors)
1TFN
    structure refinement for a 24-nucleotide rna hairpin, nmr, minimized average
    structure ribonucleic acid, hairpin, bacteriophage r17 mol_id: 1; molecule: r17c; chain: null; engineered: yes
    gi|1942336|pdb|1TFN| [1942336]
    (View GenBank report, FASTA report, ASN.1 report, Graphical view, or 1 structure link)
1RPEA
    rna (5'-d(gpgpgpapcpupgpapcpgpapupcpapcpgp cpapgpupcpupapu-3') (24-mer rna
    hairpin coat protein binding site for bacteriophage r17) (nmr, minimized average structure)
    gi|1421020|pdb|1RHT| [1421020]
    (View GenBank report, FASTA report, ASN.1 report, Graphical view, or 1 structure link)
M14428
    Bacteriophage S13 circular DNA, complete genome
    gi|216089|gb|M14428|S13CG [216089]
    (View GenBank report, FASTA report, ASN.1 report, Graphical view, 2 MEDLINE links, 12 protein links, 26 nucleotide neighbors,
    or 1 genome link)
J05393
    Bacteriophage T1 DNA N-6-adenine-methyltransferase (M.T1) gene, complete cds
    gi|166163|gb|J05393|BT1NAMTA [166163]
    (View GenBank report, FASTA report, ASN.1 report, Graphical view, 1 MEDLINE link, or 2 protein links)
L46845
    Bacteriophage T2 frd3, frd2 genes, complete cds
    gi|951387|gb|L46845|PT2FRD32G [951387]
    (View GenBank report, FASTA report, ASN.1 report, Graphical view, 2 protein links, or 17 nucleotide neighbors)
L43611
    Bacteriophage T2 fibritin (wac) gene, complete cds
    gi|903869|gb|L43611|PT2WAC [903869]
    (View GenBank report, FASTA report, ASN.1 report, Graphical view, 1 protein link, or 4 nucleotide neighbors)
M24812
    Bacteriophage T2 secondary structure RNA sequence
    gi|215796|gb|M24812|PT2RNA [215796]
    (View GenBank report, FASTA report, ASN.1 report, Graphical view, 1 MEDLINE link, or 4 nucleotide neighbors)
M22342
    Bacteriophage T2 DNA-(adenine-N6)methyltransferase (dam) gene, complete cds
    gi|215792|gb|M22342|PT2DAM [215792]
    (View GenBank report, FASTA report, ASN.1 report, Graphical view, 1 MEDLINE link, 1 protein link, or 2 nucleotide neighbors)
S57515
    orf 61.2 {intergenic region between 41 and 61} [bacteriophage T2, Genomic, 323 nt]
    gi|298524|gb|S57515|S57515 [298524]
    (View GenBank report, FASTA report, ASN.1 report, Graphical view, 1 MEDLINE link, or 1 protein link)
X05312
    Bacteriophage T2 gene 38 for receptor recognizing protein
    gi|15197|emb|X05312|MYT2G38 [15197]
    (View GenBank report, FASTA report, ASN.1 report, Graphical view, 1 MEDLINE link, or 1 protein link)
X04442
    Bacteriophage T2 gene 37 for receptor recognizing protein
    gi|15195|emb|X04442|MYT2G37 [15195]
    (View GenBank report, FASTA report, ASN.1 report, Graphical view, 1 MEDLINE link, or 1 protein link)
X12460
    Bacteriophage T2 gene 32 mRNA for single-stranded DNA binding protein
    gi|15192|emb|X12460|MYT2G32 [15192]
    (View GenBank report, FASTA report, ASN.1 report, Graphical view, 1 MEDLINE link, 2 protein links, or 14 nucleotide neighbors)
X57797
    Bacteriophage T2 gene for gp12
    gi|14875|emb|X56555|BT2GP12 [14875]
    (View GenBank report, FASTA report, ASN.1 report, Graphical view, 1 protein link, or 2 nucleotide neighbors)
X01755
    Bacteriophage T2 tail fiber gene 36
    gi|15189|emb|X01755|MYT2F36 [15189]
    (View GenBank report, FASTA report, ASN.1 report, Graphical view, 1 MEDLINE link, 2 protein links, or 1 nucleotide neighbor)

TABLE 11-continued

SEQUENCE INFORMATION FOR PHAGES MATCHING WITH TABLE 1

M14784
    Bacteriophage T3 strain amNG220B right end, tail fiber protein, lysis protein and DNA packaging proteins, complete cds
    gi|215810|gb|M14784|PT3RE [215810]
    (View GenBank report, FASTA report, ASN.1 report, Graphical view, 1 MEDLINE link, 9 protein links, or 10 nucleotide neighbors)
SEG_PT3RNAPOL
    Bacteriophage T3 RNA polymerase III gene, 5' end
    gi|710559|gb||SEG_PT3RNAPOL [710559]
    (View GenBank report, FASTA report, ASN.1 report, Graphical view, 1 MEDLINE link, 2 protein links, or 2 nucleotide neighbors)
M22610
    Bacteriophage T3 RNA polymerase III gene, 3' end
    gi|340722|gb|M22610|PT3RNAPOL2 [340722]
    (View GenBank report, FASTA report, ASN.1 report, or Graphical view)
M22609
    Bacteriophage T3 RNA polymerase III gene, 5' end
    gi|340721|gb|M22609|PT3RNAPOL1 [340721]
    (View GenBank report, FASTA report, ASN.1 report, or Graphical view)
X05031
    Bacteriophage T3 gene region 1–2.5 with primary origin of replication
    gi|15719|emb|X05031|POT3ORI [15719]
    (View GenBank report, FASTA report, ASN.1 report, Graphical view, 1 MEDLINE link, 11 protein links, or 5 nucleotide neighbors)
X03964
    Bacteriophage T3 early control region pos. 308–810 from genome left end
    gi|15718|emb|X03964|POT3EP [15718]
    (View GenBank report, FASTA report, ASN.1 report, Graphical view, 2 MEDLINE links, or 20 nucleotide neighbors)
X17255
    Bacteriophage T3 gene 1 to gene 11
    gi|15682|emb|X17255|POT3111G [15682]
    (View GenBank report, FASTA report, ASN.1 report, Graphical view, 4 MEDLINE links, 36 protein links, 17 nucleotide neighbors,
    or 1 genome link)
X15840
    Phage T3 gene 10
    gi|15625|emb|X15840|PODT3G10 [15625]
    (View GenBank report, FASTA report, ASN.1 report, Graphical view, 1 MEDLINE link, or 3 nucleotide neighbors)
X02981
    Bacteriophage T3 gene 1 for RNA polymerase
    gi|15561|emb|X02981|PODOT3P [15561]
    (View GenBank report, FASTA report, ASN.1 report, Graphical view, 1 MEDLINE link, 1 protein link, or 3 nucleotide neighbors)
J02503
    bacteriophage t3 5' end, terminally redundant sequence (trs)
    gi|215816|gb|J02503|PT3TRS1 [215816]
    (View GenBank report, FASTA report, ASN.1 report, or Graphical view)
SEG_PT3TRS
    bacteriophage t3 5' end, terminally redundant sequence (trs)
    gi|215818|gb||SEG_PT3TRS [215818]
    (View GenBank report, FASTA report, ASN.1 report, Graphical view, or 1 MEDLINE link)
J02504
    bacteriophage t3 3' end, terminally redundant sequence (trs)
    gi|215817|gb|J02504|PT3TRS2 [215817]
    (View GenBank report, FASTA report, ASN.1 report, or Graphical view)
    HYPERLINK http://www.rs.noda.sut.ac.jp/~kunisawa http://www.rs.noda.sut.ac.jp/~kunisawa
    Bacteriophage T4 genomic database compiled by Arisaka et al.
X95646
    Bacteriophage T5 DNA for region 60.5%–71% of the T5 genome
    gi|2791557|emb|AJ001191|BTJ001191 [2791557]
    (View GenBank report, FASTA report, ASN.1 report, Graphical view, 7 MEDLINE links, 12 protein links, or 6 nucleotide neighbors)
X56847
    Bacteriophage T5 genomic region encoding early genes D10–D15
    gi|15407|emb|X12930|MYT5D10 [15407]
    (View GenBank report, FASTA report, ASN.1 report, Graphical view, 1 MEDLINE link, 5 protein links, or 4 nucleotide neighbors)
AF039886
    Bacteriophage T5 subclone T5.5.3r5.18r, single pass sequence, genomic survey sequence
    gi|2811154|gb|AF039886|AF039886 [2811154]
    (View GenBank report, FASTA report, ASN.1 report, or Graphical view)
AF039885
    Bacteriophage T5 subclone T5.40f, 41f, single pass sequence, genomic survey sequence
    gi|2811153|gb|AF039885|AF039885 [2811153]
    (View GenBank report, FASTA report, ASN.1 report, or Graphical view)
AF039884
    Bacteriophage T5 subclone T5.26.fr, single pass sequence, genomic survey sequence
    gi|2811152|gb|AF039884|AF039884 [2811152]
    (View GenBank report, FASTA report, ASN.1 report, or Graphical view)
AF039883
    Bacteriophage T5 subclone 10-T5.5.7F, single pass sequence, genomic survey sequence
    gi|2811151|gb|AF039883|AF039883 [2811151]
    (View GenBank report, FASTA report, ASN.1 report, or Graphical view)

TABLE 11-continued

SEQUENCE INFORMATION FOR PHAGES MATCHING WITH TABLE 1

AF039882
    Bacteriophage T5 subclone 41-T5.5.4BF, single pass sequence, genomic survey sequence
    gi|2811150|gb|AF039882|AF039882 [2811150]
    (View GenBank report, FASTA report, ASN.1 report, or Graphical view)
AF039881
    Bacteriophage T5 subclone 39-T5.5.4aF, single pass sequence, genomic survey sequence
    gi|2811149|gb|AF039881|AF039881 [2811149]
    (View GenBank report, FASTA report, ASN.1 report, Graphical view, or 1 nucleotide neighbor)
AF039880
    Bacteriophage T5 subclone 19-T5.7.2r, single pass sequence, genomic survey sequence
    gi|2811148|gb|AF039880|AF039880 [2811148]
    (View GenBank report, FASTA report, ASN.1 report, or Graphical view)
AF039879
    Bacteriophage T5 subclone 18-T5.7.2F, single pass sequence, genomic survey sequence
    gi|2811147|gb|AF039879|AF039879 [2811147]
    (View GenBank report, FASTA report, ASN.1 report, or Graphical view)
AF039878
    Bacteriophage T5 subclone 11-T5.5.7R, single pass sequence, genomic survey sequence
    gi|2811146|gb|AF039878|AF039878 [2811146]
    (View GenBank report, FASTA report, ASN.1 report, Graphical view, or 2 nucleotide neighbors)
AF039877
    Bacteriophage T5 subclone T5.4FR, single pass sequence, genomic survey sequence
    gi|2811145|gb|AF039877|AF039877 [2811145]
    (View GenBank report, FASTA report, ASN.1 report, or Graphical view)
AF039876
    Bacteriophage T5 subclone 22-T5.16R, single pass sequence, genomic survey sequence
    gi|2811144|gb|AF039876|AF039876 [2811144]
    (View GenBank report, FASTA report, ASN.1 report, or Graphical view)
AF039875
    Bacteriophage T5 subclone 21-T5.16R, single pass sequence, genomic survey sequence
    gi|2811143|gb|AF039875|AF039875 [2811143]
    (View GenBank report, FASTA report, ASN.1 report, or Graphical view)
AF039874
    Bacteriophage T5 subclone 21-T5.16F, single pass sequence, genomic survey sequence
    gi|2811142|gb|AF039874|AF039874 [2811142]
    (View GenBank report, FASTA report, ASN.1 report, or Graphical view)
AF039873
    Bacteriophage T5 subclone 09-T5.6F, single pass sequence, genomic survey sequence
    gi|2811141|gb|AF039873|AF039873 [2811141]
    (View GenBank report, FASTA report, ASN.1 report, or Graphical view)
AF039872
    Bacteriophage T5 subclone 09-T5.6R, single pass sequence, genomic survey sequence
    gi|2811140|gb|AF039872|AF039872 [2811140]
    (View GenBank report, FASTA report, ASN.1 report, Graphical view, or 2 nucleotide neighbors)
AF039871
    Bacteriophage T5 subclone 04-T5.26.R, single pass sequence, genomic survey sequence
    gi|2811139|gb|AF039871|AF039871 [2811139]
    (View GenBank report, FASTA report, ASN.1 report, or Graphical view)
AF039870
    Bacteriophage T5 subclone 13-T5.42F, single pass sequence, genomic survey sequence
    gi|2811138|gb|AF039870|AF039870 [2811138]
    (View GenBank report, FASTA report, ASN.1 report, or Graphical view)
X69460
    Bacteriophage T5 ltf gene for L-shaped tail fibers
    gi|15415|emb|X69460|MYT5LTF [15415]
    (View GenBank report, FASTA report, ASN.1 report, Graphical view, 2 MEDLINE links, 1 protein link, or 4 nucleotide neighbors)
X03402
    Bacteriophage T5 D15 gene for 5' exonuclease
    gi|15413|emb|X03402|MYT5EXOG [15413]
    (View GenBank report, FASTA report, ASN.1 report, Graphical view, 1 MEDLINE link, 1 protein link, or 2 nucleotide neighbors)
Z11972
    Bacteriophage T5 tRNA-Tyr, tRNA-Glu, tRNA-Trp, tRNA-Phe, tRNA-Cys and
    tRNA-Asn genes, and ORFs 91aa, 90aa, 42aa and 172aa
    gi|15795|emb|Z11972|T56TRNAG [15795]
    (View GenBank report, FASTA report, ASN.1 report, Graphical view, 1 MEDLINE link, 4 protein links, or 3 nucleotide neighbors)
X03898
    Bacteriophage T5 genes for tRNA-His, -Ser and -Leu
    gi|15786|emb|X03898|STT5RN1 [15786]
    (View GenBank report, FASTA report, ASN.1 report, Graphical view, or 2 MEDLINE links)
X04177
    Bacteriophage T5 gene for transfer RNA-Gln
    gi|15421|emb|X04177|MYT5TRNQ [15421]
    (View GenBank report, FASTA report, ASN.1 report, Graphical view, 1 MEDLINE link, or 2 nucleotide neighbors)
X03899
    Bacteriophage T5 genes for tRNA-Val, -Lys, -fMet, -Pro and -Ile3
    gi|15787|emb|X03899|STT5RN2 [15787]
    (View GenBank report, FASTA report, ASN.1 report, Graphical view, or 1 MEDLINE link)

TABLE 11-continued

SEQUENCE INFORMATION FOR PHAGES MATCHING WITH TABLE 1

X03798
    Bacteriophage T5 gene for tRNA-Asp (GUC)
    gi|15472|emb|X03798|NCT5TRDG [15472]
    (View GenBank report, FASTA report, ASN.1 report, Graphical view, 1 MEDLINE link, 2 protein links, or 2 nucleotide neighbors)
Y00364
    Bacteriophage T5 tRNA gene cluster (27.8%–22.4%)
    gi|15420|emb|Y00364|MYT5TRN [15420]
    (View GenBank report, FASTA report, ASN.1 report, Graphical view, 1 MEDLINE link, or 13 nucleotide neighbors)
X03140
    Bacteriophage T5 DNA with rho-dependent transcription terminator (Hind III-P fragment)
    gi|15417|emb|X03140|MYT5RHO [15417]
    (View GenBank report, FASTA report, ASN.1 report, Graphical view, 1 MEDLINE link, 2 protein links, or 2 nucleotide neighbors)
Z35070
    Bacteriophage T6 DNA
    gi|535228|emb|Z35074|MYEREGBT6 [535228]
    (View GenBank report, FASTA report, ASN.1 report, Graphical view, 1 MEDLINE link, or 1 protein link)
AF060870
    Coliphage T6 small subunit distal tail fiber (gene 36) gene, partial cds; and large subunit distal tail fiber (gene 37) and tail fiber adhesin (gene 38) genes, complete cds
    gi|3676458|gb|AF052605|AF052605 [3676458]
    (View GenBank report, FASTA report, ASN.1 report, Graphical view, 3 protein links, or 2 nucleotide neighbors)
Z35072
    Bacteriophage T6 DNA encoding ORF19.1 gene and g19 gene
    gi|535232|emb|Z35072|MYTAILT6 [535232]
    (View GenBank report, FASTA report, ASN.1 report, Graphical view, 1 MEDLINE link, or 2 protein links)
X12488
    Bacteriophage T6 gene 32 mRNA for single-stranded DNA binding protein
    gi|15843|emb|X12488|MYT6G32 [15843]
    (View GenBank report, FASTA report, ASN.1 report, Graphical view, 1 MEDLINE link, 1 protein link, or 14 nucleotide neighbors)
Z78095
    Bacteriophage T6 DNA (1506 bp)
    gi|1488562|emb|Z78095|BPHZ78095 [1488562]
    (View GenBank report, FASTA report, ASN.1 report, Graphical view, 1 protein link, or 4 nucleotide neighbors)
Z35079
    Bacteriophage T6 DNA for Ip5, Ip6
    gi|535215|emb|Z35079|MY57BT6 [535215]
    (View GenBank report, FASTA report, ASN.1 report, Graphical view, 1 MEDLINE link, 2 protein links, or 1 nucleotide neighbor)
X68725
    *E.coli* bacteriophage T6 gene for beta-glucosyl-HMC-alpha-glucosyl-transferase
    gi|296439|emb|X68725|ECT6 [296439]
    (View GenBank report, FASTA report, ASN.1 report, Graphical view, 1 MEDLINE link, 3 protein links, or 1 nucleotide neighbor)
X69894
    Bacteriophage T6 alt gene for ADP-Ribosyltransferase
    gi|15422|emb|X69894|MYT6ADP [15422]
    (View GenBank report, FASTA report, ASN.1 report, Graphical view, 1 MEDLINE link, 1 protein link, or 1 nucleotide neighbor)
L46846
    Bacteriophage T6 frd3, frd2 genes, complete cds
    gi|951390|gb|L46846|PT6FRD32G [951390]
    (View GenBank report, FASTA report, ASN.1 report, Graphical view, or 2 protein links)
M27738
    Bacteriophage T6 translational repressor protein (regA), complete cds
    gi|215993|gb|M27738|PT6REGA [215993]
    (View GenBank report, FASTA report, ASN.1 report, Graphical view, 1 MEDLINE link, 1 protein link, or 5 nucleotide neighbors)
M38465
    Bacteriophage T6 DNA ligase gene, complete cds
    gi|215991|gb|M38465|PT6LIG55 [215991]
    (View GenBank report, FASTA report, ASN.1 report, Graphical view, 1 MEDLINE link, 1 protein link, or 2 nucleotide neighbors)
V01146
    Genome of bacteriophage T7
    gi|431187|emb|V01146|T7CG [431187]
    (View GenBank report, FASTA report, ASN.1 report, Graphical view, 13 MEDLINE links, 60 protein links, 105 nucleotide neighbors, or 1 genome link)
X60322
    Bacteriophage alpha3 genes A, B, K, C, D, E, J, F, G, H
    gi|14775|emb|X60322|BACALPHA [14775]
    (View GenBank report, FASTA report, ASN.1 report, Graphical view, 1 MEDLINE link, 10 protein links, 22 nucleotide neighbors, or 1 genome link)
X13332
    Bacteriophage alpha3 DNA for origin of replication
    gi|15093|emb|X13332|MIA3ORPL [15093]
    (View GenBank report, FASTA report, ASN.1 report, Graphical view, or 1 MEDLINE link)
X12611
    Bacteriophage alpha3 gene for protein A part, finger domain
    gi|15092|emb|X12611|MIA3AFIN [15092]
    (View GenBank report, FASTA report, ASN.1 report, Graphical view, 1 MEDLINE link, 1 protein link, or 6 nucleotide neighbors)

TABLE 11-continued

SEQUENCE INFORMATION FOR PHAGES MATCHING WITH TABLE 1

X15721
    Bacteriophage alpha3 deletion mutation DNA for the origin region (-ori) of replication
    gi|14774|emb|X15721|BA3DMOR9 [14774]
    (View GenBank report, FASTA report, ASN.1 report, Graphical view, 1 MEDLINE link, or 11 nucleotide neighbors)
X15720
    Bacteriophage alpha3 deletion mutant DNA for the origin region (-ori) of replication
    gi|14773|emb|X15720|BA3DMOR8 [14773]
    (View GenBank report, FASTA report, ASN.1 report, Graphical view, 1 MEDLINE link, or 1 nucleotide neighbor)
X15719
    Bacteriophage alpha3 insertion mutant DNA for the origin region (-ori) of replication
    gi|14772|emb|X15719|BA3DMOR7 [14772]
    (View GenBank report, FASTA report, ASN.1 report, Graphical view, 1 MEDLINE link, or 10 nucleotide neighbors)
X15718
    Bacteriophage alpha3 deletion mutation DNA for origin region (-ori) of replication
    gi|14771|emb|X15718|BA3DMOR6 [14771]
    (View GenBank report, FASTA report, ASN.1 report, Graphical view, 1 MEDLINE link, or 11 nucleotide neighbors)
X15717
    Bacteriophage alpha3 deletion mutant DNA for origin region (-ori) of replication
    gi|14770|emb|X15717|BA3DMOR5 [14770]
    (View GenBank report, FASTA report, ASN.1 report, Graphical view, 1 MEDLINE link, or 9 nucleotide neighbors)
X15716
    Bacteriophage alpha3 deletion mutant DNA for origin region (-ori) of replication
    gi|14769|emb|X15716|BA3DMOR4 [14769]
    (View GenBank report, FASTA report, ASN.1 report, Graphical view, 1 MEDLINE link, or 10 nucleotide neighbors)
X15715
    Bacteriophage alpha3 deletion mutant DNA for origin region (-ori) of of replication
    gi|14768|emb|X15715|BA3DMOR3 [14768]
    (View GenBank report, FASTA report, ASN.1 report, Graphical view, 1 MEDLINE link, or 11 nucleotide neighbors)
X15714
    Bacteriophage alpha3 deletion mutant DNA for origin region (-ori) of replication
    gi|14767|emb|X15714|BA3DMOR2 [14767]
    (View GenBank report, FASTA report, ASN.1 report, Graphical view, 1 MEDLINE link, or 11 nucleotide neighbors)
X15713
    Bacteriophage alpha3 deletion mutant DNA for the origin region (-ori) of replication
    gi|14766|emb|X15713|BA3DMOR1 [14766]
    (View GenBank report, FASTA report, ASN.1 report, Graphical view, 1 MEDLINE link, or 11 nucleotide neighbors)
X62059
    Bacteriophage alpha3 origin of cDNA synthesis (oriGA)
    gi|14763|emb|X62059|AL3ORIGA [14763]
    (View GenBank report, FASTA report, ASN.1 report, Graphical view, 1 MEDLINE link, or 13 nucleotide neighbors)
X62058
    Bacteriophage alpha3 origin of cDNA synthesis (oriAA)
    gi|14762|emb|X62058|AL3ORIAA [14762]
    (View GenBank report, FASTA report, ASN.1 report, Graphical view, 1 MEDLINE link, or 13 nucleotide neighbors)
J02444
    Bacteriophage alpha3 origin of DNA replication
    gi|166103|gb|J02444|AL3ORI [166103]
    (View GenBank report, FASTA report, ASN.1 report, Graphical view, 1 MEDLINE link, 2 protein links, or 12 nucleotide neighbors)
M25640
    Bacteriophage alpha-3 H protein gene, complete cds
    gi|166101|gb|M25640|AL3HP [166101]
    (View GenBank report, FASTA report, ASN.1 report, Graphical view, 1 MEDLINE link, 1 protein link, or 13 nucleotide neighbors)
M10631
    Bacteriophage alpha-3 cleavage site for phage phi-X174 gene A protein
    gi|166099|gb|M10631|AL3CSA [166099]
    (View GenBank report, FASTA report, ASN.1 report, Graphical view, 1 MEDLINE link, 1 protein link, or 3 nucleotide neighbors)
X00774
    Bacteriophage alpha-3 gene J sequence
    gi|15431|emb|X00774|NCBA3J [15431]
    (View GenBank report, FASTA report, ASN.1 report, Graphical view, 1 MEDLINE link, 3 protein links, or 2 nucleotide neighbors)
M25640
    Bacteriophage alpha-3 H protein gene, complete cds
    gi|166101|gb|M25640|AL3HP [166101]
    (View GenBank report, FASTA report, ASN.1 report, Graphical view, 1 MEDLINE link, 1 protein link, or 13 nucleotide neighbors)
M10631
    Bacteriophage alpha-3 cleavage site for phage phi-X174 gene A protein
    gi|166099|gb|M10631|AL3CSA [166099]
    (View GenBank report, FASTA report, ASN.1 report, Graphical view, 1 MEDLINE link, 1 protein link, or 3 nucleotide nieghbors)
J02459
    Bacteriophage lambda, complete genome
    gi|215104|gb|J02459|LAMCG [215104]
    (View GenBank report, FASTA report, ASN.1 report, Graphical view, 87 MEDLINE links, 67 protein links, 190 nucleotide neighbors, or 1 genome link)

TABLE 11-continued

SEQUENCE INFORMATION FOR PHAGES MATCHING WITH TABLE 1

J02482
    Bacteriophage phi-X174, complete genome
    gi|216019|gb|J02482|PX1CG [216019]
    (View GenBank report, FASTA report, ASN.1 report, Graphical view, 23 MEDLINE links, 11 protein links, 26 nucleotide neighbors, or 1 genome link)
J02454
    Bacteriophage G4, complete genome
    gi|215415|gb|J02454|PG4CG [215415]
    (View GenBank report, FASTA report, ASN.1 report, Graphical view, 6 MEDLINE links, 11 protein links, 20 nucleotide neighbors, or 1 genome link)
X60323
    Bacteriophage phiK complete genome
    gi|1478118|emb|X60323|BPHIKCG [1478118]
    (View GenBank report, FASTA report, ASN.1 report, Graphical view, 10 protein links, 18 nucleotide neighbors, or 1 genome link)
L42820
    Bacteriophage BF23 tail protein (hrs) gene, complete cds
    gi|1048680|gb|L42820|BBFHRS [1048680]
    (View GenBank report, FASTA report, ASN.1 report, Graphical view, 1 MEDLINE link, 1 protein link, or 1 nucleotide neighbor)
X54455
    Bacteriophage BF23 gene 17 and gene 18
    gi|14797|emb|X54455|BF231718G [14797]
    (View GenBank report, FASTA report, ASN.1 report, Graphical view, 2 protein links, or 2 nucleotide neighbors)
M37097
    Bacteriophage BF23 DNA, right end of terminal repetition
    gi|166115|gb|M37097|BBFRIGH [166115]
    (View GenBank report, FASTA report, ASN.1 report, Graphical view, 1 MEDLINE link, or 2 nucleotide neighbors)
M37096
    Bacteriophage BF23 DNA, left end of terminal repetition
    gi|166114|gb|M37096|BBFLEFT [166114]
    (View GenBank report, FASTA report, ASN.1 report, Graphical view, 1 MEDLINE link, or 1 nucleotide neighbor)
M37095
    Bacteriophage BF23 A2–A3 gene, complete cds, and A1 gene, 5' end
    gi|166110|gb|M37095|BBFA2A3 [166110]
    (View GenBank report, FASTA report, ASN.1 report, Graphical view, 2 MEDLINE links, 3 protein links, or 1 nucleotide neighbor)
AF056281
    Bacteriophage BF23 clone bf23.mac5/6.1, genomic survey sequence
    gi|3090930|gb|AF056281|AF056281 [3090930]
    (View GenBank report, FASTA report, ASN.1 report, or Graphical view)
AF056280
    Bacteriophage BF23 clone bf23.mac3, genomic survey sequence
    gi|3090929|gb|AF056280|AF056280 [3090929]
    (View GenBank report, FASTA report, ASN.1 report, or Graphical view)
AF056279
    Bacteriophage BF23 clone bf23.mac18/21.34, genomic survey sequence
    gi|3090928|gb|AF056279|AF056279 [3090928]
    (View GenBank report, FASTA report, ASN.1 report, or Graphical view)
AF056278
    Bacteriophage BF23 clone bf23.mac16/19.33, genomic survey sequence
    gi|3090927|gb|AF056278|AF056278 [3090927]
    (View GenBank report, FASTA report, ASN.1 report, or Graphical view)
AF056277
    Bacteriophage BF23 clone bf23.mac16/19-33, genomic survey sequence
    gi|3090926|gb|AF056277|AF056277 [3090926]
    (View GenBank report, FASTA report, ASN.1 report, or Graphical view)
AF056276
    Bacteriophage BF23 clone bf23.mac12/9-9, genomic survey sequence
    gi|3090925|gb|AF056276|AF056276 [3090925]
    (View GenBank report, FASTA report, ASN.1 report, or Graphical view)
AF056275
    Bacteriophage BF23 clone bf23.mac11/14-24, genomic survey sequence
    gi|3090924|gb|AF056275|AF056275 [3090924]
    (View GenBank report, FASTA report, ASN.1 report, or Graphical view)
AF056274
    Bacteriophage BF23 clone bf23.57r64r, genomic survey sequence
    gi|3090923|gb|AF056274|AF056274 [3090923]
    (View GenBank report, FASTA report, ASN.1 report, Graphical view, or 3 nucleotide neighbors)
AF056273
    Bacteriophage BF23 clone bf23.54fr, genomic survey sequence
    gi|3090922|gb|AF056273|AF056273 [3090922]
    (View GenBank report, FASTA report, ASN.1 report, or Graphical view)
AF056272
    Bacteriophage BF23 clone bf23.47fr.mac10/7, genomic survey sequence
    gi|3090921|gb|AF056272|AF056272 [3090921]
    (View GenBank report, FASTA report, ASN.1 report, or Graphical view)

TABLE 11-continued

SEQUENCE INFORMATION FOR PHAGES MATCHING WITH TABLE 1

AF056271
    Bacteriophage BF23 clone bf23.23.66r, genomic survey sequence
    gi|3090920|gb|AF056271|AF056271 [3090920]
    (View GenBank report, FASTA report, ASN.1 report, or Graphical view)
AF056270
    Bacteriophage BF23 clone bf23.23.64f, genomic survey sequence
    gi|3090919|gb|AF056270|AF056270 [3090919]
    (View GenBank report, FASTA report, ASN.1 report, or Graphical view)
AF056269
    Bacteriophage BF23 clone bf23.23.60r, genomic survey sequence
    gi|3090918|gb|AF056269|AF056269 [3090918]
    (View GenBank report, FASTA report, ASN.1 report, or Graphical view)
AF056268
    Bacteriophage BF23 clone bf23.23.60f, genomic survey sequence
    gi|3090917|gb|AF056268|AF056268 [3090917]
    (View GenBank report, FASTA report, ASN.1 report, Graphical view, or 1 nucleotide neighbor)
AF056267
    Bacteriophage BF23 clone bf23.23.59r, genomic survey sequence
    gi|3090916|gb|AF056267|AF056267 [3090916]
    (View GenBank report, FASTA report, ASN.1 report, or Graphical view)
AF056266
    Bacteriophage BF23 clone bf23.23.59f, genomic survey sequence
    gi|3090915|gb|AF056266|AF056266 [3090915]
    (View GenBank report, FASTA report, ASN.1 report, or Graphical view)
AF056265
    Bacteriophage BF23 clone bf23.23.56r, genomic survey sequence
    gi|3090914|gb|AF056265|AF056265 [3090914]
    (View GenBank report, FASTA report, ASN.1 report, or Graphical view)
AF056264
    Bacteriophage BF23 clone bf23.23.56f, genomic survey sequence
    gi|3090913|gb|AF056264|AF056264 [3090913]
    (View GenBank report, FASTA report, ASN.1 report, or Graphical view)
AF056263
    Bacteriophage BF23 clone bf23.23.68f55r, genomic survey sequence
    gi|2090912|gb|AF056263|AF056263 [3090912]
    (View GenBank report, FASTA report, ASN.1 report, or Graphical view)
AF056262
    Bacteriophage BF23 clone bf23.23.43fr.66f, genomic survey sequence
    gi|3090911|gb|AF056262|AF056262 [3090911]
    (View GenBank report, FASTA report, ASN.1 report, or Graphical view)
AF056261
    Bacteriophage BF23 clone bf23.23.2fr, genomic survey sequence
    gi|3090910|gb|AF056261|AF056261 [3090910]
    (View GenBank report, FASTA report, ASN.1 report, or Graphical view)
AF056260
    Bacteriophage BF23 clone bf23.23.55.f, genomic survey sequence
    gi|3090909|gb|AF056260|AF056260 [3090909]
    (View GenBank report, FASTA report, ASN.1 report, or Graphical view)
AF056259
    Bacteriophage BF23 clone bf23.23.53.r, genomic survey sequence
    gi|3090908|gb|AF056259|AF056259 [3090908]
    (View GenBank report, FASTA report, ASN.1 report, or Graphical view)
AF056258
    Bacteriophage BF23 clone bf23.23.53.f, genomic survey sequence
    gi|3090907|gb|AF056258|AF056258 [3090907]
    (View GenBank report, FASTA report, ASN.1 report, or Graphical view)
AF056257
    Bacteriophage BF23 clone bf23.23.52.r, genomic survey sequence
    gi|3090906|gb|AF056257|AF056257 [3090906]
    (View GenBank report, FASTA report, ASN.1 report, or Graphical view)
AF056256
    Bacteriophage BF23 clone bf23.23.52.f, genomic survey sequence
    gi|3090905|gb|AF056256|AF056256 [3090905]
    (View GenBank report, FASTA report, ASN.1 report, or Graphical view)
AF056255
    Bacteriophage BF23 clone bf23.23.49.r, genomic survey sequence
    gi|3090904|gb|AF056255|AF056255 [3090904]
    (View GenBank report, FASTA report, ASN.1 report, or Graphical view)
AF056254
    Bacteriophage BF23 clone bf23.23.49.f, genomic survey sequence
    gi|3090903|gb|AF056254|AF056254 [3090903]
    (View GenBank report, FASTA report, ASN.1 report, or Graphical view)
AF056253
    Bacteriophage BF23 clone bf23.23.48.r, genomic survey sequence
    gi|3090902|gb|AF056253|AF056253 [3090902]
    (View GenBank report, FASTA report, ASN.1 report, or Graphical view)

TABLE 11-continued

SEQUENCE INFORMATION FOR PHAGES MATCHING WITH TABLE 1

AF056252
    Bacteriophage BF23 clone bf23.23.48.f, genomic survey sequence
    gi|3090901|gb|AF056252|AF056252 [3090901]
    (View GenBank report, FASTA report, ASN.1 report, or Graphical view)
AF056251
    Bacteriophage BF23 clone bf23.23.44.r, genomic survey sequence
    gi|3090900|gb|AF056251|AF056251 [3090900]
    (View GenBank report, FASTA report, ASN.1 report, or Graphical view)
AF056250
    Bacteriophage BF23 clone bf23.23.41.f, genomic survey sequence
    gi|3090899|gb|AF056250|AF056250 [3090899]
    (View GenBank report, FASTA report, ASN.1 report, or Graphical view)
AF056249
    Bacteriophage BF23 clone bf23.23.22.a.r, genomic survey sequence
    gi|3090898|gb|AF056249|AF056249 [3090898]
    (View GenBank report, FASTA report, ASN.1 report, or Graphical view)
AF056248
    Bacteriophage BF23 clone bf23.23.22.a.f, genomic survey sequence
    gi|3090897|gb|AF056248|AF056248 [3090897]
    (View GenBank report, FASTA report, ASN.1 report, or Graphical view)
AF056247
    Bacteriophage BF23 clone bf23.23.68.r, genomic survey sequence
    gi|3090896|gb|AF056247|AF056247 [3090896]
    (View GenBank report, FASTA report, ASN.1 report, or Graphical view)
Z50114
    Bacteriophage BF23 DNA for putative tail protein gene
    gi|2464952|emb|Z50114|BF23LATE [2464952]
    (View GenBank report, FASTA report, ASN.1 report, Graphical view, or 1 protein link)
D12824
    Bacteriophage BF23 genes for minor tail protein gp24 and major tail protein gp25, complete cds
    gi|520578|dbj|D12824|BBF2TAIL [520578]
    (View GenBank report, FASTA report, ASN.1 report, Graphical view, 1 MEDLINE link, 2 protein links, or 3 nucleotide neighbors)
Z34953
    Bacteriophage K3 ip9, ip7 and ip8 genes
    gi|535261|emb|Z34953|MYK3IP978 [535261]
    (View GenBank report, FASTA report, ASN.1 report, Graphical view, 1 MEDLINE link, 3 protein links, or 1 nucleotide neighbor)
Z35075
    Bacteriophage K3 DNA for Ip3 and Ip4
    gi|535229|emb|Z35075|MYEORF64K [535229]
    (View GenBank report, FASTA report, ASN.1 report, Graphical view, 1 MEDLINE link, or 2 protein links)
X05560
    Bacteriophage K3 gene 38 for receptor recognizing protein
    gi|15112|emb|X05560|MYK3G38 [15112]
    (View GenBank report, FASTA report, ASN.1 report, Graphical view, 1 MEDLINE link, or 1 protein link)
X04747
    Bacteriophage K3 gene 37 for receptor recognizing protein
    gi|15110|emb|X04747|MYK3G37 [15110]
    (View GenBank report, FASTA report, ASN.1 report, Graphical view, 1 MEDLINE link, 1 protein link, or 2 nucleotide neighbors)
X01754
    Bacteriophage K3 tail fiber gene 36
    gi|15108|emb|X01754|MYK3F36 [15108]
    (View GenBank report, FASTA report, ASN.1 report, Graphical view, 1 MEDLINE link, or 2 protein links)
M16812
    Bacteriophage K3 't' lysis gene, complete cds
    gi|215503|gb|M16812|PK3LYST [215503]
    (View GenBank report, FASTA report, ASN.1 report, Graphical view, 1 MEDLINE link, 1 protein link, or 4 nucleotide neighbors)
L46833
    Bacteriophage K3 frd3, frd2 genes, complete cds
    gi|951377|gb|L46833|PK3FRD32G [951377]
    (View GenBank report, FASTA report, ASN.1 report, Graphical view, 2 protein links, or 2 nucleotide neighbors)
L43613
    Bacteriophage K3 fibritin (wac) gene, complete cds
    gi|903861|gb|L43613|PK3WAC [903861]
    (View GenBank report, FASTA report, ASN.1 report, Graphical view, 1 protein link, or 4 nucleotide neighbors)
X01753
    Bacteriophage Ox2 tail fiber gene 36
    gi|15122|emb|X01753|MYOX2F36 [15122]
    (View GenBank report, FASTA report, ASN.1 report, Graphical view, 1 MEDLINE link, 2 protein links, or 1 nucleotide neighbor)
L43612
    Bacteriophage Ox2 fibritin (wac) gene, complete cds
    gi|903848|gb|L43612|OX2WAC [903848]
    (View GenBank report, FASTA report, ASN.1 report, Graphical view, 1 protein link, or 4 nucleotide neighbors)
Z46880
    Bacteriophage OX2 stp gene
    gi|599663|emb|Z46880|BPOX2STP [599663]
    (View GenBank report, FASTA report, ASN.1 report, Graphical view, 1 MEDLINE link, 1 protein link, or 4 nucleotide neighbors)

TABLE 11-continued

SEQUENCE INFORMATION FOR PHAGES MATCHING WITH TABLE 1

X05675
    Bacteriophage Ox2 gene 38 for receptor-recognizing protein and flanking regions
    gi|15124|emb|X05675|MYOX2G38 [15124]
    (View GenBank report, FASTA report, ASN.1 report, Graphical view, 1 MEDLINE link, 3 protein links, or 1 nucleotide neighbor)
M33533
    Bacteriophage RB18 translational repressor protein (regA) and Orf43.1, complete cds
    gi|216083|gb|M33533|RB18REGA [216083]
    (View GenBank report, FASTA report, ASN.1 report, Graphical view, 1 MEDLINE link, 2 protein links, or 2 nucleotide neighbors)
AF033329
    Bacteriophage RB18 single-stranded binding protein (gene 32) gene, partial cds, and 5' region
    gi|2645788|gb|AF033329|AF033329 [2645788]
    (View GenBank report, FASTA report, ASN.1 report, Graphical view, 1 protein link, or 11 nucleotide neighbors)
M86231
    Bacteriophage RB69 gene 62, 3' end; RegA (regA) gene, complete cds
    gi|215354|gb|M86231|P6962REGA [215354]
    (View GenBank report, FASTA report, ASN.1 report, Graphical view, 1 MEDLINE link, 2 protein links, or 1 nucleotide neighbor)
AF033332
    Bacteriophage RB69 single-stranded binding protein (gene 32) gene, partial cds, and 5' region
    gi|2645794|gb|AF033332|AF033332 [2645794]
    (View GenBank report, FASTA report, ASN.1 report, Graphical view, 1 protein link, or 12 nucleotide neighbors)
U34036
    Bacteriophage RB69 DNA polymerase (43) gene, complete cds
    gi|1237125|gb|U34036|BRU34036 [1237125]
    (View GenBank report, FASTA report, ASN.1 report, Graphical view, 1 MEDLINE link, or 1 protein link)
V01145
    Bacteriophage H1 genome fragment Each Thymine given in this sequence represents a HMU-residue
    (HMU = 5-hydroxymethyluracil)
    gi|15557|emb|V01145|PODOH1 [15557]
    (View GenBank report, FASTA report, ASN.1 report, Graphical view, or 1 MEDLINE link)
X05676
    Bacteriophage M1 gene 38 for receptor recognizing protein and flanking regions
    gi|15114|emb|X05676|MYM1G38 [15114]
    (View GenBank report, FASTA report, ASN.1 report, Graphical view, 1 MEDLINE link, 3 protein links, or 1 nucleotide neighbor)
AF034575
    Bacteriophage M1 putative integrase (int) gene, complete cds, and attP region, complete sequence
    gi|2662472|gb|AF034575|AF034575 [2662472]
    (View GenBank report, FASTA report, ASN.1 report, Graphical view, 1 MEDLINE link, or 1 protein link)
AF033321
    Bacteriophage M1 single-stranded binding protein (gene 32) gene, partial cds, and 5' region
    gi|2645772|gb|AF033321|AF033321 [2645772]
    (View GenBank report, FASTA report, ASN.1 report, Graphical view, 1 protein link, or 17 nucleotide neighbors)
X55190
    Bacteriophage TuIa 37 and 38 genes for receptor-recognizing proteins 37 and 38 (respectively), partial cds
    gi|14860|emb|X55190|BPTUIA [14860]
    (View GenBank report, FASTA report, ASN.1 report, Graphical view, 1 MEDLINE link, 2 protein links, or 2 nucleotide neighbors)
AF033334
    Bacteriophage TuIb single-stranded binding protein (gene 32) gene, partial cds, and 5' region
    gi|2645798|gb|AF033334|AF033334 [2645798]
    (View GenBank report, FASTA report, ASN.1 report, Graphical view, or 5 nucleotide neighbors)
X55191
    Bacteriophage TuIb 37 gene for receptor-recognizing protein 37 (partial cds), 38 gene for receptor-recognizing protein 38,
    and t gene (partial cds)
    gi|14863|emb|X55191|BPTUIB [14863]
    (View GenBank report, FASTA report, ASN.1 report, Graphical view, 1 MEDLINE link, 3 protein links, or 3 nucleotide neighbors)
X13065
    Bacteriophage phi80 early region
    gi|14800|emb|X13065|BP80ER [14800]
    (View GenBank report, FASTA report, ASN.1 report, Graphical view, 1 MEDLINE link, 8 protein links, or 6 nucleotide neighbors)
D00360
    Bacteriophage phi80 cor gene
    gi|217782|dbj|D00360|P8O80COR [217782]
    (View GenBank report, FASTA report, ASN.1 report, Graphical view, or 1 protein link)
X01639
    Bacteriophage phi 80 DNA-fragment with replication origin
    gi|15828|emb|X01639|XXPHI80 [15828]
    (View GenBank report, FASTA report, ASN.1 report, Graphical view, 1 MEDLINE link, or 25 nucleotide neighbors)
X04051
    Lambdoid bacteriophage phi 80 int-xis region (integrase-excisionase region)
    gi|15770|emb|X04051|STPHI80X [15770]
    (View GenBank report, FASTA report, ASN.1 report, Graphical view, 1 MEDLINE link, 2 protein links, or 1 nucleotide neighbor)
X06751
    Phage Phi80 DNA for major coat protein
    gi|15768|emb|X06751|STPHI80C [15768]
    (View GenBank report, FASTA report, ASN.1 report, Graphical view, 1 MEDLINE link, 1 protein link, or 11 nucleotide neighbors)

TABLE 11-continued

SEQUENCE INFORMATION FOR PHAGES MATCHING WITH TABLE 1

X75949
    Bacteriophage phi80 DNA for ORF x171.8 and ORF x171.28'
    gi|458811|emb|X75949|ECORF171B [458811]
    (View GenBank report, FASTA report, ASN.1 report, Graphical view, 1 MEDLINE link, 2 protein links, or 28 nucleotide neighbors)
L40418
    Bacteriophage phi-80 gene, complete cds
    gi|1019107|gb|L40418|P80A [1019107]
    (View GenBank report, FASTA report, ASN.1 report, Graphical view, 1 MEDLINE link, or 1 protein link)
M24831
    Bacteriophage phi-80 Tyr-tRNA gene, 3' end
    gi|215363|gb|M24831|P80TGY [215363]
    (View GenBank report, FASTA report, ASN.1 report, Graphical view, 1 MEDLINE link, or 43 nucleotide neighbors)
M10670
    Bacteriophage phi-80 replication origin
    gi|215361|gb|M10670|P80ORI [215361]
    (View GenBank report, FASTA report, ASN.1 report, Graphical view, 1 MEDLINE link, 1 protein link, or 1 nucleotide neighbor)
M24825
    Bacteriophage phi-80 RNA fragment
    gi|215360|gb|M24825|P80M3A [215360]
    (View GenBank report, FASTA report, ASN.1 report, Graphical view, 1 MEDLINE link, or 1 nucleotide neighbor)
M11919
    Bacteriophage phi-80 cI immunity region encoding the N gene
    gi|215358|gb|M11919|P80CI [215358]
    (View GenBank report, FASTA report, ASN.1 report, Graphical view, 1 MEDLINE link, 1 protein link, or 2 nucleotide neighbors)
M10891
    Bacteriophage phi-80 attP site DNA
    gi|215357|gb|M10891|P80ATTP [215357]
    (View GenBank report, FASTA report, ASN.1 report, Graphical view, 1 MEDLINE link, or 1 nucleotide neighbor)
M19473
    Bacteriophage 933J (from *E.coli*) proviral Shiga-like toxin type 1 subunits A and B genes, complete cds
    gi|215072|gb|M19473|J93SLTI [215072]
    (View GenBank report, FASTA report, ASN.1 report, Graphical view, 2 MEDLINE links, 2 protein links, or 20 nucleotide neighbors)
Y10775
    Bacteriophage 933W ileX, stx2A and stx2B genes
    gi|1938206|emb|Y10775|BP933ILEX [1938206]
    (View GenBank report, FASTA report, ASN.1 report, Graphical view, 2 protein links, or 36 nucleotide neighbors)
X83722
    Bacteriophage 933W slt-IIB gene
    gi|1490229|emb|X83722|B933WSLT [1490229]
    (View GenBank report, FASTA report, ASN.1 report, Graphical view, 2 protein links, or 20 nucleotide neighbors)
X07865
    Bacteriophage 933W slt-II gene for Shiga-like toxin typeII subunit A and B
    gi|14892|emb|X07865|BWSLTII [14892]
    (View GenBank report, FASTA report, ASN.1 report, Graphical view, 2 protein links, or 29 nucleotide neighbors)
M16625
    Bacteriophage H19B (from *E.coli*) sltIA and sltIB genes encoding Shiga-like toxin I subunits A and B, complete cds
    gi|215043|gb|M16625|H19BSLT [215043]
    (View GenBank report, FASTA report, ASN.1 report, Graphical view, 1 MEDLINE link, 2 protein links, or 24 nucleotide neighbors)
M17358
    Bacteriophage H19B shiga-like toxin-1 (SLT-1) A and B subunit DNA, complete cds
    gi|215046|gb|M17358|H19BSLTA [215046]
    (View GenBank report, FASTA report, ASN.1 report, Graphical view, 1 MEDLINE link, 2 protein links, or 20 nucleotide neighbors)
U29728
    Bacteriophage N4 single-stranded DNA-binding protein (N4SSB) gene, complete cds
    gi|939708|gb|U29728|BNU29728 [939708]
    (View GenBank report, FASTA report, ASN.1 report, Graphical view, 2 MEDLINE links, or 1 protein link)
J02580
    Bacteriophage PA-2 (*E.coli* porcine strain isolate) Rz gene, 5' end; ORF2, outer membrane porin protein (lc) and ORF1 genes, complete cds
    gi|215366|gb|J02580|PA2LC [215366]
    (View GenBank report, FASTA report, ASN.1 report, Graphical view, 1 MEDLINE link, 4 protein links, or 4 nucleotide neighbors)
U32222
    Bacteriophage 186, complete sequence
    gi|3337249|gb|U32222|B1U32222 [3337249]
    (View GenBank report, FASTA report, ASN.1 report, Graphical view, 6 MEDLINE links, 46 protein links, or 5 nucleotide neighbors)
X51522
    Bacteriophage P4 complete DNA genome
    gi|450916|emb|X51522|MYP4CG [450916]
    (View GenBank report, FASTA report, ASN.1 report, Graphical view, 3 MEDLINE links, 13 protein links, 6 nucleotide neighbors,
    or 1 genome link)
X92588
    Bacteriophage 82 orf33, orf151, orf56, orf96, rus, orf45, and Q genes
    gi|1051111|emb|X92588|BAC82HOLL [1051111]
    (View GenBank report, FASTA report, ASN.1 report, Graphical view, 7 protein links, or 1 nucleotide neighbor)
J02803
    Bacteriophage 82 antitermination protein (Q) gene, complete cds
    gi|215364|gb|J02803|P82Q [215364]
    (View GenBank report, FASTA report, ASN.1 report, Graphical view, 1 MEDLINE link, or 1 protein link)

TABLE 11-continued

SEQUENCE INFORMATION FOR PHAGES MATCHING WITH TABLE 1

U02466
    Bacteriophage HK022 (cro), (cII) and (O) genes, complete cds, (P) gene, partial cds
    gi|407285|gb|U02466|BHU02466 [407285]
    (View GenBank report, FASTA report, ASN.1 report, Graphical view, 1 MEDLINE link, 5 protein links, or 1 nucleotide neighbor)
M26291
    Bacteriophage D108 regulatory DNA-binding protein (ner) gene, complete cds
    gi|166194|gb|M26291|D18NER [166194]
    (View GenBank report, FASTA report, ASN.1 report, Graphical view, 1 MEDLINE link, 1 protein link, or 1 nucleotide neighbor)
M11272
    Bacteriophage D108 left-end DNA
    gi|166193|gb|M11272|D18LEDNA [166193]
    (View GenBank report, FASTA report, ASN.1 report, Graphical view, 1 MEDLINE link, or 2 nucleotide neighbors)
M18902
    Bacteriophage D108 kil gene encoding a replication protein, 3' end; and containing three ORFs, complete cds
    gi|166191|gb|M18902|D18KIL [166191]
    (View GenBank report, FASTA report, ASN.1 report, Graphical view, 1 MEDLINE link, 1 protein link, or 3 nucleotide neighbors)
M10191
    Bacteriophage D108, left end with Mu A protein binding sites L1 and L2
    gi|166190|gb|M10191|D18BSL [166190]
    (View GenBank report, FASTA report, ASN.1 report, Graphical view, 1 MEDLINE link, or 5 nucleotide neighbors)
J02447
    bacteriophage d108 gene a 5' end
    gi|166189|gb|J02447|D18AAA [166189]
    (View GenBank report, FASTA report, ASN.1 report, Graphical view, or 1 MEDLINE link)
V00865
    Bacteriophage D108 fragment from genes A and ner (C-terminus of ner and N-terminus of A)
    gi|15437|emb|V00865|NCD108 [15437]
    (View GenBank report, FASTA report, ASN.1 report, Graphical view, 1 MEDLINE link, or 2 protein links)
X01914
    Bacteriophage IKe gene for DNA binding protein
    gi|14957|emb|X01914|INIKEDBP [14957]
    (View GenBank report, FASTA report, ASN.1 report, Graphical view, 1 MEDLINE link, 1 protein link, or 2 nucleotide neighbors)
AF064539
    Bacteriophage N15, complete genome
    gi|3192683|gb|AF064539|AF064539 [3192683]
    (View GenBank report, FASTA report, ASN.1 report, Graphical view, 2 MEDLINE links, 60 protein links, 26 nucleotide neighbors,
    or 1 genome link)
U02303
    Bacteriophage If1, complete genome
    gi|3676280|gb|U02303|B2U02303 [3676280]
    (View GenBank report, FASTA report, ASN.1 report, Graphical view, 10 protein links, or 1 genome link)
AF007792
    Bacteriophage Mu late morphogenetic region
    gi|3551775|gb|AF007792|AF007792 [3551775]
    (View GenBank report, FASTA report, ASN.1 report, Graphical view, or 1 nucleotide neighbor)
U24159
    Bacteriophage HP1 strain HP1c1, complete genome
    gi|1046235|gb|U24159|BHU24159 [1046235]
    (View GenBank report, FASTA report, ASN.1 report, Graphical view, 6 MEDLINE links, 41 protein links, 8 nucleotide neighbors,
    or 1 genome link)
Z71579
    Bacteriophage S2 type A 5.6 kb DNA fragment
    gi|1679806|emb|Z71579|BPHS1ADNA [1679806]
    (View GenBank report, FASTA report, ASN.1 report, Graphical view, 3 MEDLINE links, 9 protein links, or 9 nucleotide neighbors)
X53238
    Klebsiella sp. bacteriophage K11 gene 1 for RNA polymerase
    gi|14984|emb|X53238|KSK11RPO [14984]
    (View GenBank report, FASTA report, ASN.1 report, Graphical view, 1 MEDLINE link, 1 protein link, or 1 nucleotide neighbor)
X85010
    Bacteriophage A511 ply511 gene
    gi|853748|emb|X85010|BPA511PLY [853748]
    (View GenBank report, FASTA report, ASN.1 report, Graphical view, 1 MEDLINE link, 3 protein links, or 1 nucleotide neighbor)
U29728
    Bacteriophage N4 single-stranded DNA-binding protein (N4SSB) gene, complete cds
    gi|939708|gb|U29728|BNU29728 [939708]
    (View GenBank report, FASTA report, ASN.1 report, Graphical view, 2 MEDLINE links, or 1 protein link)
J02445
    bacteriophage bo1 3'-terminal region rna
    gi|166152|gb|J02445|BO1TR3 [166152]
    (View GenBank report, FASTA report, ASN.1 report, Graphical view, 1 MEDLINE link, or 5 nucleotide neighbors)
L06183
    Bacteriophage L5 (from *Leuconostoc oenos*) genome
    gi|289353|gb|L06183|BL5GENM [289353]
    (View GenBank report, FASTA report, ASN.1 report, Graphical view, or 1 genome link)

TABLE 11-continued

SEQUENCE INFORMATION FOR PHAGES MATCHING WITH TABLE 1

AF074945
    Mycoplasma arthritidis bacteriophage MAV1, complete genome
    gi|3511243|gb|AF074945|AF074945 [3511243]
    (View GenBank report, FASTA report, ASN.1 report, Graphical view, 15 protein links, 3 nucleotide neighbors, or 1 genome link)
L13696
    Bacteriophage L2 (from Mycoplasma), complete genome
    gi|289338|gb|L13696|BL2CG [289338]
    (View GenBank report, FASTA report, ASN.1 report, Graphical view, 3 MEDLINE links, 14 protein links, or 1 genome link)
X80191
    Bacteriophage PP7 mRNA for maturation, coat, lysis and replicase proteins
    gi|517237|emb|X80191|BPP7PR [517237]
    (View GenBank report, FASTA report, ASN.1 report, Graphical view, 1 MEDLINE link, 4 protein links, or 1 genome link)
M19377
    Bacteriophage Pf3 from *Pseudomonas aeruginosa* (New York strain), complete genome
    gi|215380|gb|M19377|PF3COMNY [215380]
    (View GenBank report, FASTA report, ASN.1 report, Graphical view, 1 MEDLINE link, 9 protein links, or 5 nucleotide neighbors)
M11912
    Bacteriophage Pf3 from *Pseudomonas aeruginosa* (Nijmegen strain), complete genome
    gi|215371|gb|M11912|PF3COMN [215371]
    (View GenBank report, FASTA report, ASN.1 report, Graphical view, 1 MEDLINE link, 9 protein links, 5 nucleotide neighbors, or 1 genome link)
V00605
    Bacteriophage Pf1 gene encoding DNA binding protein
    gi|14970|emb|V00605|INOPF1 [14970]
    (View GenBank report, FASTA report, ASN.1 report, Graphical view, 1 protein link, or 1 nucleotide neighbor)
L05626
    Bacteriophage PR4 capsid protein (P6) gene, complete cds
    gi|215735|gb|L05626|PR4P6MAJA [215735]
    (View GenBank report, FASTA report, ASN.1 report, Graphical view, 1 MEDLINE link, 1 protein link, or 1 nucleotide neighbor)
D13409
    Bacteriophage phiCTX (isolated from *Pseudomonas aeruginosa*) cosR, attP, int genes
    gi|217776|dbj|D13409|BPHCOSR [217776]
    (View GenBank report, FASTA report, ASN.1 report, Graphical view, 1 MEDLINE link, 3 protein links, or 3 nucleotide neighbors)
D13408
    Bacteriophage phiCTX (isolated from *Pseudomonas aeruginosa*) cosL, ctx genes
    gi|217775|dbj|D13408|BPHCOSLCTX [217775]
    (View GenBank report, FASTA report, ASN.1 report, Graphical view, 2 MEDLINE links, or 3 nucleotide neighbors)
M24832
    Bacteriophage f2 coat protein gene, partial cds
    gi|166228|gb|M24832|F2CRNACA [166228]
    (View GenBank report, FASTA report, ASN.1 report, Graphical view, 1 MEDLINE link, 1 protein link, or 4 nucleotide neighbors)
S72011
    Bacteriophage 21 isocitrate dehydrogenase (icd) and integrase (int) genes, partial cds
    gi|2618967|gb|AF017629|AF017629 [2618967]
    (View GenBank report, FASTA report, ASN.1 report, Graphical view, 1 MEDLINE link, 2 protein links, or 44 nucleotide neighbors)
AF017628
    Bacteriophage 21 isocitrate dehydrogenase (icd) and integrase (int) genes, partial cds
    gi|2618964|gb|AF017628|AF017628 [2618964]
    (View GenBank report, FASTA report, ASN.1 report, Graphical view, 1 MEDLINE link, 2 protein links, or 44 nucleotide neighbors)
AF017627
    Bacteriophage 21 isocitrate dehydrogenase (icd) and integrase (int) genes, partial cds
    gi|2618961|gb|AF017627|AF017627 [2618961]
    (View GenBank report, FASTA report, ASN.1 report, Graphical view, 1 MEDLINE link, 2 protein links, or 44 nucleotide neighbors)
AF017626
    Bacteriophage 21 isocitrate dehydrogenase (icd) gene, partial cds; and integrase (int) gene, partial cds
    gi|2618958|gb|AF017626|AF017626 [2618958]
    (View GenBank report, FASTA report, ASN.1 report, Graphical view, 1 MEDLINE link, 2 protein links, or 49 nucleotide neighbors)
AF017625
    Bacteriophage 21 isocitrate dehydrogenase (icd) and integrase (int) genes, partial cds
    gi|2618955|gb|AF017625|AF017625 [2618955]
    (View GenBank report, FASTA report, ASN.1 report, Graphical view, 1 MEDLINE link, 2 protein links, or 44 nucleotide neighbors)
AF017624
    Bacteriophage 21 isocitrate dehydrogenase (icd) and integrase (int) genes, partial cds
    gi|2618952|gb|AF017624|AF017624 [2618952]
    (View GenBank report, FASTA report, ASN.1 report, Graphical view, 1 MEDLINE link, 2 protein links, or 44 nucleotide neighbors)
AF017623
    Bacteriophage 21 isocitrate dehydrogenase (icd) and integrase (int) genes, partial cds
    gi|2618949|gb|AF017623|AF017623 [2618949]
    (View GenBank report, FASTA report, ASN.1 report, Graphical view, 1 MEDLINE link, 2 protein links, or 44 nucleotide neighbors)
AF017622
    Bacteriophage 21 isocitrate dehydrogenase (icd) and integrase (int) genes, partial cds
    gi|2618946|gb|AF017622|AF017622 [2618946]
    (View GenBank report, FASTA report, ASN.1 report, Graphical view, 1 MEDLINE link, 2 protein links, or 44 nucleotide neighbors)
AF017621
    Bacteriophage 21 isocitrate dehydrogenase (icd) and integrase (int) genes, partial cds
    gi|2618943|gb|AF017621|AF017621 [2618943]
    (View GenBank report, FASTA report, ASN.1 report, Graphical view, 1 MEDLINE link, 2 protein links, or 44 nucleotide neighbors)

TABLE 11-continued

SEQUENCE INFORMATION FOR PHAGES MATCHING WITH TABLE 1

D26449
    Bacteriophage PS17 FI gene for tail sheath protein (gpFI) and FII gene for tail tube protein (gpFII), complete cds
    gi|452162|dbj|D26449|BPSFIFII [452162]
    (View GenBank report, FASTA report, ASN.1 report, Graphical view, or 2 protein links)
X87627
    Bacteriophage D3112 A and B genes
    gi|974768|emb|X87627|BPD3112AB [974768]
    (View GenBank report, FASTA report, ASN.1 report, Graphical view, 1 MEDLINE link, 2 protein links, or 1 nucleotide neighbor)
U32623
    Bacteriophage D3 transcriptional activator CII (cII) gene, complete cds
    gi|984852|gb|U32623|BDU32623 [984852]
    (View GenBank report, FASTA report, ASN.1 report, Graphical view, 1 protein link, or 1 nucleotide neighbor)
L34781
    Bacteriophage phi 11 holin homologue (ORF3) gene, complete cds and peptidoglycan hydrolase (lytA) gene, partial cds
    gi|511838|gb|L34781|BPHHOLIN [511838]
    (View GenBank report, FASTA report, ASN.1 report, Graphical view, 1 MEDLINE link, 4 protein links, or 2 nucleotide neighbors)
L14810
    Bacteriophage P22 (gp10) gene, complete cds, and (gp26) gene, complete cds
    gi|294053|gb|L14810|P22GP1026X [294053]
    (View GenBank report, FASTA report, ASN.1 report, Graphical view, 1 MEDLINE link, 2 protein links, or 2 nucleotide neighbors)
X87420
    Bacteriophage ES18 genes 24, c2, cro, c1, 18, and oL and oR operators
    gi|1143407|emb|X87420|BPES18GEN [1143407]
    (View GenBank report, FASTA report, ASN.1 report, Graphical view, 5 protein links, or 9 nucleotide neighbors)
L42820
    Bacteriophage BF23 tail protein (hrs) gene, complete cds
    gi|1048680|gb|L42820|BBFHRS [1048680]
    (View GenBank report, FASTA report, ASN.1 report, Graphical view, 1 MEDLINE link, 1 protein link, or 1 nucleotide neighbor)
X14980
    Bacteriophage PRD1 XV gene for protein P15 (lytic enzyme)
    gi|15802|emb|X14980|TEPRD1XV [15802]
    (View GenBank report, FASTA report, ASN.1 report, Graphical view, 1 MEDLINE link, 1 protein link, or 4 nucleotide neighbors)
X06321
    Bacteriophage PRD1 gene 8 for DNA terminal protein
    gi|15800|emb|X06321|TEPRD18 [15800]
    (View GenBank report, FASTA report, ASN.1 report, Graphical view, 1 MEDLINE link, 2 protein links, or 10 nucleotide neighbors)
X14336
    Filamentous Bacteriophage I2-2 genome
    gi|14920|emb|X14336|INBI22 [14920]
    (View GenBank report, FASTA report, ASN.1 report, Graphical view, 1 MEDLINE link, 9 protein links, 1 nucleotide neighbor, or 1 genome link)
L05001
    Bacteriophage X glucosyl transferase gene, complete cds
    gi|216044|gb|L05001|PXFCLUSYLT [216044]
    (View GenBank report, FASTA report, ASN.1 report, Graphical view, 1 MEDLINE link, or 1 protein link)
M29479
    Bacteriophage p4 sid and psu genes partial cds, and delta gene, complete cds
    gi|215701|gb|M29479|PP4SDP [215701]
    (View GenBank report, FASTA report, ASN.1 report, Graphical view, 3 protein links, or 4 nucleotide neighbors)
SEG_PP4PSUSID
    Bacteriophage P4 capsid size determination protein (sid) gene, 5' end
    gi|215698|gb||SEG_PP4PSUSID [215698]
    (View GenBank report, FASTA report, ASN.1 report, Graphical view, 1 MEDLINE link, 2 protein links, or 1 nucleotide neighbor)
M29650
    Bacteriophage P4 polarity suppression protein (psu) gene, complete cds
    gi|215697|gb|M29650|PP4PSUSID2 [215697]
    (View GenBank report, FASTA report, ASN.1 report, or Graphical view)
M29651
    Bacteriophage P4 capsid size determination protein (sid) gene, 5' end
    gi|215696|gb|M29651|PP4PSUSID1 [215696]
    (View GenBank report, FASTA report, ASN.1 report, or Graphical view)
M27748
    Bacteriophage P4 gop, beta, and cII genes, complete cds and int gene, 3' end
    gi|215691|gb|M27748|PP4GOPBC [215691]
    (View GenBank report, FASTA report, ASN.1 report, Graphical view, 1 MEDLINE link, 4 protein links, or 1 nucleotide neighbor)
K02750
    Bacteriophage IKe, complete genome
    gi|215061|gb|K02750|IKECG [215061]
    (View GenBank report, FASTA report, ASN.1 report, Graphical view, 1 MEDLINE link, 10 protein links, 4 nucleotide neighbors, or 1 genome link)
L40418
    Bacteriophage phi-80 gene, complete cds
    gi|1019107|gb|L40418|P80A [1019107]
    (View GenBank report, FASTA report, ASN.1 report, Graphical view, 1 MEDLINE link, or 1 protein link)

TABLE 11-continued

SEQUENCE INFORMATION FOR PHAGES MATCHING WITH TABLE 1

AF032122
  Bacteriophage SfII integrase (int) gene, partial cds; and bactoprenol glucosyl transferase (bgt), and glucosyl tranferase II (gtrII) genes, complete cds
  gi|2465412|gb|AF021347|AF021347 [2465412]
  (View GenBank report, FASTA report, ASN.1 report, Graphical view, 1 MEDLINE link, 4 protein links, or 2 nucleotide neighbors)
M35825
  Bacteriophage SF6 fragment D lysozyme gene, complete cds
  gi|216105|gb|M35825|SF6LYZ [216105]
  (View GenBank report, FASTA report, ASN.1 report, Graphical view, or 1 protein link)
Z35479
  Bacteriophage C16 ip1 gene
  gi|534936|emb|Z35479|BC16IP1 [534936]
  (View GenBank report, FASTA report, ASN.1 report, Graphical view, 1 MEDLINE link, 1 protein link, or 2 nucleotide neighbors)
X12638
  Bacteriophage 21 DNA for gene 2
  gi|296141|emb|X12638|B21GENE2 [296141]
  (View GenBank report, FASTA report, ASN.1 report, Graphical view, 1 MEDLINE link, 1 protein link, or 1 nucleotide neighbor)
X02501
  Bacteriophage 21 DNA for left end sequence with genes 1 and 2
  gi|15825|emb|X02501|XXPHA21 [15825]
  (View GenBank report, FASTA report, ASN.1 report, Graphical view, 1 MEDLINE link, 2 protein links, or 3 nucleotide neighbors)
M65239
  Bacteriophage 21 lysis genes S, R, and Rz, complete cds
  gi|215466|gb|M65239|PH2LYSGEN [215466]
  (View GenBank report, FASTA report, ASN.1 report, Graphical view, 1 MEDLINE link, 3 protein links, or 1 nucleotide neighbor)
M58702
  Bacteriophage 21 late gene regulatory region
  gi|215465|gb|M58702|PH2LATEGE [215465]
  (View GenBank report, FASTA report, ASN.1 report, Graphical view, or 1 MEDLINE link)
M81255
  Bacteriophage 21 head gene operon
  gi|215454|gb|M81255|PH2HEADTL [215454]
  (View GenBank report, FASTA report, ASN.1 report, Graphical view, 2 MEDLINE links, 10 protein links, or 4 nucleotide neighbors)
M23775
  Bacteriophage 21 glycoprotein 1 gene, complete cds, and glycoprotein gene, 5' end
  gi|215451|gb|M23775|PH2GPA [215451]
  (View GenBank report, FASTA report, ASN.1 report, Graphical view, 1 MEDLINE link, 2 protein links, or 3 nucleotide neighbors)
M61865
  Bacteriophage 21 excisionase (xis), integrase (int) and isocitrate dehydrogenase (icd), complete cds
  gi|215448|gb|M61865|PH22XISAA [215448]
  (View GenBank report, FASTA report, ASN.1 report, Graphical view, 2 protein links, or 9 nucleotide neighbors)
S72011
  Bacteriophage 21 isocitrate dehydrogenase (icd) and integrase (int) genes, partial cds
  gi|2618967|gb|AF017629|AF017629 [2618967]
  (View GenBank report, FASTA report, ASN.1 report, Graphical view, 1 MEDLINE link, 2 protein links, or 44 nucleotide neighbors)
AF017628
  Bacteriophage 21 isocitrate dehydrogenase (icd) and integrase (int) genes, partial cds
  gi|2618964|gb|AF017628|AF017628 [2618964]
  (View GenBank report, FASTA report, ASN.1 report, Graphical view, 1 MEDLINE link, 2 protein links, or 44 nucleotide neighbors)
AF017627
  Bacteriophage 21 isocitrate dehydrogenase (icd) and integrase (int) genes, partial cds
  gi|2618961|gb|AF017627|AF017627 [2618961]
  (View GenBank report, FASTA report, ASN.1 report, Graphical view, 1 MEDLINE link, 2 protein links, or 44 nucleotide neighbors)
AF017626
  Bacteriophage 21 isocitrate dehydrogenase (icd) gene, partial cds; and integrase (int) gene, partial cds
  gi|2618958|gb|AF017626|AF017626 [2618958]
  (View GenBank report, FASTA report, ASN.1 report, Graphical view, 1 MEDLINE link, 2 protein links, or 49 nucleotide neighbors)
AF017625
  Bacteriophage 21 isocitrate dehydrogenase (icd) and integrase (int) genes, partial cds
  gi|2618955|gb|AF017625|AF017625 [2618955]
  (View GenBank report, FASTA report, ASN.1 report, Graphical view, 1 MEDLINE link, 2 protein links, or 44 nucleotide neighbors)
AF017624
  Bacteriophage 21 isocitrate dehydrogenase (icd) and integrase (int) genes, partial cds
  gi|2618952|gb|AF017624|AF017624 [2618952]
  (View GenBank report, FASTA report, ASN.1 report, Graphical view, 1 MEDLINE link, 2 protein links, or 44 nucleotide neighbors)
AF017623
  Bacteriophage 21 isocitrate dehydrogenase (icd) and integrase (int) genes, partial cds
  gi|2618949|gb|AF017623|AF017623 [2618949]
  (View GenBank report, FASTA report, ASN.1 report, Graphical view, 1 MEDLINE link, 2 protein links, or 44 nucleotide neighbors)
AF017622
  Bacteriophage 21 isocitrate dehydrogenase (icd) and integrase (int) genes, partial cds
  gi|2618946|gb|AF017622|AF017622 [2618946]
  (View GenBank report, FASTA report, ASN.1 report, Graphical view, 1 MEDLINE link, 2 protein links, or 44 nucleotide neighbors)
AF017621
  Bacteriophage 21 isocitrate dehydrogenase (icd) and integrase (int) genes, partial cds
  gi|2618943|gb|AF017621|AF017621 [2618943]
  (View GenBank report, FASTA report, ASN.1 report, Graphical view, 1 MEDLINE link, 2 protein links, or 44 nucleotide neighbors)

TABLE 11-continued

SEQUENCE INFORMATION FOR PHAGES MATCHING WITH TABLE 1

M57455
    Bacteriophage 42D (clone pDB17) (from *Staphylococcus aureus*) staphylokinase gene, complete cds
    gi|215344|gb|M57455|P42STK [215344]
    (View GenBank report, FASTA report, ASN.1 report, Graphical view, 1 protein link, or 9 nucleotide neighbors)
Y12633
    Bacteriophage 85 DNA, promoter sequence of unknown gene
    gi|2058285|emb|Y12633|B85PROM [2058285]
    (View GenBank report, FASTA report, ASN.1 report, or Graphical view)
X98146
    Bacteriophage P1 DNA sequence around the Op88 operator
    gi|1359513|emb|X98146|BP1OP88OP [1359513]
    (View GenBank report, FASTA report, ASN.1 report, Graphical view, or 1 nucleotide neighbor)
Y07739
    Staphylococcus phage Twort holTW, plyTW genes
    gi|2764979|emb|Y07739|BPTWGHOLG [2764979]
    (View GenBank report, FASTA report, ASN.1 report, Graphical view, or 2 protein links)
L07580
    Bacteriophage phi-11 rinA and rinB genes, required for the activation of Staphylococcal phage phi-11 int expression
    gi|166160|gb|L07580|BPHRINAB [166160]
    (View GenBank report, FASTA report, ASN.1 report, Graphical view, 1 MEDLINE link, or 2 protein links)
M34832
    Bacteriophage phi-11 integrase (int) and excisionase (xis) genes, complete cds
    gi|166157|gb|M34832|BPHINTXIS [166157]
    (View GenBank report, FASTA report, ASN.1 report, Graphical view, 1 MEDLINE link, 2 protein links, or 2 nucleotide neighbors)
M20394
    Bacteriophage phi-11 *S.aureus* attachment site (attP)
    gi|166156|gb|M20394|BPHATTP [166156]
    (View GenBank report, FASTA report, ASN.1 report, Graphical view, 1 MEDLINE link, or 4 nucleotide neighbors)
X23128
    Bacteriophage phi-13 integrase gene
    gi|758228|emb|X82312|PHI13INT [758228]
    (View GenBank report, FASTA report, ASN.1 report, Graphical view, 1 protein link, or 3 nucleotide neighbors)
X61719
    *S.aureus* phi-13 lysogen right chromosome/bacteriophage DNA junction
    gi|46625|emb|X61719|SAP13RJNC [46625]
    (View GenBank report, FASTA report, ASN.1 report, Graphical view, or 1 MEDLINE link)
X61718
    *S.aureus* phi-13 lysogen left chromosomal/bacteriophage DNA junction
    gi|46624|emb|X61718|SAP13LJNC [46624]
    (View GenBank report, FASTA report, ASN.1 report, Graphical view, or 1 MEDLINE link)
X61717
    Bacteriophage phi-13 core sequence for attachment
    gi|14799|emb|X61717|BP13ATTP [14799]
    (View GenBank report, FASTA report, ASN.1 report, Graphical view, 2 MEDLINE links, or 3 nucleotide neighbors)
U01875
    Bacteriophage phi-13 putative regulatory region and integrase (int) gene, partial cds
    gi|437118|gb|U01875|U01875 [437118]
    (View GenBank report, FASTA report, ASN.1 report, Graphical view, 3 MEDLINE links, or 4 nucleotide neighbors)
X67739
    *S.aureus* Bacteriophage phi-42 attP gene
    gi|14809|emb|X67739|BPATTPA [14809]
    (View GenBank report, FASTA report, ASN.1 report, Graphical view, 1 MEDLINE link, or 3 nucleotide neighbors)
U01872
    Bacteriophage phi-42 integrase (int) gene, complete cds
    gi|437115|gb|U01872|U01872 [437115]
    (View GenBank report, FASTA report, ASN.1 report, Graphical view, 3 MEDLINE links, 2 protein links, or 3 nucleotide neighbors)
X94423
    *Staphylococcus aureus* bacteriophage phi-42 DNA with ORFs (restriction modification system)
    gi|1771597|emb|X94423|SARMS [1771597]
    (View GenBank report, FASTA report, ASN.1 report, Graphical view, 2 protein links, or 1 nucleotide neighbor)
M27965
    Bacteriophage L54a (from *S.aureus*) int and xis genes, complete cds
    gi|215096|gb|M27965|L54INTXIS [215096]
    (View GenBank report, FASTA report, ASN.1 report, Graphical view, MEDLINE 1 link, 2 protein links, or 3 nucleotide neighbors)
U72397
    Bacteriophage 80 alpha holin and amidase genes, complete cds
    gi|1763241|gb|U72397|B8U72397 [1763241]
    (View GenBank report, FASTA report, ASN.1 report, Graphical view, 2 protein links, or 2 nucleotide neighbors)
AB009866
    Bacteriophage phi PVL proviral DNA, complete sequence
    gi|3341907|dbj|AB009866|AB009866 [3341907]
    (View GenBank report, FASTA report, ASN.1 report, Graphical view, 63 protein links, or 1 nucleotide neighbor)
Z47794
    Bacteriophage Cp-1 DNA, complete genome
    gi|2288892|emb|Z47794|BPCP1XX [2288892]
    (View GenBank report, FASTA report, ASN.1 report, Graphical view, 3 MEDLINE links, 28 protein links, 1 nucleotide neighbor, or 1 genome link)

TABLE 11-continued

SEQUENCE INFORMATION FOR PHAGES MATCHING WITH TABLE 1

SEG_CP7RSIT
    Bacteriophage Cp-7 (*S.pneumoniae*) 5' inverted terminal repeat
    gi|166186|gb||SEG_CP7RSIT [166186]
    (View GenBank report, FASTA report, ASN.1 report, Graphical view, or 1 MEDLINE link)
M11635
    Bacteriophage Cp-7 (*S.pneumoniae*) DNA, 3' inverted terminal repeat
    gi|166185|gb|M11635|CP7RSIT2 [166185]
    (View GenBank report, FASTA report, ASN.1 report, or Graphical view)
M11636
    Bacteriophage Cp-7 (*S.pneumoniae*) 5' inverted terminal repeat
    gi|166184|gb|M11636|CP7RSIT1 [166184]
    (View GenBank report, FASTA report, ASN.1 report, or Graphical view)
SEG_CP5RSIT
    Bacteriophage Cp-5 (*S.pneumoniae*), 5' inverted terminal repeat
    gi|166181|gb||SEG_CP5RSIT [166181]
    (View GenBank report, FASTA report, ASN.1 report, Graphical view, or 1 MEDLINE link)
M11633
    Bacteriophage Cp-5 (*S.pneumoniae*) 3' inverted terminal repeat
    gi|166180|gb|M11633|CP5RSIT2 [166180]
    (View GenBank report, FASTA report, ASN.1 report, or Graphical view)
M11634
    Bacteriophage Cp-5 (*S.pneumoniae*), 5' inverted terminal repeat
    gi|166179|gb|M11634|CP5RSIT1 [166179]
    (View GenBank report, FASTA report, ASN.1 report, or Graphical view)
M34780
    Bacteriophage Cp-9 muramidase (cpl9) gene
    gi|166187|gb|M34780|CP9CPL [166187]
    (View GenBank report, FASTA report, ASN.1 report, Graphical view, 1 MEDLINE link, 1 protein link, or 1 nucleotide neighbor)
M34652
    Bacteriophage HB-3 amidase (hbl) gene, complete cds
    gi|215055|gb|M34652|HB3HBLA [215055]
    (View GenBank report, FASTA report, ASN.1 report, Graphical view, 1 MEDLINE link, or 1 protein link)
U64984
    *Streptococcus pyogenes* phage T12 repressor, excisionase (xis), integrase (int) and erythrogenic toxin A precursor (speA) genes, complete cds
    gi|1877426|gb|U40453|SPU40453 [1877426]
    (View GenBank report, FASTA report, ASN.1 report, Graphical view, 2 MEDLINE links, 4 protein links, or 22 nucleotide neighbors)
X12375
    Phage CP-T1 (*Vibrio cholerae*) DNA for packaging signal (pac site)
    gi|15435|emb|X12375|NCCPPAC [15435]
    (View GenBank report, FASTA report, ASN.1 report, Graphical view, 1 MEDLINE link, or 1 protein link)
AF087814
    *Vibrio cholerae* filamentous bacteriophage fs-2 DNA, complete genome sequence
    gi|3702207|dbj|AB002632|AB002632 [3702207]
    (View GenBank report, FASTA report, ASN.1 report, Graphical view, 1 MEDLINE link, 9 protein links, or 1 genome link)
D83518
    Bacteriophage KVP40 gene for major capsid protein precursor, complete cds
    gi|3046858|dbj|D83518|D83518 [3046858]
    (View GenBank report, FASTA report, ASN.1 report, Graphical view, 1 MEDLINE link, or 1 protein link)
AF033322
    Bacteriophage PST single-stranded binding protein (gene 32) gene, partial cds, and 5' region
    gi|2645774|gb|AF033322|AF033322 [2645774]
    (View GenBank report, FASTA report, ASN.1 report, Graphical view, 1 protein link, or 17 nucleotide neighbors)
X94331
    Bacteriophage L cro, 24, c2, and c1 genes
    gi|1469213|emb|X94331|BLCRO24C [1469213]
    (View GenBank report, FASTA report, ASN.1 report, Graphical view, 1 MEDLINE link, or 4 protein links)
U82619
    *Shigella flexneri* bacteriophage V glucosyl transferase (gtr), integrase (int) and excisionase (xis) genes, complete cds
    gi|2465470|gb|U82619|SFU82619 [2465470]
    (View GenBank report, FASTA report, ASN.1 report, Graphical view, 1 MEDLINE link, 8 protein links, or 1 nucleotide neighbor)

TABLE 12

NCBI Entrez Nucleotide QUERY
Key words: bacteriophage and lysis
56 citations found (all selected)

AJ011581

Bacteriophage Ps119 lysis genes 13, 19, 15, and packaging gene 3, complete cds
gi|3676084|emb|AJ011581|BPS011581 [3676084]
(View GenBank report, FASTA report, ASN.1 report, Graphical view, 5 protein links, or 1 nucleotide neighbor)

AJ011580

Bacteriophage PS34 lysis genes 13, 19, 15, antiterminator gene 23, and packaging gene 3, complete cds
gi|3676078|emb|AJ011580|BPS011580 [3676078]

TABLE 12-continued

NCBI Entrez Nucleotide QUERY
Key words: bacteriophage and lysis
56 citations found (all selected)

(View GenBank report, FASTA report, ASN.1 report, Graphical view,
5 protein links, or 2 nucleotide neighbors)
AJ011579

Bacteriophage PS3 lysis genes 13, 19, 15, and packaging gene 3
gi|3676073|emb|AJ011579|BPS011579 [3676073]
(View GenBank report, FASTA report, ASN.1 report, Graphical view,
4 protein links, or 1 nucleotide neighbor)
AF034975

Bacteriophage H-19B essential recombination function
protein (crf), kil protein (kil), regulatory protein
cIII (cIII), protein gp17 (17), N protein (N), cI protein (cI),
cro protein (cro). cII protein (cII), O protein (O),
P protein (P), ren protein (ren), Roi (roi), Q protein (Q),
Shig-like toxin A (slt-IA) and B (slt-IB) subunits,
and putative holin protein (S) genes, complete cds
gi|2668751|gb|AF034975| [2668751]
(View GenBank report, FASTA report, ASN.1 report, Graphical view,
1 MEDLINE link, 20 protein links, or 30 nucleotide neighbors)
U37314

Bacteriophage lambda Rz1 protein precursor (Rz1) gene, complete cds
gi|1017780|gb|U37314|BLU37314 [1017780]
(View GenBank report, FASTA report, ASN.1 report, Graphical view,
2 MEDLINE links, 1 protein link, or 9 nucleotide neighbors)
U00005

E. coli hflA locus encoding the hflX, hflK and hflC genes,
hfq gene, complete cds; miaA gene, partial cds
gi|436153|gb|U00005|ECOHFLA [4361531]
(View GenBank report, FASTA report, ASN.1 report, Graphical view,
4 MEDLINE links, 5 protein links, or 8 nucleotide neighbors)
U32222

Bacteriophage 186, complete sequence
gi|3337249|gb|U32222|B1U32222 [3337249]
(View GenBank report, FASTA report, ASN.1 report, Graphical view,
6 MEDLINE links, 46 protein links, or 5 nucleotide neighbors)
AF064539

Bacteriophage N15, complete genome
gi|3192683|gb|AF064539|AF064539 [3192683]
(View GenBank report, FASTA report, ASN.1 report, Graphical view,
2 MEDLINE links, 60 protein links, 26 nucleotide neighbors,
or 1 genome link)
AF063097

Bacteriophage P2, complete genome
gi|3139086|gb|AF063097|AF063097 [3139086]
(View GenBank report, FASTA report, ASN.1 report, Graphical view,
21 MEDLINE links, 42 protein links, 3 nucleotide neighbors,
or 1 genome link)
Z97974

Bacteriophage phiadh lys, hol, intG, rad, and tec genes
gi|2707950|emb|Z97974|BPHIADH [2707950]
(View GenBank report, FASTA report, ASN.1 report, Graphical view,
2 MEDLINE links, 9 protein links, or 1 nucleotide neighbor)
AF059243

Bacteriophage NL95, complete genome
gi|3088545|gb|AF059243|AF059243 [3088545]
(View GenBank report, FASTA report, ASN.1 report, Graphical view,
2 MEDLINE links, 4 protein links, 3 nucleotide neighbors,
or 1 genome link)
AF052431

Bacteriophage M11 A-protein, coat protein, A1-protein,
and replicase genes, complete cds
gi|2981208|gb|AF052431| [2981208]
(View GenBank report, FASTA report, ASN.1 report, Graphical view,
2 MEDLINE links, 4 protein links, or 8 nucleotide neighbors)

TABLE 12-continued

NCBI Entrez Nucleotide QUERY
Key words: bacteriophage and lysis
56 citations found (all selected)

Y07739

Staphylococcus phage Twort holTW, plyTW genes
gi|2764979|emb|Y07739|BPTWGHOLG [2764979]
(View GenBank report, FASTA report, ASN.1 report, Graphical view,
or 2 protein links)
X94331

Bacteriophage L cro, 24, c2, and c1 genes
gi|1469213|emb|X94331|BLCRO24C [1469213]
(View GenBank report, FASTA report, ASN.1 report, Graphical view,
1 MEDLINE link, or 4 protein links)
X78401

Bacteriophage P22 right and lysin genes
gi|793848|emb|X78410|LGHOLLYS [793848]
(View GenBank report, FASTA report, ASN.1 report, Graphical view,
1 MEDLINE link, 2 protein links, or 1 nucleotide neighbor)
X99260

Bacteriophage B103 genomic sequence
gi|142922|emb|X99260|BB103G [1429229]
(View GenBank report, FASTA report, ASN.1 report, Graphical view,
1 MEDLINE link, 17 protein links, or 12 nucleotide neighbors)
AJ000741

Bacteriophage P1 darA operon
gi|2462938|emb|AJ000741|BPAJ7641 [2462938]
(View GenBank report, FASTA report, ASN.1 report, Graphical view,
1 MEDLINE link, 10 protein links, or 31 nucleotide neighbors)
X87420

Bacteriophage ES18 genes 24, c2, cro, c1, 18,
and oL and oR operators
gi|1143407|emb|X87420|BPES18GEN [1143407]
(View GenBank report, FASTA report, ASN.1 report, Graphical view,
5 protein links, or 9 nucleotide neighbors)
L35561

Bacteriophage phi-105 ORFs 1–3
gi|532218|gb|L35561|PH5ORFHTR [532218]
(View GenBank report, FASTA report, ASN.1 report, Graphical view,
1 MEDLINE link, or 3 protein links)
D10027

Group II RNA coliphage GA genome
gi|217784|dbj|D10027|PGAXX [217784]
(View GenBank report, FASTA report, 1 report, Graphical view,
1 MEDLINE link, 3 protein links, 5 nucleotide neighbors,
or 1 genome link)
V01128

Bacteriophage phi-X174 (cs70 mutation) complete genome
gi|5535|emb|V01128|PHIX174 [15535]
(View GenBank report, FASTA report, ASN.1 report, Graphical view,
4 MEDLINE links, 11 protein links, or 26 nucleotide neighbors)
S81763 coat gene . . . replicase gene [bacteriophage KU1,
host = Escherichia coli,
group II RNA phage, Genomic RNA, 3 genes, 120 nt]
gi|438766|gb|S81763|S81763 [1438766]
(View GenBank report, FASTA report, ASN.1 report, Graphical view,
or 1 MEDLINE link)
U38906

Bacteriophage r1t integrase, repressor protein (rro),
dUTPase, holin and lysin genes, complete cds
gi|353517|gb|U38906|BRU38906 [1353517]
(View GenBank report, FASTA report, ASN.1 report, Graphical view,
2 MEDLINE links, 50 protein links, or 3 nucleotide neighbors)
X91149

Bacteriophage phi-C31 DNA cos region
gi|1107473|emb|X91149|APHIC31C [1107473]

TABLE 12-continued

NCBI Entrez Nucleotide QUERY
Key words: bacteriophage and lysis
56 citations found (all selected)

(View GenBank report, FASTA report, ASN.1 report, Graphical view,
1 MEDLINE link, 6 protein links, or 1 nucleotide neighbor)
V00642 phage MS2 genome
gi|15081|emb|V00642|LEMS2X [15081]
(View GenBank report, FASTA report, ASN.1 report, Graphical view,
8 MEDLINE links, 4 protein links, or 20 nucleotide neighbors)
V01146

Genome of bacteriophage T7
gi|431187|emb|V01146|T7CG [431187]
(View GenBank report, FASTA report, ASN.1 report, Graphical view,
13 MEDLINE links, 60 protein links, 105 nucleotide neighbors,
or 1 genome link)
X78401

Bacteriophage P22 right operon, orf 48,
replication genes 18 and 12, nin region genes,
ninG phosphatase, late control gene 23, orf 60, complete
cds, late control region, start of lysis gene 13
gi|512343|emb|X78401|POP22NIN [512343]
(View GenBank report, FASTA report, ASN.1 report, Graphical view,
2 MEDLINE links, 13 protein links, or 4 nucleotide neighbors)
Y00408

Bacteriophage T4 gene t for lysis protein
gi|5368|emb|Y00408|MYT4T [15368]
(View GenBank report, FASTA report, ASN.1 report, Graphical view,
1 MEDLINE link, 1 protein link, or 3 nucleotide neighbors)
Z26590

Bacteriophage mv4 lysA and lysB genes
gi|410500|emb|Z26590|MV4LYSAB [410500]
(View GenBank report, FASTA report, ASN.1 report, Graphical view,
or 4 protein links)
X07809

Phage phiX174 lysis (E) gene upstream region
gi|15094|emb|X07809|MIPHIXE [15094]
(View GenBank report, FASTA report, ASN.1 report, Graphical view,
1 MEDLINE link, 2 protein links, or 4 nucleotide neighbors)
Z34528

Lactococcal bacteriophage c2 lysin gene
gi|506455|emb|Z34528|LBC2LYSIN [506455]
(View GenBank report, FASTA report, ASN.1 report, Graphical view,
1 MEDLINE link, 1 protein link, or 4 nucleotide neighbors)
X15031

Bacteriophage fr RNA genome
gi|15071|emb|X15031|LEBFRX [15071]
(View GenBank report, FASTA report, ASN.1 report, Graphical view,
1 MEDLINE link, 4 protein links, 9 nucleotide neighbors,
or 1 genome link)
X80191

Bacteriophage PP7 mRNA for maturation, coat,
lysis and replicase proteins
gi|517237|emb|X80191|BPP7PR [517237]
(View GenBank report, FASTA report, ASN.1 report, Graphical view,
1 MEDLINE link, 4 protein links, or 1 genome link)
X85010

Bacteriophage A511 ply511 gene
gi|853748|emb|X85010|BPA511PLY [853748]
(View GenBank report, FASTA report, ASN.1 report, Graphical view,
1 MEDLINE link, 3 protein links, or 1 nucleotide neighbor)
X85009

Bacteriophage A500 hol500 and ply500 genes
gi|853744|emb|X85009|BPA500PLY [853744]
(View GenBank report, FASTA report, ASN.1 report, Graphical view,
1 MEDLINE link, 3 protein links, or 4 nucleotide neighbors)

X85008

Bacteriophage A118 hol118 and ply118 genes
gi|853740|emb|X85008|BPA118PLY [853740]
(View GenBank report, FASTA report, ASN.1 report, Graphical view,
1 MEDLINE link, 3 protein links, or 1 nucleotide neighbor)
Z35638

Bacteriophage phi-X174 genes for lysis protein and beta-lactamase
gi|520996|emb|Z35638|BPLYSPR [520996]
(View GenBank report, FASTA report, ASN.1 report, Graphical view,
1 MEDLINE link, 2 protein links, or 516 nucleotide neighbors)
J02459

Bacteriophage lambda, complete genome
gi|215104|gb|J02459|LAMCG [215104]
(View GenBank report, FASTA report, ASN.1 report, Graphical view,
87 MEDLINE links, 67 protein links, 190 nucleotide neighbors,
or 1 genome link)
X87674

Bacteriophage P1 lydA & lydB genes
gi|974763|emb|X87674|BACP1LYD [974763]
(View GenBank report, FASTA report, ASN.1 report, Graphical view,
1 MEDLINE link, 2 protein links, or 2 nucleotide neighbors)
X87673

Bacteriophage P1 gene 17
gi|974761|emb|X87673|BACP117 [974761]
(View GenBank report, FASTA report, ASN.1 report, Graphical view,
1 MEDLINE link, 1 protein link, or 1 nucleotide neighbor)
M14784

Bacteriophage T3 strain amNG220B right end,
tail fiber protein, lysis protein and
DNA packaging proteins, complete cds
gi|215810|gb|M14784|PT3RE [215810]
(View GenBank report, FASTA report, ASN.1 report, Graphical view,
1 MEDLINE link, 9 protein links, or 10 nucleotide neighbors)
M11813

Bacteriophage PZA (from B. subtilis), complete genome
gi|216046|gb|M11813|PZACG [216046]
(View GenBank report, FASTA report, ASN.1 report, Graphical view,
3 MEDLINE links, 27 protein links, 17 nucleotide neighbors,
or 1 genome link)
M16812

Bacteriophage K3 't' lysis gene, complete cds
gi|215503|gb|M16812|PK3LYST [215503]
(View GenBank report, FASTA report, ASN.1 report, Graphical view,
1 MEDLINE link, 1 protein link, or 4 nucleotide neighbors)
J04356

Bacteriophage P22 proteins 15 (complete cds),
and 19 (3' end) genes
gi|215265|gb|J04356|P2215P [215265]
(View GenBank report, FASTA report, ASN.1 report, Graphical view,
1 MEDLINE link, 3 protein links, or 2 nucleotide neighbors)
J04343

Bacteriophage JP34 coat and lysis protein genes,
complete cds, and replicase protein gene, 5' end
gi|215076|gb|J04343|JP3COLY [215076]
(View GenBank report, FASTA report, ASN.1 report, Graphical view,
1 MEDLINE link, 3 protein links, or 2 nucleotide neighbors)
J02482

Bacteriophage phi-X174, complete genome
gi|216019|gb|J02482|PX1CG [216019]
(View GenBank report, FASTA report, ASN.1 report, Graphical view,
23 MEDLINE links, 11 protein links, 26 nucleotide neighbors,
or 1 genome link)

TABLE 12-continued

NCBI Entrez Nucleotide QUERY
Key words: bacteriophage and lysis
56 citations found (all selected)

M99441

Bacteriophage T4 anti-sigma 70 protein (asiA) gene,
complete cds and lysis protein, 3' end
gi|215820|gb|M99441|PT4ASIA [215820]
(View GenBank report, FASTA report, ASN.1 report, Graphical view,
3 MEDLINE links, 2 protein links, or 2 nucleotide neighbors)

M65239

Bacteriophage 21 lysis genes S, R. and Rz, complete cds
gi|215466|gb|M65239|PH2LYSGEN [215466]
(View GenBank report, FASTA report, ASN.1 report, Graphical view,
1 MEDLINE link, 3 protein links, or 1 nucleotide neighbor)

M10637

Phage G4 D/E overlapping gene system, encoding D
(morphogenetic) and E (lysis) proteins
gi|215427|gb|M10637|PG4DE [215427]
(View GenBank report, FASTA report, ASN.1 report, Graphical view,
1 MEDLINE link, 2 protein links, or 12 nucleotide neighbors)

J02454

Bacteriophage G4, complete genome
gi|215415|gb|J02454|PG4CG [215415]
(View GenBank report, FASTA report, ASN.1 report, Graphical view,
6 MEDLINE links, 11 protein links, 20 nucleotide neighbors,
or 1 genome link)

J02580

Bacteriophage PA-2 (*E. coli* porcine strain isolate)
Rz gene, 5' end; ORF2, outer membrane porin
protein (lc) and ORF1 genes, complete cds
gi|215366|gb|J02580|PA2LC [215366]
(View GenBank report, FASTA report, ASN.1 report, Graphical view,
1 MEDLINE link, 4 protein links, or 4 nucleotide neighbors)

M14782

Bacillus phage phi-29 head morphogenesis, major head protein,
head fiber protein, tail protein, upper collar protein,
lower collar protein, pre-neck appendage protein,
morphogenesis(13), lysis, morphogenesis(15),
encapsidation genes, complete cds
gi|215323|gb|M14782|P29LATE2 [215323]
(View GenBank report, FASTA report, ASN.1 report, Graphical view,
1 MEDLINE link, 11 protein links, or 11 nucleotide neighbors)

M10997

Bacteriophage P22 lysis genes 13 and 19, complete cds
gi|215262|gb|M10997|P221319 [215262]
(View GenBank report, FASTA report, ASN.1 report, Graphical view,
1 MEDLINE link, 2 protein links, or 3 nucleotide neighbors)

J02467

Bacteriophage MS2, complete genome
gi|215232|gb|J02467|MS2CG [215232]
(View GenBank report, FASTA report, ASN.1 report, Graphical view,
8 MEDLINE links, 4 protein links, 20 nucleotide neighbors,
or 1 genome link)

M14035

Bacteriophage lambda lysis S gene with mutations
leading to nonlethality of S in the plasmid pRG1
gi|215180|gb|M14035|LAMLYS [215180]
(View GenBank report, FASTA report, ASN.1 report, Graphical view,
1 MEDLINE link, 1 protein link, or 14 nucleotide neighbors)

U04309

Bacteriophage phi-LC3 putative holin (lysA) gene
and putative murein hydrotase (lysB) gene. complete cds
gi|530796|gb|U04309|BPU04309 [530796]
(View GenBank report, FASTA report, ASN.1 report, Graphical view,
1 MEDLINE link, 2 protein links or 1 nucleotide neighbor)

TABLE 13

NCBI Entrez Nucleotide QUERY
Key word: holin
51 citations found (all selected)

AF034975

Bacteriophage H-19B essential recombination function protein (erf), kil
protein (kil), regulatory protein cIII (cIII), protein gp17 (17), N
protein (N), cI protein (cI), cro protein (cro), cII protein (cII), O
protein (O), P protein (P), ren protein (ren), Roi (roi), Q protein (Q),
Shiga-like toxin A (slt-IA) and B (slt-IB) subunits, and putative holin
protein (S) genes, complete cds
gi|2668751|gb|AF034975|[2668751]
(View GenBank report, FASTA report, ASN.1 report, Graphical view, 1 MEDLINE
link, 20 protein links, or 30 nucleotide neighbors)

U52961

Staphylococcus aureus holin-like protein LrgA (lrgA) and LrgB (lrgB)
genes, complete cds
gi|1841516|gb|52961|SAU52961 [1841516]
(View GenBank report, FASTA report, ASN.1 report, Graphical view, 1 MEDLINE
link, 2 protein links, or 1 nucleotide neighbor)

U28154

*Haemophilus somnus* cryptic prophage genes, capsid scaffolding protein
gene, partial cds, major capsid protein precursor, endonuclease, capsid
completion protein, tail synthesis proteins, holin, and lysozyme genes,
complete cds
gi|1765928|gb|U28154|HSU28154 [1765928]
(View GenBank report, FASTA report, ASN.1 report, Graphical view, 1 MEDLINE
link, or 13 protein links)

TABLE 13-continued

NCBI Entrez Nucleotide QUERY
Key word: holin
51 citations found (all selected)

AF032122

*Streptococcus thermiophilus* bacteriophage Sfi19 central region of genome
gi|2935682|gb|AF032122|[2935682]
(View GenBank report, FASTA report, ASN.1 report, Graphical view, 1 MEDLINE
link, 14 protein links, or 2 nucleotide neighbors)
AF032121

*Streptococcus thermophilus* bacteriophage Sfi21 central region of genome
gi|2935667|gb|AF032121|AF032121 [2935667]
(View GenBank report, FASTA report, ASN.1 report, Graphical view, 1 MEDLINE
link, 14 protein links, or 2 nucleotide neighbors)
AF021803

*Bacillus subtilis* 168 prophage SPbeta N-acetylmuramoyl-L-alanine amidase
(blyA), holin-like protein (bhlA), holin-like protein (bhlB), and yolK
genes, complete cds; and yolJ gene, partial cds
gi|2997594|gb|AF021803|AF021803 [2997594]
(View GenBankreport, FASTA report, ASN.1 report, Graphical view, 1 MEDLINE
link, 5 protein links, or 1 nucleotide neighbor)
AF057033

*Streptococcus thermophilus* bacteriophage sfi11 gp502 (orf502), gp284
(orf284), gp129 (orf129), gp193 (orf193), gp119 (orf119), gp348
(orf348), gp53 (orf53), gp113 (orf113), gp104 (orf104), gp114 (orf114),
gp128 (orf128), gp168 (orf168), gp117 (orf117), gp105 (orf105), putative
minor tail protein (orf1510), putative minor structural protein
(orf512), putative minor structural protein (orf1000),gp373 (orf373),
gp57 (orf57), putative anti-receptor (orf695), putative minor structural
protein (orf669), gp149 (orf149), putative holin (orf141), putative
holin (orf187), and lysin (orf288) genes, complete cds
gi|3320432|gb|AF057033|AF057033 [3320432]
(View GenBank report, FASTA report, ASN.1 report, Graphical view, 25 protein
links, or 1 nucleotide neighbor)
U32222

Bacteriophage 186, complete sequence
gi|3337249|gb|U32222|B1U32222 [3337249]
(View GenBank report, FASTA report, ASN.1 report, Graphical view, 6 MEDLINE
links, 46 protein links, or 5 nucleotide neighbors)
AB009866

Bacteriophage phi PVL proviral DNA, complete sequence
gi|3341907|dbj|AB009866|AB009866 [3341907]
(View GenBank report,FASTA reportASN. i report,Graphical view,63 protein
links, or 1 nucleotide neighbor)
AF009630

Bacteriophage bIL170, complete genome
gi|3282260|gb|AF009630|AF009630 [3282260]
(View GenBank report, FASTA report, ASN.1 report, Graphical view, 63 protein
links, 3 nucleotide neighbors, or 1 genome link)
AF064539

Bacteriophage N15, complete genome
gi|3192683|gb|AF064539|AF064539 |3192683|
(View GenBank report, FASTA report, ASN.1 report, Graphical view, 21 MEDLINE
links, 60 protein links, 26 nucleotide neighbors, or 1 genome link)
AF063097

Bacteriophage P2, complete genome
gi|3139886|gb|AF063097|AF063097 [3139086]
(View GenBank report, FASTA report, ASN.1 report, Graphical view, 21 MEDLINE
links, 42 protein links, 3 nucleotide neighbors, or 1 genome link)
Z97974

Bacteriophage phiadh lys, hol, intG, rad, and tec genes
gi|2707950|emb|Z97974|BPH1ADH [2707950]
(View GenBank report, FASTA report, ASN.1 report, Graphical view, 2 MEDLINE
links, 9 protein links, or 1 nucleotide neighbor)
X95646

*Streptococcus thermophilus* bacteriophage Sfi21 DNA; lysogeny module,
8141 bp
gi|2292747|emb|X95646|BSFI21LYS [2292747]

TABLE 13-continued

NCBI Entrez Nucleotide QUERY
Key word: holin
51 citations found (all selected)

(View GenBank report, FASTA report, ASN.1 report, Graphical view,2 MEDLINE
links, 19 protein links, or 3 nucleotide neighbors)
SEG_LLHLYSINO Bacteriophage LL-H structural protein gene, partial cds; minor
structurai protein gp61 (g57), unknown protein, unknown protein,
structurai protein (g20), unknown protein, unknown protein, major capsid
protein (g34), main tail protein gp19 (g17), holin (hol), muramidase
(mur), unknown protein, unknown protein, unknown protein, unknown
protein, unknown protein, and unknown protein genes, complete cds;
unknown protein gene, partial cds; and unknown protein, unknown protein,
unknown protein, unknown protein, unknown protein, minor structural
protein gp75 (g70), minor structural protein gp89 (g88), minor
structural protein gp58 (g71), unknown protein, unknown protein, unknown
protein, and unknown protein genes, complete cds
gi|1004337|gb|ISEG_LHLYSIN0 [1004337]
(View GenBank report, FASTA report, ASN.1 report, Graphical view,4 MEDLINE
links, 31 protein links, or 1 nucleotide neighbor)
M96254

Bacteriophage LL-H holin (hol), muramidase (mur), and unknown protein
genes, complete cds
gi|1004336|gb|M96254|LLHLYSIN03 [1004336]
(View GenBank report, FASTA report, ASN.1 report, or Graphical view)
Y07740

*Staphylococcus phage* 187 ply187 and hol187 genes
gi|2764982|emb|Y07740|BP187PLYH [2764982]
(View GenBank report, FASTA report, ASN.1 report, Graphical view, or 2
protein links)
U88974

*Streptococcus thermophilus* bacteriophage 01205 DNA sequence
gi|2444080|gb|U88974| [2444080]
(View Ge#ank report,FASTA repoMSN.1 report,Graphical view,1 MEDLINE
link, 57 protein links, or 6 nucieotide neighbors)
Z99117

*Bacillus subtilis* complete genome (section 14 of 21): from 2599451 to
2812870
gi|2634966|emb|Z99117|BSUB0014 [2634966]
(View GenBank report,FASTA report, ASN.1 report, Graphical view, 233
pro#in links, 51 nucleotide neighbors, or 1 genome link)
Z99115

*Bacillus subtilis* complete genome (section 12 of 21): from 2195541 to
2409220
gi|2634478|emb|Z99115|BSUB0012 [2634478]
(View GenBank report, FASTA report, ASN.1 report, Graphical view, 244
protein links, 64 nucleotide neighbors, or 1 genome link)
Z99110

*Bacillus subtilis* complete genome (section 7 of 21): from 1194391 to
1411140
gi|2633472|emb|Z99110|BSUB0007 [2633472]
(View GenBank report, FASTA repot, ASN.1 report, Graphical view, 226
protein links, 31 nucleotide neighbors, or 1 genome link)
X78410

Bacteriophage phiadh holin and lysin genes
gi|793848|emb|X78410|LGHOLLYS [793848]
(View GenBank report, FASTA report, ASN.1 report, Graphical view, 1 MEDLINE
link, 2 protein links, or 1 nucleotide neighbor)
Z93946

Bacteriophage Dp-1 dph and pal genes and 5 open reading frames
gi|1934760|emb|Z93946|BPDPIORFS [1934760]
(View GenBank report, FASTA report, ASN.1 report, Graphical view, or 6
protein links)
AF011378

Bacteriophage skI complete genome
gi|2392824|gb|AF011378|AF011378 [2392824]
(View GenBank report, FASTA report, ASN.1 report, Graphical view, 54 protein
links, 2 nucleotide neighbors, or 1 genome link)

TABLE 13-continued

NCBI Entrez Nucleotide QUERY
Key word: holin
51 citations found (all selected)

Z47794

Bacteriophage Cp-1 DNA, complete genome
gi|2288892|emb|Z47794|BPCPIXX [2288892]
(View GenBank report, FASTA report, ASN.1 report, Graphical view, 3 MEDLINE
links, 28 protein links, 1 nucleotide neighbor, or 1 genome link)
L35561

Bacteriophage phi-105 ORFs 1-3
gi|532218 |gb|L35561|PH5ORFHTR [532218]
(View GenBank report, FASTA report, ASN.1 report, Graphical view, 1 MEDLINE
link, or 3 protein links)
D49712

*Bacillus licheniformis* DNA for ORFs, xpaL2 homologous protein and xpaL1
homologous protein, complete and partial cds
gi|1514423|dbj|D49712|D49712 [1514423]
(View GenBank report, FASTA report, ASN.1 report, Graphical view, 2 MEDLINE
links, or 4 protein links)
X90511

*Lactobacillus bacteriophage* phig le DNA for Rorf1621, Holin, Lysin, and
Rorf175 genes
gi|1926386|emb|X90511|LBPHIHOL [1926386]
(View GenBank report, FASTA report, ASN.1 report, Graphical view, 4 protein
links, or 1 nucleotide neighbor)
X98106

*Lactobacillus bacteriophage* phig le complete genomic DNA
gi|1926320|emb|X98106|LBPHIG1E [1926320]
(View GenBank report, FASTA report, ASN.1 report, Graphical view, 1 MEDLINE
link, 50 protein links, or 4 nucleotide neighbors)
U72397

Bacteriophage 80 alpha holin and amidase genes, complete cds
gi|1763241|gb|U723971B8U72397 [1763241]
(View GenBank report, FASTA report, ASN.1 report, Graphical view, 2 protein
links, or 2 nucleotide neighbors)
U38906

Bacteriophage rlt integrase, repressor protein (rro), dUTPase, holin and
lysin genes, complete cds
gi|1353517|gb|U38906|BRU38906 [1353517]
(View GenBank report, FASTA report, ASN.1 report, Graphical view, 2 MEDLINE
links, 50 protein links, or 3 nucleotide neighbors)
X91149

Bacteriophage phi-C31 DNA cos region
gi|107473|emb|X91149|APHIC31C [1107473]
(View GenBank report, FASTA report, ASN.1 report,Graphical view,1 MEDLINE
link, 6 protein links, or 1 nucleotide neighbor)
U24159

Bacteriophage HP1 strain HP1c1, complete genome
gi|1046235|gb|U24159|BHU24159 [1046235]
(View GenBank report, FASTA report, ASN.1 report, Graphical view, 6 MEDLINE
links, 41 protein links, 8 nucleotide neighbors, or 1 genome link)
Z26590

Bacteriophage mv4 lysA and lysB genes
gi|410500|emb|Z26590|MV4LYSAB [410500]
(View GenBank report, FASTA report, ASN.1 report, Graphical view, or 4
protein links)
Z70177

*B. subtilis* DNA (28 kb PBSX/skin element region)
gi|1225934|emb|Z70177|BSPBSXSE [1225934]
(View GenBank report, FASTA report, ASN.1 report, Graphical view, 32 protein
links, or 4 nucleotide neighbors)
Z36941

*B. subtilis* defective prophage PBSX xhlA, xhlB, and xylA genes
gi|535793|emb|736941|BSPBSXXHL [535793]
(View GenBank report, FASTA report, ASN.1 report, Graphical view, 4 protein
links, or 5 nucleotide neighbors)

TABLE 13-continued

NCBI Entrez Nucleotide QUERY
Key word: holin
51 citations found (all selected)

X89234

*L. innocua* DNA for phagelysin and holin gene
gi|1134844|emb|X89234|LICPLYHOL [1134844]
(View GenBank report, FASTA report, ASN.1 report, Graphical view, 1 MEDLINE link, 2 protein links, or 4 nucleotide neighbors)
X85010

Bacleriophage A511 ply511 gene
gi|853748|emb|X85010|BPA511PLY [853748]
(View GenBank report, FASTA report, ASN.1 report, Graphical view, 1 MEDLINE link, 3 protein links, or 1 nucleotide neighbor)
X85009

Bacteriophage A500 hol500 and ply500 genes
gi|853744|emb|X85009|BPA500PLY [853744]
(View GenBank report, FASTA report, ASN.1 report, Graphical view, 1 MEDLINE link, 3 protein links, or 4 nucleotide neighbors)
X85008

Bacteriophage A118 hol118 and ply118 genes
gi|853740|emb|X85008|BPA118PLY [853740]
(View GenBank report, FASTA report, ASN.1 report, Graphical view, 1 MEDLINE link, 3 protein links, or 1 nucleotide neighbor)
L34781

Bacteriophage phi 11 holin homologue (ORF3) gene, complete cds and
peptidoglycan hydrolase (lytA) gene, partial cds
gi|511838|gb|L34781|BPHHOLIN [511838]
(View GenBank report, FASTA report, ASN.1 report, Graphical view, 1 MEDLINE link, 4 protein links, or 2 nucleotide neighbors)
U11698

*Serratia marcescens* SM6 extracellular secretory protein (nucE), putative
phage lysozyme (nucD), and transcriptional activator (nucC) genes,
complete cds
gi|509550|gb|U11698|SMU11698 [509550]
(View GenBank report, FASTA report, ASN.1 report, Graphical view, 1 MEDLINE link, 3 protein links, or 1 nucleotide neighbor)
U31763

*Serratia marcescens* phage-holin analog protein (regA), putative phage
lysozyme (regB), and transcriptional activator (regC) genes, complete
cds
gi|965068|gb|U31763|SMU31763 [965068]
(View GenBank report, FASTA report, ASN.1 report, Graphical view, 1 MEDLINE link, 3 protein iinks, or 1 nucleotide neighbor)
X87674

Bacteriophage P1 lydA & lydB genes
gi|974763|emb|X87674|BACP1LYD [974763]
(View GenBank report, FASTA report, ASN.1 report, Graphical view, 1 MEDLINE link, 2 protein links, or 2 nucleotide neighbors)
L48605

Bacteriophage c2 complete genome
gi|1146276|gb|L48605|C2PVCG [1146276]
(View GenBank report, FASTA report, ASN.1 report, Graphical View, 3 MEDLINE links, 39 protein links, 3 nucleotide neighbors, or 1 genome link)
L33769

Bacteriophage bIL67 DNA polymerase subunit (ORF3-5), essential
recombination protein (ORF13), lysin (ORF24), minor tail protein
(ORF31), terminase subunit (ORF32), holin (ORF37), uuknown protein (ORF
1–2, 6–12, 14–23, 25–30, 33–36), complete genome
gi|522252|gb|L33769|L67CG [522252]
(View GenBank report, FASTA report, ASN.1 report, Graphical view, 1 MEDLINE link, 37 protein links, 2 nucleotide neighbors, or 1 genome link)
L31348

Bacteriophage Tuc2009 integrase (int) gene, complete cds; lysin (lys)
gene, 3' end
gi|508612|gb|L31348|TU21NT [508612]
(View GenBank report, FASTA report, ASN.1 report, Graphical view, 2 MEDLINE links, 3 protein links, or 3 nucleotide neighbors)

TABLE 13-continued

NCBI Entrez Nucleotide QUERY
Key word: holin
51 citations found (all selected)

L31364

Bacteriophage Tuc2009 holin (S) gene, complete cds; lysin (lys) gene,
complete cds
gi|496281|gb|L31364|TU2SLYS [496281]
(View GenBank report, FASTA report, ASN.1 report, Graphical view, 1 MEDLINE
link, 2 protein links, or 1 nucleotide neighbor)
L31366

Bacteriophage Tuc2009 structural protein (mp2) gene, complete cds
gi|496278|gb|L31366|TU2MP2A [496278]
(View GenBank report, FASTA report, ASN.1 report, Graphical View, 1 MEDLINE
link, 2 protein links, or 1 nucleotide neighbor)
L31365

Bacteriophage Tuc2009 structural protein (mp1) gene, complete cds
gi|496276|gb|L31365|TU2MP1A [496276]
(View GenBank report, FASTA report, ASN.1 report, Graphical view, 1 MEDLINE
link, or 1 protein link)
U04309

Bacteriophage phi-LC3 putative holin (lysA) gene and putative murein
hydrolase (lysB) gene, complete cds
gi|530796|gb|U04309|BPU04309 [530796]
(View GenBank report, FASTA report, ASN.1 report, Graphical view, 1 MEDLINE
link, 2 protein links, or 1 nucleotide neighbor)

TABLE 14

NCBI Entrez Nucle tide QUERY
Key word: bacteriophage and kil
5 citations found (all selected)

AF034975

Bacteriophage H-19B essential recombination function protein (erf), kil
protein (kil), regulatory protein cIII (cIII), protein gp17 (17), N
protein (N), cI protein (cI), cro protein (cro), cII protein (cII), O
protein (O), P protein (P), ren protein (ren), Roi (roi), Q protein (Q),
Shiga-like toxin A (slt-IA) and B (slt-IB) subunits, and putative holin
protein (S) genes, complete cds
gi|2668751|gb|AF034975| [2668751]
(View GenBank report, FASTA report, ASN.1 report, Graphical view, 1 MEDLINE
link, 20 protein links, or 30 nucleotide neighbors)
X15637

Bacteriophage P22 P(L) operon encompassing ral, 17, kil and arf genes
gi|15646|emb|X15637|POP22PL [15646]
(View GenBank report, FASTA report, ASN.1 report, Graphical view, 1 MEDLINE
link, 7 protein links, or 2 nucleotide neighbors)
J02459

Bacteriophage lambda, complete genome
gi|215104|gb|J02459|LAMCG [215104]
(View GenBank report,FASTA report, ASN.1 report, Graphical view, 87 MEDLINE
links, 67 protein links, 190 nucleotide neighbors, or 1 genome link)
M64097

Bacteriophage Mu left end
gi|215543|gb|M64097|PMULEFTEN [215543]
(View GenBank report, FASTA report, ASN.1 report, Graphical view, 2 MEDLINE
links, 39 protein links, or 15 nucleotide neighbors)
M18902

Bacteriophage D108 kil gene encoding a replication protein, 3' end; and
containing three ORFs, complete cds
gi|166191|gb|M18902|D18KIL [166191]
(View GenBank report, FASTA report, ASN.1 report, Graphical view, 1 MEDLINE
link, 1 protein link, or 3 nucleotide neighbors)

What is claimed is:

1. A method for identifying at least one target for antibacterial agents, comprising contacting a bacterial protein with a bacterial growth inhibitory bacteriophage polypeptide;

determining whether said bacterial growth inhibitory bacteriophage polypeptide binds to said bacterial protein; and identifying any said bacterial protein bound by said bacterial growth inhibitory bacteriophage polypeptide wherein binding of said bacterial growth inhibitory bacteriophage polypeptide to said bacterial protein is indicative that said bacterial protein is a said target.

2. The method of claim 1, wherein said determining comprises identifying at least one bacterial protein which binds to said bacterial growth inhibitory bacteriophage polypeptide using affinity chromatography on a solid matrix.

3. The method of claim 1, wherein said method further comprises identifying a bacterial nucleic acid sequence encoding said target of said bacterial growth inhibitory bacteriophage polypeptide.

4. The method of claim 1, wherein said determining is performed for a plurality of bacterial growth inhibitory bacteriophage polypeptides.

5. The method of claim 1, wherein said determining is performed using bacterial growth inhibitory bacteriophage polypeptides from a plurality of different bacteriophages.

6. The method of claim 5, wherein said plurality of different bacteriophage is at least 3 different bacteriophages.

7. The method of claim 5, wherein said plurality of different bacteriophage is at least 5 different bacteriophages.

8. The method of claim 5, wherein said plurality of different bacteriophage is at least 10 different bacteriophages.

9. The method of claim 1, wherein said at least one target is a plurality of targets.

10. The method of claim 9, wherein said plurality of targets is from a plurality of different bacteria.

* * * * *